United States Patent
Goto et al.

(10) Patent No.: US 9,617,477 B2
(45) Date of Patent: *Apr. 11, 2017

(54) COMPOUND HAVING FOUR POLYMERIZABLE GROUPS, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Yasuyuki Goto, Tokyo (JP); Maiko Matsukuma, Chiba (JP); Junichi Yamashita, Chiba (JP)

(73) Assignees: JNC CORPORATION, Tokyo (JP); JNC PETROCHEMICAL CORPORATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/820,567

(22) Filed: Aug. 7, 2015

(65) Prior Publication Data

US 2015/0344784 A1 Dec. 3, 2015

Related U.S. Application Data

(62) Division of application No. 13/726,204, filed on Dec. 23, 2012, now Pat. No. 9,157,027.

(30) Foreign Application Priority Data

Apr. 24, 2012 (JP) .................................. 2012-099145
Nov. 12, 2012 (JP) .................................. 2012-248617

(51) Int. Cl.
| | | |
|---|---|---|
| C09K 19/20 | (2006.01) | |
| C09K 19/30 | (2006.01) | |
| C09K 19/38 | (2006.01) | |
| C07C 69/80 | (2006.01) | |
| C09K 19/54 | (2006.01) | |
| C09K 19/12 | (2006.01) | |
| C09K 19/34 | (2006.01) | |
| C09K 19/16 | (2006.01) | |
| C07C 69/54 | (2006.01) | |
| C07C 69/017 | (2006.01) | |
| C07C 69/96 | (2006.01) | |
| C07C 69/007 | (2006.01) | |
| C07C 69/618 | (2006.01) | |

(Continued)

(52) U.S. Cl.
CPC .......... *C09K 19/542* (2013.01); *C07C 69/007* (2013.01); *C07C 69/017* (2013.01); *C07C 69/54* (2013.01); *C07C 69/618* (2013.01); *C07C 69/96* (2013.01); *C09K 19/12* (2013.01); *C09K 19/16* (2013.01); *C09K 19/2014* (2013.01); *C09K 19/3001* (2013.01); *C09K 19/3066* (2013.01); *C09K 19/3068* (2013.01); *C09K 19/3402* (2013.01); *C07C 69/80* (2013.01); *C07C 2101/14* (2013.01); *C09K 19/18* (2013.01); *C09K 19/20* (2013.01); *C09K 19/2007* (2013.01); *C09K 19/3003* (2013.01); *C09K 19/3028* (2013.01); *C09K 19/3809* (2013.01); *C09K 2019/0448* (2013.01); *C09K 2019/122* (2013.01); *C09K 2019/123* (2013.01); *C09K 2019/3077* (2013.01); *C09K 2019/3083* (2013.01); *C09K 2019/3422* (2013.01); *C09K 2019/3425* (2013.01); *C09K 2019/548* (2013.01)

(58) Field of Classification Search
CPC ........ C09K 19/12; C09K 19/16; C09K 19/18; C09K 19/20; C09K 19/2007; C09K 19/2014; C09K 19/3028; C09K 19/3003; C09K 19/3809; C09K 2019/0448; C09K 2019/122; C09K 2019/123; C07C 69/54; C07C 69/80; C07C 45/71; C08F 16/36; C08F 20/18
See application file for complete search history.

(56) References Cited

U.S. PATENT DOCUMENTS

| 8,968,597 | B2 * | 3/2015 | Furusato | ................ | C09K 19/56 |
| | | | | | 252/299.6 |
| 9,157,027 | B2 * | 10/2015 | Goto | ...................... | C09K 19/12 |

FOREIGN PATENT DOCUMENTS

| CN | 102249866 | 11/2011 |
| CN | 102314015 | 1/2012 |

(Continued)

OTHER PUBLICATIONS

CAPLUS 1965:43718.*

(Continued)

*Primary Examiner* — Shean C Wu
(74) *Attorney, Agent, or Firm* — Jianq Chyun IP Office

(57) ABSTRACT

A compound represented by formula (1), a liquid crystal composition, a liquid crystal display device are described.

(1)

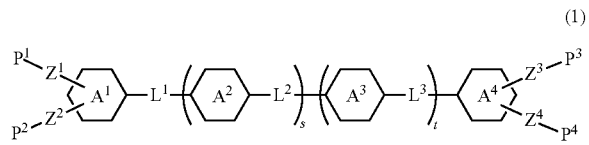

In formula (1), for example, the ring $A^1$ and the ring $A^4$ are phenylene or cyclohexylene; $Z^1$, $Z^2$, $Z^3$ and $Z^4$ are a single bond or alkylene having 1 to 6 carbons; $L^1$ is a single bond; s and t are 0; and $P^1$, $P^2$, $P^3$ and $P^4$ are a polymerizable group.

17 Claims, No Drawings

(51) Int. Cl.
*C09K 19/18* (2006.01)
*C09K 19/04* (2006.01)

(56) References Cited

FOREIGN PATENT DOCUMENTS

| | | | |
|---|---|---|---|
| JP | 2001233837 A | * | 8/2001 |
| JP | 2012-025667 | | 2/2012 |
| WO | 2011/036985 | | 3/2011 |

OTHER PUBLICATIONS

"Office Action of China Counterpart Application", issued on Nov. 5, 2015, pp. 1-23, with English translation thereof.
"Office Action of China Counterpart Application" with English translation, issued on May 27, 2016, p. 1-p. 18.
"Office Action of Taiwan Counterpart Application" with English translation, issued on Jun. 17, 2016, p. 1-p. 11.
"Office Action of China Counterpart Application" with English translation, issued on Aug. 11, 2016, p. 1-p. 13.
"Office Action of Taiwan Counterpart Application" with English translation thereof, issued on Dec. 12, 2016, pp. 1-8.

* cited by examiner

COMPOUND HAVING FOUR POLYMERIZABLE GROUPS, LIQUID CRYSTAL COMPOSITION AND LIQUID CRYSTAL DISPLAY DEVICE

CROSS-REFERENCE TO RELATED APPLICATIONS

This application is a divisional of and claims the priority benefit of U.S. application Ser. No. 13/726,204, filed on Dec. 23, 2012, now allowed, which claims the priority benefit of Japan application serial no. 2012-099145, filed on Apr. 24, 2012, and Japan application serial no. 2012-248617, filed on Nov. 12, 2012. The entirety of each of the above-mentioned patent applications is hereby incorporated by reference herein and made a part of this specification.

BACKGROUND OF THE INVENTION

Technical Field

The invention relates to a polymerizable compound having four groups that can be polymerized by light or heat, and a liquid crystal composition including the polymerizable compound. The invention also relates to a liquid crystal display device in which the orientation of liquid crystal molecules is fixed by sealing the liquid crystal composition between substrates, and then polymerizing the polymerizable compound while a voltage applied to the substrates is adjusted.

Technical Background

A liquid crystal display device utilizes optical anisotropy, dielectric anisotropy and so forth of liquid crystal molecules in a liquid crystal composition. A classification based on the operating mode for liquid crystal molecules includes a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a fringe field switching (FFS) mode and a vertical alignment (VA) mode.

A liquid crystal display device having a mode in which a polymer is used in combination with a liquid crystal composition is known. The mode is, for example, a polymer sustained alignment (PSA) mode or a polymer stabilized (PS) mode. In a liquid crystal display device having this mode, a liquid crystal composition to which a polymerizable compound is added is poured into a display device. A polymer is formed in the liquid crystal composition by the irradiation with ultraviolet light which polymerizes the polymerizable compound, while a voltage is applied between electrodes. With this method, a liquid crystal display device is obtained in which the response time is decreased and the image burn-in is improved.

This method can be applied to a variety of operating modes of liquid crystal display devices, and modes such as PS-TN, PS-IPS, PS-FFS, PSA-VA and PSA-OCB are known. A polymerizable compound used for these kinds of modes seems to have a high ability to orient liquid crystal molecules, but its solubility in a liquid crystal composition is not reported to be high. Improvement of the solubility in a liquid crystal composition has been tried until now, but there is a tendency that the polymerization reactivity is decreased as the solubility increases. Thus, the development of a polymerizable compound having a suitable balance between the solubility and the polymerization reactivity has been expected.

PRIOR ART

Patent Document

Patent document No. 1: JP 2001-233837 A.
Patent document No. 2: JP 2003-321430 A.
Patent document No. 3: JP 2010-189282 A.
Patent document No. 4: JP 2003-307720 A.
Patent document No. 5: JP 2004-131704 A.
Patent document No. 6: JP 2010-536894 A.
Patent document No. 7: JP 2010-537256 A.

SUMMARY OF THE INVENTION

Subject to be Solved by the Invention

The first object of the invention is to provide a polymerizable compound having a suitable polymerization reactivity, a high conversion yield and a high solubility in a liquid crystal composition. The second object is to provide a liquid crystal composition including the compound and having physical properties such as a high maximum temperature of a nematic phase, a low minimum temperature of a nematic phase, a small viscosity, a suitable optical anisotropy, a large dielectric anisotropy, a suitable elastic constant, a large specific resistance and a suitable pretilt. The object is to provide a liquid crystal composition having a suitable balance between at least two of the physical properties. The third object is to provide a liquid crystal display device containing the composition and having a wide temperature range in which the device can be used, a short response time, a large voltage holding ratio, a low threshold voltage, a large contrast ratio and a long service life.

Means for Solving the Subject

The invention concerns a compound represented by formula (1), a liquid crystal composition including the compound, and a liquid crystal display device containing the composition.

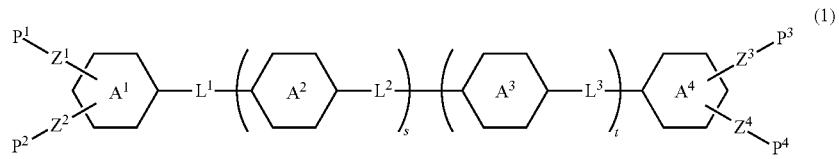

In formula (1), the ring $A^1$, the ring $A^2$, the ring $A^3$ and the ring $A^4$ are independently phenylene or cyclohexylene, and in these groups at least one hydrogen may be replaced by alkyl having 1 to 10 carbons, fluorine, $-CF_2H$ or $-CF_3$;

$Z^1$, $Z^2$, $Z^3$ and $Z^4$ are independently a single bond or alkylene having 1 to 6 carbons, and in the alkylene at least one —CH$_2$— may be replaced by —O—, —COO—, —CH=CH— or —C≡C—;

L$^1$, L$^2$ and L$^3$ are independently a single bond, —COO—, —CH=CH—, —CH—CH—COO—, —C(CH$_3$)=CH—COO—, —CH=C(CH$_3$)—COO—, —C(CH$_3$)=C(CH$_3$)—COO—, —C≡C—, —COCH=CH—, —C(CH$_3$)=C(CH$_3$)—, —CH=CH—CH$_2$O—, —CH=CH—OCH$_2$— or —CO—, and when any one of L$^1$, L$^2$ and L$^3$ is —COO—, the rest of L$^1$, L$^2$ or L$^3$ is a single bond, —CH=CH—, —CH=CH—COO—, —C(CH$_3$)=CH—COO—, —CH=C(CH$_3$)—COO—, —C(CH$_3$)=C(CH$_3$)—COO—, —C≡C—, —COCH=CH—, —C(CH$_3$)=C(CH$_3$)—, —CH=CH—CH$_2$O—, —CH=CH—OCH$_2$— or —CO—;

s and t are independently 0 or 1, and the sum of s and t is 0, 1 or 2;

P$^1$, P$^2$, P$^3$ and P$^4$ are a polymerizable group; and when L$^1$ is a single bond and s and t are 0, an alkyl substituent at the 2-position of the ring A$^1$ and an alkyl substituent at the 2-position of the ring A$^4$ may be bonded with each other to form a ring.

Effect of the Invention

The first advantage of the invention is to provide the polymerizable compound having a suitable polymerization reactivity, a high conversion yield and a high solubility in a liquid crystal composition. The second advantage is to provide the liquid crystal composition including the compound and having physical properties such as a high maximum temperature of a nematic phase, a low minimum temperature of a nematic phase, a small viscosity, a suitable optical anisotropy, a large dielectric anisotropy, a suitable elastic constant, a large specific resistance and a suitable pretilt. The advantage is to provide the liquid crystal composition having a suitable balance between at least two of the physical properties. The third advantage is to provide the liquid crystal display device containing the composition and having a wide temperature range in which the device can be used, a short response time, a large voltage holding ratio, a low threshold voltage, a large contrast ratio and a long service life.

DESCRIPTION OF THE EMBODIMENTS

Usage of the terms in this specification is described as follows. A liquid crystal compound is a generic term for a compound having a liquid crystal phase such as a nematic phase or a smectic phase, and also for a compound having no liquid crystal phases but useful as a component of a liquid crystal composition. A polymerizable compound is a compound that gives a polymer by polymerization. A liquid crystal compound, a polymerizable compound, a liquid crystal composition and a liquid crystal display device may be abbreviated to a compound, a compound, a composition and a device, respectively. A liquid crystal display device is a generic term for a liquid crystal display panel and a liquid crystal display module. A clearing point is the transition temperature between a liquid crystal phase and an isotropic phase of a liquid crystal compound. The minimum temperature of a liquid crystal phase is the transition temperature between solids and a liquid crystal phase (a smectic phase, a nematic phase or the like) of a liquid crystal compound. The maximum temperature of a nematic phase is the transition temperature between a nematic phase and an isotropic phase of a liquid crystal composition, and may be abbreviated to the maximum temperature. The minimum temperature of a nematic phase may be abbreviated to the minimum temperature.

A compound represented by formula (1) may be abbreviated to the compound (1). This abbreviation may apply to a compound represented by formula (2) or the like. A group represented by formula (P-1) may be abbreviated to the group (P-1). This abbreviation may apply to a compound represented by formula (M-1) or the like. The compound (1) means one compound or at least two compounds represented by formula (1). In formulas (1) to (14), the symbol A$^1$, B$^1$, C$^1$ or the like surrounded by a hexagonal shape corresponds to the ring A$^1$, the ring B$^1$, the ring C$^1$ or the like, respectively. The symbol R$^3$ is used in a plurality of formulas such as formula (2) and formula (3). Two groups represented by arbitrary two of R$^3$ may be the same or different in these compounds. Two of the symbol C$^2$ is present in one formula when q is 2 in formula (5). Two rings represented by two of the symbol C$^2$ may be the same or different in this compound. The same rule applies to symbols such as R$^5$ and Y$^4$. The contents of liquid crystal compounds in a liquid crystal composition means a weight percentage (% by weight) based on the total weight of the liquid crystal compounds (the weight of the liquid crystal composition from which a polymerizable compound and an additive are excluded).

The expression "at least one of 'A' may be replaced by 'B'" means that the position of 'A' is arbitrary when the number of 'A' is one, and that the positions of 'A' can be selected without any restriction also when the numbers of 'A' are two or more. The expression "at least one of A may be replaced by B, C or D" includes cases where arbitrary A has been replaced by B, where arbitrary A has been replaced by C, and where arbitrary A has been replaced by D, and also cases where a plurality of A are replaced by at least two of B, C and D. For example, "alkyl in which at least one of —CH$_2$— may be replaced by —O— or —CH=CH—" includes alkyl, alkenyl, alkoxy, alkoxyalkyl, alkoxyalkenyl and alkenyloxyalkyl. Incidentally, it is undesirable that two successive —CH$_2$— should be replaced by —O— to give —O—O—. It is also undesirable that —CH$_2$— of a methyl moiety (—CH$_2$—H) in alkyl and so forth should be replaced by —O— to give —O—H.

2-Fluoro-1,4-phenylene means the following two divalent groups. Fluorine may be facing left or facing right in a structural formula. The rule applies to an asymmetric divalent group such as tetrahydropyran-2,5-diyl.

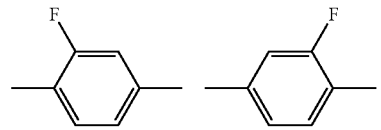

The same rule applies to a trivalent six-membered ring described below.

In the compound (1), the ring A$^1$ and the ring A$^4$ are represented by a trivalent six-membered ring described below. The symbol L means L$^1$ or L$^3$.

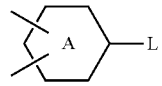

In the ring $A^1$ and the ring $A^4$, two oblique lines crossing a hexagonal shape mean that the bonding positions on the six-membered ring can be arbitrarily selected. When the six-membered ring is a benzene ring, typical examples of the ring $A^1$ and the ring $A^4$ are the group (N-1), the group (N-2) and the group (N-3).

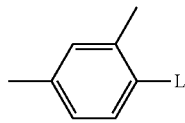
(N-1)

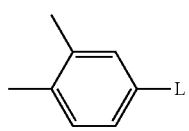
(N-2)

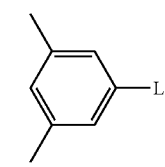
(N-3)

In the bonding groups $Z^1$, $Z^2$, $Z^3$, $Z^4$, $L^1$, $L^2$ and $L^3$ of the compound (1), —COO—, —CH=CH—COO—, —C(CH$_3$)=CH—COO—, —CH=C(CH$_3$)—COO—, —C(CH$_3$)=C(CH$_3$)—COO—, —COCH=CH—, —CH=CH—CH$_2$O— or —CH=CH—OCH$_2$— is not restricted to the direction described in definitions and may also mean —OCO—, —OCO—CH=CH—, —OCO—C(CH$_3$)=CH—, —OCO—CH=C(CH$_3$)—, —OCO—C(CH$_3$)=C(CH$_3$)—, —CH=CH—CO—, —OCH$_2$—CH=CH— or —CH$_2$O—CH=CH—.

The invention includes the contents described in the following items 1 to 18.

Item 1. A compound represented by formula (1):

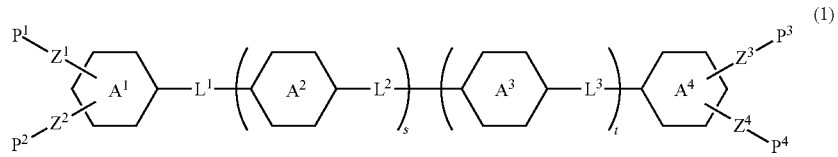
(1)

in formula, the ring $A^1$, the ring $A^2$, the ring $A^3$ and the ring $A^4$ are independently phenylene or cyclohexylene, and in these groups at least one hydrogen may be replaced by alkyl having 1 to 10 carbons, fluorine, —CF$_2$H or —CF$_3$;

$Z^1$, $Z^2$, $Z^3$ and $Z^4$ are independently a single bond or alkylene having 1 to 6 carbons, and in the alkylene at least one —CH$_2$— may be replaced by —O—, —COO—, —CH=CH— or —C≡C—;

$L^1$, $L^2$ and $L^3$ are independently a single bond, —COO—, —CH=CH—, —CH=CH—COO—, —C(CH$_3$)=CH—COO—, —CH=C(CH$_3$)—COO—, —C(CH$_3$)=C(CH$_3$)—COO—, —CH=C—, —COCH=CH—, —C(CH$_3$)=C(OH$_3$)—, —CH=CH—CH$_2$O—, —CH=CH—OCH$_2$— or —CO—, and when any one of $L^1$, $L^2$ and $L^3$ is —COO—, the rest of $L^1$, $L^2$ or $L^3$ is a single bond, —CH=CH—, —CH=CH—COO—, —C(CH$_3$)=CH—COO—, —CH=C(CH$_3$)—COO—, —C(CH$_3$)=C(CH$_3$)—COO—, —C≡C—, —COCH=CH—, —C(CH$_3$)=C(CH$_3$)—, —CH=CH—CH$_2$O—, —CH=CH—OCH$_2$— or —CO—;

s and t are independently 0 or 1, and the sum of s and t is 0, 1 or 2;

$P^2$, $P^3$ and $P^4$ are independently a polymerizable group; and when $L^1$ is a single bond and s and t are 0, an alkyl substituent at the 2-position of the ring $A^1$ and an alkyl substituent at the 2-position of the ring $A^4$ may be bonded with each other to form a ring.

Item 2. The compound according to item 1, wherein in formula (1) according to item 1, $P^1$, $P^2$, $P^3$ and $P^4$ are the group (P-1):

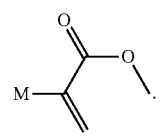
(P-1)

In the group (P-1), M is hydrogen, fluorine, —CH$_3$ or —CF$_3$.

Item 3. The compound according to item 2, wherein the compound is represented by any one of formulas (1-1) to (1-6):

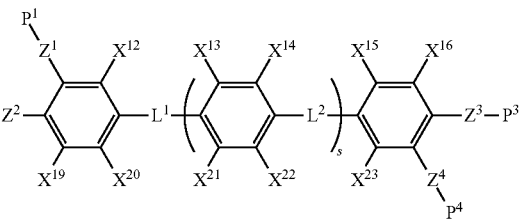
(1-1)

-continued

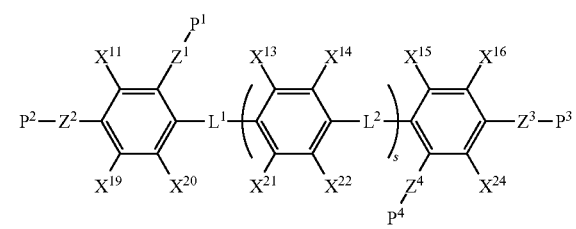
(1-2)

(1-3)
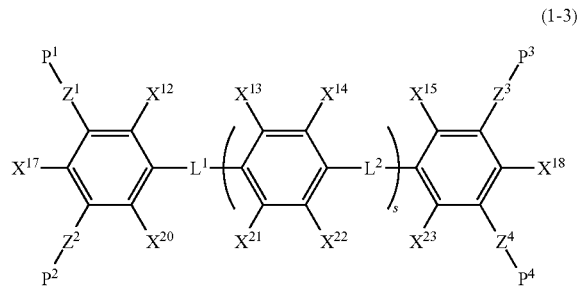

(1-4)
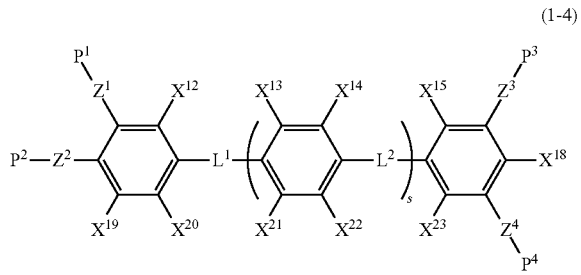

(1-5)
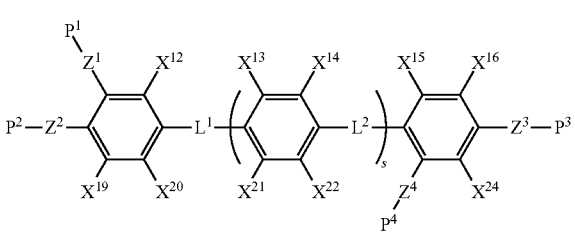

(1-6)
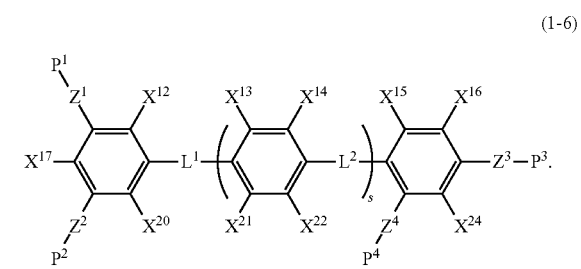

In these formulas, $Z^1$, $Z^2$, $Z^3$ and $Z^4$ are independently a single bond or alkylene having 1 to 6 carbons, and in the alkylene at least one —$CH_2$— may be replaced by —O—, —COO—, —CH=CH— or $L^1$ and $L^2$ are independently a single bond, —COO—, —CH=CH—, —CH=CH—COO—, —C($CH_3$)=CH—COO—, —CH=C($CH_3$)—COO—, —C($CH_3$)=C($CH_3$)—COO—, —C≡C—, —COCH=CH—, —C($CH_3$)=C($CH_3$)—, —CH=CH—$CH_2$O—, —CH=CH—O$CH_2$— or —CO—, and when any one of $L^1$ and $L^2$ is —COO—, the rest of $L^1$ or $L^2$ is a single bond, —CH=CH—, —CH=CH—COO—, —C($CH_3$)=CH—COO—, —CH=C($CH_3$)—COO—, —C($CH_3$)=C($CH_3$)—COO—, —C≡C—, —COCH=CH—, —C($CH_3$)=C($CH_3$)—, —CH=CH—$CH_2$O—, —CH=CH—O$CH_2$— or —CO—; $X^{11}$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$ and $X^{24}$ are independently hydrogen, alkyl having 1 to 10 carbons, fluorine, —$CF_2H$ or —$CF_3$; s is 0 or 1; and $P^1$, $P^2$, $P^3$ and $P^4$ are the group (P-1):

(P-1)
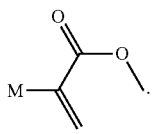

In the group (P-1), M is hydrogen, fluorine, —$CH_3$ or —$CF_3$.

Item 4. The compound according to item 3, wherein in formulas (1-1) to (1-6) according to item 3, s is 0.

Item 5. The compound according to item 3, wherein in formulas (1-1) to (1-6) according to item 3, $Z^1$, $Z^2$, $Z^3$ and $Z^4$ are independently a single bond; s is 0 or 1; $L^1$ is a single bond; $L^2$ is a single bond, —COO—, —CH=CH—, —CH=CH—COO—, —C($CH_3$)=CH—COO—, —OH=O($CH_3$)—COO—, —C($CH_3$)=C($CH_3$)—COO—, —C≡C—, —COCH=CH—, —C($CH_3$) ($CH_3$)—, —CH=CH—$CH_2$O—, —CH=CH—O$CH_2$— or —CO—; and P is $CH_2$=CH—COO— or $CH_2$=C($CH_3$)—COO—.

Item 6. The compound according to item 3, wherein in formulas (1-1) to (1-6) according to item 3, $Z^1$, $Z^2$, $Z^3$ and $Z^4$ are independently —COO—, —$CH_2$O—, —$CH_2CH_2$O— or —CH=CHO—; s is 0 or 1; $L^1$ is a single bond; $L^2$ is a single bond, —COO—, —CH=CH—, —CH=CH—COO—, —C($CH_3$)=CH—COO—, —CH=C($CH_3$)—COO—, —C($CH_3$)=C($CH_3$)—COO—, —C≡C—, —COCH=CH—, —C($CH_3$)=C($CH_3$)—CH=CH—$CH_2$O—, —CH=CH—O$CH_2$— or —CO—; and P is $CH_2$=CH—COO— or $CH_2$=C($CH_3$)—COO—.

Item 7. The compound according to item 3, wherein in formulas (1-1) to (1-3) according to item 3, $Z^1$, $Z^2$, $Z^3$ and $Z^4$ are independently a single bond; s is 0 or 1; $L^1$ is a single bond; $L^2$ is a single bond, —COO—, —CH=CH— or —CH=CHCOO—; and P is $CH_2$=CH—COO— or $CH_2$=C($CH_3$)—COO—.

Item 8. The compound according to item 3, wherein in formulas (1-1) to (1-3) according to item 3, $Z^1$, $Z^2$, $Z^3$ and $Z^4$ are independently —$CH_2CH_2$O— or —CH=CHO—; s is 0 or 1; $L^1$ is a single bond; $L^2$ is a single bond, —COO—, —CH=CH— or —CH=CHCOO—; and P is $CH_2$=CH—COO— or $CH_2$=C($CH_3$)—COO—.

Item 9. A polymer obtained from the compound according to any one of items 1 to 8.

Item 10. A liquid crystal composition including at least one selected from the group consisting of the compound according to any one of items 1 to 8 and the polymer according to item 9.

Item 11. The liquid crystal composition according to item 10, further including at least one compound selected from the group consisting of compounds represented by formulas (2), (3) and (4):

(2)
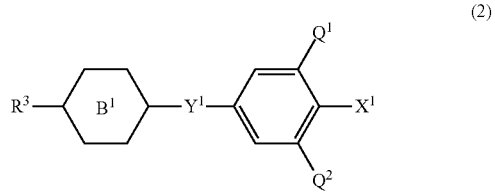

-continued

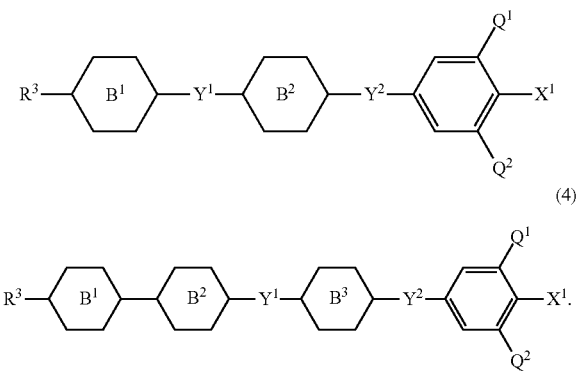
(3)
(4)

In the formulas, $R^3$ is alkyl having 1 to 10 carbons or alkenyl having 2 to 10 carbons, and in these groups at least one hydrogen may be replaced by fluorine and at least one —$CH_2$— may be replaced by —O—;

$X^1$ is independently fluorine, chlorine, —$OCF_3$, —$OCHF_2$, —$CF_3$, —$CHF_2$, —$CH_2F$, —$OCF_2CHF_2$ or —$OCF_2CHFCF_3$;

the ring $B^1$, the ring $B^2$ and the ring $B^3$ are independently 1,4-cyclohexylene, 1,3-dioxane-2,5-diyl, pyrimidine-2,5-diyl, tetrahydropyran-2,5-diyl, or 1,4-phenylene in which at least one hydrogen may be replaced by fluorine;

$Y^1$ and $Y^2$ are independently —$(CH_2)_2$—, —$(CH_2)_4$—, —COO—, —$CF_2O$—, —$OCF_2$—, —CH=CH—, —C≡C—, —$CH_2O$— or a single bond; and $Q^1$ and $Q^2$ are independently hydrogen or fluorine.

Item 12. The liquid crystal composition according to item 10 or 11, further including at least one compound selected from the group consisting of compounds represented by formula (5):

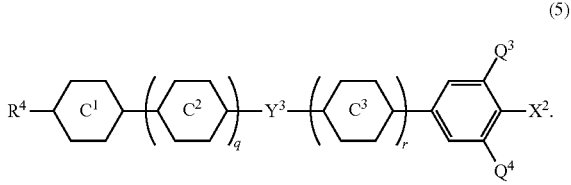
(5)

In the formulas, $R^4$ is alkyl having 1 to 10 carbons or alkenyl having 2 to 10 carbons, and in these groups at least one hydrogen may be replaced by fluorine and at least one —$CH_2$— may be replaced by —O—;

$X^2$ is —CN or —C≡C—CN;

the ring $C^1$, the ring $C^2$ and the ring $C^3$ are independently 1,4-cyclohexylene, 1,4-phenylene in which at least one hydrogen may be replaced by fluorine, 1,3-dioxane-2,5-diyl, tetrahydropyran-2,5-diyl or pyrimidine-2,5-diyl;

$Y^3$ is —$(CH_2)_2$—, —COO—, —$CF_2O$—, —$OCF_2$—, —C≡C—, —$CH_2O$— or a single bond;

$Q^3$ and $Q^4$ are independently hydrogen or fluorine; and q is 0, 1 or 2, and r is 0 or 1.

Item 13. The liquid crystal composition according to item 10, further including at least one compound selected from the group consisting of compounds represented by formulas (6), (7), (8), (9), (10) and (11):

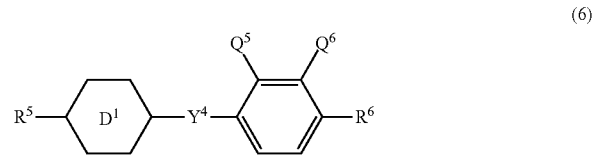
(6)

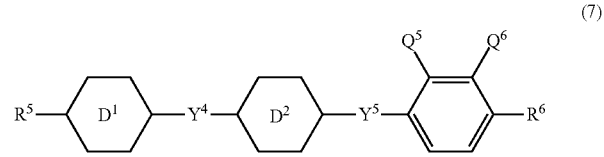
(7)

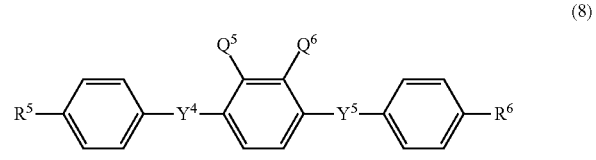
(8)

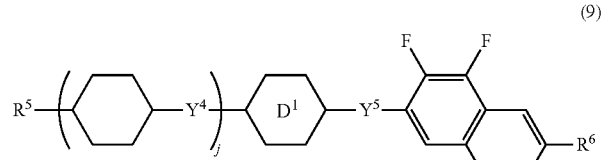
(9)

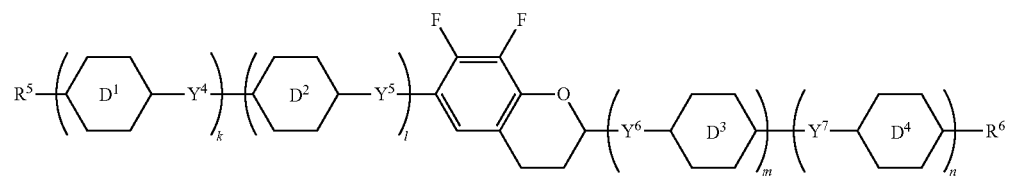
(10)

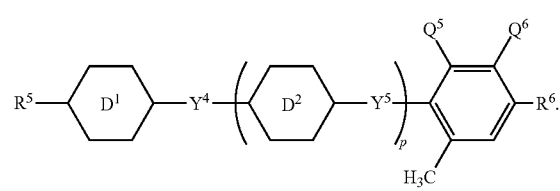
(11)

In these formulas, $R^5$ and $R^6$ are independently alkyl having 1 to 10 carbons or alkenyl having 2 to 10 carbons, and in these groups at least one hydrogen may be replaced by fluorine and at least one —CH$_2$— may be replaced by —O—;

the ring $D^1$, the ring $D^2$, the ring $D^3$ and the ring $D^4$ are independently 1,4-cyclohexylene, 1,4-cyclohexenylene, 1,4-phenylene in which at least one hydrogen may be replaced by fluorine, tetrahydropyran-2,5-diyl or decahydro-2,6-naphthalene;

$Y^4$, $Y^5$, $Y^6$ and $Y^7$ are independently —(CH$_2$)$_2$—, —COO—, —CH$_2$O—, —OCF$_2$—, —OCF$_2$(CH$_2$)$_2$— or a single bond;

$Q^5$ and $Q^6$ are independently fluorine or chlorine; and j, k, l, m, n and p are independently 0 or 1, and the sum of k, l, m and n is 1 or 2.

Item 14. The liquid crystal composition according to item 10, further including at least one compound selected from the group consisting of compounds represented by formulas (12), (13) and (14):

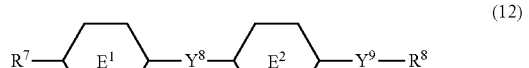

(12)

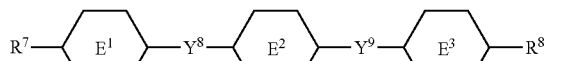

(13)

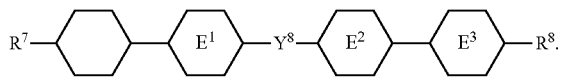

(14)

In these formulas, $R^7$ and $R^8$ are independently alkyl having 1 to 10 carbons or alkenyl having 2 to 10 carbons, and in these groups at least one hydrogen may be replaced by fluorine and at least one —CH$_2$— may be replaced by —O—;

the ring $E^1$, the ring $E^2$ and the ring $E^3$ are independently 1,4-cyclohexylene, pyrimidine-2,5-diyl, 1,4-phenylene, 2-fluoro-1,4-phenylene or 2,5-difluoro-1,4-phenylene; and $Y^8$ and $Y^9$ are independently —C≡C—, —COO—, —(CH$_2$)$_2$—, —CH=CH— or a single bond.

Item 15. The liquid crystal composition according to item 11, further including at least one compound selected from the group consisting of compounds represented by formulas (12), (13) and (14) according to item 14.

Item 16. The liquid crystal composition according to item 12, further including at least one compound selected from the group consisting of compounds represented by formulas (12), (13) and (14) according to item 14.

Item 17. The liquid crystal composition according to item 13, further including at least one compound selected from the group consisting of compounds represented by formulas (12), (13) and (14) according to item 14.

Item 18. A liquid crystal display device containing the liquid crystal composition according to any one of items 10 to 17.

The invention includes the following aspects 1) to 7): 1) the composition described above, further including an optically active compound; 2) the composition described above, further including an additive such as an antioxidant, an ultraviolet light absorber, a light stabilizer, a thermal stabilizer and/or an antifoaming agent; 3) an AM device containing the composition described above; 4) a device containing the composition described above and having a mode of PS-TN, PS-IPS, PS-FFS, PSA-VA or PSA-OCB; 5) a transmission type device containing the composition described above; 6) use of the composition described above as a composition having a nematic phase; and 7) use as an optically active composition by the addition of an optically active compound to the composition described above.

The invention also includes the following aspects 8) to 11): 8) use of a composition including a compound represented by formula (1) and at least one compound selected from the group consisting of compounds represented by formulas (2), (3) and (4), in a liquid crystal display device having a PSA mode; 9) use of a composition including a compound represented by formula (1) and at least one compound selected from the group consisting of compounds represented by formula (5), in a liquid crystal display device having a PSA mode; 10) use of a composition including a compound represented by formula (1) and at least one compound selected from the group consisting of compounds represented by formulas (6), (7), (8), (9), (10) and (11), in a liquid crystal display device having a PSA mode; and 11) use of a composition including a compound represented by formula (1) and at least one compound selected from the group consisting of compounds represented by formulas (12), (13) and (14), in a liquid crystal display device having a PSA mode.

The compounds, synthetic methods, liquid crystal compositions, polymerization and liquid crystal display devices in the invention will be explained in this order.

1. The compound (1)

Desirable examples of the compound (1) of the invention will be explained. Desirable examples of the terminal group, the ring structure, the bonding group and the substituent in the compound (1) can be applied to the sub-formulas of the compound (1). Physical properties such as a clearing point, the minimum temperature of a liquid crystal phase, optical anisotropy and dielectric anisotropy can be arbitrarily adjusted by a suitable combination of the kinds of the ring $A^1$ to the ring $A^4$, $Z^1$ to $Z^4$, $L^1$ to $L^3$ and $P^1$ to $P^4$ in the compound (1). The compound (1) may contain isotopes such as $^2$H (deuterium) and $^{13}$C in a larger amount than the amount of the natural abundance, since there are no major differences in physical properties of the compound. Main effects of the kinds of $Z^1$ and so forth on the physical properties of the compound (1) will be explained below.

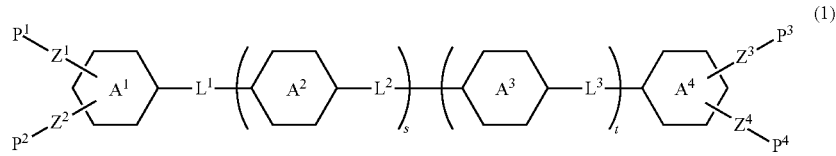

(1)

In formula (1), the ring $A^1$, the ring $A^2$, the ring $A^3$ and the ring $A^4$ are independently phenylene or cyclohexylene, and in these groups at least one hydrogen may be replaced by fluorine, alkyl having 1 to 10 carbons, —$CF_2H$ or —$CF_3$.

Desirable examples of the ring $A^1$ or the ring $A^4$ are the group (N-1), the group (N-2) and the group (N-3). The group (N-1), (N-2) or (N-3) with at least one hydrogen having been replaced by fluorine, —$CF_2H$ or —$CF_3$ is also desirable. A more desirable example of the ring $A^1$ or the ring $A^4$ is the group (N-2).

Desirable examples of the groups (N-1), (N-2) and (N-3) with at least one hydrogen having been replaced by fluorine, —$CF_2H$ or —$CF_3$ are the groups (R-1) to (R-12). L means $L^1$ or $L^3$.

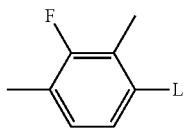
(R-1)

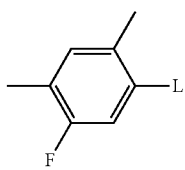
(R-2)

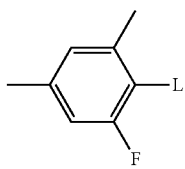
(R-3)

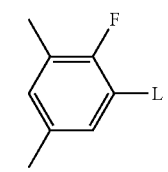
(R-4)

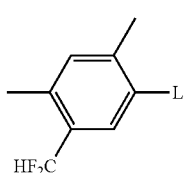
(R-5)

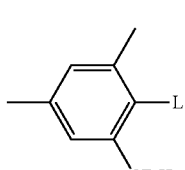
(R-6)

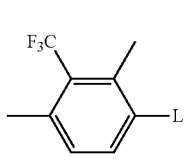
(R-7)

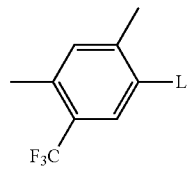
(R-8)

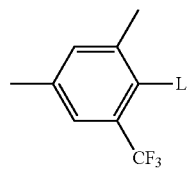
(R-9)

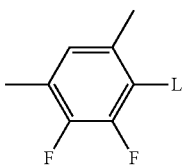
(R-10)

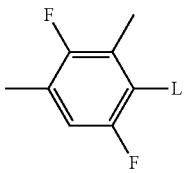
(R-11)

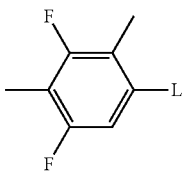
(R-12)

A desirable combination of the ring $A^1$ and the ring $A^4$ is the group (N-1) and the group (N-1), the group (N-2) and the group (N-2), or the group (N-3) and the group (N-3). A more desirable combination is the group (N-2) and the group (N-2).

A desirable example of the ring $A^2$ or the ring $A^3$ is 1,4-phenylene, 1,4-cyclohexylene, 2-fluoro-1,4-phenylene, 2,3-difluoro-1,4-phenylene, 2-methyl-1,4-phenylene, 2-difluoromethyl-1,4-phenylene or 2-trifluoromethyl-1,4-phenylene. A more desirable example is 1,4-phenylene, 1,4-cyclohexylene, 2-fluoro-1,4-phenylene or 2,3-difluoro-1,4-phenylene. The most desirable example is 1,4-phenylene.

In formula (1), $Z^1$, $Z^2$, $Z^3$ and $Z^4$ are independently a single bond or alkylene having 1 to 6 carbons, and in the alkylene at least one —$CH_2$— may be replaced by —O—, —COO—, —CH=CH— or —C≡C—.

Desirable examples of $Z^1$, $Z^2$, $Z^3$ or $Z^4$ are a single bond, —COO—, —$CH_2$—, —$CH_2O$—, —$(CH_2)_2$—, —$(CH_2)_2$—O—, —CH=CH—, —CH=CHO—, —C≡C—, —C≡CO—, —$(CH_2)_3$—, —$(CH_2)_3O$—, —$(CH_2)_4$— and —$(CH_2)_4$—O—. More desirable examples are a single bond, —$CH_2$—, —$(CH_2)_2$—O—, —CH=CH— and —CH=CHO—. The most desirable example is a single bond.

When $Z^1$, $Z^2$, $Z^3$ and $Z^4$ are a single bond, —$CH_2$—, —$(CH_2)_2$—, —$(CH_2)_2$—O—, —CH=CH—, —CH=CHO—, —$CH_2O$—, —$(CH_2)_3$—O—, —$(CH_2)_4$— or —$(CH_2)_4$—O—, the viscosity is small. When $Z^1$, $Z^2$, $Z^3$ or $Z^4$ is a single bond, —$(CH_2)_2$—, —$(CH_2)_2O$—, —CH═CH— or —CH═CHO—, the viscosity is smaller. When the bonding group is —CH═CH— or —CH═CHO—, the temperature range of a liquid crystal phase is wide and the elastic constant is large. When the bonding group is —CH—CH—, —CH═CHO— or —C≡C—, the optical anisotropy is large. When $Z^1$, $Z^2$, $Z^3$ or $Z^4$ is a single bond, —CH$_2$—, —(CH$_2$)$_2$—, —(CH$_2$)$_2$—O—, —(CH$_2$)$_4$— or —(CH$_2$)$_3$—O—, the chemical stability is high. When $Z^1$, $Z^2$, $Z^3$ or $Z^4$ is a group having a double bond such as —CH═CH—, the configuration may be a cis-form or a trans-form.

In formula (1), $L^1$, $L^2$ and $L^3$ are independently a single bond, —COO—, —CH—CH—, —CH═CH—COO—, —C(CH$_3$)═CH—COO—, —CH═C(CH$_3$)—COO—, —C(CH$_3$)═C(CH$_3$)—COO—, —C≡C—, —COCH═CH—, —C(CH$_3$)═C(CH$_3$)—, —CH—CH—CH$_2$O—, —CH═CH—OCH$_2$— or —CO—, and when any one of $L^1$, $L^2$ and $L^3$ is —COO—, the rest of $L^1$, $L^2$ or $L^3$ is a single bond, —CH═CH—, —CH—CH—COO—, —C(CH$_3$)═CH—COO—, —CH═C(CH$_3$)—COO—, —C(CH$_3$)═C(CH$_3$)—COO—, —C≡C—, —COCH═CH—, —C(CH$_3$)═C(CH$_3$)—, —CH═CH—CH$_2$O—, —CH═CH—OCH$_2$— or —CO—.

Desirable examples of $L^1$, $L^2$ or $L^3$ are a single bond, —COO—, —CH═CH—, —C≡C—, —CH═CH—COO— and —C(CH$_3$)═C(CH$_3$)—. More desirable examples are a single bond and —CH═CH—. The most desirable example is a single bond.

When $L^1$, $L^2$ or $L^3$ is a single bond, the viscosity is small. When $L^1$, $L^2$ or $L^3$ is —CH═CH—, —CH═CH—COO—, —C≡C—, —COCH═CH— or —C(CH$_3$)═C(CH$_3$)—, the temperature range of a liquid crystal phase is wide and the elastic constant is large. When $L^1$, $L^2$ or $L^3$ is —CH═CH—, —CH═CH—COO—, —C≡C—, —COCH═CH— or —C(CH$_3$)═C(CH$_3$)—, the optical anisotropy is large. When $L^1$, $L^2$ or $L^3$ is a single bond, the chemical stability is high. When $L^1$, $L^2$ or $L^3$ is a group having a double bond such as —CH═CH—, the configuration may be a cis-form or a trans-form.

In formula (1), $P^1$, $P^2$, $P^3$ and $P^4$ are polymerizable groups. Desirable examples of the polymerizable groups are an acryloyloxy group, a methacryloyloxy group, an acrylamido group, a methacrylamide group, a vinyloxy group, a vinylcarbonyl group, an epoxy group, an oxetanyl group, a 3,4-epoxycyclohexyl group and a maleimido group. In these groups, at least one hydrogen may be replaced by fluorine. A desirable example of $P^1$, $P^2$, $P^3$ or $P^4$ is the group (P-1).

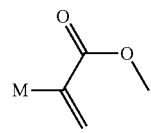

(P-1)

In the group (P-1), M is hydrogen, fluorine, —CH$_3$ or —CF$_3$. Desirable M is hydrogen or —CH$_3$ (namely, (P-1) is CH$_2$═CH—COO— or CH$_2$═C(CH$_3$)—COO—).

In formula (1), s and t are independently 0 or 1, and the sum of s and t is 0, 1 or 2. When the sum of s and t is 0, the viscosity is small. When the sum of s and t is 1 or 2, the maximum temperature is high.

In formula (1), when $L^1$ is a single bond and s and t are 0, an alkyl substituent at the 2-position of the ring $A^1$ and an alkyl substituent at the 2-position of the ring $A^4$ may be bonded with each other to form a ring.

A desirable example of the compound (1) is the compound (1-A) or (1-B).

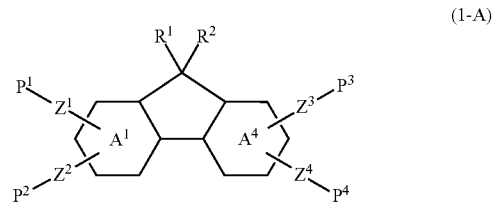

(1-A)

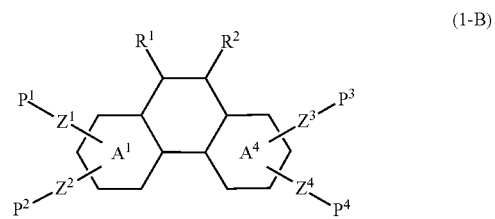

(1-B)

In the compounds (1-A) and (1-8), $R^1$ and $R^2$ are independently hydrogen or alkyl. The sum of the number of carbon in $R^1$, the number of carbon in $R^2$ and the number of carbon that connects the ring $A^1$ and the ring $A^4$ is 2 to 20.

As described above, a compound having objective physical properties can be obtained by a suitable selection of the kinds of ring structures, terminal groups, bonding groups and so forth. Accordingly, the compound (1) is useful as the component of a liquid crystal composition for use in a liquid crystal display device having a mode such as PS-TN, PS-IPS, PS-FFS, PSA-VA or PSA-OCB.

Desirable examples of the compound (1) are the compounds (1-1) to (1-6). A more desirable example is the compound (1-1), (1-2) or (1-3). The most desirable example is the compound (1-1).

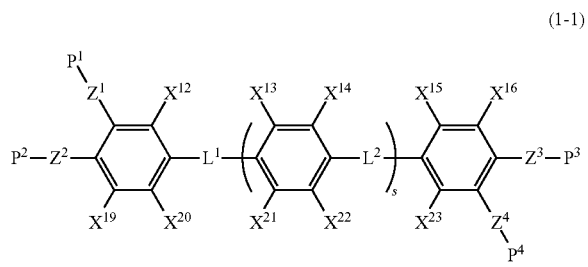

(1-1)

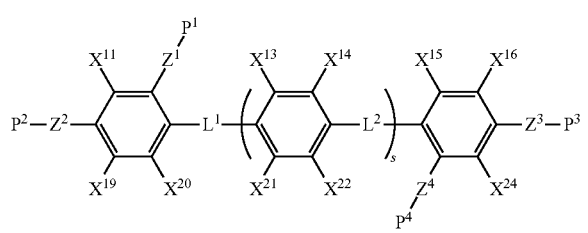

(1-2)

-continued (1-3)
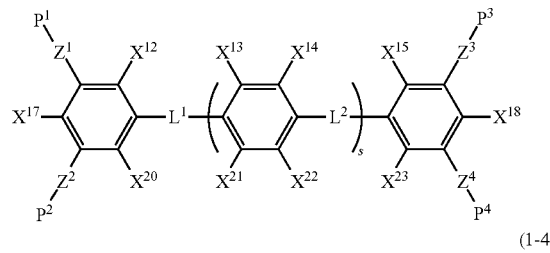

(1-4)
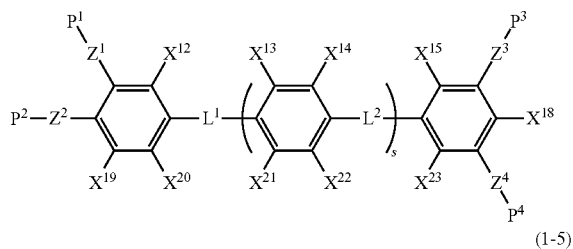

(1-5)
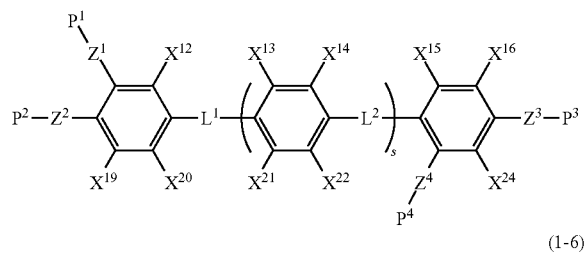

(1-6)
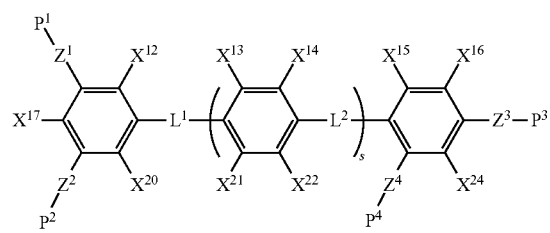

In these compounds, the definitions of $Z^1$, $Z^2$, $Z^3$, $Z^4$, $L^1$, $L^2$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$ s, $P^1$, $P^2$, $P^3$ and $P^4$ are just the same as described previously.

A desirable example of the compound (1-1) is the compound (1-1-a).

(1-1-a)
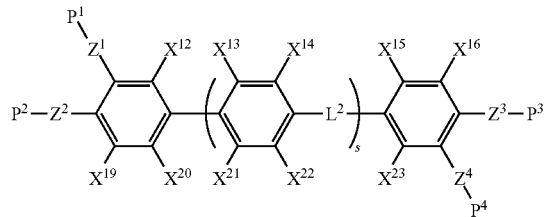

In the compound (1-1-a), $Z^1$, $Z^2$, $Z^3$ and $Z^4$ are independently a single bond, —CH$_2$CH$_2$O— or —CH=CHO—; s is 0 or 1; $L^2$ is a single bond, —COO—, —CH=CH—, —CH=CH—COO— or —C≡C—; $X^{12}$, $X^{13}$, $X^{14}$, $X^{15}$, $X^{16}$, $X^{19}$, $X^{20}$, $X^{21}$, $X^{22}$ and $X^{23}$ are independently hydrogen, alkyl having 1 to 10 carbons, fluorine, —CF$_2$H or —CF$_3$; and $P^1$, $P^2$, $P^3$ and $P^4$ are independently CH$_2$=CH—COO— or CH$_2$=C(CH$_3$)—COO—.

A more desirable example of the compound (1-1) is the compound (1-1-b).

(1-1-b)
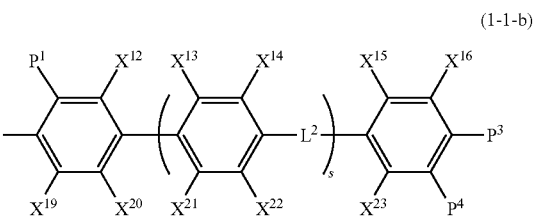

In the compound (1-1-b), $L^2$ is a single bond, —COO—, —CH=CH— or —CH=CH—COO—; s is 0 or 1; $X^{12}$, $X^{13}$, $X^{14}$, $X^{15}$, $X^{16}$, $X^{19}$, $X^{20}$, $X^{21}$, $X^{22}$ and $X^{23}$ are independently hydrogen, alkyl having 1 to 10 carbons, fluorine, —CF$_2$H or —CF$_3$; and $P^1$, $P^2$, $P^3$ and $P^4$ are independently CH$_2$=CH—COO— or CH$_2$=C(CH$_3$)—COO—.

The most desirable example of the compound (1-1) is the compound (1-1-c).

(1-1-c)
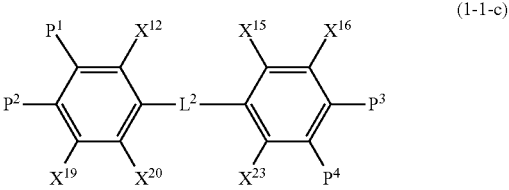

In the compound (1-1-c), $L^2$ is a single bond, —OCO— or —CH=CH—; $X^{12}$, $X^{15}$, $X^{16}$, $X^{19}$, $X^{20}$ and $X^{23}$ are independently hydrogen, alkyl having 1 to 10 carbons, fluorine, —CF$_2$H or —CF$_3$; and $P^1$, $P^2$, $P^3$ and $P^4$ are independently CH$_2$=CH—COO— or CH$_2$=C(CH$_3$)—COO—.

2. Synthetic Methods

The method for synthesizing the compound (1) will be explained. The compound (1) can be prepared by a suitable combination of methods in synthetic organic chemistry. Methods of introducing objective terminal groups, rings and bonding groups into starting materials are described in books as Houben-Wyle, Methoden der Organische Chemie (Georg-Thieme Verlag, Stuttgart), Organic Syntheses (John Wily & Sons, Inc.), Organic Reactions (John Wily & Sons Inc.), Comprehensive Organic Synthesis (Pergamon Press) and Shin Jikken Kagaku Kouza (New Experimental Chemistry Course, in English; Maruzen Co., Ltd., Japan).

2-1. Formation of the Bonding Group L

Examples of the formation of the bonding group $L^1$, $L^2$ and $L^3$ in the compound (1) are shown in the following schemes. In these schemes, MSG$^1$ (or MSG$^2$) is a monovalent organic group having at least one ring. Monovalent organic groups represented by a plurality of the MSG$^1$ (or MSG$^2$) may be the same or different. The compounds (1A) to (1R) correspond to the compound (1).

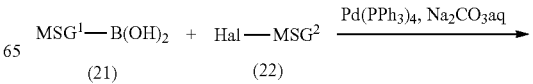

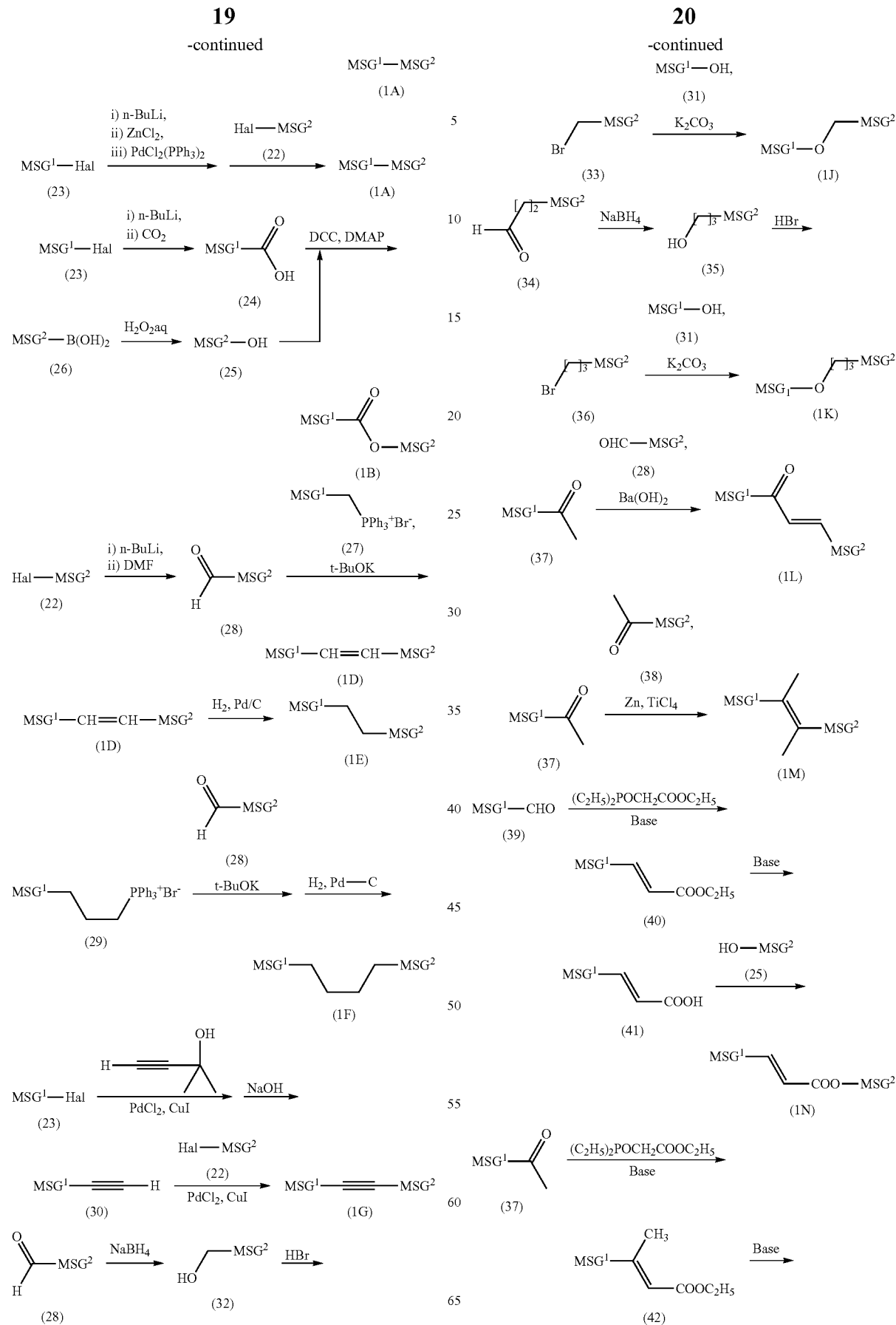

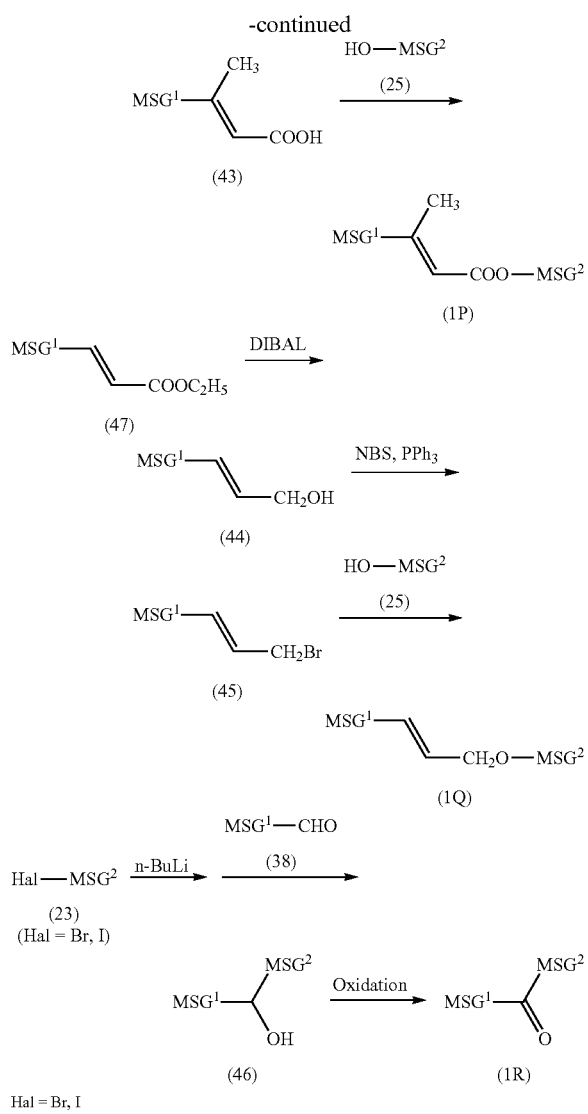

(I) Formation of a Single Bond

The compound (1A) is prepared by the reaction of the arylboronic acid (21) with the compound (22) prepared by a known method in the presence of a catalyst such as tetrakis(triphenylphosphine)palladium in an aqueous solution of a carbonate. This compound (1A) can also be prepared by the reaction of the compound (23) prepared by a known method with n-butyllithium, and further with zinc chloride, and then by the reaction with the compound (22) in the presence of a catalyst such as dichlorobis(triphenylphosphine)palladium.

(II) Formation of —COO—

The carboxylic acid (24) is prepared by the reaction of the compound (23) with n-butyllithium and then with carbon dioxide. The dehydration condensation of the compound (24) and the phenol (25) prepared by a known method, in the presence of DCC (1,3-dicyclohexylcarbodiimide) and DMAP (N,N-dimethyl-4-aminopyridine) gives the compound (1B).

(III) Formation of —CH=CH—

The compound (23) is treated with n-butyllithium, and then reacted with a formamide such as N,N-dimethylformamide (DMF) to give the aldehyde (28). The phosphonium salt (27) prepared by a known method is treated with a base such as potassium tert-butoxide, and the resulting phosphorus ylide is allowed to react with the aldehyde (28) to give the compound (1D). Since the cis-isomer is formed depending on the reaction conditions, the cis-isomer is isomerized to the trans-isomer by a known method as required.

(IV) Formation of —(CH$_2$)$_2$—

The compound (1E) is prepared by the hydrogenation of the compound (1D) in the presence of a catalyst such as palladium on carbon.

(V) Formation of —(CH$_2$)$_4$—

The compound having —(CH$_2$)$_2$—CH=CH— is obtained according to the procedure described in item (III) except for the replacement of the phosphonium salt (27) with the phosphonium salt (29). The compound (1F) is prepared by the catalytic hydrogenation of this compound.

(VI) Formation of —C≡C—

The reaction of the compound (23) with 2-methyl-3-butyn-2-ol in the presence of a catalyst of dichloropalladium and a copper halide, followed by the deprotection of the product under basic conditions gives the compound (30). The compound (1G) is prepared by the reaction of the compound (30) with the compound (22) in the presence of a catalyst of dichloropalladium and a copper halide.

(VII) Formation of —CH$_2$O—

The compound (28) is reduced with a reducing agent such as sodium borohydride to give the compound (32). The compound (32) is halogenated with hydrobromic acid or the like, giving the compound (33). The compound (33) is allowed to react with the compound (31) in the presence of potassium carbonate or the like, giving the compound (1J).

(VIII) Formation of —(CH$_2$)$_3$—O—

The compound (1K) is prepared according to the procedure described in item (VII) except for the replacement of the compound (28) with the compound (34).

(IX) Formation of —COCH=CH—

The compound (1L) is prepared by a reaction of the compound (37) with the compound (28) in the presence of barium hydroxide.

(X) Formation of —C(CH$_3$)=C(CH$_3$)—

The compound (1M) is prepared by a reaction of the compound (37) with the compound (38) in the presence of zinc and titanium chloride.

(XI) Formation of —CH=CH—COO—

A phosphorus ylide is prepared by a treatment to ethyl diethylphosphonoacetate with a base such as sodium hydride. The phosphorus ylide is allowed to react with the aldehyde (39) to give the ester (40). The ester (40) is hydrolyzed in the presence of a base such as sodium hydroxide to give the carboxylic acid (41). The compound (1N) is prepared by the dehydration condensation of this compound and the alcohol (25).

(XII) Formation of —C(CH$_3$)=CH—COO—

A phosphorus ylide is prepared by a treatment to ethyl diethylphosphonoacetate with a base such as sodium hydride. The phosphorus ylide is allowed to react with the methyl ketone (37) to give the ester (42). The ester (42) is hydrolyzed in the presence of a base such as sodium hydroxide to give the carboxylic acid (43). The compound (1P) is prepared by the dehydration condensation of this compound and the alcohol (25).

(XIII) Formation of —CH=CH—CH$_2$O—

The ester (47) is reduced with diisobutylaluminum hydride (DIBAL) to give the alcohol (44). The reaction of the alcohol (44) with N-bromosuccinimide (NBS) in the presence of triphenylphosphine gives the bromide (45). The compound (1Q) is prepared by the dehydration condensation of this compound and the compound (25).

(XX) Formation of —CO—

The alcohol (46) is obtained by a reaction of the compound (23) with n-butyl lithium, and then with the aldehyde (38). The alcohol (46) is allowed to react with an oxidant such as the Jones reagent to give the compound (1R).

2-2. Formation of the Polymerizable Group

Examples of the method for forming the polymerizable groups described below are shown in the schemes described below. In these schemes, $MSG^1$ is a monovalent organic group having at least one ring. The compounds (1S) to (1X) correspond to the compound (1).

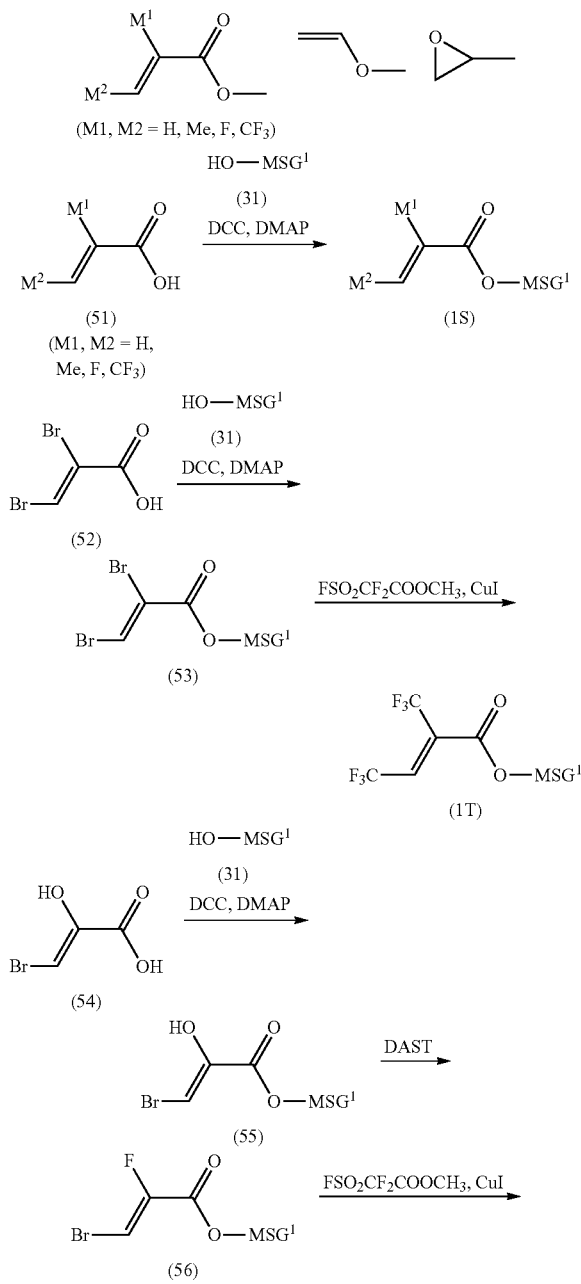

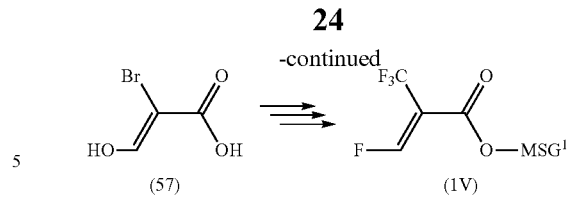

(I) Formation of $M^2CH{=}CM^1$-COO—

The carboxylic acid (51) shown in the above scheme, where both $M^1$ and $M^2$ are not —$CF_3$, where $M^1$ is fluorine and $M^2$ is not —$CF_3$, or where $M^1$ is —$CF_3$ and $M^2$ is not fluorine, is commercially available. The dehydration condensation of this carboxylic acid (51) and the compound (31) in the presence of DCC and DMAP gives the compound (1S).

When both $M^1$ and $M^2$ are —$CF_3$, the dehydration condensation of the carboxylic acid (52) and the compound (31) in the presence of DCC and DMAP gives the compound (53). The compound (53) is allowed to react with methyl 2,2-difluoro-2-(fluorosulfonyl)acetate in the presence of a catalytic amount of copper iodide to give the compound (1T).

When $M^1$ is fluorine and $M^2$ is —$CF_3$, the dehydration condensation of the carboxylic acid (54) and the compound (31) in the presence of DCC and DMAP gives the compound (55). The compound (55) is fluorinated with a fluorinating agent such as DAST to give the compound (56). The compound (1U) is prepared by the reaction of the compound (56) with methyl 2,2-difluoro-2-(fluorosulfonyl)acetate in the presence of a catalytic amount of copper iodide.

When $M^1$ is —$CF_3$ and $M^2$ is fluorine, the compound (1V) is prepared according to the method described above, using the carboxylic acid (57) as a starting material.

(II) Formation of a Vinyloxy Group

The compound (1W) is prepared by the reaction of the compound (31) with vinyl bromide in the presence of potassium carbonate or the like.

(III) Formation of an Epoxy Group

The compound (1X) is prepared by the oxidation of the vinyl compound (58) prepared by known methods with meta-chloroperbenzoic acid (mCPBA) or the like.

2-3. Formation of the Bonding Group Z

Examples of the method for forming the bonding groups $Z^1$ to $Z^4$ in the compound (1) are shown in the following schemes. In these schemes, $MSG^1$ is a monovalent organic group having at least one ring. The compound (1Y) corresponds to the compound (1).

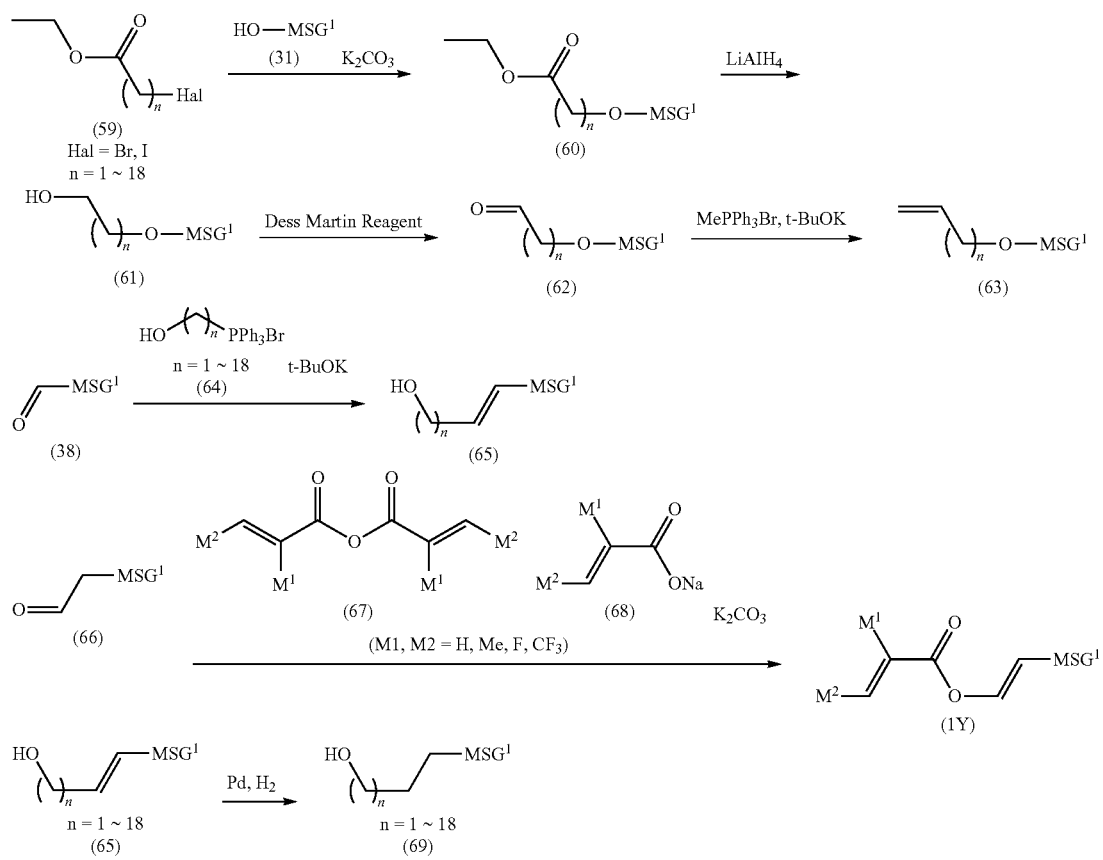

(I) Formation of —CH$_2$O—

The reaction of the compound (59) prepared by a known method with the compound (31) in the presence of potassium carbonate or the like gives the compound (60). The compound (60) is reduced with a reducing agent such as lithium aluminum hydride to give the compound (61). The compound (61) is oxidized with an oxidizing agent such as the Dess-Martin reagent to give the aldehyde (62). A phosphorus ylide generated by a treatment to methyltriphenylphosphonium bromide with a base such as potassium tert-butoxide is allowed to react with the aldehyde (62) to give the compound (63).

When M$^2$CH=CM$^1$-COO— is to be introduced to the compound (61), the dehydration condensation of the compound (61) and the compound (51) is carried out according to the method described above. When a vinyloxy group is to be introduced to the compound (61), the reaction of the compound (61) with vinyl bromide is carried out according to the method described above. When an epoxy group is to be introduced to the compound (63), the epoxidation of the compound (63) is carried out according to the method described above.

(II) Formation of —CH=CH—

A phosphorus ylide generated by a treatment to the phosphonium salt (64) prepared by a known method with a base such as potassium tert-butoxide is allowed to react with the aldehyde (38) to give the compound (65). When M$^2$CH=CM$^1$-COO— is to be introduced to the compound (65), the dehydration condensation of the compound (65) and the compound (51) is carried out according to the method described above. When a vinyloxy group is to be introduced to the compound (65), the reaction of the compound (65) with vinyl bromide is carried out according to the method described above. When an epoxy group is to be introduced to the compound (65), the conversion of —CH$_2$OH to —CH$_2$—CH=CH$_2$ and then the epoxidation are carried out according to the method described above.

Introduction of M$^2$CH=CW—COO— may be carried out as follows: The compound (1Y) is prepared by the reaction of the aldehyde (66) prepared by a known method and the acid anhydride (67) and the sodium carboxylate (68) in the presence of potassium carbonate or the like.

(III) Formation of —CH$_2$CH$_2$—

The compound (69) is prepared by the hydrogenation of the compound (65) in the presence of a catalyst such as palladium on carbon. The method for introducing M$^2$CH=CM$^1$-COO—, a vinyloxy group or an epoxy group to this alcohol is described above.

2-4. Formation of the ring A$^1$ and the ring A$^4$

With regard to a trivalent benzene ring, starting materials are commercially available or their synthetic methods are well known. For example, 4-bromocatechol (T-1), 5-bromoresorcinol (T-5) and 4-bromoresorcinol (T-8) can be utilized as starting materials.

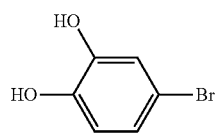

(T-1)

(T-5)
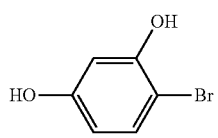

(T-8)
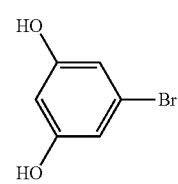

The compound (1) has a suitable polymerization reactivity, a high conversion yield and a high solubility in a liquid crystal composition, in comparison with similar compounds. The compound (1) has a suitable balance between at least two of these physical properties. Accordingly, the compound (1) can be added to a liquid crystal composition for use in a PSA mode.

3. Liquid Crystal Compositions

The liquid crystal composition of the invention includes at least one compound (1) as a component. The composition may further include other polymerizable compound that is different from the compound (1). Desirable examples of other polymerizable compound are acrylates, methacrylates, vinyl compounds, vinyloxy compounds, propenyl ethers, epoxy compounds (oxiranes, oxetanes) and vinyl ketones. More desirable examples are a compound having at least one acryloyloxy and a compound having at least one methacryloyloxy. More desirable examples also include a compound having both acryloyloxy and methacryloyloxy.

Additional examples of other polymerizable compound are the compounds (M-1) to (M-12). In the compounds (M-1) to (M-12), $R^{20}$ is hydrogen or methyl, s is 0 or 1, and t and u are independently an integer from 1 to 10. The symbol F in parentheses means hydrogen or fluorine.

(M-1)
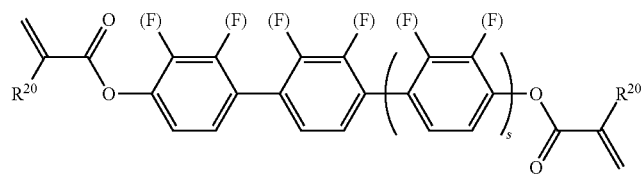

(M-2)
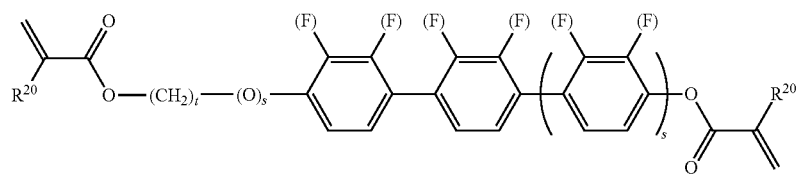

(M-3)
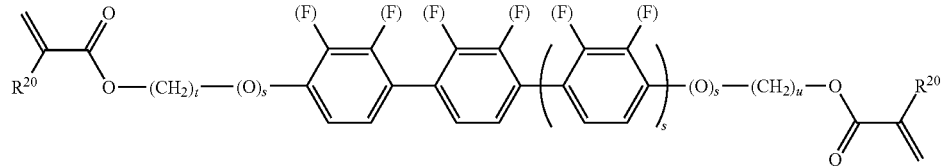

(M-4)
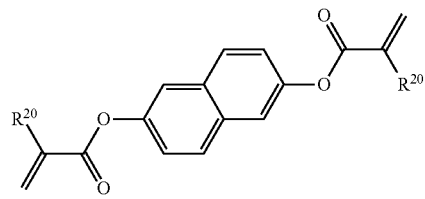

(M-5)
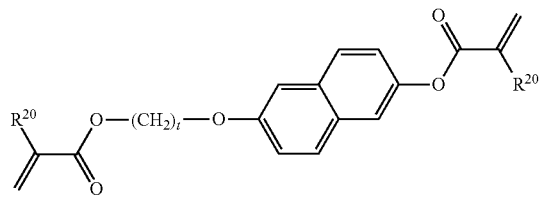

(M-6)
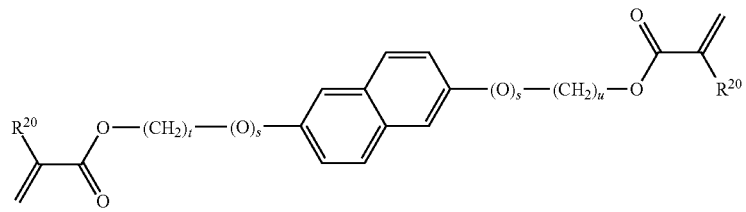

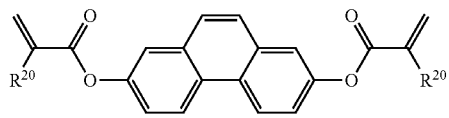
(M-7)

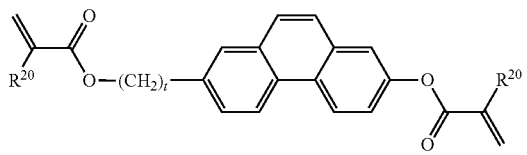
(M-8)

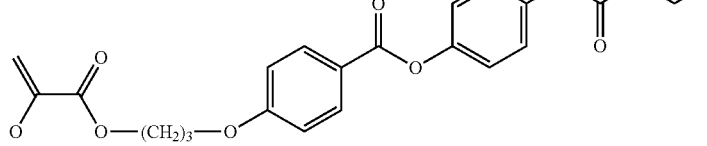
(M-9)

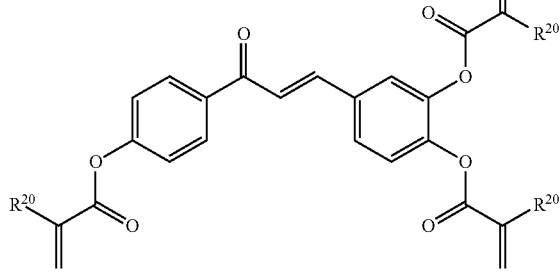
(M-10)

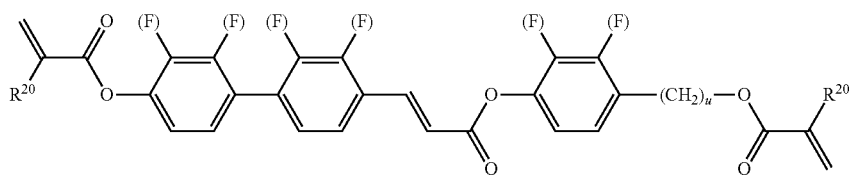
(M-11)

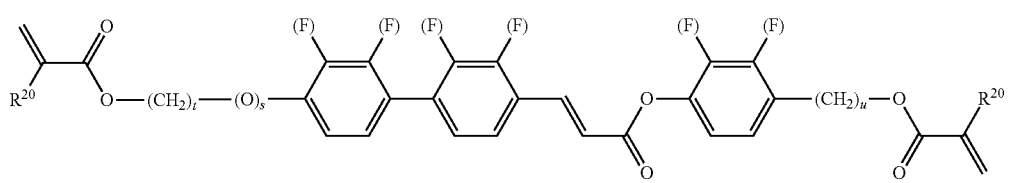
(M-12)

The liquid crystal composition includes at least one compound (1), and may further include a liquid crystal compound. When a liquid crystal display device for use in a mode such as PS-TN, PS-IPS, PS-FFS, PSA-VA or PSA-OCB is targeted, it is desirable that the composition should include the compound (1) as a component A, and should further include compounds selected from components B, C, D and E that will be shown below. The component B is selected from the compounds (2) to (4). The component C is the compound (5). The component D is selected from the compounds (6) to (11). The component E is selected from the compounds (12) to (14). It is desirable that the components B, C, D and E should be selected in consideration of positive or negative dielectric anisotropy, the magnitude of dielectric anisotropy and so forth when such kind of composition is to be prepared. The composition in which the component is suitably selected has a high maximum temperature, a low minimum temperature, a small viscosity, a suitable (large or small) optical anisotropy, a large positive or negative dielectric anisotropy and a suitable (large or small) elastic constant.

In such a composition, the added amount of the compound (1) (namely, the component A) is in the range of 0.05% by weight to 20% by weight based on the total weight of the liquid crystal compounds. A more desirable added amount is in the range of 0.1% by weight to 10% by weight. The most desirable added amount is in the range of 0.2% by weight to 1% by weight. At least one of other polymerizable compounds that are different from the compound (1) may further be added. In this case, it is desirable that the total added amount of the compound (1) and other polymerizable compound should be within the range described above. The physical properties of the resulting polymer can be adjusted by a suitable selection of other polymerizable compound.

Examples of other polymerizable compounds are acrylates, methacrylates and so forth, as having been explained previously. The examples also include the compounds (M-1) to (M-12).

The component B includes a compound having halogen or a fluorine-containing group at the right terminal. Desirable examples of the component B include the compounds (2-1) to (2-16), the compounds (3-1) to (3-118) and the compounds (4-1) to (4-56).

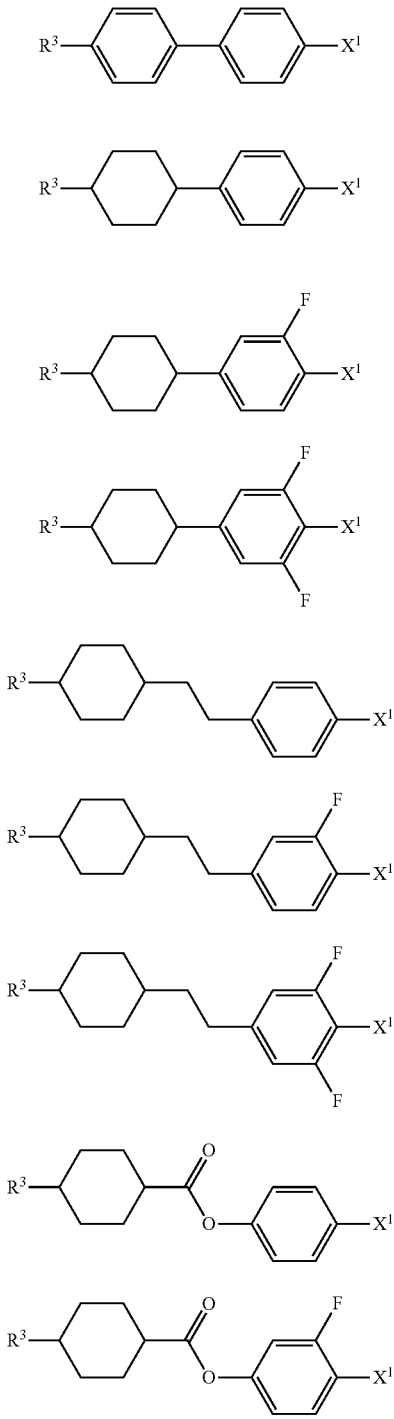

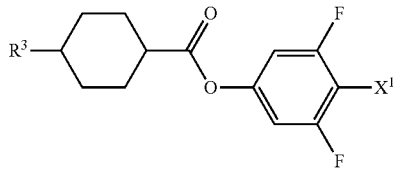

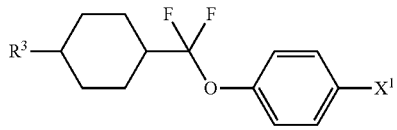

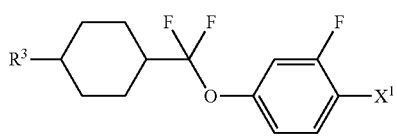

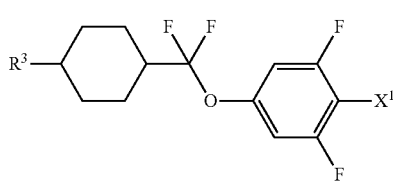

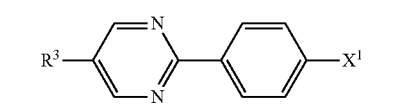

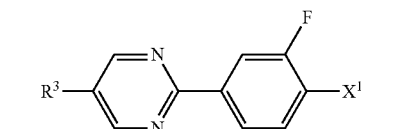

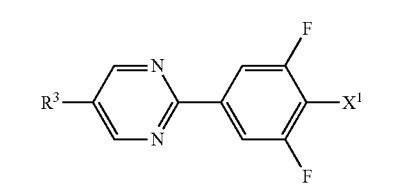

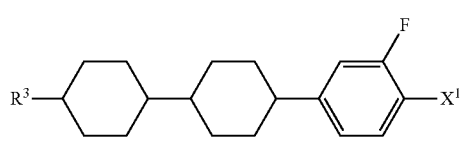

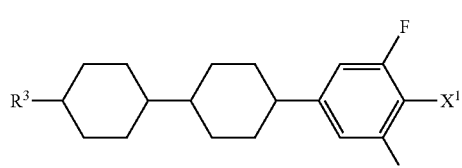

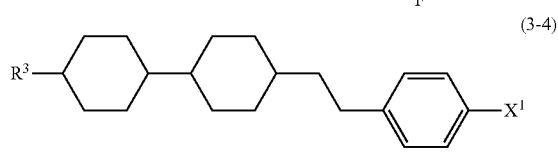

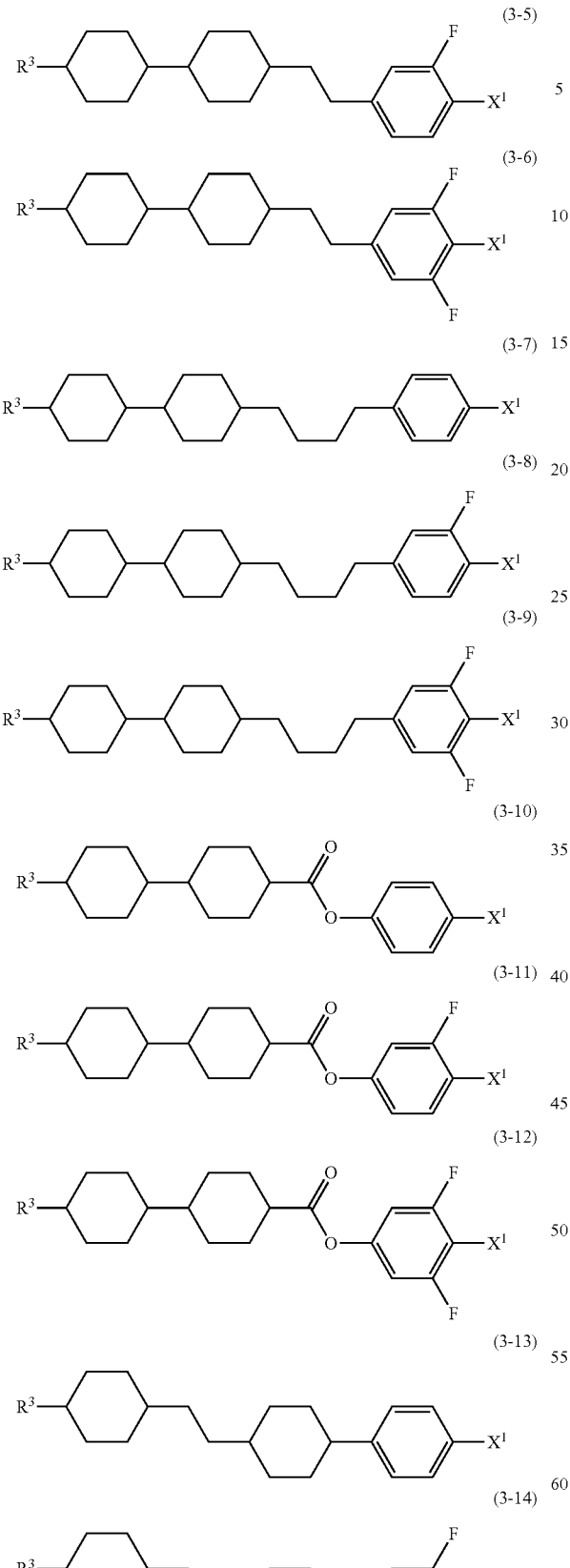
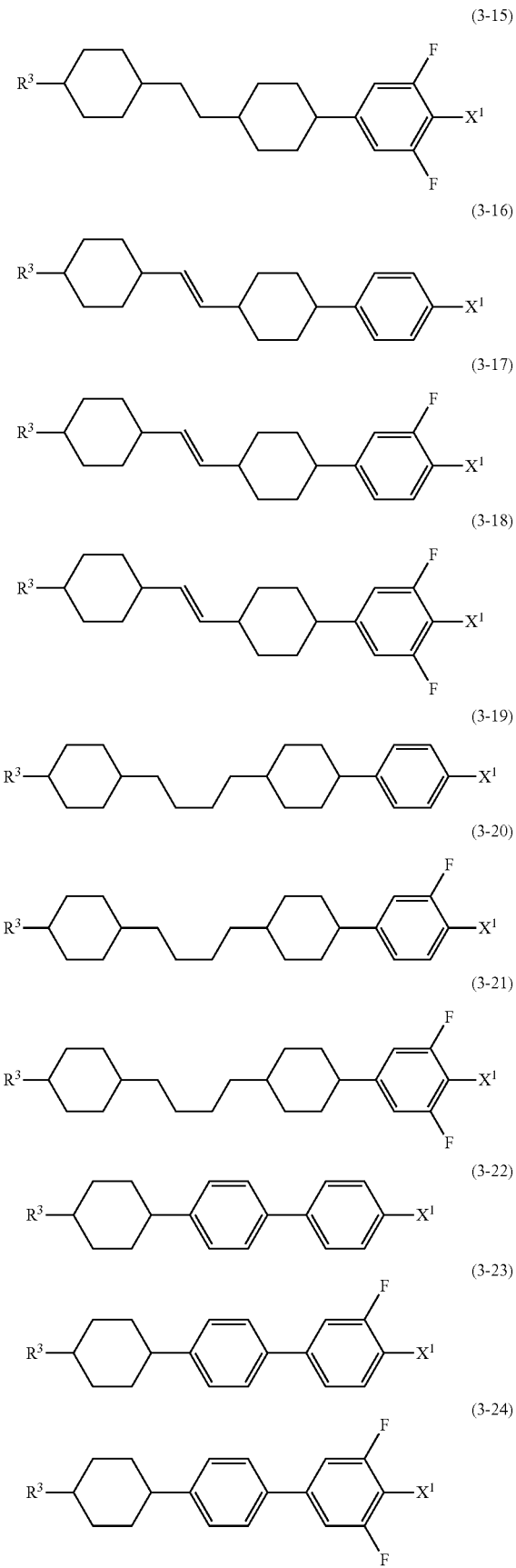

(3-25)
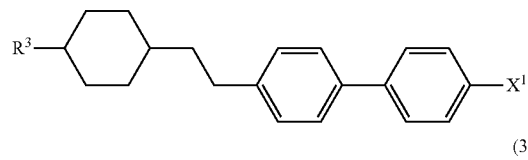
(3-26)
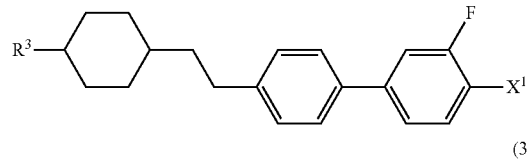
(3-27)
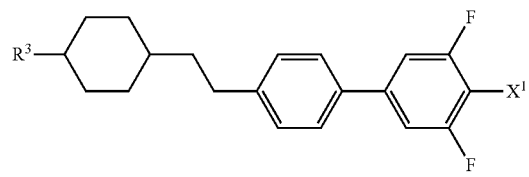
(3-28)
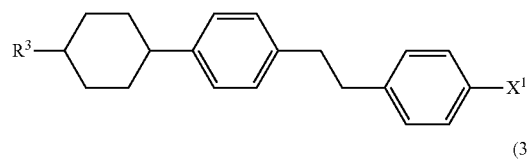
(3-29)
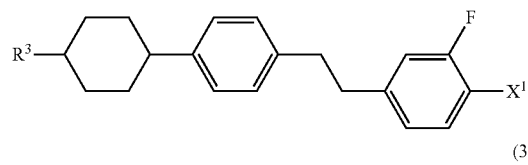
(3-30)
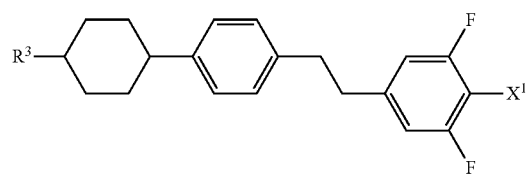
(3-31)
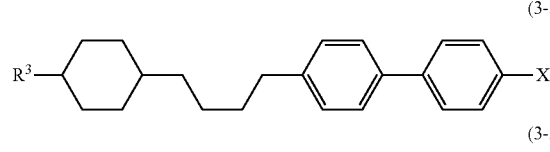
(3-32)
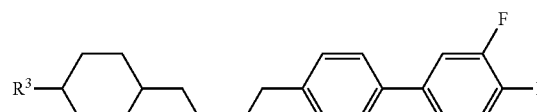
(3-33)
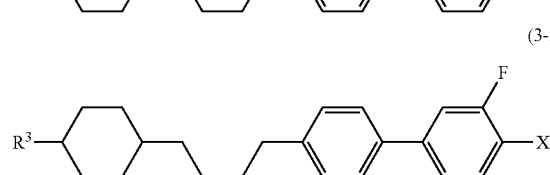
(3-34)
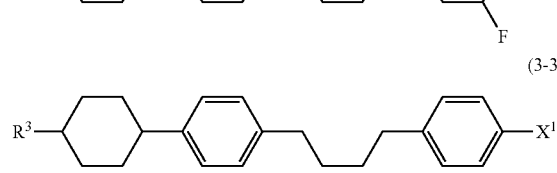
(3-35)
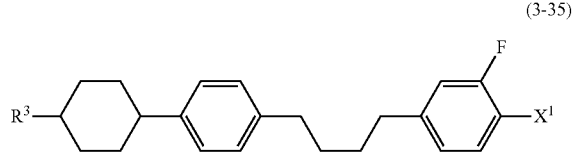
(3-36)
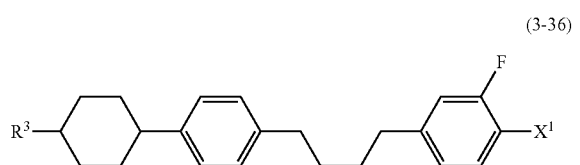
(3-37)
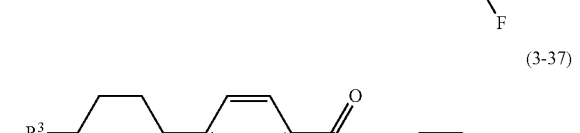
(3-38)
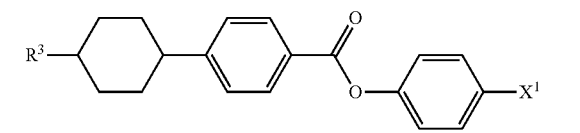
(3-39)
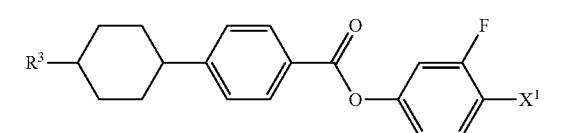
(3-40)
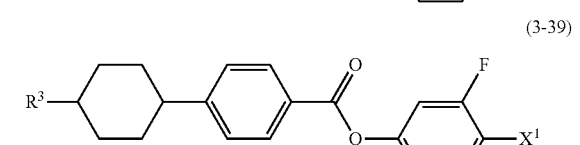
(3-41)
(3-42)
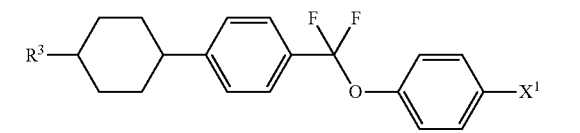
(3-43)
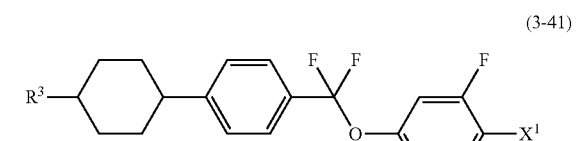

(3-44) 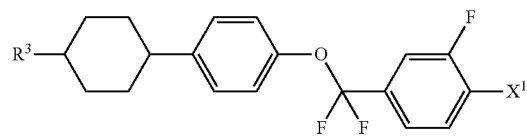
(3-45) 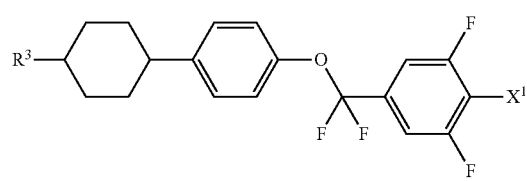
(3-46) 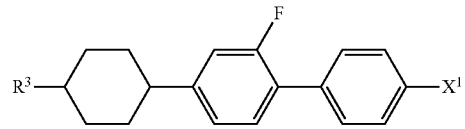
(3-47) 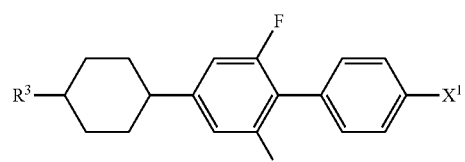
(3-48) 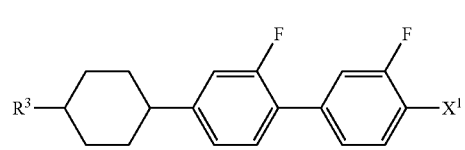
(3-49) 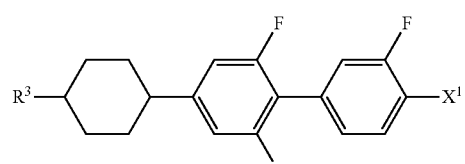
(3-50) 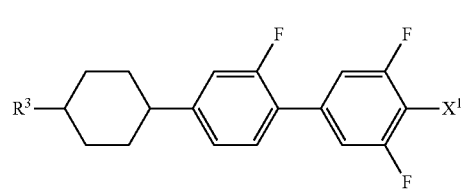
(3-51) 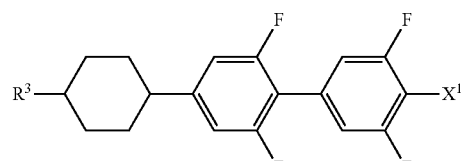
(3-52) 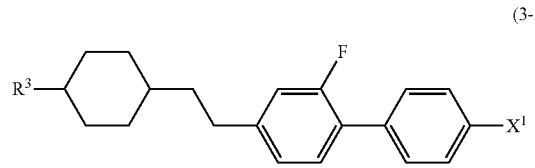
(3-53) 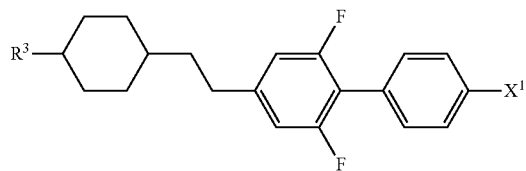
(3-54) 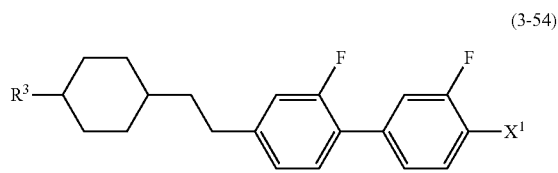
(3-55) 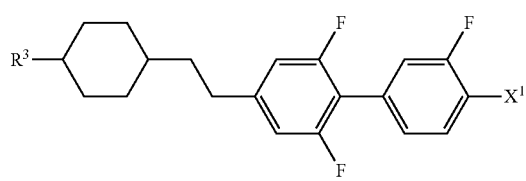
(3-56) 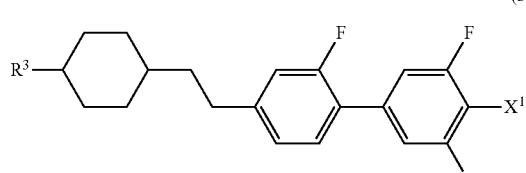
(3-57) 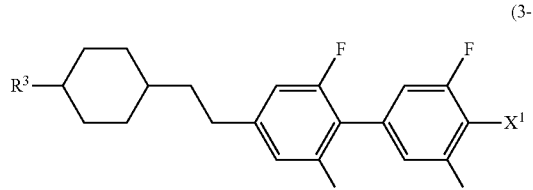
(3-58) 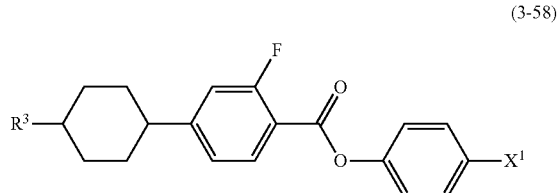
(3-59) 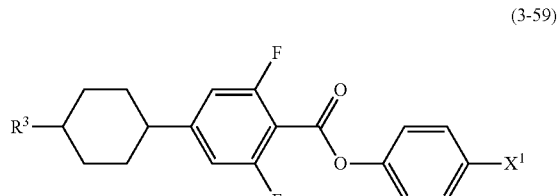
(3-60) 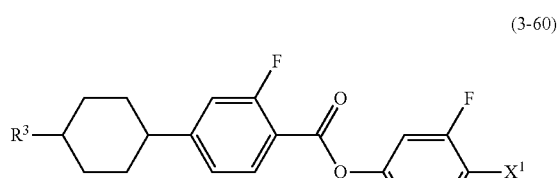

(3-61) 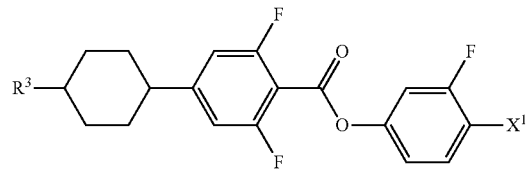
(3-62) 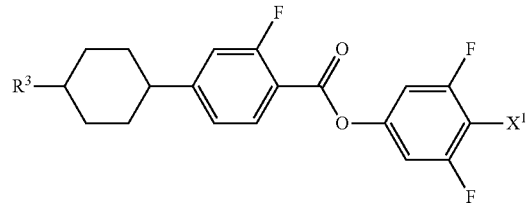
(3-63) 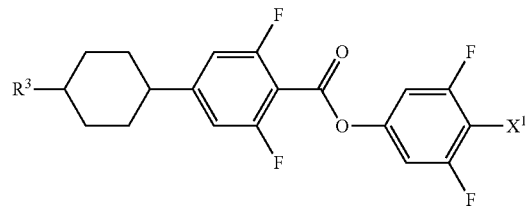
(3-64) 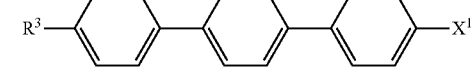
(3-65) 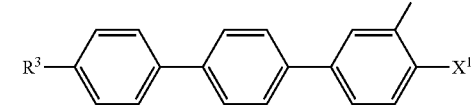
(3-66) 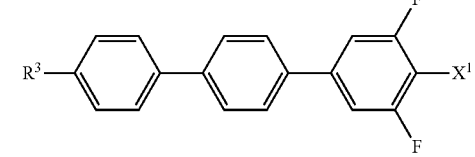
(3-67) 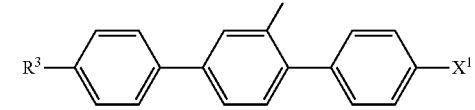
(3-68) 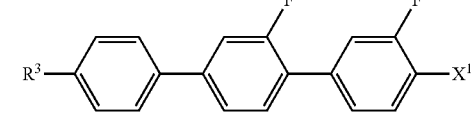
(3-69) 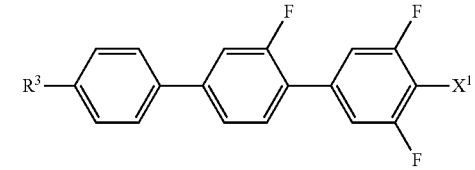
(3-70) 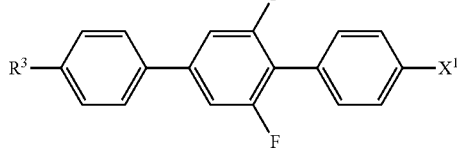
(3-71) 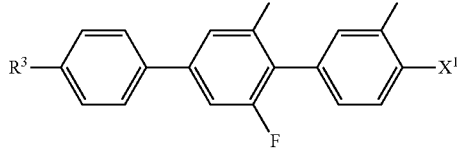
(3-72) 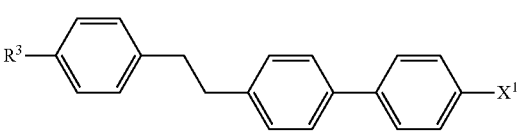
(3-73) 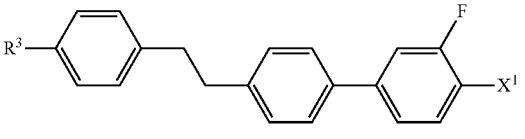
(3-74) 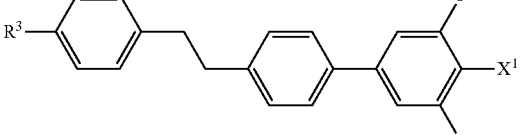
(3-75) 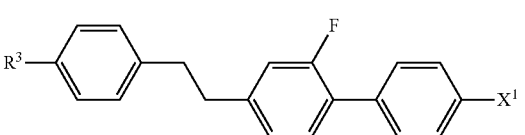
(3-76) 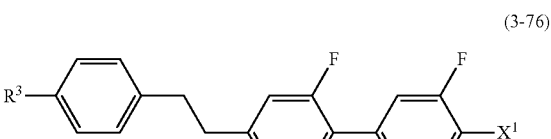
(3-77) 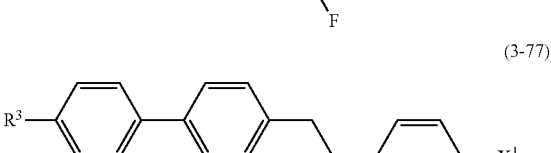
(3-78) 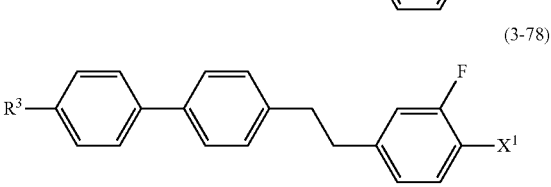

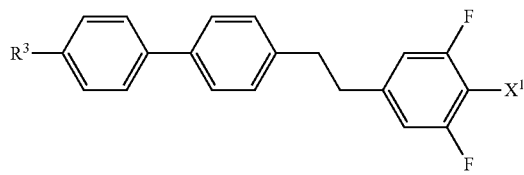 (3-79)
 (3-80)
(3-81)
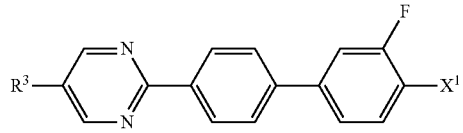 (3-82)
(3-83)
(3-84)
(3-85)
(3-86)
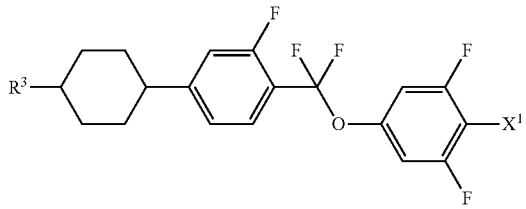 (3-87)
(3-88)
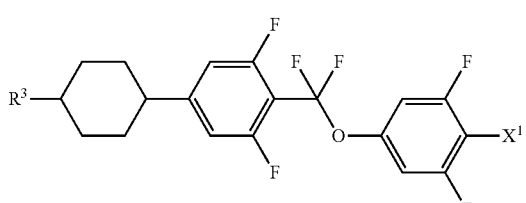 (3-89)
(3-90)
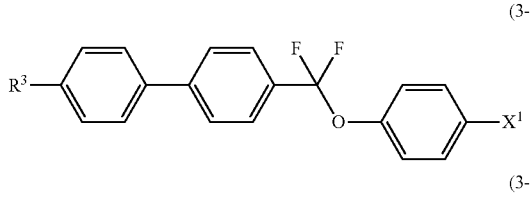 (3-91)
(3-92)
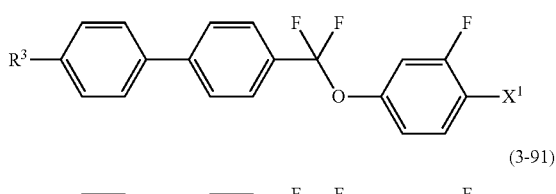 (3-93)
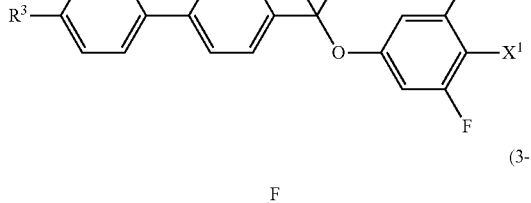 (3-94)
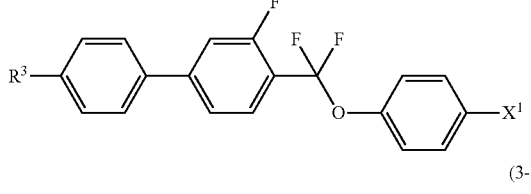
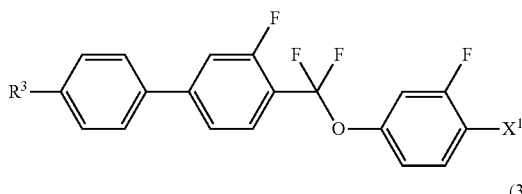
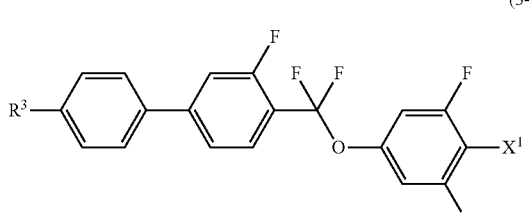

(3-95) 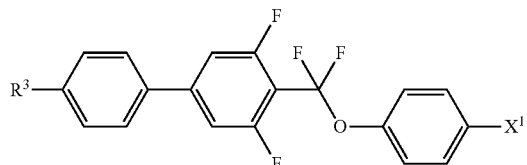
(3-96) 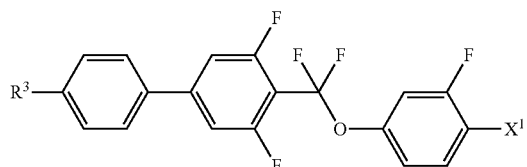
(3-97) 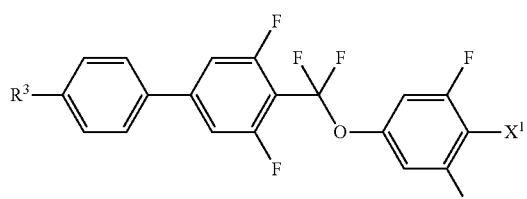
(3-98) 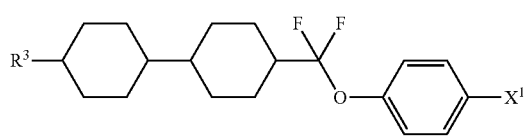
(3-99) 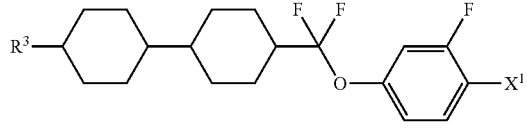
(3-100) 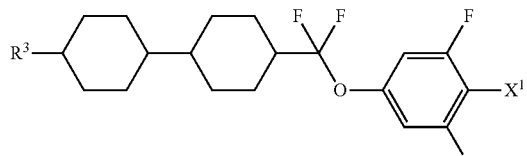
(3-101) 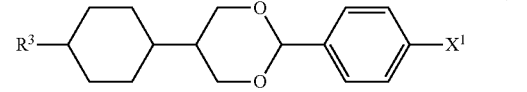
(3-102) 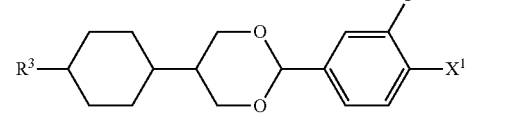
(3-103) 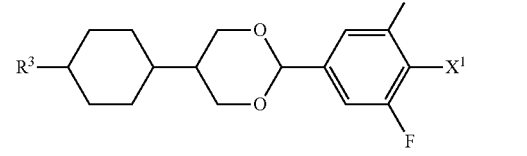
(3-104) 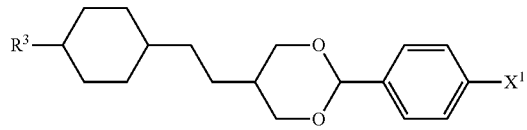
(3-105) 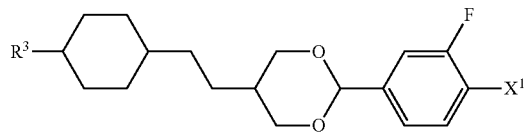
(3-106) 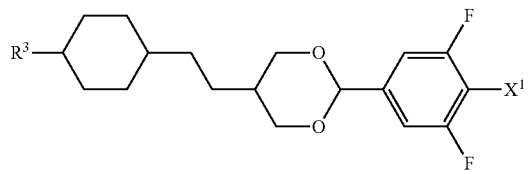
(3-107) 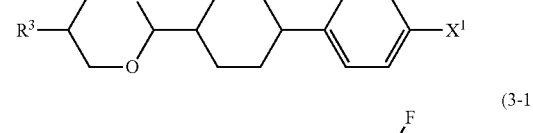
(3-108) 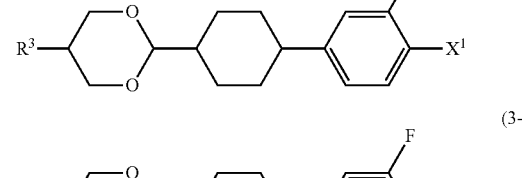
(3-109) 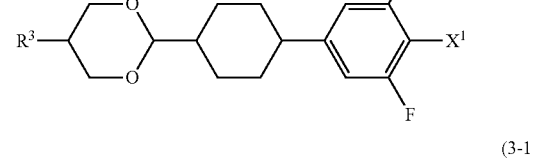
(3-110) 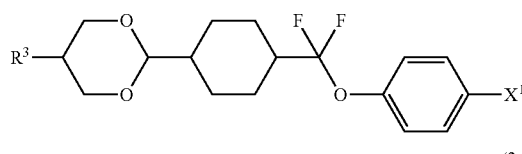
(3-111) 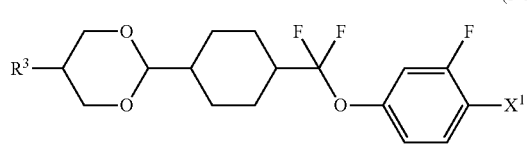
(3-112) 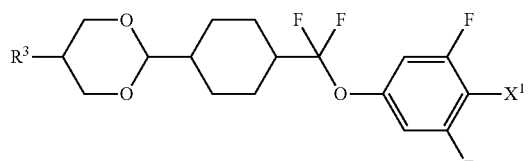

(3-113) 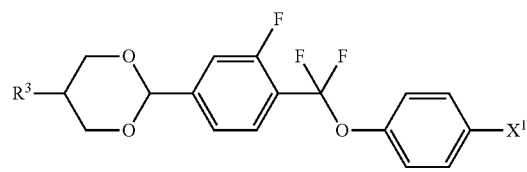
(3-114) 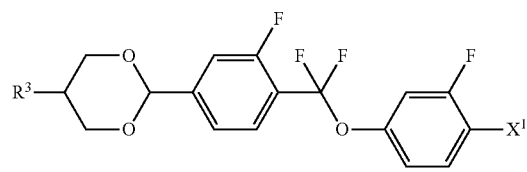
(3-115) 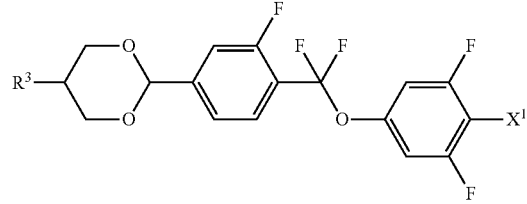
(3-116) 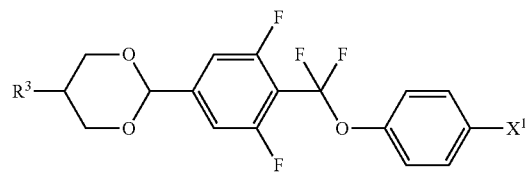
(3-117) 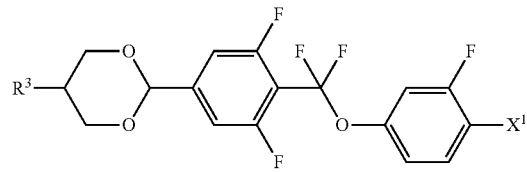
(3-118) 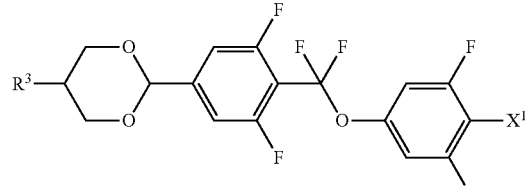
(4-1) 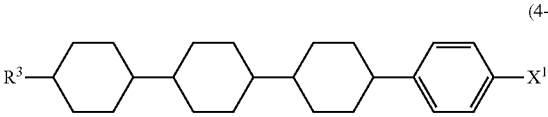
(4-2) 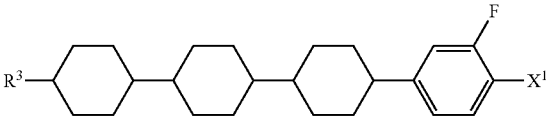
(4-3) 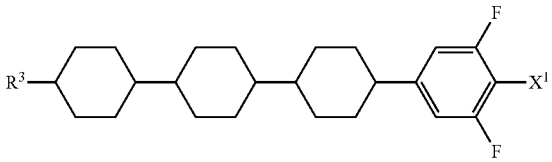
(4-4) 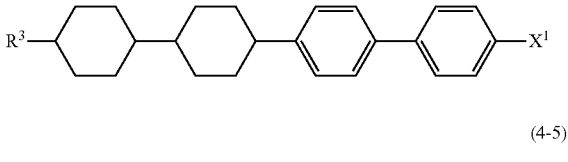
(4-5) 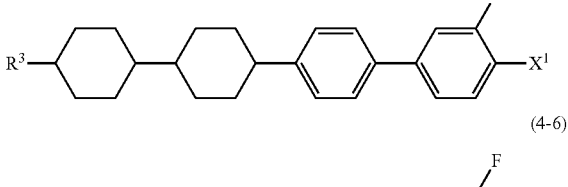
(4-6) 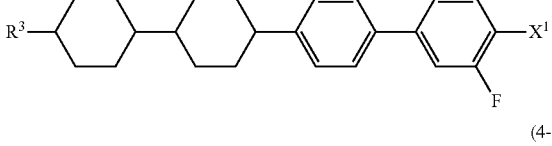
(4-7) 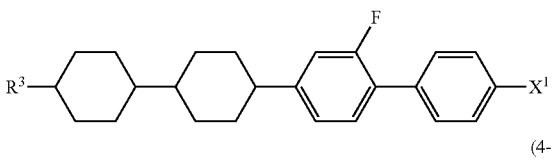
(4-8) 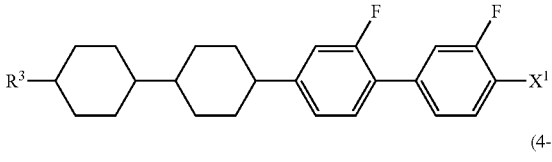
(4-9) 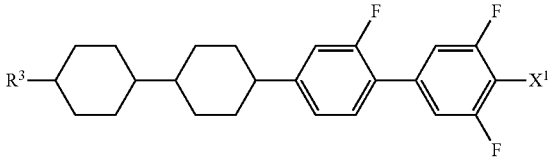
(4-10) 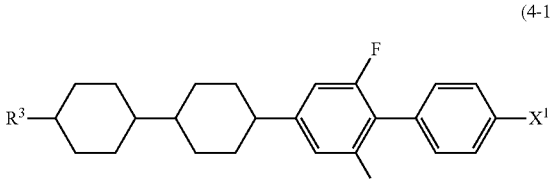
(4-11) 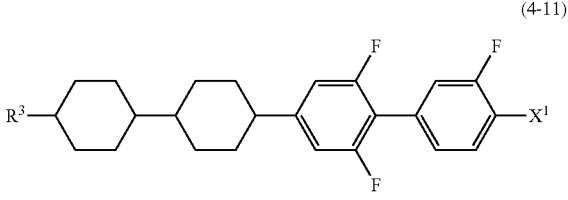

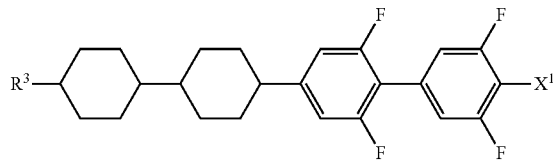
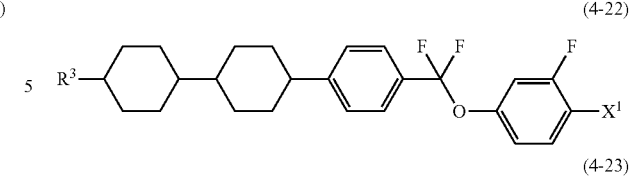

(4-31) 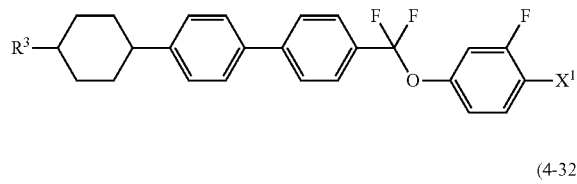
(4-32) 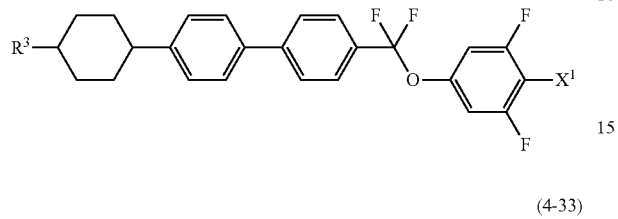
(4-33) 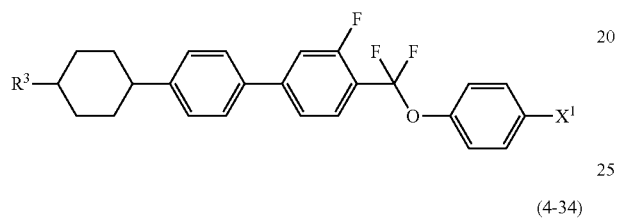
(4-34) 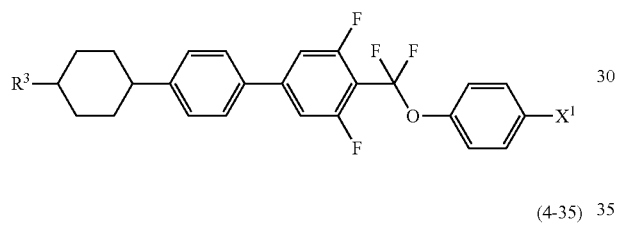
(4-35) 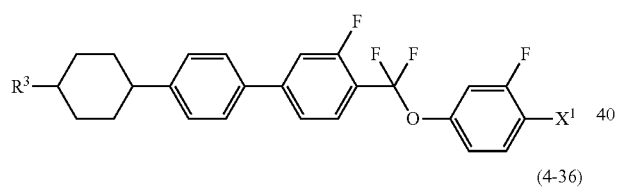
(4-36) 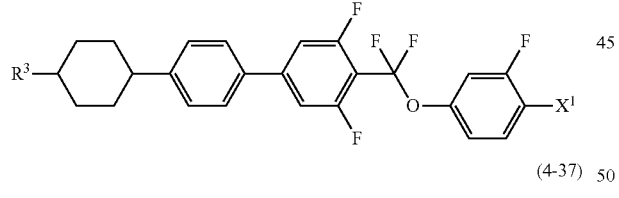
(4-37) 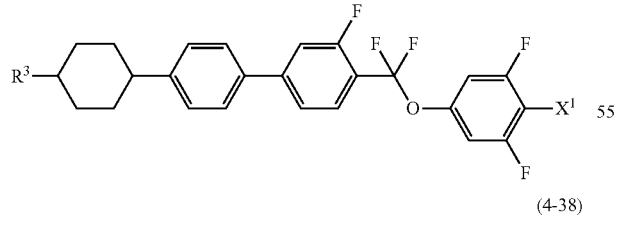
(4-38) 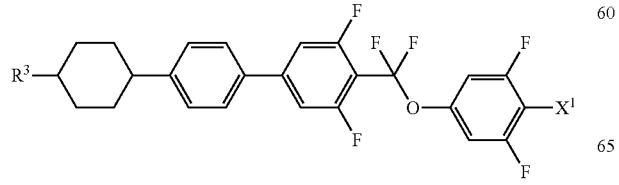
(4-39) 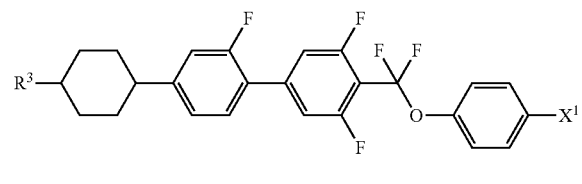
(4-40) 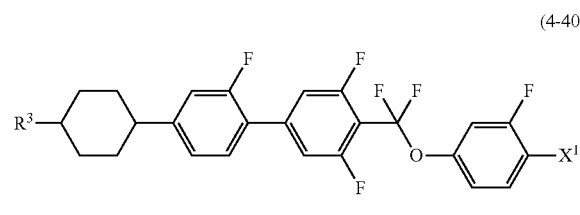
(4-41) 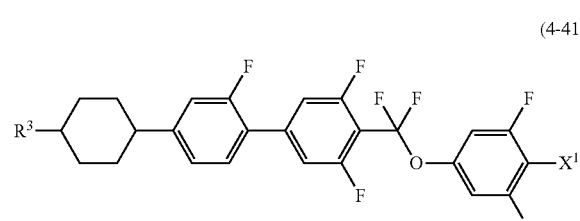
(4-42) 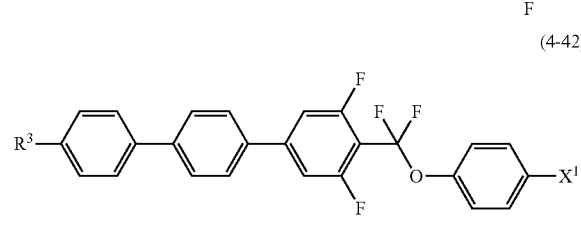
(4-43) 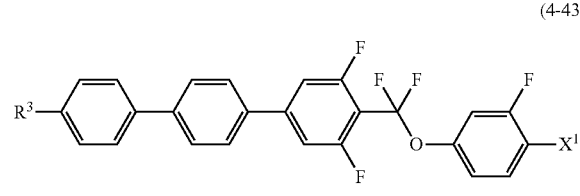
(4-44) 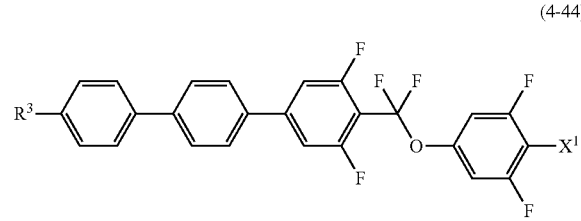
(4-45) 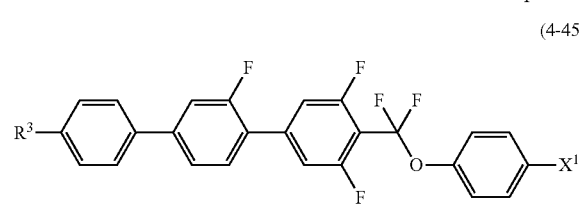
(4-46) 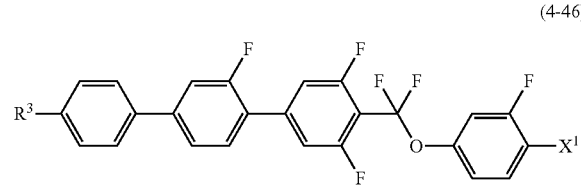

-continued (4-47)
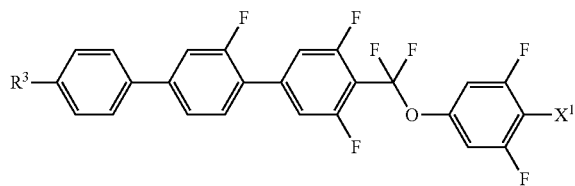

(4-48)
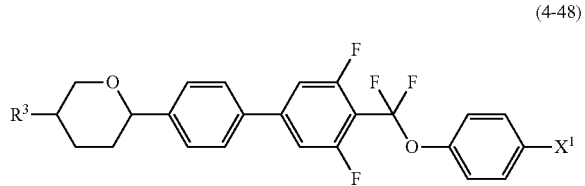

(4-49)
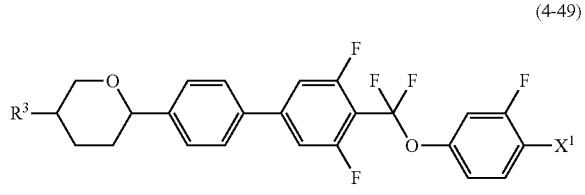

(4-50)
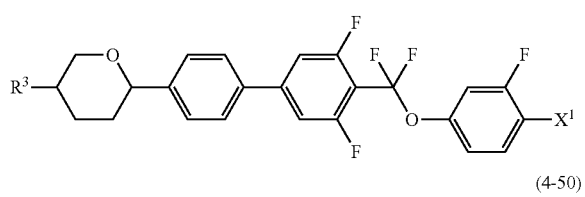

(4-51)
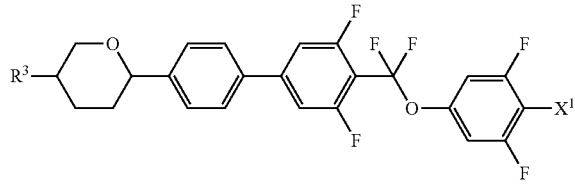

(4-52)
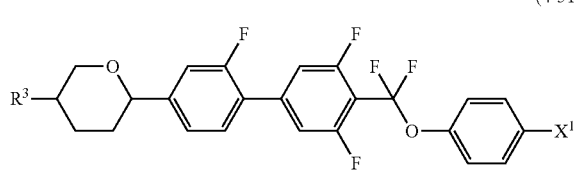

(4-53)
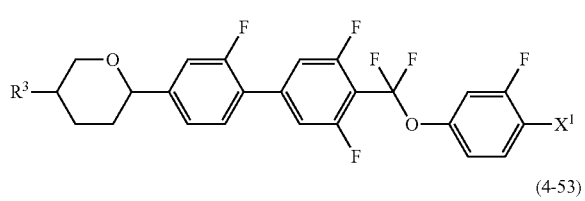

(4-54)
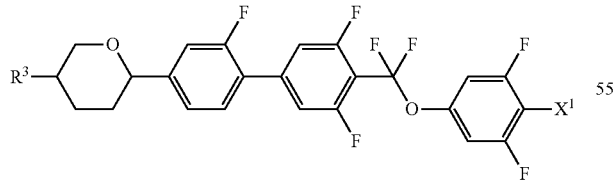

-continued (4-55)
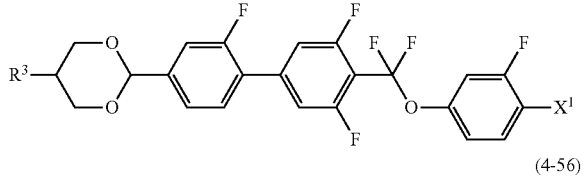

(4-56)
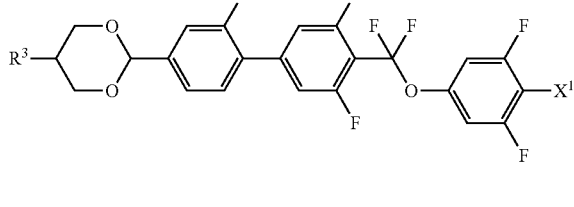

In these compounds (the component B), the definitions of $R^3$ and $X^1$ are just the same as described previously.

The component B is used for the preparation of a composition for use in modes of PS-IPS, PS-FFS, PSA-OCB and so forth, since its dielectric anisotropy is positive and its stability to heat, light or the like is quite excellent. The content of the component B is suitably in the range of 1% by weight to 99% by weight, preferably in the range of 10% by weight to 97% by weight, more preferably in the range of 40% by weight to 95% by weight, based on the total weight of the liquid crystal compounds. In this composition, the viscosity can be adjusted by further addition of the component E selected from the compounds (12) to (14). It is desirable that the content of the component B should be 30% by weight or less based on the total weight of the liquid crystal compounds when the component B is added to a composition having negative dielectric anisotropy. The elastic constant of the composition can be adjusted and the voltage-transmittance curve of a device can be adjusted by the addition of the component B.

The component C is the compound (5) where the right-terminal group is —C≡N or —C≡C—C≡N. Desirable examples of the component C include the compounds (5-1) to (5-64).

(5-1)
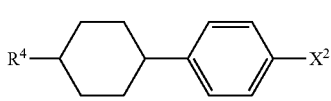

(5-2)

(5-3)
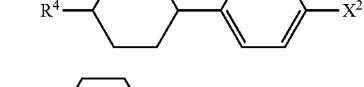

(5-4)
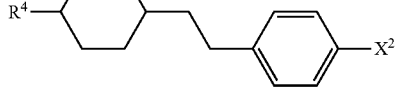

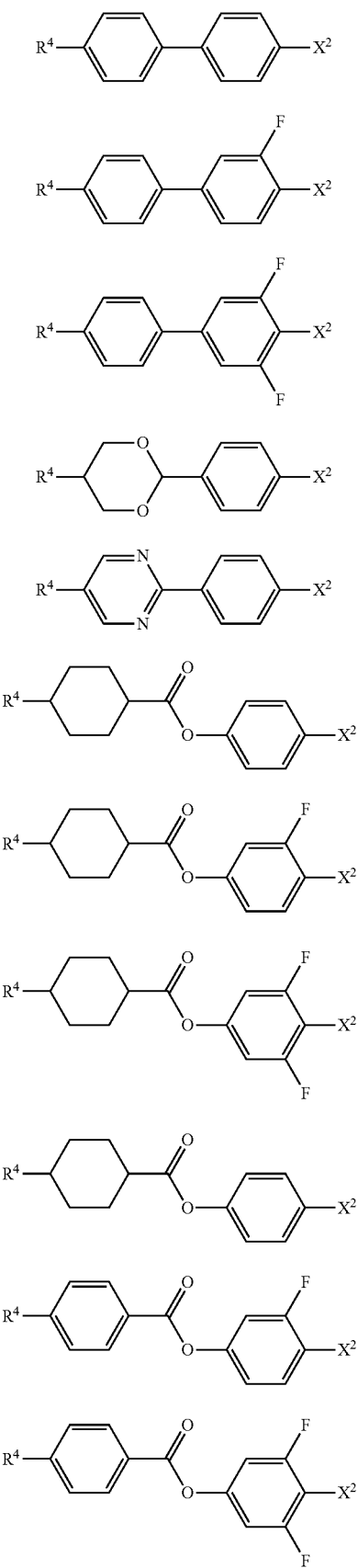
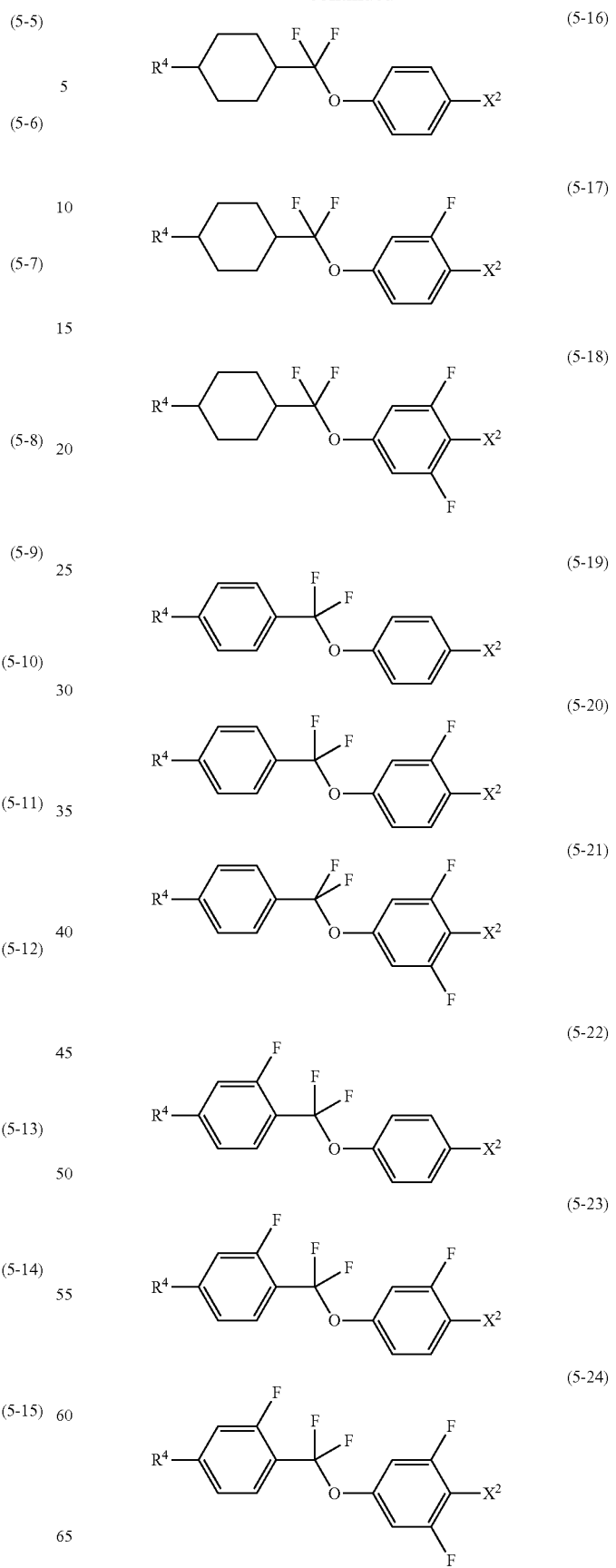

(5-25)
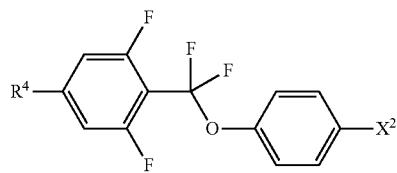
(5-26)
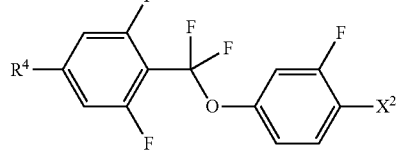
(5-27)
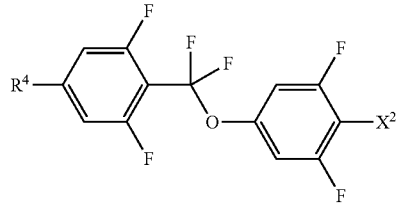
(5-28)
(5-29)
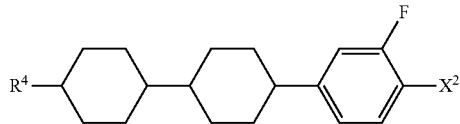
(5-30)
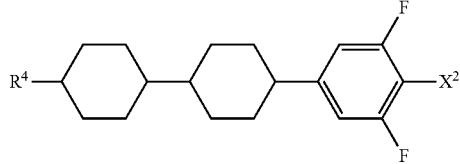
(5-31)
(5-32)
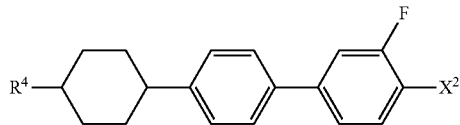
(5-33)
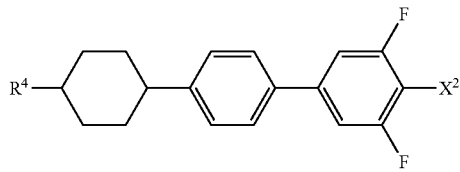
(5-34)
(5-35)
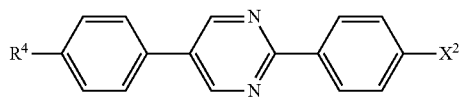
(5-36)
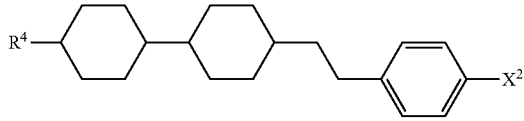
(5-37)
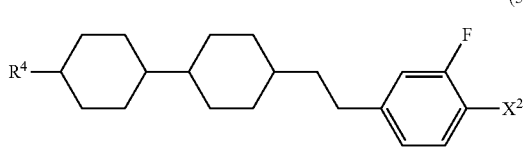
(5-38)
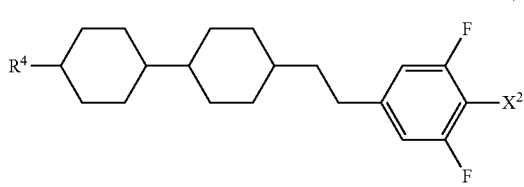
(5-39)
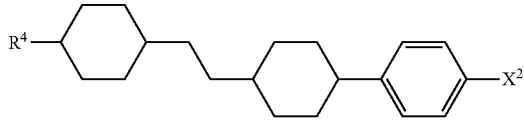
(5-40)
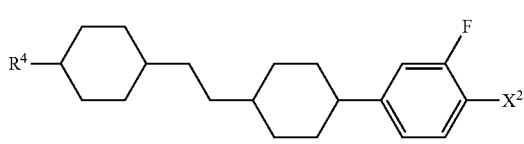
(5-41)
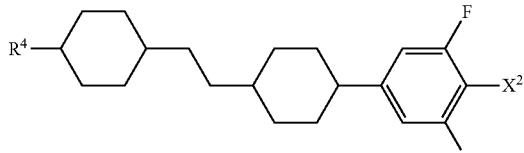
(5-42)
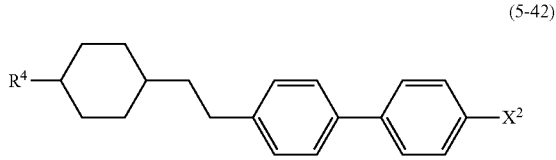
(5-43)
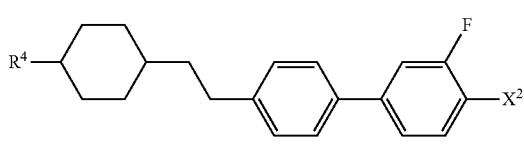
(5-44)
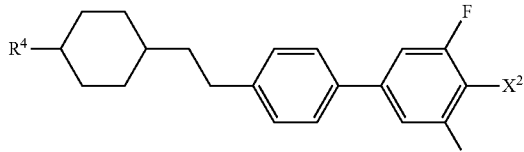

(5-45) 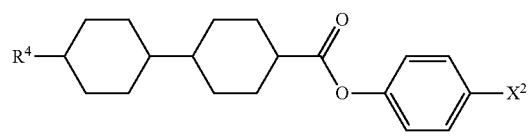
(5-46) 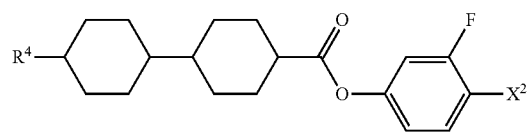
(5-47) 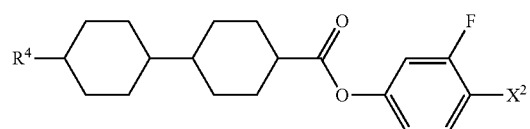
(5-48) 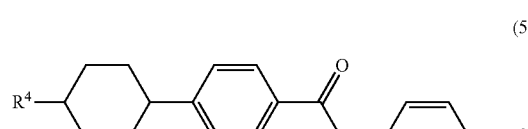
(5-49) 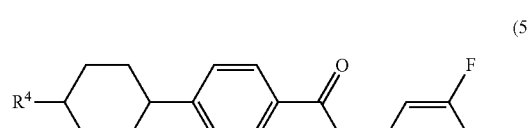
(5-50) 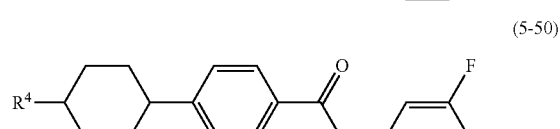
(5-51) 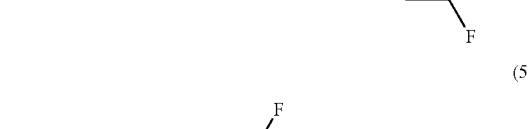
(5-52) 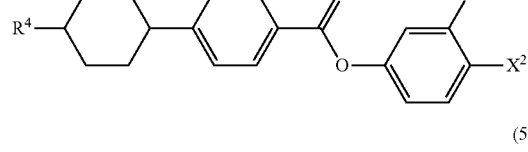
(5-53) 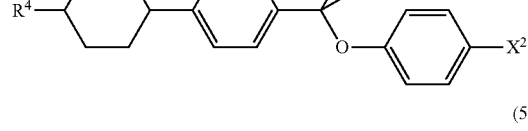
(5-54) 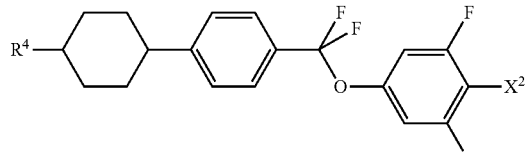
(5-55) 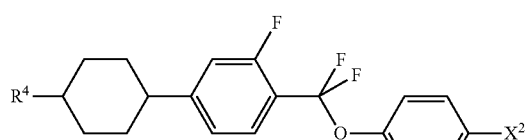
(5-56) 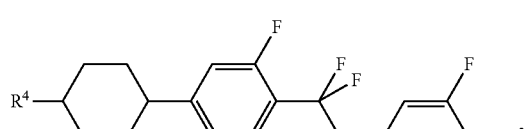
(5-57) 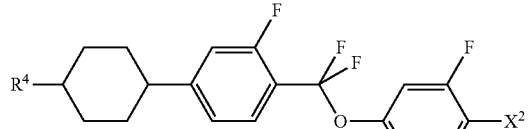
(5-58) 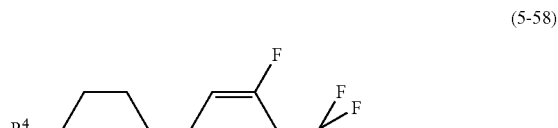
(5-59) 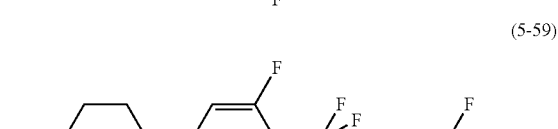
(5-60) 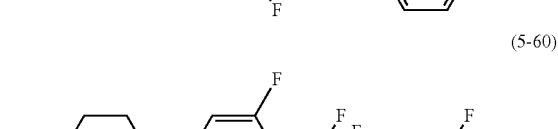
(5-61) 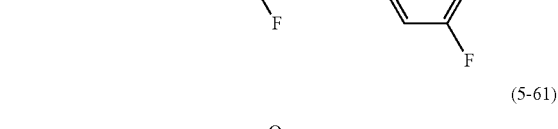

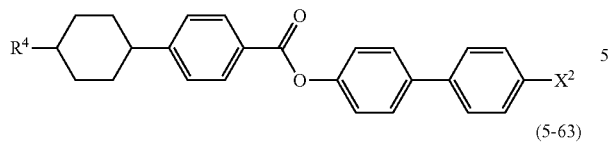
(5-62)

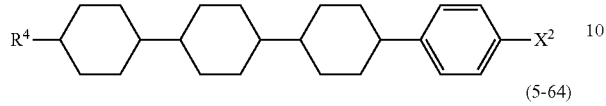
(5-63)

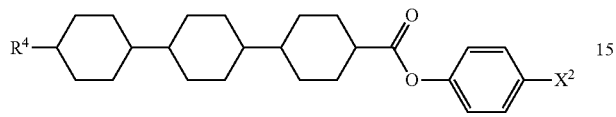
(5-64)

In these compounds (the component C), the definitions of R⁴ and X² are just the same as described previously.

The component C is mainly used for the preparation of a composition for use in a PS-TN mode and so forth, since the dielectric anisotropy is positive and its value is large. The dielectric anisotropy of the composition can be increased by addition of the component C. The component C has the effect of increasing the temperature range of a liquid crystal phase, adjusting the viscosity and adjusting the optical anisotropy. The component C is useful for adjusting the voltage-transmittance curve of a device.

The content of the component C is suitably in the range of 1% by weight to 99% by weight, preferably in the range of 10 by weight to 97% by weight, more preferably 40% by weight to 95% by weight, based on the total weight of the liquid crystal compounds, in the preparation of a composition for use in a mode of PS-TN or the like. In this composition, the temperature range of a liquid crystal phase, the viscosity, the optical anisotropy, the dielectric anisotropy or the like can be adjusted by addition of the component E. It is desirable that the content of the component C should be 30% by weight or less based on the total weight of the liquid crystal compounds when the component C is added to a composition having negative dielectric anisotropy. The elastic constant of the composition can be adjusted and the voltage-transmittance curve of a device can be adjusted by the addition of the component C.

The component D is selected from the compounds (6) to (11). These compounds have a benzene ring substituted with two halogens in the lateral positions, such as 2,3-difluoro-1,4-phenylene. Desirable examples of the component D include the compounds (6-1) to (6-6), the compounds (7-1) to (7-15), the compound (8-1), the compounds (9-1) to (9-3), the compounds (10-1) to (10-11) and the compounds (11-1) to (11-10).

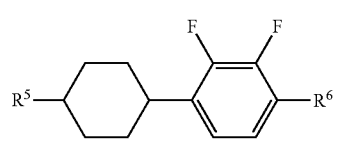
(6-1)

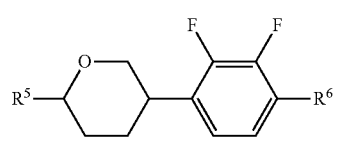
(6-2)

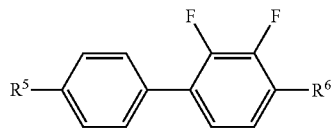
(6-3)

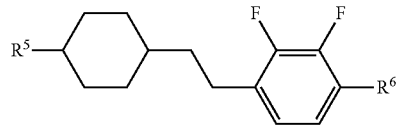
(6-4)

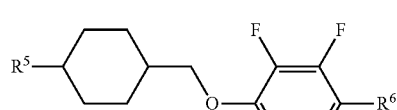
(6-5)

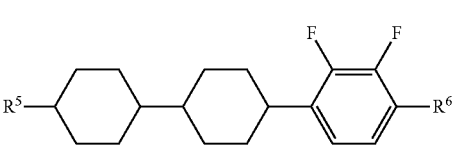
(6-6)

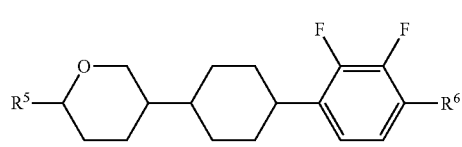
(7-1)

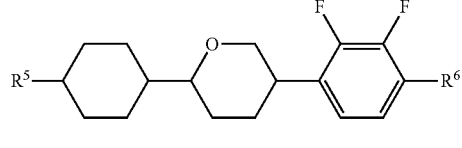
(7-2)

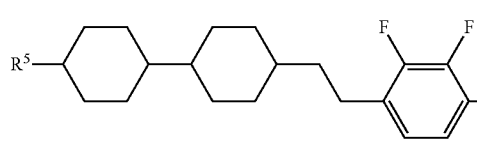
(7-3)

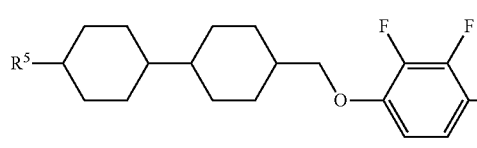
(7-4)

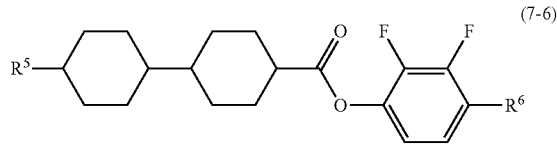
(7-5)

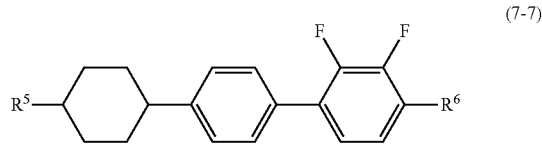
(7-6)

(7-7)

(7-8)
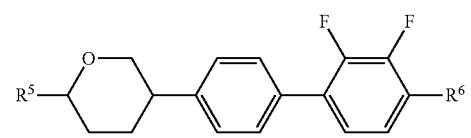
(7-9)
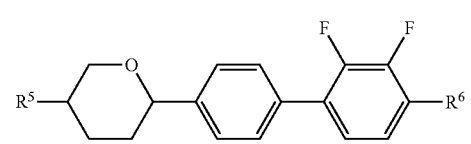
(7-10)
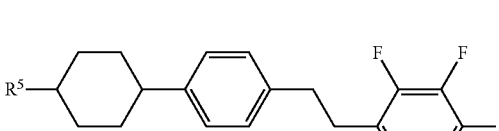
(7-11)
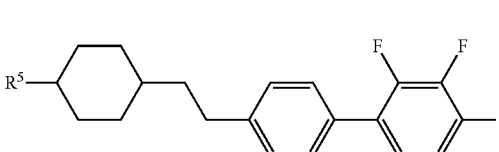
(7-12)
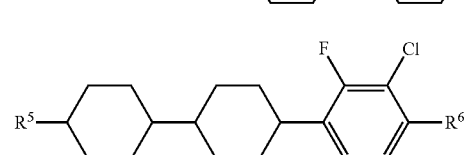
(7-13)
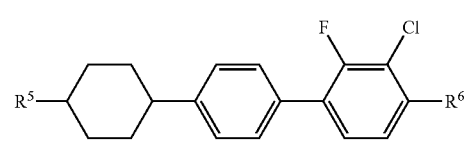
(7-14)
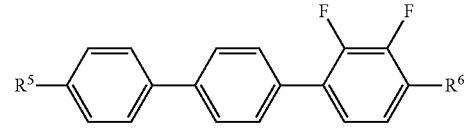
(7-15)
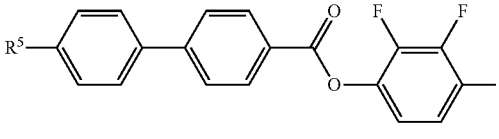
(8-1)
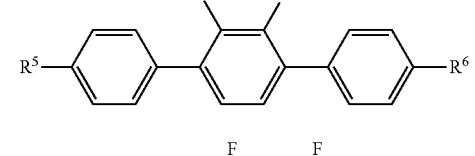
(9-1)
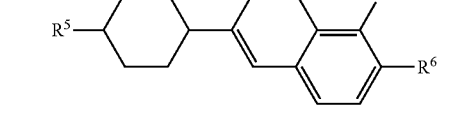
(9-2)
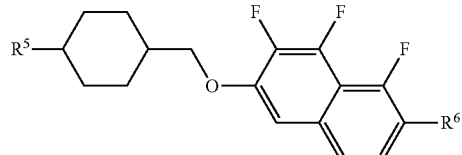
(9-3)
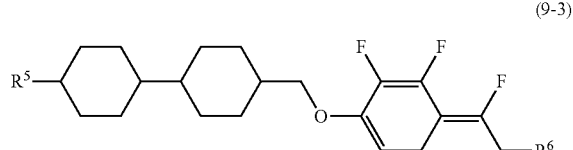
(10-1)
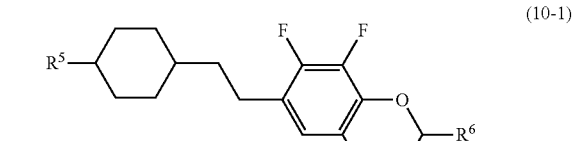
(10-2)
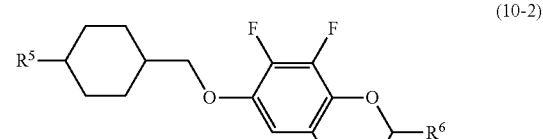
(10-3)
(10-4)
(10-5)
(10-6)
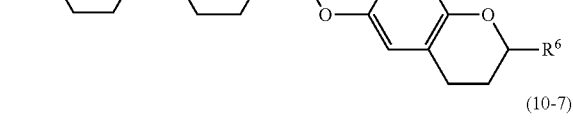
(10-7)
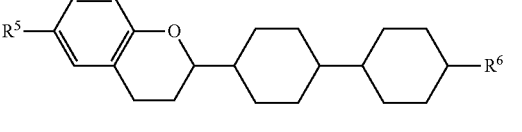

(10-8)
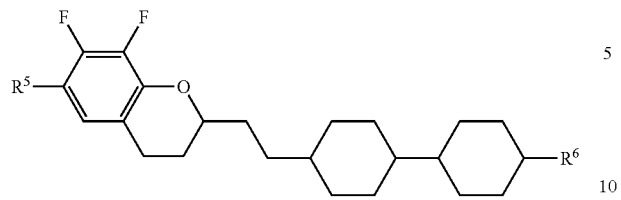

(10-9)
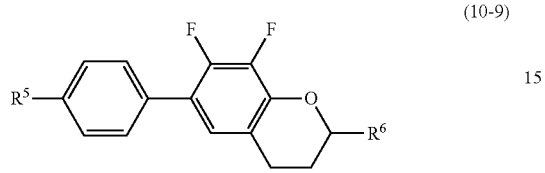

(10-10)
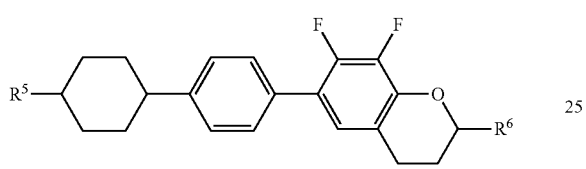

(10-11)
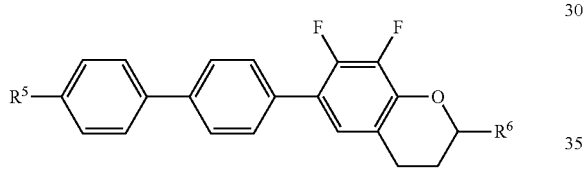

(11-1)
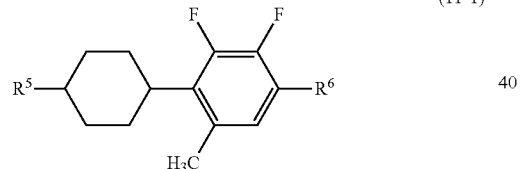

(11-2)
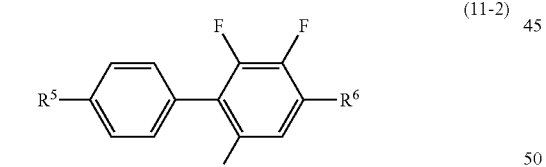

(11-3)
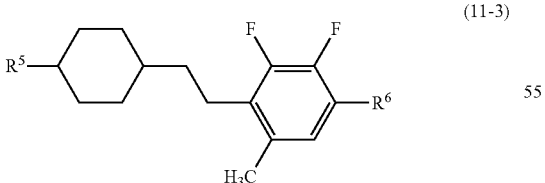

(11-4)
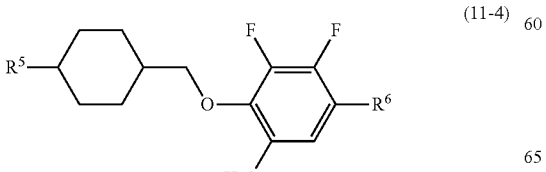

(11-5)
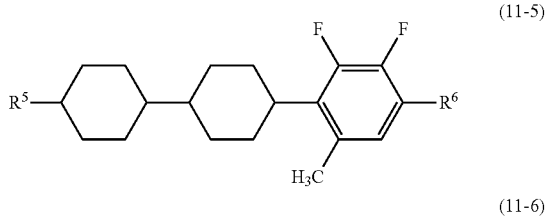

(11-6)
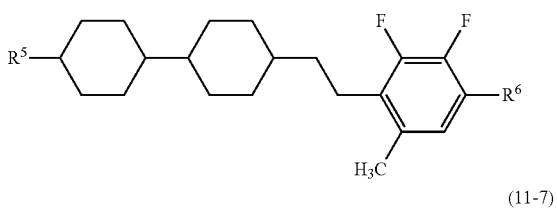

(11-7)
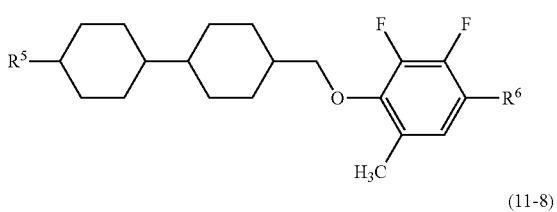

(11-8)
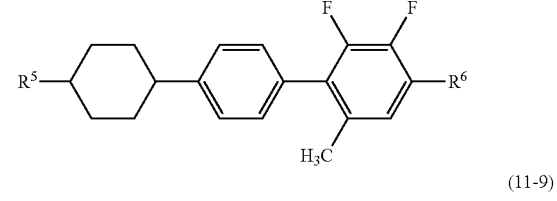

(11-9)
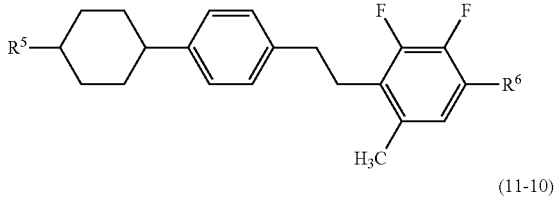

(11-10)
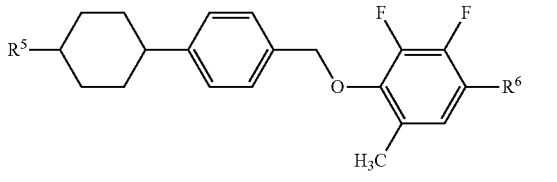

In these compounds (the component D), the definitions of $R^5$ and $R^6$ are just the same as described previously.

The component D is a compound having a negative dielectric anisotropy. The component D is used for the preparation of a composition for use in modes of PS-IPS, PS-FFS, PSA-VA and so forth. As the content of the component D is increased, the dielectric anisotropy of the composition increases negatively, but the viscosity increases. Thus, it is desirable that the content should decrease as long as the required value of the threshold voltage of a device is satisfied. Accordingly, the content is preferably 40% by weight or more in order to ensure adequate voltage drive, in consideration that the absolute value of the dielectric anisotropy is about 5.

In the component D, the compound (6) is mainly effective in adjusting the viscosity, adjusting the optical anisotropy or adjusting the dielectric anisotropy, since it is a two-ring compound. The compounds (7) and (8) are effective in increasing the maximum temperature, increasing the optical anisotropy or increasing the dielectric anisotropy, since they are three-ring compounds. The compounds (9) to (11) are effective in increasing the dielectric anisotropy.

The content of the component D is preferably 40% by weight or more, and more preferably in the range of 50% by weight to 95% by weight, based on the total weight of the liquid crystal compounds, in the preparation of a composition for use in modes of PS-IPS, PS-FFS, PSA-VA and so forth. The elastic constant of the composition can be adjusted and the voltage-transmittance curve of a device can be adjusted by the addition of the component D. It is desirable that the content of the component D should be 30% by weight or less based on the total weight of the liquid crystal compounds when the component D is added to a composition having positive dielectric anisotropy.

The component E includes a compound where two terminal groups are alkyl or the like. Desirable examples of the component E include the compounds (12-1) to (12-11), the compounds (13-1) to (13-19) and the compounds (14-1) to (14-6).

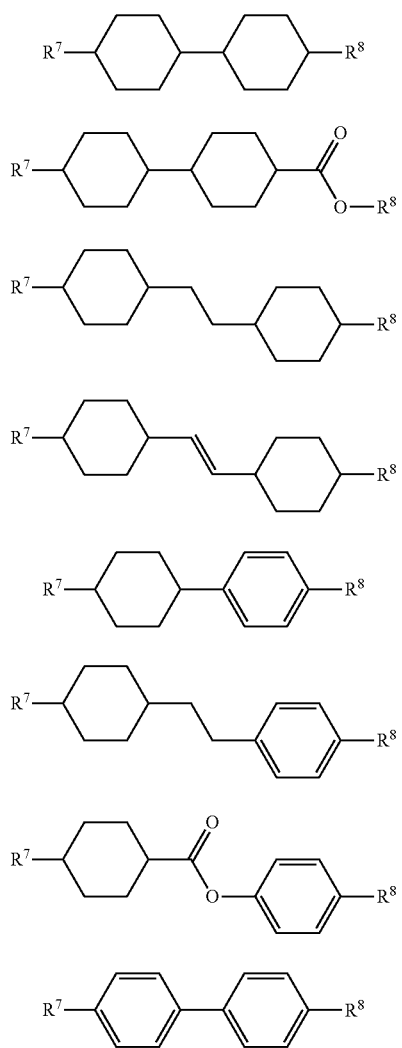

-continued

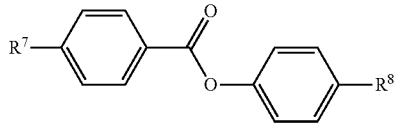
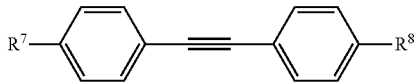
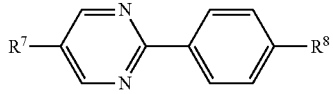
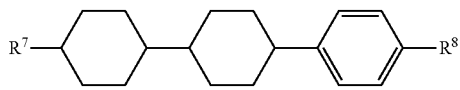
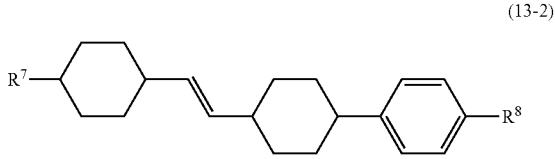
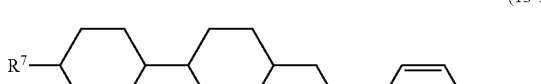
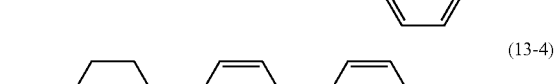
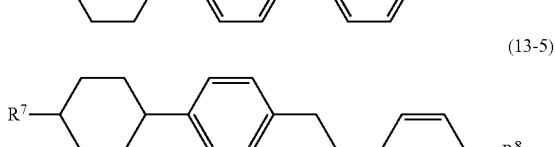
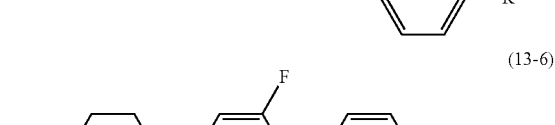
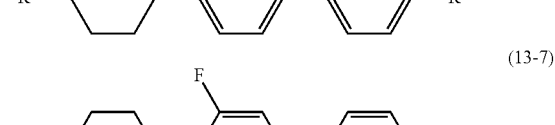
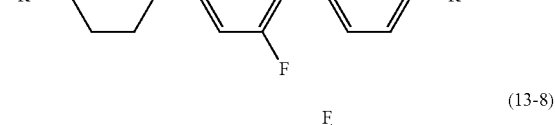
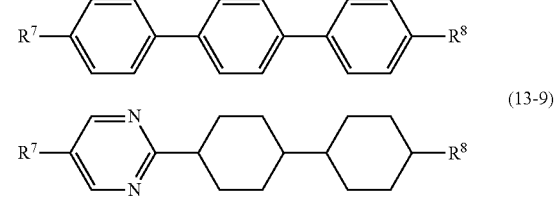

-continued

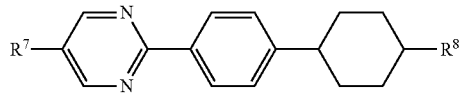
(13-10)

(13-11)

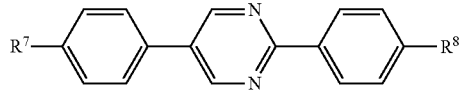
(13-12)

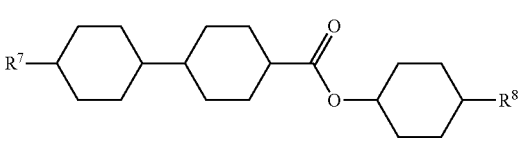
(13-13)

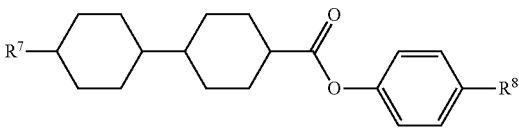
(13-14)

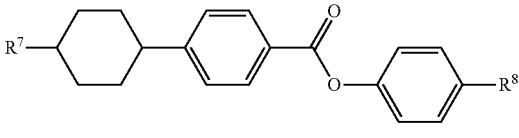
(13-15)

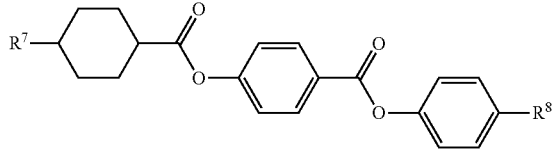
(13-16)

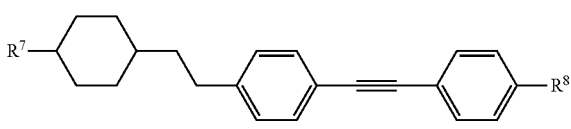
(13-17)

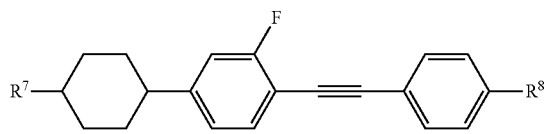
(13-18)

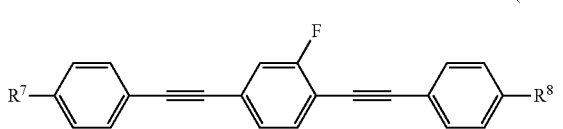
(13-19)

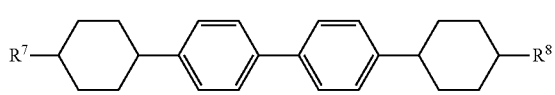
(14-1)

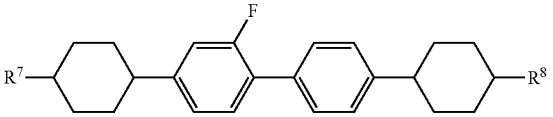
(14-2)

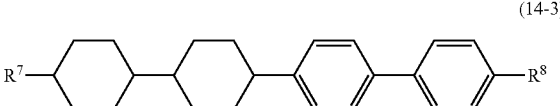
(14-3)

(14-4)

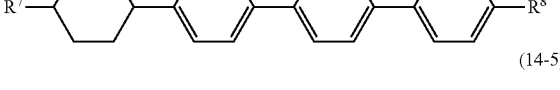
(14-5)

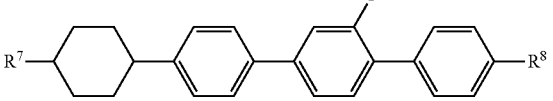
(14-6)

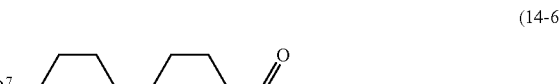

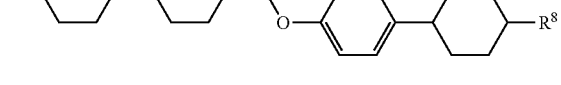

In these compounds (component E), the definitions of $R^7$ and $R^8$ are just the same as described previously.

The component E is nearly neutral, since the absolute value of its dielectric anisotropy is small. The compound (12) is mainly effective in adjusting the viscosity or adjusting the optical anisotropy. The compounds (13) and (14) are effective in increasing the temperature range of a nematic phase due to an increase in the maximum temperature, or adjusting the optical anisotropy.

As the content of the component E is increased, the viscosity of the composition decreases, but the dielectric anisotropy decreases. Thus, it is desirable that the content should increase as long as the required value of the threshold voltage of a device is satisfied. Accordingly, the content of the component E is preferably 30% by weight or more, and more preferably 40% by weight or more based on the total weight of the liquid crystal compounds, in the preparation of a composition for use in modes of PS-IPS, PSA-VA and so forth.

The preparation of the liquid crystal composition is carried out according to a known method such as the mutual dissolution of necessary components at higher temperatures than room temperature. An additive may be added to the composition, depending on its intended use. Examples of the additive are an optically active compound, an antioxidant, an ultraviolet light absorber, a light stabilizer, a thermal stabilizer, an antifoaming agent and so forth. These kinds of additives are well known to a person of ordinary skill in the art, and have been described in the literature.

An optically active compound is effective in inducing a helical structure in liquid crystal molecules, giving a necessary twist angle and thus preventing a reverse twist. A helical pitch can be adjusted by addition of the optically active compound. Two or more optically active compounds may be added for the purpose of adjusting the temperature dependence of the helical pitch. Desirable examples of the optically active compound include the following compounds (Op-1) to (Op-18). In the compound (Op-18), the ring J is 1,4-cyclohexylene or 1,4-phenylene, and $R^{24}$ is alkyl having 1 to 10 carbons.
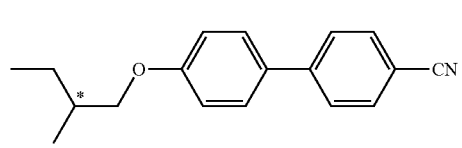
(Op-1)
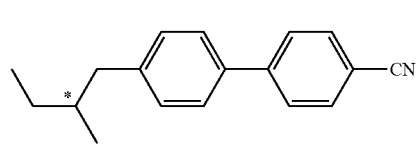
(Op-2)
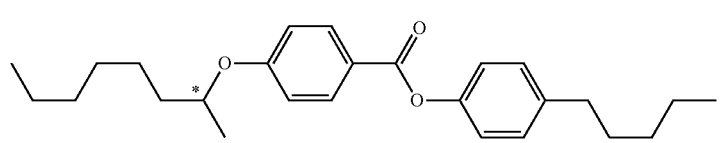
(Op-3)
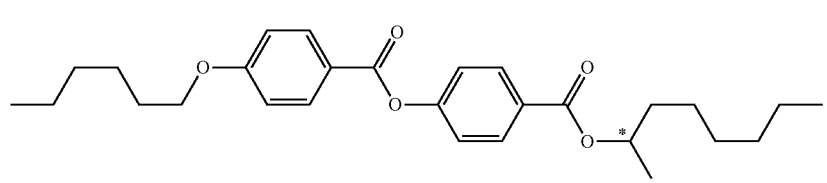
(Op-4)
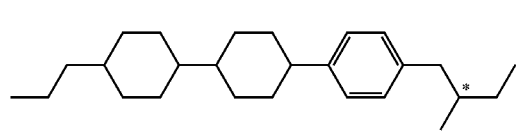
(Op-5)
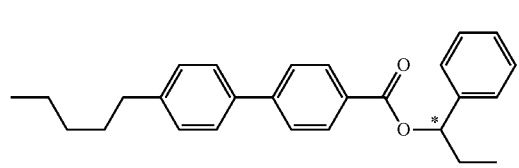
(Op-6)
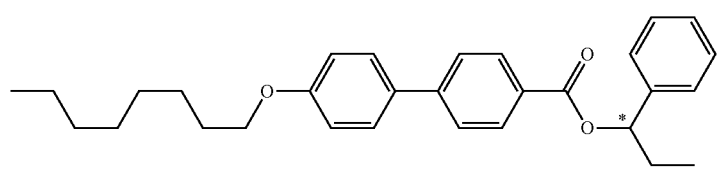
(Op-7)
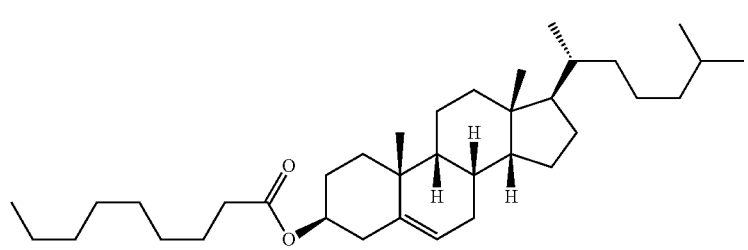
(Op-8)
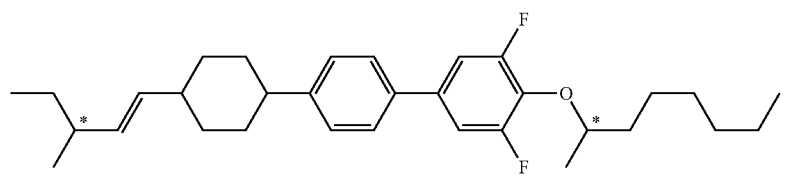
(Op-9)
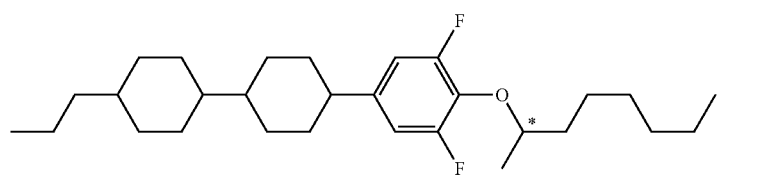
(Op-10)

(Op-11)
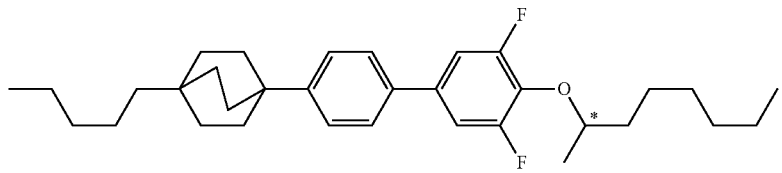

(Op-12)
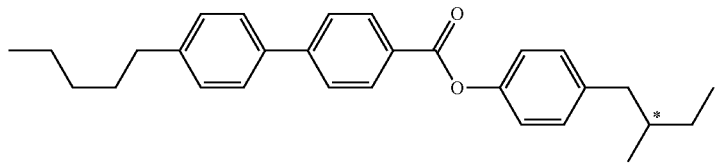

(Op-13)
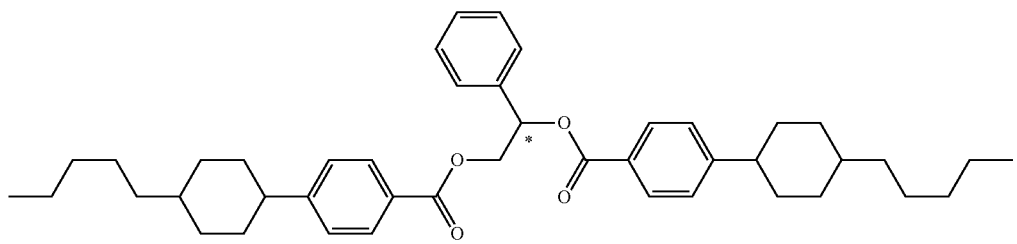

(Op-14)
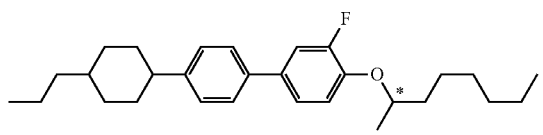

(Op-15)
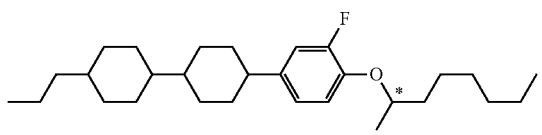

(Op-16)
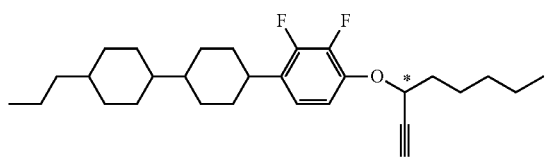

(Op-17)
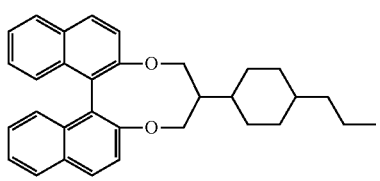

(Op-18)
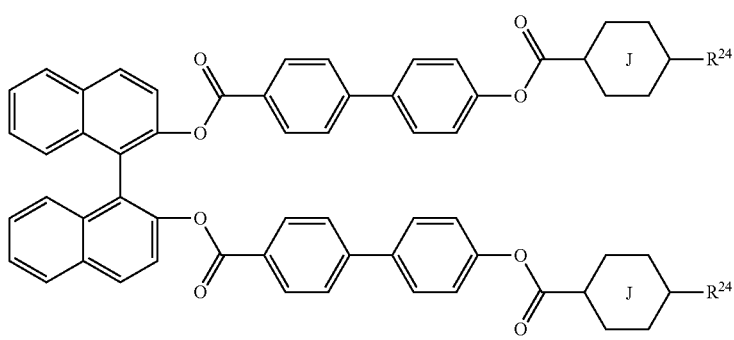

An antioxidant is effective in maintaining a large voltage holding ratio. Desirable examples of the antioxidant include the compounds (AO-1) and (AO-2) described below; Irganox 415, Irganox 565, Irganox 1010, Irganox 1035, Irganox 3114 and Irganox 1098 (trade names, from BASF). An ultraviolet light absorber is effective for preventing a decrease in the maximum temperature. Desirable examples of the ultraviolet light absorber include a benzophenone derivative, a benzoate derivative and a triazole derivative. Specific examples include the compounds (AO-3) and (AO-4) described below; Tinuvin 329, Tinuvin P, Tinuvin 326, Tinuvin 234, Tinuvin 213, Tinuvin 400, Tinuvin 328 and Tinuvin 99-2 (trade names, from BASF); and 1,4-diazabicyclo[2.2.2]octane (DABCO).

A light stabilizer such as an amine having steric hindrance is desirable for maintaining a large voltage holding ratio. Desirable examples of the light stabilizer include the compounds (AO-5) and (AO-6) described below; Tinuvin 144, Tinuvin 765 and Tinuvin 770DF (trade names, from BASF). A thermal stabilizer is also effective in maintaining a large voltage holding ratio, and a desirable example include Irgafos 168 (trade name, from BASF). An antifoaming agent is effective in preventing foam formation. Desirable examples of the antifoaming agent include dimethyl silicone oil and methyl phenyl silicone oil.

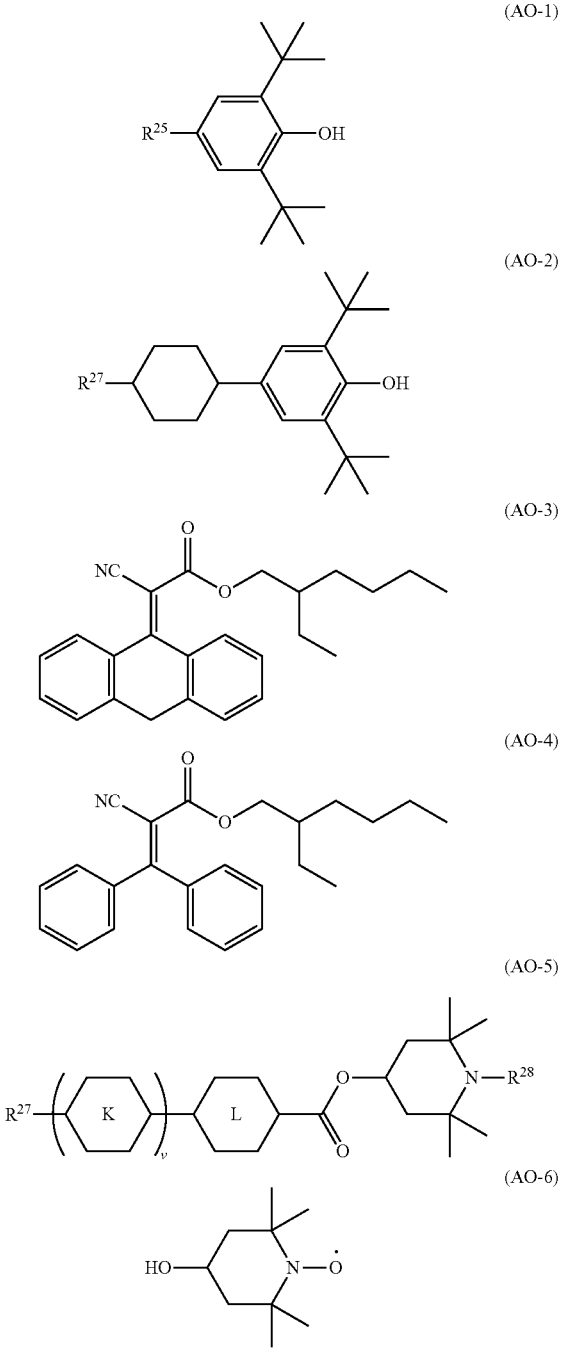

In the compound (AO-1), $R^{25}$ is alkyl having 1 to 20 carbons, alkoxy having 1 to 20 carbons, —COOR$^{26}$ or —CH$_2$CH$_2$COOR$^{26}$; $R^{26}$ is alkyl having 1 to 20 carbons. In the compounds (AO-2) and (AO-5), $R^{27}$ is alkyl having 1 to 20 carbons. In the compound (AO-5), the ring K and the ring L are 1,4-cyclohexylene or 1,4-phenylene, v is 0, 1 or 2, and $R^{28}$ is hydrogen, methyl or O•.

4. Polymerization

The compound (1) has a suitable polymerization reactivity, a high conversion yield and a high solubility in a liquid crystal composition. A liquid crystal composition including a polymer is formed by the polymerization of a liquid crystal composition including the compound (1) and liquid crystal compounds. This is because the compound (1) gives the polymer in the liquid crystal composition by the polymerization. The polymer is effective in inducing pretilt in liquid crystal molecules. It is desirable that the polymerization is carried out at a temperature in which the liquid crystal composition exhibits a liquid crystal phase. The polymerization proceeds on heating or on irradiation with light, for instance. A desirable reaction is the photopolymerization. It is desirable that the photopolymerization should be carried out at 100° C. or lower to prevent thermal polymerization from occurring simultaneously. The polymerization may be carried out while an electric or magnetic field is applied.

The polymerization reactivity and the conversion yield of the compound (1) can be adjusted. The compound (1) is suitable for radical polymerization. The compound (1) can be smoothly polymerized by the addition of a polymerization initiator. The amount of the compound (1) remained can be reduced by the optimization of the reaction temperature. Examples of photo-radical polymerization initiators are TPO, 1173 and 4265 of Darocur series, and 184, 369, 500, 651, 784, 819, 907, 1300, 1700, 1800, 1850 and 2959 of Irgacure series, from Ciba Specialty Chemicals.

Additional examples of the photo-radical polymerization initiators are 4-methoxyphenyl-2,4-bis(trichloromethyl)triazine, 2-(4-butoxystyryl)-5-trichloromethyl-1,3,4-oxadiazole, 9-phenylacridine, 9,10-benzphenazine, a mixture of benzophenone/Michler's ketone, a mixture of hexaarylbiimidazole/mercaptobenzimidazole, 1-(4-isopropylphenyl)-2-hydroxy-2-methylpropan-1-one, benzyldimethylketal, 2-methyl-1-[4-(methylthio)phenyl]-2-morphorinopropan-1-one, a mixture of 2,4-diethylxanthone/methyl p-dimethylaminobenzoate and a mixture of benzophenone/methyltriethanolamine.

The polymerization can be carried out by irradiation with ultraviolet light while an electric field is applied, after a photo-radical polymerization initiator had been added to a liquid crystal composition. However, the unreacted polymerization initiator or the degradation product of a polymerization initiator may cause a poor display such as image burn-in to a device. The photopolymerization may be carried out without a polymerization initiator to avoid this. Desirable wavelengths of the irradiated light are in the range of 150 nm to 500 nm. More desirable wavelengths are in the range of 250 nm to 450 nm, and the most desirable wavelengths are in the range of 300 nm to 400 nm.

5. Liquid Crystal Display Devices

The effect of a polymer in a liquid crystal display device is interpreted as follows. A liquid crystal composition is a mixture of liquid crystal compounds, a polymerizable compound and so forth. By applying an electric field to the liquid crystal composition, the liquid crystal molecules are aligned in the direction of the electric field. The polymerizable compound is also aligned similarly following this alignment. Under the condition, the polymerizable compound is polymerized by irradiation of the liquid crystal composition with ultraviolet light, as a result of which a polymer network is formed in the liquid crystal composition. The liquid crystal molecules are stabilized as being aligned in the direction of the electric field by the effect of the network. The effect is maintained even when the electric field is removed. The response time of the device is decreased accordingly.

It is desirable that the polymerization of the liquid crystal composition should be carried out in a display device. One example is as follows. A display device is prepared, which has two glass substrates equipped with transparent electrodes and alignment films. A liquid crystal composition, which includes the compound (1), a liquid crystal compound, an additive and so forth as components, is prepared. The composition is poured into the display device. The compound (1) is polymerized by irradiating the display device with ultraviolet light while an electric field is applied. The polymerization gives a liquid crystal composition including a polymer. A liquid crystal display device having a PSA mode can be easily made by this method. A rubbing treatment for the alignment film may be eliminated in this method. Incidentally, a method in which liquid crystal molecules are stabilized without an electric field may alternatively be employed.

A liquid crystal display device having a PSA mode is made when the added amount of the polymerizable compound is in the range of 0.1% by weight to 2% by weight based on the total weight of the liquid crystal compounds. The device having a PSA mode can be driven by means of a driving mode such as an active matrix (AM) or a passive matrix (PM). Such kind of device can be applied to any type of a reflection type, a transmission type and a semi-transmission type. A device having a polymer dispersed mode can also be made by increasing the added amount of the polymerizable compound.

EXAMPLES

The invention will be explained in more detail based on the following examples. The invention is not limited by these examples.

1. Examples of the Compound (1)

The compound (1) was prepared by the procedures described in Example 1 and so forth. Compounds prepared herein were identified by means of NMR analysis and so forth. The physical properties of the compounds were measured by the methods described below.

NMR Analysis

A model DRX-500 apparatus (made by Bruker BioSpin Corporation) was used for the measurement. In the measurement of $^1$H-NMR, a sample was dissolved in a deuterated solvent such as $CDCl_3$, and the measurement was carried out at room temperature, 500 MHz and an accumulation of 16 scans. Tetramethylsilane (TMS) was used as an internal standard. In the measurement of $^{19}$F-NMR, $CFCl_3$ was used as an internal standard, and an accumulation of 24 scans was performed. In the explanation of the nuclear magnetic resonance spectra, the symbols s, d, t, q, quin, sex, m and br stand for a singlet, a doublet, a triplet, a quartet, a quintet, a sextet, a multiplet and line-broadening, respectively.

HPLC analysis

Model Prominence (LC-20AD; SPD-20A) made by Shimadzu Corporation was used for the measurement. A column YMC-Pack ODS-A (length: 150 mm, bore: 4.6 mm, particle size: 5 µm) made by YMC Co., Ltd. was used. Acetonitrile and water were suitably mixed and used as eluent. A UV detector, a RI detector or a Corona detector, etc., was suitably used as a detector. A wavelength for the UV detector was 254 nm. A sample was dissolved in acetonitrile to give a 0.1% by weight solution, and then 1 microliter of the solution was injected into the sample injector. Model C-R7Aplus made by Shimadzu Corporation was used as a recorder.

Ultraviolet and Visible Spectrophotometric Analysis

Model PharmaSpec UV-1700 made by Shimadzu Corporation was used for measurement. Wavelengths in the range of 190 nm to 700 nm were used for the detection. A sample was dissolved in acetonitrile, giving a 0.01 mmol/L solution, which was placed in a quartz cell (optical path length: 1 cm) and measured.

Sample for Measurement

A compound itself was used as a sample when the phase structure and the transition temperature (the clearing point, the melting point, the starting temperature of polymerization, and so forth) were measured. A mixture of the compound and a mother liquid crystal was used as a sample when physical properties such as the maximum temperature of a nematic phase, viscosity, optical anisotropy and dielectric anisotropy were measured.

Measurement Method

Physical properties were measured according to the following methods. Most of them were methods described in the JEITA standards (JEITA-ED-2521B) which was deliberated and established by Japan Electronics and Information Technology Industries Association (abbreviated to JEITA), or modified versions thereof. No thin film transistor (TFT) was attached to the TN device used for measurement.

(1) Phase Structure

A sample was placed on a hot plate of a melting point apparatus (Hot Stage Model FP-52 made by Mettler Toledo International Inc.) equipped with a polarizing microscope, and the phase conditions and their changes were observed with the polarizing microscope while the sample was heated at the rate of 3° C. per minute, and the kinds of the phases were specified.

(2) Transition Temperature (° C.)

A Perkin-Elmer differential scanning calorimeter, a Diamond DSC system or a X-DSC7000 high sensitivity differential scanning analyzer made by SII NanoTechnology Inc. was used for the measurement. A sample was heated and then cooled at the rate of 3° C. per minute, and the starting point of an endothermic peak or an exothermic peak caused by the phase change of the sample was obtained by means of the extrapolation, and thus the transition temperature was determined. The transition temperature of a compound, from solid to a liquid crystal phase such as a smectic phase or a nematic phase, may be abbreviated to "the minimum temperature of a liquid crystal phase". The transition temperature of a compound from a liquid crystal phase to liquid may be abbreviated to "a clearing point". The melting point and the starting temperature of polymerization of a compound were also measured by use of this apparatus.

The symbol C stood for crystals. When the kinds of crystals were distinguishable, each was expressed as $C_1$ and $C_2$. The symbols S and N stood for a smectic phase and a nematic phase, respectively. When a smectic A phase, a smectic B phase, a smectic C phase or a smectic F was distinguishable in the smectic phases, it was expressed as $S_A$, $S_B$, $S_C$ or $S_F$, respectively. The symbol I stood for a liquid (isotropic). Transition temperatures were expressed as, for example, "C 50.0 N 100.0 Iso", which means that the transition temperature from crystals to a nematic phase was 50.0° C., and the transition temperature from the nematic phase to a liquid was 100.0° C.

(3) Maximum Temperature of a Nematic Phase ($T_{NI}$ or NI; ° C.)

A sample was placed on a hot plate in a melting point apparatus equipped with a polarizing microscope and was heated at the rate of 1° C. per minute. The temperature was measured when a part of the sample began to change from a nematic phase to an isotropic liquid. The upper limit of the temperature range of the nematic phase may be abbreviated to "the maximum temperature." The symbol $T_{NI}$ means that the sample was a mixture of a compound and a mother liquid crystal. The symbol NI means that the sample was a mixture of a compound and the component B, C, D or E.

(4) Minimum Temperature of a Nematic Phase ($T_C$; ° C.)

A sample having a nematic phase was kept in freezers at temperatures of 0° C., −10° C., −20° C., −30° C. and −40° C. for 10 days, and then the liquid crystal phases were observed. For example, when the sample maintained the nematic phase at −20° C. and changed to crystals or a smectic phase at −30° C., $T_C$ was expressed as ≤−20° C. The lower limit of the temperature range of the nematic phase may be abbreviated to "the minimum temperature."

(5) Viscosity (Bulk Viscosity; η; Measured at 20° C.; mPa·s)

An E-type viscometer was used for the measurement.

(6) Optical Anisotropy (Refractive Index Anisotropy; Δn; Measured at 25° C.)

The measurement was carried out using an Abbe refractometer with a polarizing plate attached to the ocular, using light at a wavelength of 589 nanometers. The surface of the main prism was rubbed in one direction, and then a sample was placed on the main prism. The refractive index ($n_∥$) was measured when the direction of the polarized light was parallel to that of the rubbing. The refractive index ($n_{⊥95}$) was measured when the direction of polarized light was perpendicular to that of the rubbing. The value of the optical anisotropy (Δn) was calculated from the equation: $Δn = n_∥ − n_⊥$.

(7) Specific Resistance (ρ; Measured at 25° C.; Ω cm)

A sample of 1.0 milliliter was poured into a vessel equipped with electrodes. DC voltage (10 V) was applied to the vessel, and the DC current was measured after 10 seconds. The specific resistance was calculated from the following equation: (specific resistance) =[(voltage)×(electric capacity of vessel)]/[(DC current)×(dielectric constant in vacuum)].

(8) Voltage Holding Ratio (VHR-1; Measured at 25° C.; %)

A TN device used for measurement had a polyimide-alignment film, and the distance between the two glass substrates (cell gap) was 5 micrometers. A sample was poured into the device, and then the device was sealed with an adhesive curable on irradiation with ultraviolet light. A pulse voltage (60 microseconds at 5 V) was applied to the device to charge it. The attenuating voltage was measured for 16.7 milliseconds with a high-speed voltmeter, and the area A between the voltage curve and the transverse axis in a unit cycle was obtained. The area B was the area without attenuation. The voltage holding ratio was a percentage of the area A relative to the area B.

(9) Voltage Holding Ratio (VHR-2; Measured at 80° C.; %)

A voltage holding ratio was measured in the same way except for the replacement of 25° C. with 80° C. and the results are shown using the symbol VHR-2.

The measurement methods are sometimes different for samples of which the dielectric anisotropy is positive or negative. Next, the measurement methods used when the dielectric anisotropy is positive are described in (10) to (14). The measurement methods used when the dielectric anisotropy is negative are described in (15) to (19).

(10) Viscosity (rotational viscosity; γ1; measured at 25° C.; mPa·S)

Measurement was carried out according to the method described in M. Imai, et al., Molecular Crystals and Liquid Crystals, Vol. 259, 37 (1995). A sample was poured into a TN device in which the twist angle was 0 degrees and the distance between the two glass substrates (cell gap) was 5 micrometers. Voltages were applied stepwise to the device in the range of 16 to 19.5 volts, with increments of 0.5 volt. After a period of 0.2 second with no voltage, a voltage was applied repeatedly under the condition of only one rectangular wave (rectangular pulse; 0.2 second) and then no voltage (2 seconds). The peak current and the peak time of the transient current generated by the applied voltage were measured. The value of rotational viscosity was obtained from the measured values and the calculating equation (8) on page 40 of the paper presented by M. Imai, et al. The value of dielectric anisotropy necessary for this calculation was obtained by use of the device that had been used for the measurement of rotational viscosity, according to the method described below.

(11) Dielectric Anisotropy (Δ∈; Measured at 25° C.)

The sample was poured into a TN device in which the distance between the two glass substrates (cell gap) was 9 micrometers and the twist angle was 80 degrees. Sine waves (10 V, 1 kHz) were applied to this device, and the dielectric constant ($∈_∥$) in the major axis direction of the liquid crystal molecules was measured after 2 seconds. Sine waves (0.5V, 1 kHz) were applied to the device and the dielectric constant ($∈_⊥$) in the minor axis direction of the liquid crystal molecules was measured after 2 seconds. The value of dielectric anisotropy was calculated from the equation: $Δ∈ = ∈_∥ − ∈_⊥$.

(12) Elastic Constant (K; Measured at 25° C.; pN)

A LCR meter Model HP 4284-A made by Yokokawa Hewlett-Packard, Ltd. was used for the measurement. The sample was poured into a homogeneous device in which the distance between the two glass substrates (cell gap) was 20 micrometers. Electric charges of 0 volts to 20 volts were applied to the device, and the electrostatic capacity and the applied voltage were measured. The measured values of the electric capacity (C) and the applied voltage (V) were fitted to the equation (2.98) and the equation (2.101) in page 75 of the "Ekisho Debaisu Handobukku" (Liquid Crystal Device Handbook, in English; The Nikkan Kogyo Shimbun, Ltd., Japan) and the values of $K_{11}$ and $K_{33}$ were obtained from the equation (2.99). Next, the value of $K_{22}$ was calculated from the equation (3.18) in page 171 and the values of $K_{11}$ and $K_{33}$ thus obtained. The elastic constant K was an average value of $K_{11}$, $K_{22}$ and $K_{33}$.

(13) Threshold Voltage (Vth; Measured at 25° C.; V)

The measurement was carried out with an LCD evaluation system Model LCD-5100 made by Otsuka Electronics Co., Ltd. The light source was a halogen lamp. The sample was poured into a TN device having a normally white mode, in which the distance between the two glass substrates (cell gap) was about 4.45/Δn (micrometers) and the twist angle was 80 degrees. The voltages applied to the device (32 Hz, rectangular waves) were increased stepwise from 0 V to 10 V, with increments of 0.02 V. During the increase, the device was irradiated with light in the perpendicular direction, and the amount of light passing through the device was measured. A voltage-transmittance curve was drawn, in which the maximum amount of light corresponded to 100% transmittance and the minimum amount of light corresponded to 0% transmittance. The threshold voltage was voltage at 90% transmittance.

(14) Response Time (τ; Measured at 25° C.; Millisecond)

Measurement was carried out with an LCD evaluation system Model LCD-5100 made by Otsuka Electronics Co., Ltd. The light source was a halogen lamp. The low-pass filter was set at 5 kHz. A sample was poured into a TN device having a normally white mode, in which the cell gap between the two glass substrates was 5.0 micrometers and the twist angle was 80 degrees. Rectangular waves (60 Hz, 5 V, 0.5 second) were applied to this device. The device was simultaneously irradiated with light in the perpendicular direction, and the amount of light passing through the device was measured. The maximum amount of light corresponded to 100% transmittance, and the minimum amount of light corresponded to 0% transmittance. Rise time ($\tau_r$; millisecond) was the time required for a change from 90% to 10% transmittance. Fall time ($\tau_f$; millisecond) was the time required for a change from 10% to 90% transmittance. The response time was the sum of the rise time and the fall time thus obtained.

(15) Viscosity (Rotational Viscosity; γ1; Measured at 25° C.; mPa·s)

The measurement was carried out according to the method described in M. Imai, et al., Molecular Crystals and Liquid Crystals, Vol. 259, p. 37 (1995). The sample was poured into a VA device in which the distance between the two glass substrates (cell gap) was 20 micrometers. Voltages were applied stepwise to the device in the range of 30 V to 50 V, with increments of 1 volt. After a period of 0.2 second with no voltage, a voltage was applied repeatedly under the condition of only one rectangular wave (rectangular pulse; 0.2 second) and then no voltage (2 seconds). The peak current and the peak time of the transient current generated by the applied voltage were measured. The value of rotational viscosity was obtained from the measured values and the calculating equation (8) on page 40 of the paper presented by M. Imai, et al. The value of the dielectric anisotropy necessary for the present calculation was obtained by the method described below, under the heading "Dielectric anisotropy."

(16) Dielectric Anisotropy ($\Delta\epsilon$; Measured at 25° C.)

The value of dielectric anisotropy was calculated from the equation: $\Delta\epsilon=\epsilon_{\parallel}-\epsilon_{\perp}$. Dielectric constants ($\epsilon_{\parallel}$ and $\epsilon_{\perp}$) were measured as follows.

1) Measurement of the dielectric constant $\epsilon_{\parallel}$: A solution of 0.16 mL of octadecyltriethoxysilane in 20 mL ethanol was applied to a thoroughly cleaned glass substrates. The glass substrates were rotated with a spinner, and then heated at 150° C. for one hour. The sample was poured into a VA device in which the distance between the two glass substrates (cell gap) was 4 micrometers, and then the device was sealed with an adhesive curable on irradiation with ultraviolet light. Sine waves (0.5 V, 1 kHz) were applied to the device, and the dielectric constant ($\epsilon_{\parallel}$) in the major axis direction of liquid crystal molecules was measured after 2 seconds.

2) Measurement of the dielectric constant $\epsilon_{\perp}$: A polyimide solution was applied to a thoroughly cleaned glass substrate. The glass substrates were burned, and then the resulting alignment film was subjected to rubbing. A sample was poured into a TN device in which the distance between the two glass substrates (cell gap) was 9 micrometers and the twist angle was 80 degrees. Sine waves (0.5 V, 1 kHz) were applied to the device, and the dielectric constant ($\epsilon_{\perp}$) in the minor axis direction of liquid crystal molecules was measured after 2 seconds.

(17) Elastic Constant ($K_{11}$ and $K_{33}$; Measured at 25° C.; pN)

An elastic constant measurement system Model EC-1 made by Toyo Corporation was used for the measurement. The sample was poured into a homeotropic device in which the distance between the two glass substrates (cell gap) was 20 micrometers. Electric charges of 20 volts to 0 volts were applied to the device, and the electrostatic capacity and applied voltage were measured. The values of the electrostatic capacity (C) and the applied voltage (V) were fitted to the equation (2.98) and the equation (2.101) in page 75 of the "Ekisho Debaisu Handobukku" (Liquid Crystal Device Handbook, in English; The Nikkan Kogyo Shimbun, Ltd., Japan), and the value of the elastic constant was obtained from the equation (2.100).

(18) Threshold Voltage (Vth; Measured at 25° C.; V)

The measurement was carried out with an LCD evaluation system Model LCD-5100 made by Otsuka Electronics Co., Ltd. The light source was a halogen lamp. The sample was poured into a VA device having a normally black mode, in which the distance between the two glass substrates (cell gap) was 4 micrometers and the rubbing direction was antiparallel, and then the device was sealed with an adhesive curable on irradiation with ultraviolet light. Voltages applied to the device (60 Hz, rectangular waves) were increased stepwise from 0 V to 20 V, with increments of 0.02 V. During the increase, the device was irradiated with light in the perpendicular direction, and the amount of light passing through the device was measured. A voltage-transmittance curve was drawn, in which the maximum amount of light corresponded to 100% transmittance and the minimum amount of light corresponded to 0% transmittance. The threshold voltage was voltage at 10% transmittance.

(19) Response Time ($\tau$; Measured at 25° C.; Millisecond): The measurement was carried out with an LCD evaluation system Model LCD-5100 made by Otsuka Electronics Co., Ltd. The light source was a halogen lamp. The low-pass filter was set at 5 kHz. The sample was poured into a PVA device having a normally black mode, in which the cell gap between two glass substrates was 3.2 micrometers, and a rubbing direction was antiparallel, and then the device was sealed with an adhesive curable on irradiation with ultraviolet light. A voltage that was a little more than the threshold voltage was applied to the device for 1 minute, and then the device was irradiated with ultraviolet light of 23.5 mW/cm$^2$ for 8 minutes while a voltage of 5.6 V was applied. Rectangular waves (60 Hz, 10V, 0.5 second) were applied to the device. The device was simultaneously irradiated with light in the perpendicular direction, and the amount of light passing through the device was measured. The maximum amount of light corresponded to 100% transmittance, and the minimum amount of light corresponded to 0% transmittance. The response time was the period of time required for the change from 90% to 10% transmittance (fall time: millisecond).

Example 1

[1,1'-Biphenyl]-3,3',4,4'-tetrayl tetrakis(2-methylacrylate), the compound (1-1-1), was prepared according to the scheme described below.

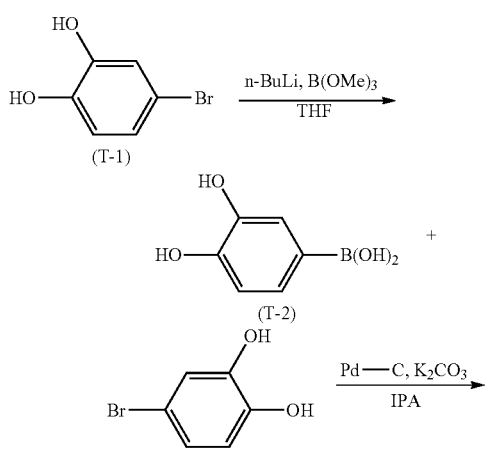

-continued

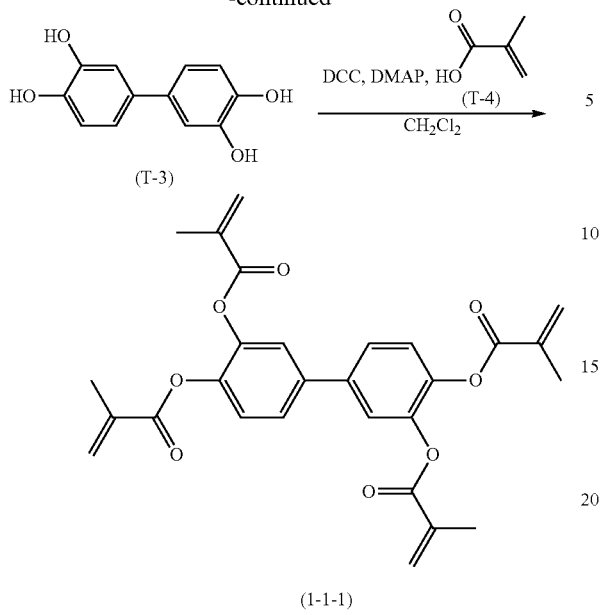

(T-3)

(1-1-1)

Preparation of 3,4-dihydroxyphenylboronic acid (T-2)

4-Bromocatechol (T-1) (18.8 g; made by Tokyo Chemical Industry Co., Ltd.) was dissolved in dry THF (200 ml), which was cooled to −70° C. n-BuLi (72 ml) was added under an atmosphere of nitrogen and the stirring was continued at −70° C. for 2 hours. Trimethyl borate (15.6 g) in a THF solution was then slowly added dropwise at −70° C., and the mixture was warmed to room temperature and stirred for 16 hours. After the completion of the reaction, 2N HCl (100 ml) was added and the mixture was extracted with toluene. The extract was washed with water and brine, and dried over anhydrous magnesium sulfate. The extract was concentrated under reduced pressure to give pale brown solids. The solids were recrystallized (heptane:toluene=4:1 by volume) to give 3,4-dihydroxyphenylboronic acid (T-2; 9.7 g; yield 63%) as colorless crystals.

Preparation of [1,1'-biphenyl]-3,3',4,4'-tetraol (T-3)

The compound (T-2) (9.7 g) obtained in the above procedure and the compound (T-1) (12.5 g) were dissolved in isopropanol (IPA), and palladium on carbon (0.38 g) and potassium carbonate (18.4 g) were added, and then the mixture was heated under reflux for 6 hours. After the completion of the reaction, palladium on carbon was filtered and the filtrate was extracted with ethyl acetate. The extract was washed with a saturated aqueous solution of sodium hydrogencarbonate, water and brine. The extract was dried over anhydrous magnesium sulfate, and concentrated under reduced pressure to give pale brown solids. The solids was purified by silica gel column chromatography (toluene:ethyl acetate=20:1 by volume), and then recrystallization (toluene:heptane=1:4 by volume) to give [1,1'-biphenyl]-3,3',4,4'-tetraol (T-3) (12.5 g; yield 86%) as colorless crystals.

Preparation of the Compound (1-1-1)

The compound (T-3) (12.5 g) obtained in the above procedure, methacrylic acid (T-4) (21.7 g) and dimethylaminopyridine (DMAP) (30.8 g) were dissolved in dichloromethane. Dicyclohexylcarbodiimide (DCC) (30.7 g) was added as a solid to the solution under ice-cooling, and the stirring was continued at room temperature for 12 hours. After the completion of the reaction, the resulting insoluble matter was filtered and the filtrate was extracted with dichloromethane. The extract was washed with water and brine, dried over anhydrous magnesium sulfate, and concentrated under reduced pressure to give colorless oil. The oil was purified by silica gel column chromatography (toluene:ethyl acetate=20:1 by volume), and then recrystallization (heptane:ethanol=1:1 by volume) to give the compound (1-1-1) (15.2 g; yield 54%) as colorless crystals.

$^1$H-NMR (δ ppm; CDCl$_3$): 7.63(s, 2H), 7.57(d, 2H), 7.32(d, 2H), 6.43(d, 4H), 6.18(d, 4H) and 2.01(s, 12H).

The physical properties of the compound (1-1-1) were as follows: Melting point: 75° C.; starting temperature of polymerization: 140° C.

Example 2

[1,1'-Biphenyl]-2,2',4,4'-tetrayl tetrakis(2-methylacrylate), the compound (1-2-1), was prepared according to the scheme described below.

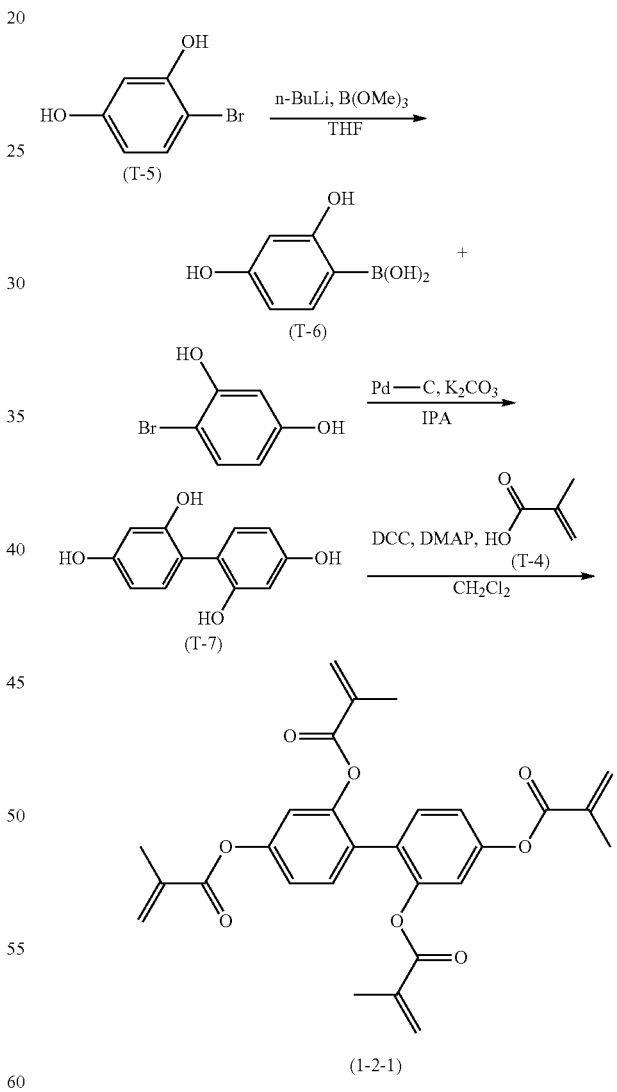

(1-2-1)

[1,1'-Biphenyl]-2,2',4,4'-tetrayl tetrakis(2-methylacrylate), the compound (1-2-1) (6.37 g; yield 13%) was obtained as colorless crystals in the same way as described in Example 1 from 5-bromoresorcinol (T-5) (18.8 g; made by Tokyo Chemical Industry Co., Ltd.) and methacrylic acid (T-4) (9.29 g).

$^1$H-NMR (δ ppm; CDCl$_3$): 7.73(d, 2H), 7.24(s, 2H), 6.96(d, 2H), 6.42(d, 4H), 6.16(d, 4H) and 2.00(s, 12H).

The physical properties of the compound (1-2-1) were as follows: Melting point: 85° C.; starting temperature of polymerization: 133° C.

Example 3

[1,1'-Biphenyl]-3,3',5,5'-tetrayl tetrakis(2-methylacrylate), the compound (1-3-1), was prepared according to the scheme described below.

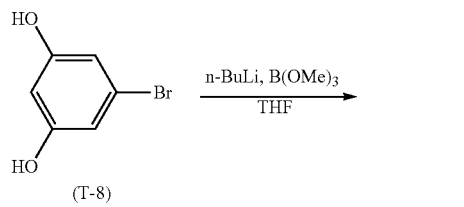

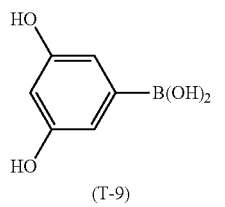

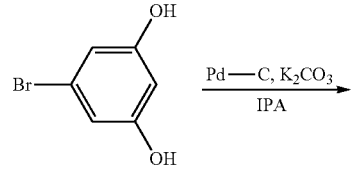

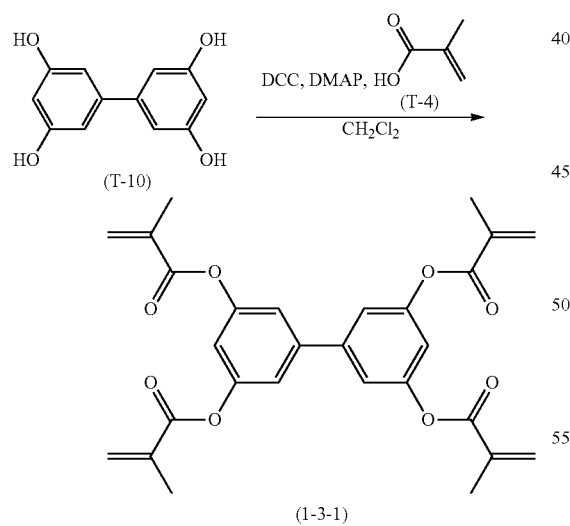

The compound (1-3-1) (17.6 g; yield 36%) was obtained as colorless crystals in the same way as described in Example 1 from 4-bromoresorcinol (T-8) (18.8 g; made by Tokyo Chemical Industry Co., Ltd.) and methacrylic acid (T-4) (9.8 g).

$^1$H-NMR (δ ppm; CDCl$_3$): 7.47(s, 4H), 7.26(s, 2H), 6.43(d, 4H), 6.19(d, 4H) and 2.01(s, 12H).

The physical properties of the compound (1-3-1) were as follows: Melting point: 97° C.; starting temperature of polymerization: 117° C.

Example 4

The Compound (1-1-31)

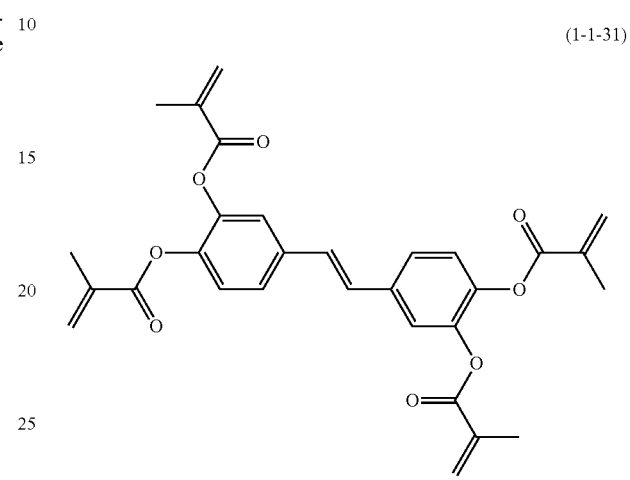

Melting point: 159.3° C.

$^1$H-NMR (CDCl$_3$; δ ppm): 7.40(d, 2H), 7.37(dd, 2H), 7.25(d, 2H), 7.06(s, 2H), 6.30(d, 4H), 5.74(d, 4H) and 2.01(d, 12H).

Example 5

The Compound (1-1-55)

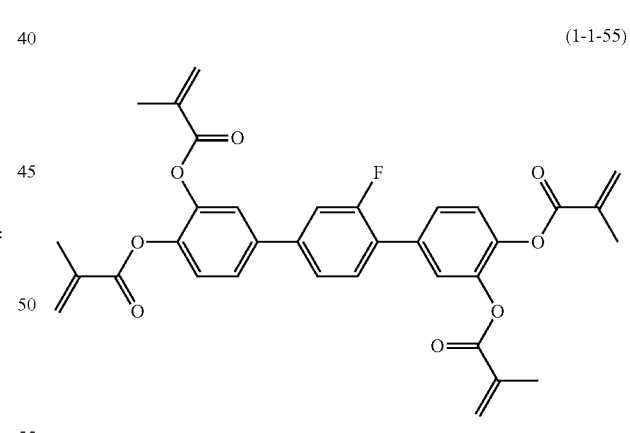

Melting point: 129.0° C.

$^1$H-NMR (CDCl$_3$; δ ppm): 7.53-7.50(m, 4H), 7.43(dd, 1H), 7.39-7.34(m, 4H), 6.32(s, 4H), 5.76(s, 4H) and 2.03(d, 12H).

The compounds (1-1-1) to (1-1-96), the compounds (1-2-1) to (1-2-90), the compounds (1-3-1) to (1-3-79), the compounds (1-4-1) to (1-4-46), the compounds (1-5-1) to (1-5-46), the compounds (1-6-1) to (1-6-46), the compounds (1-A-1) to (1-A-16) and the compounds (1-B-1) to (1-B-16) shown below can be prepared by synthetic methods similar to those described in Examples 1 to 3.

| | |
|---|---|
| 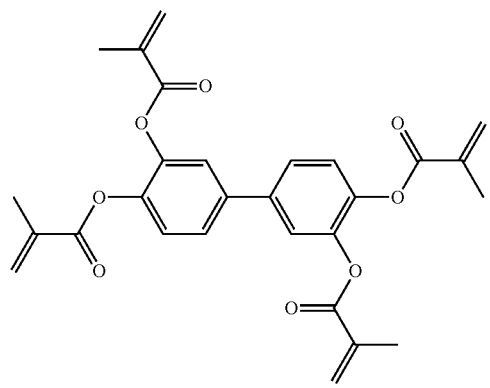 (1-1-1) | 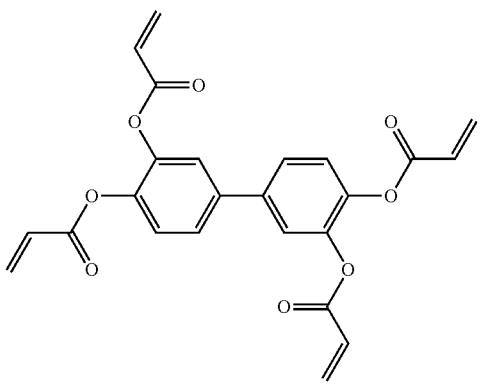 (1-1-2) |
| 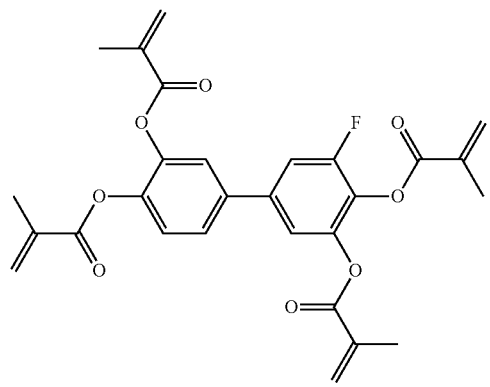 [SMILES: C=C(C)C(=O)Oc1ccc(-c2ccc(OC(=O)C(=C)C)c(OC(=O)C(=C)C)c2)cc1OC(=O)C(=C)C] (1-1-3) | 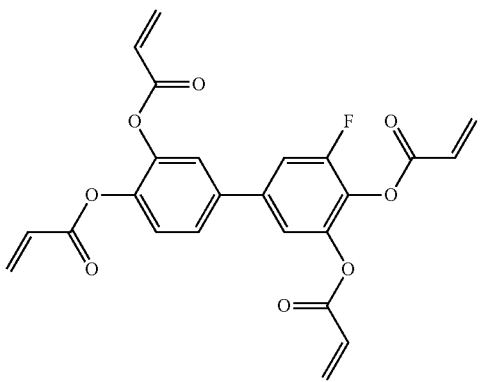 (1-1-4) |
| 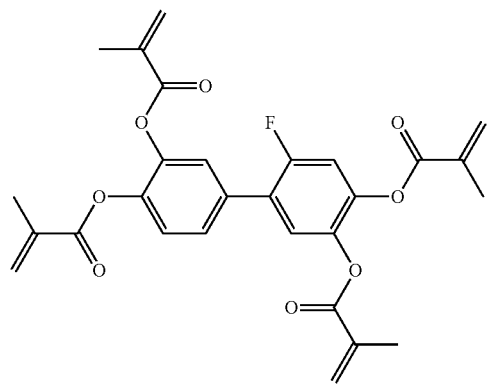 (1-1-5) | 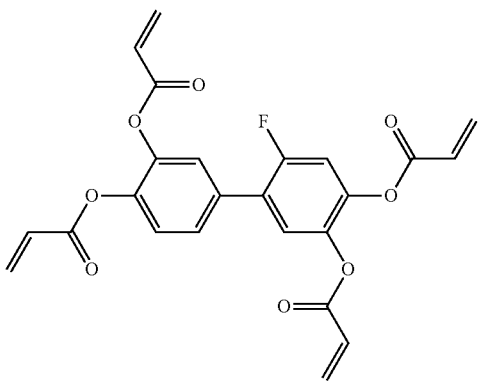 (1-1-6) |
| 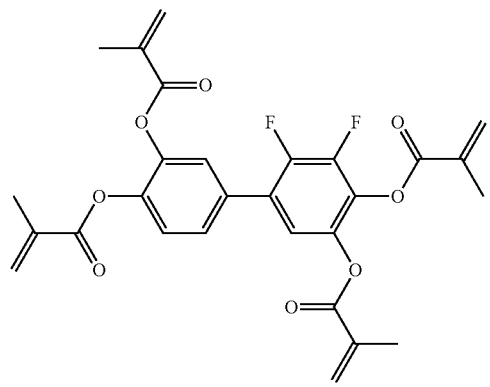 (1-1-7) | 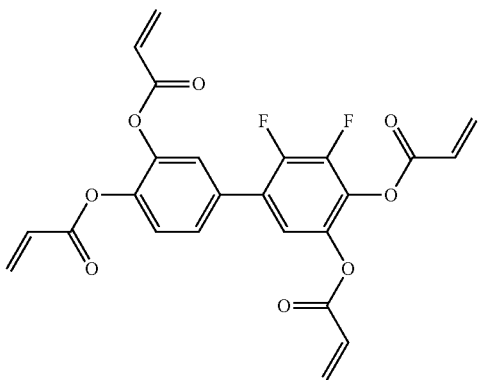 (1-1-8) |

-continued
(1-1-9)
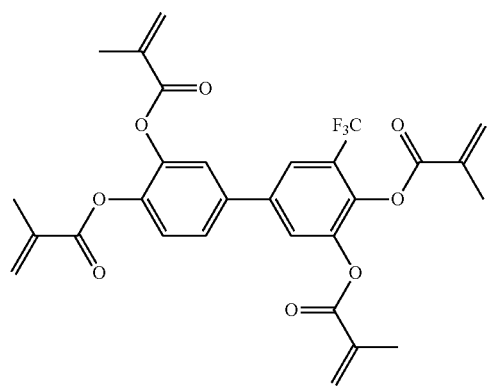
(1-1-10)
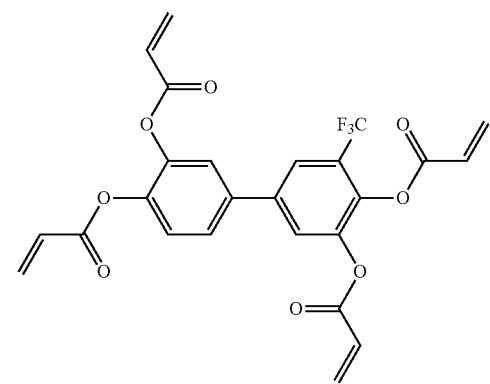
(1-1-11)
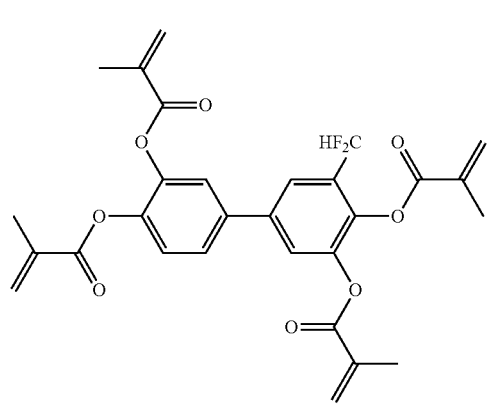
(1-1-12)
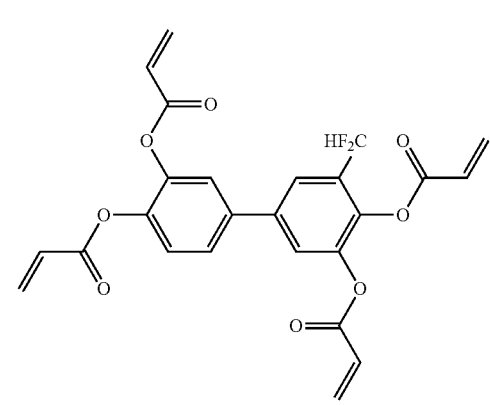
(1-1-13)
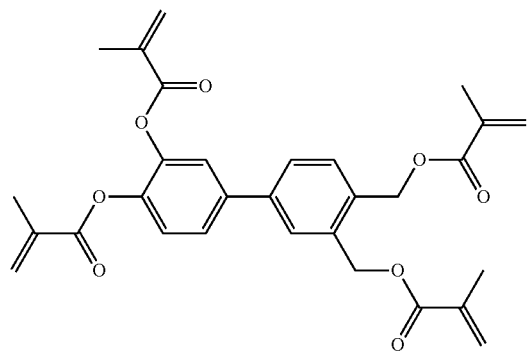
(1-1-14)
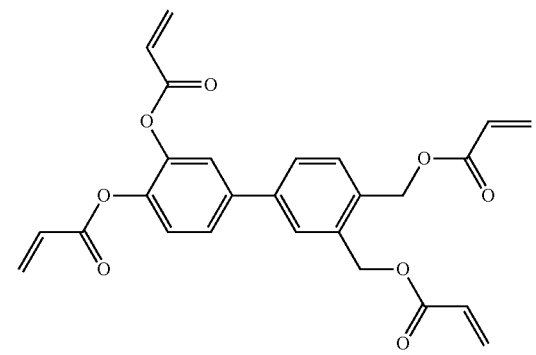
(1-1-15)
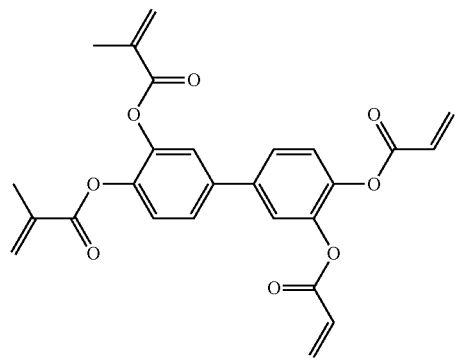
(1-1-16)
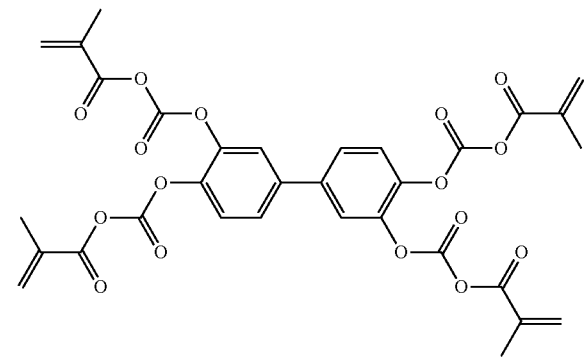

-continued
(1-1-17)
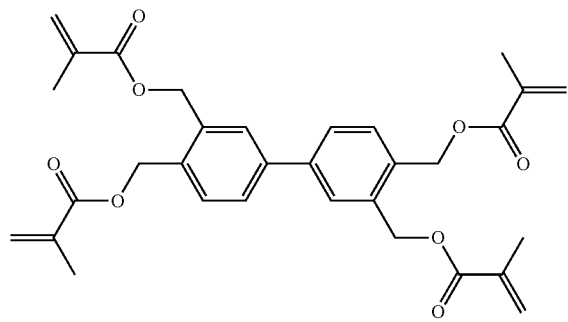
(1-1-18)
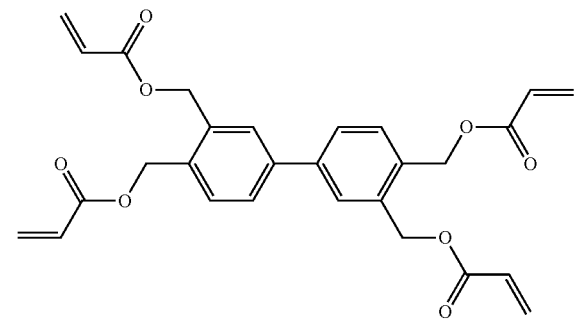
(1-1-19)
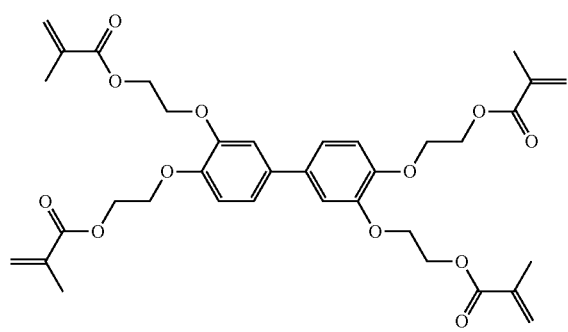
(1-1-20)
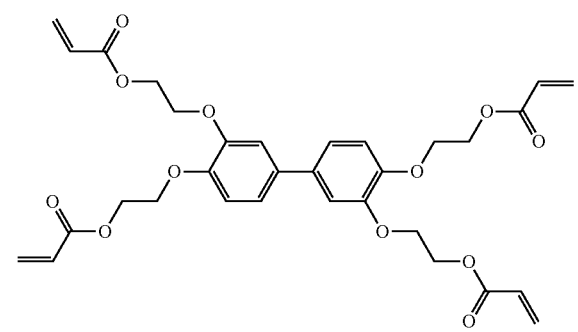
(1-1-21)
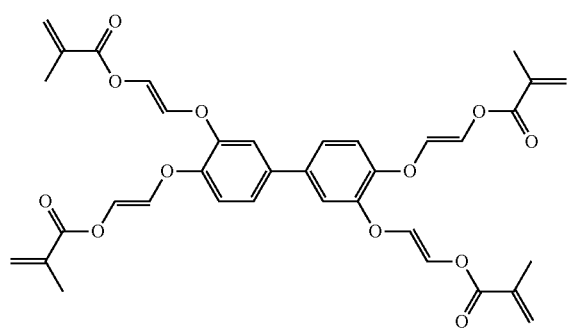
(1-1-22)
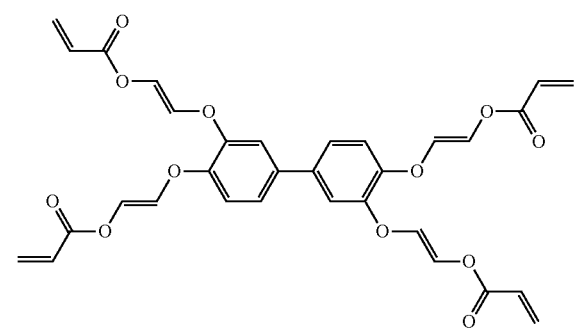
(1-1-23)
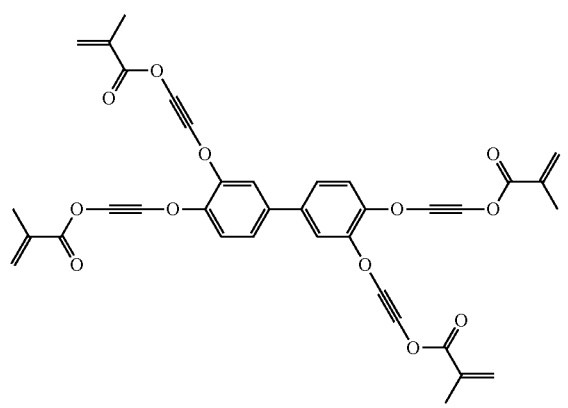
(1-1-24)
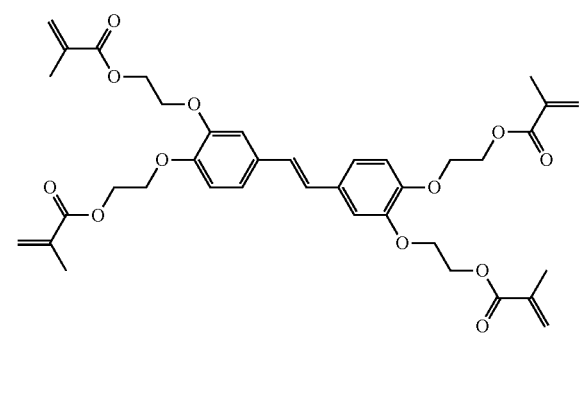

-continued
(1-1-25)
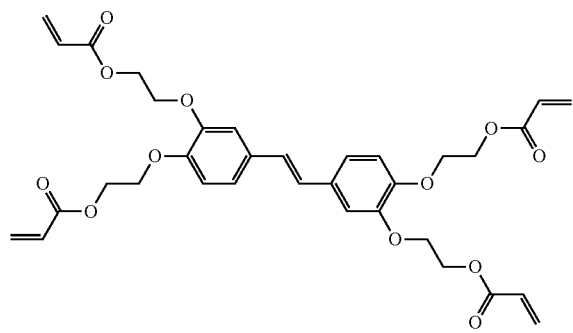
(1-1-26)
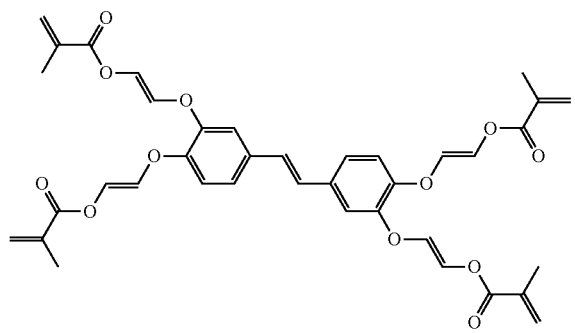
(1-1-27)
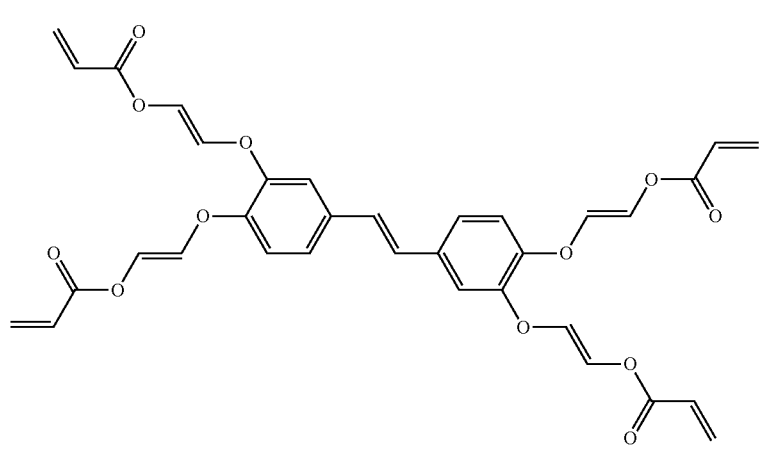
(1-1-28)
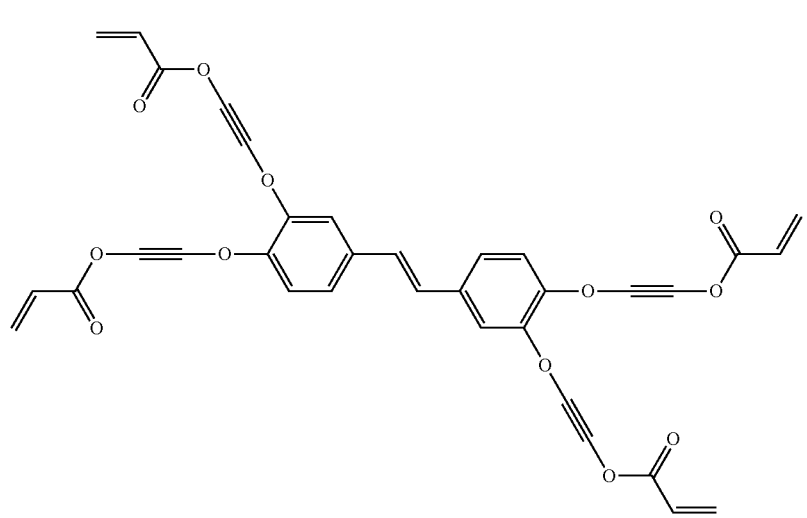

-continued
(1-1-29)
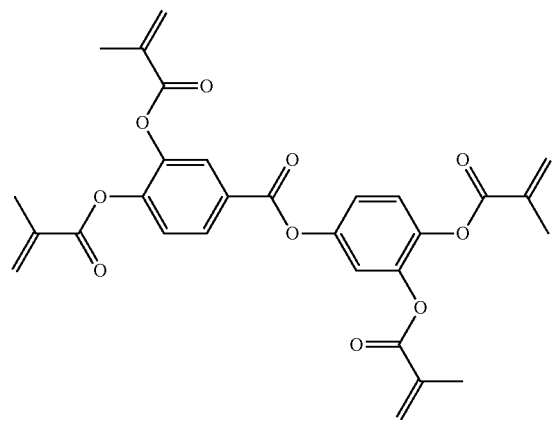
(1-1-30)
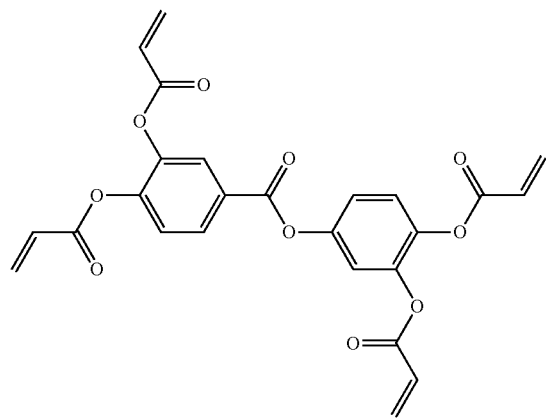
(1-1-31)
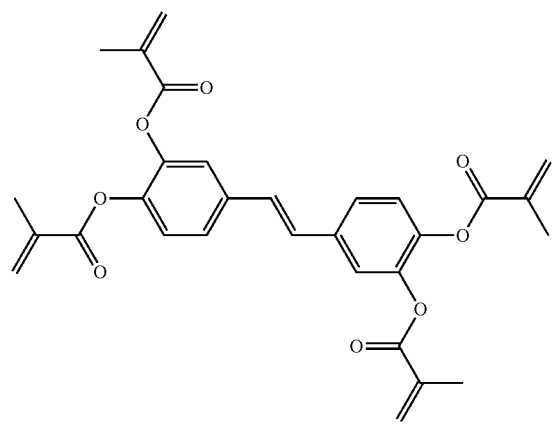
(1-1-32)
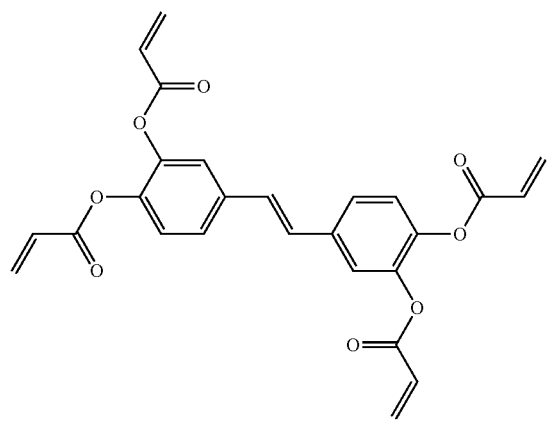
(1-1-33)
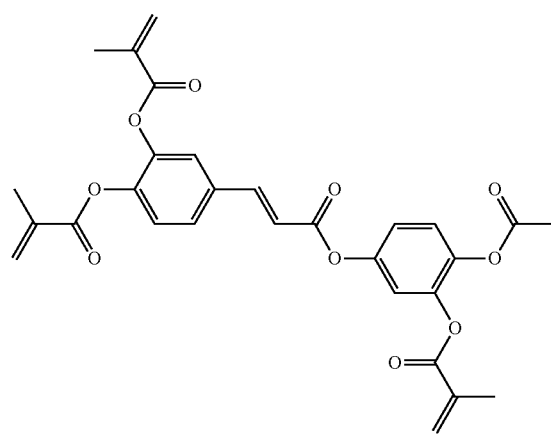
(1-1-34)
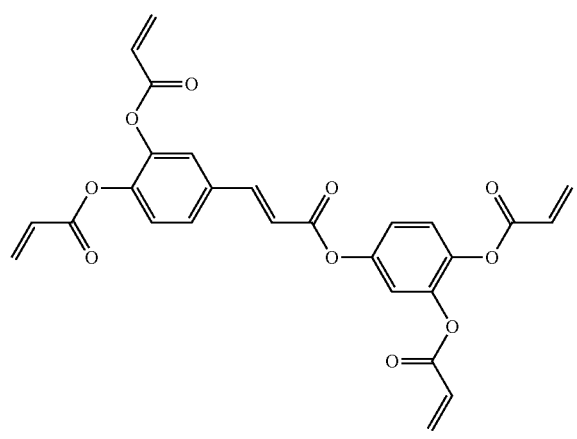

-continued
(1-1-35)
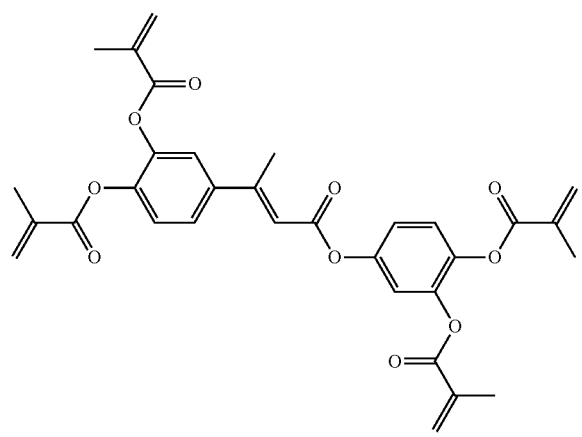
(1-1-36)
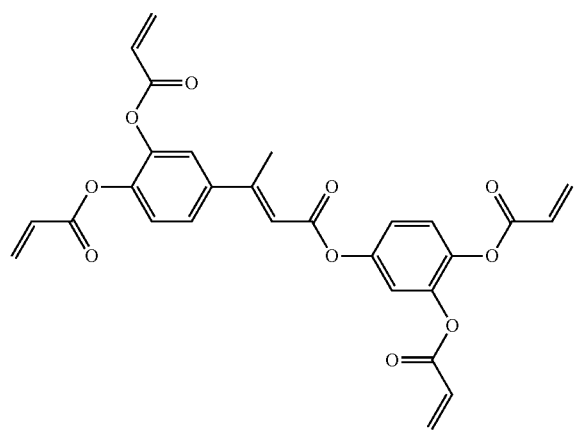
(1-1-37)
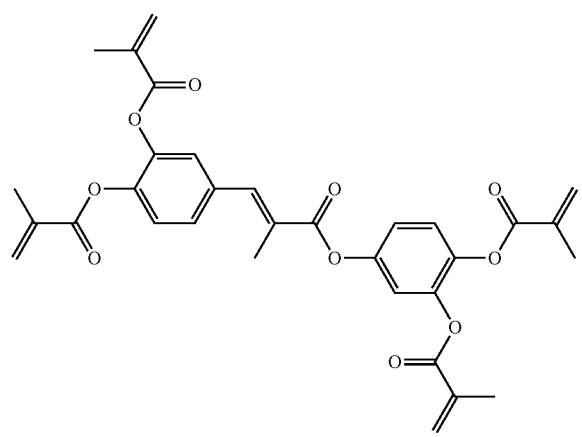
(1-1-38)
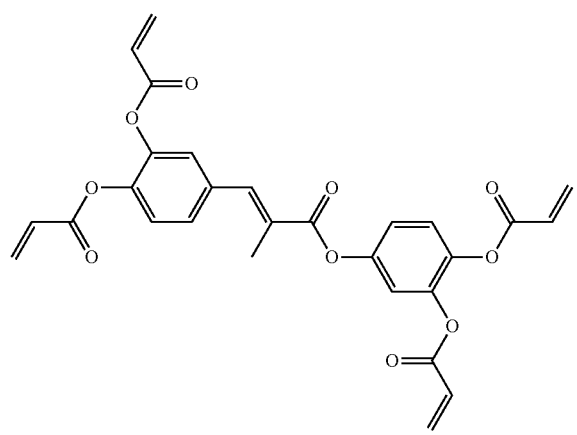
(1-1-39)
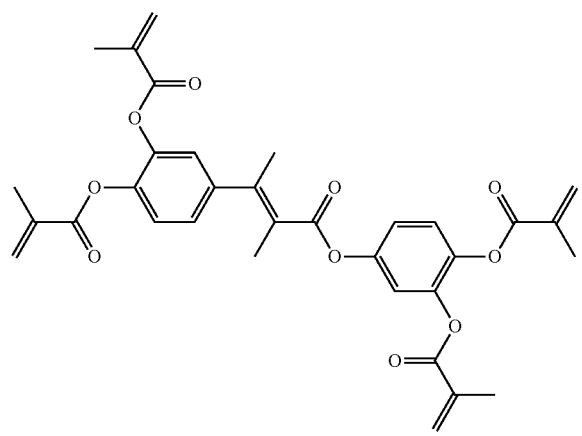
(1-1-40)
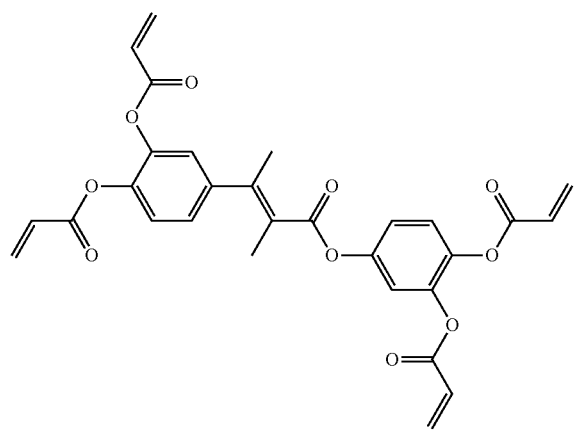

(1-1-41)
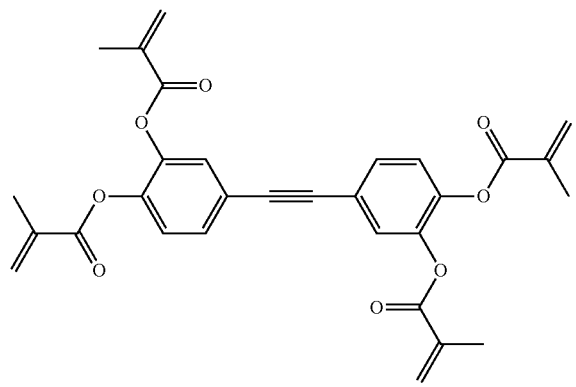
(1-1-42)
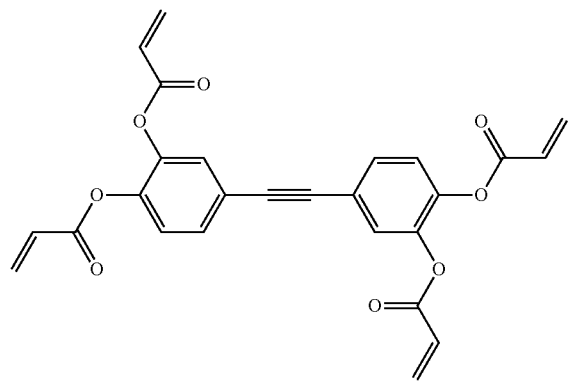
(1-1-43)
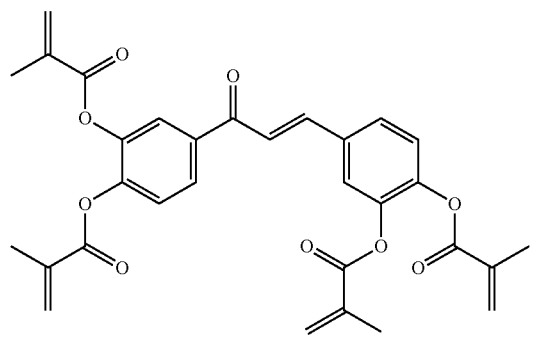
(1-1-44)
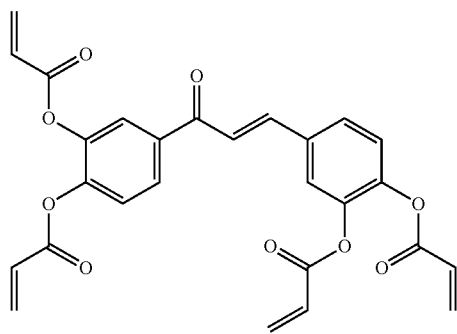
(1-1-45)
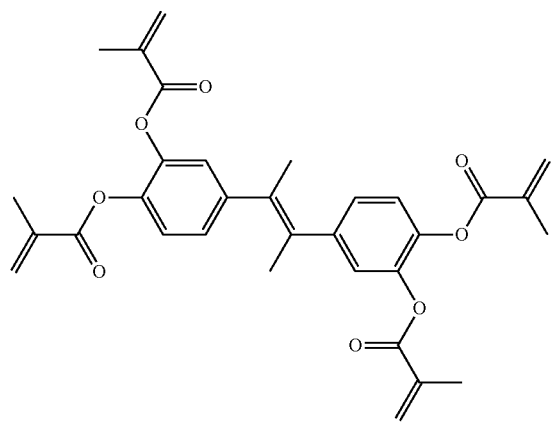
(1-1-46)
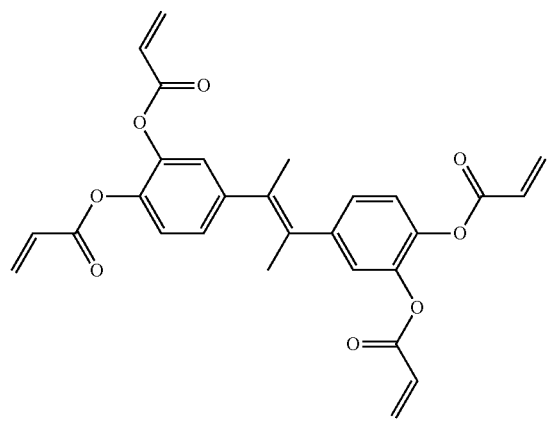
(1-1-47)
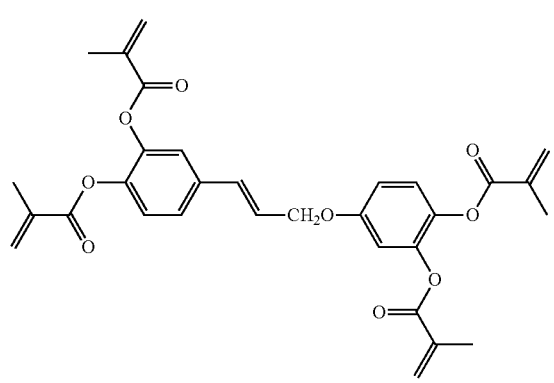
(1-1-48)
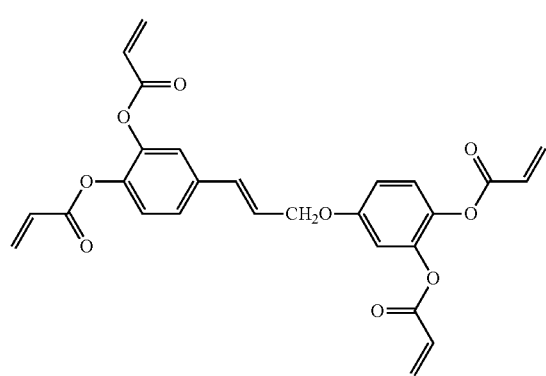

-continued
(1-1-49)
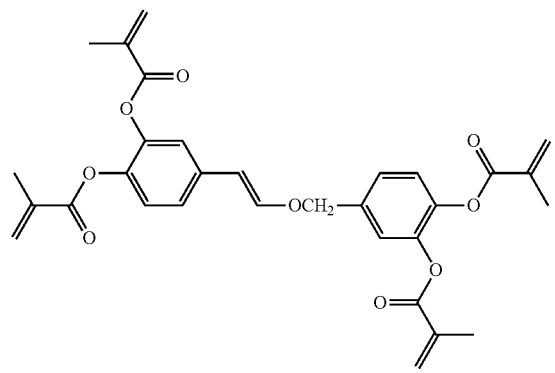
(1-1-50)
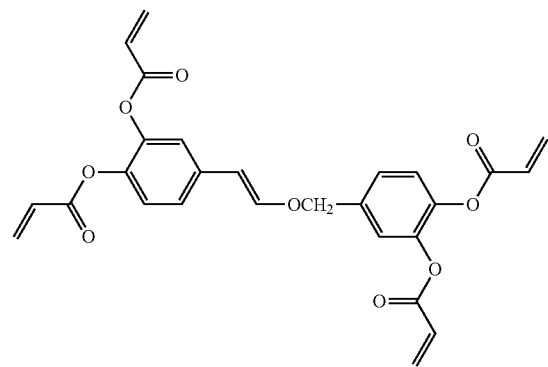
(1-1-51)
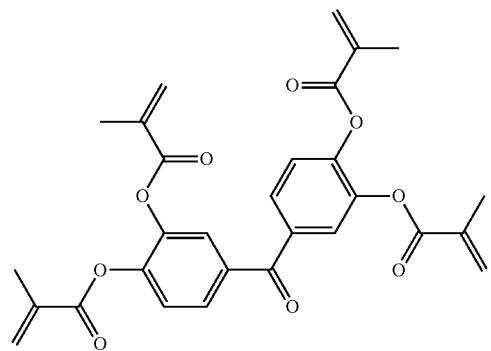
(1-1-52)
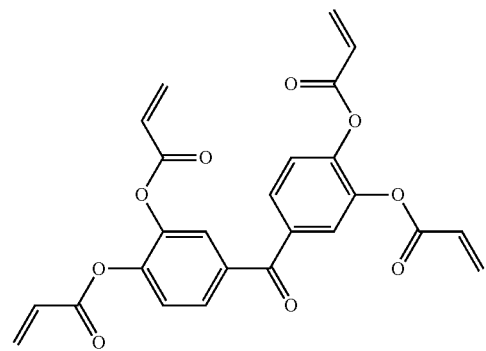
(1-1-53)
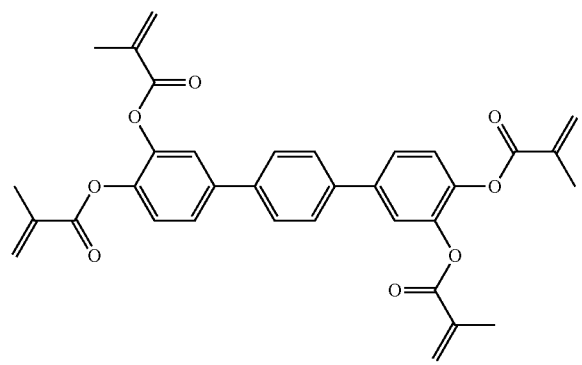
(1-1-54)
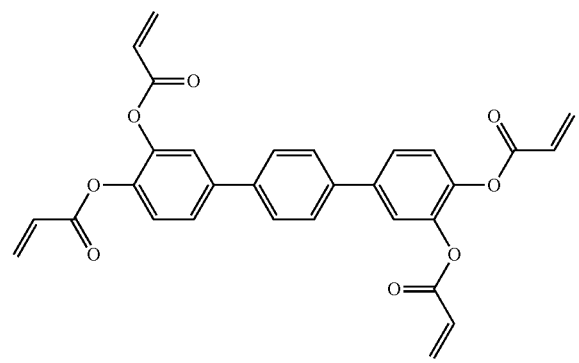
(1-1-55)
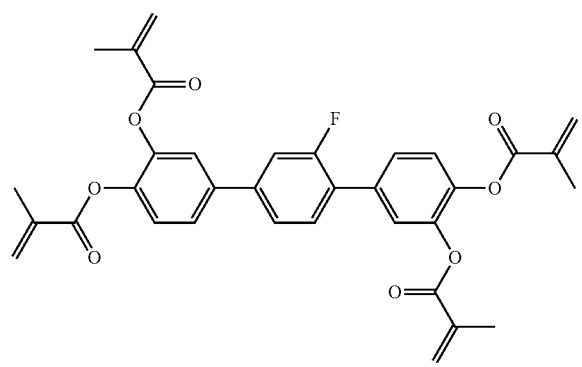
(1-1-56)
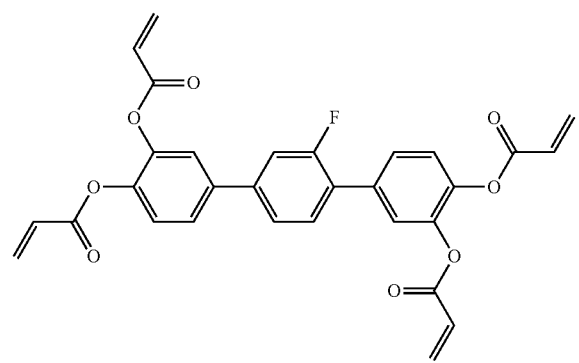

-continued
(1-1-57)
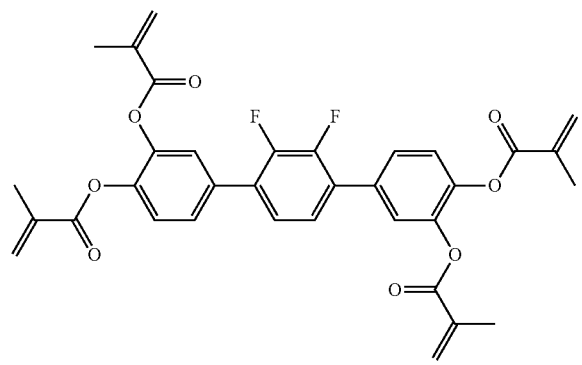
(1-1-58)
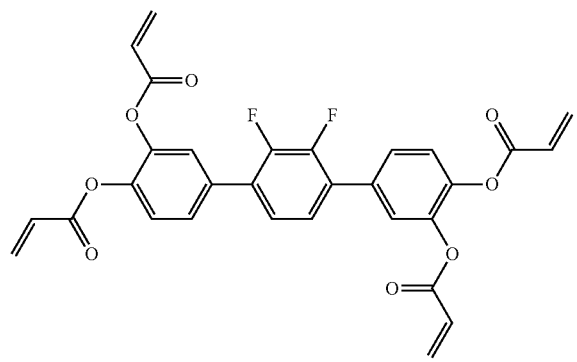
(1-1-59)
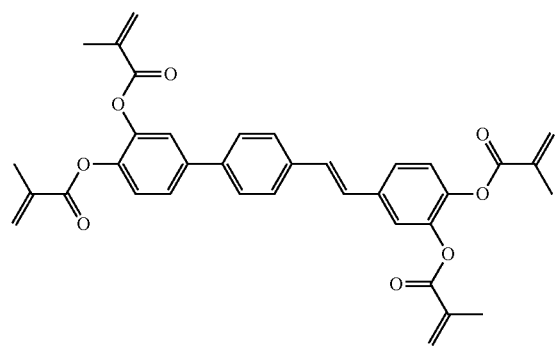
(1-1-60)
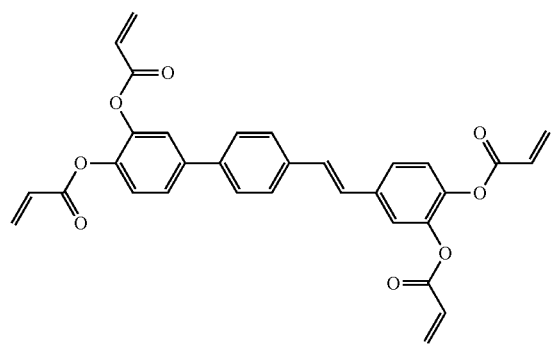
(1-1-61)
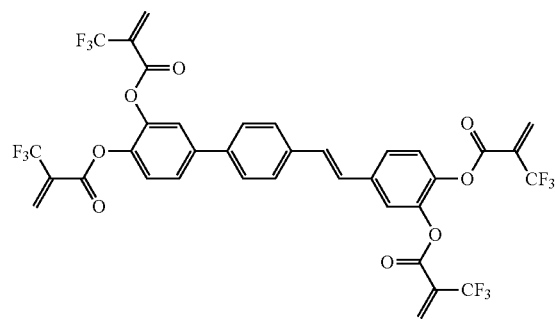
(1-1-62)
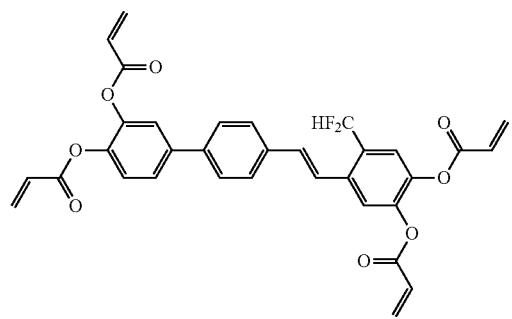
(1-1-63)
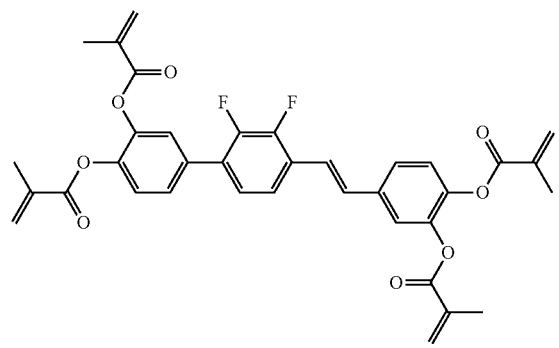
(1-1-64)
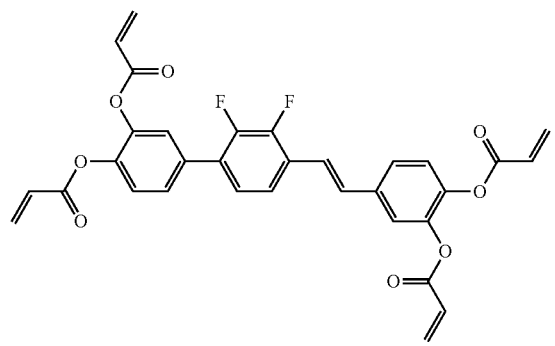

-continued
(1-1-65)
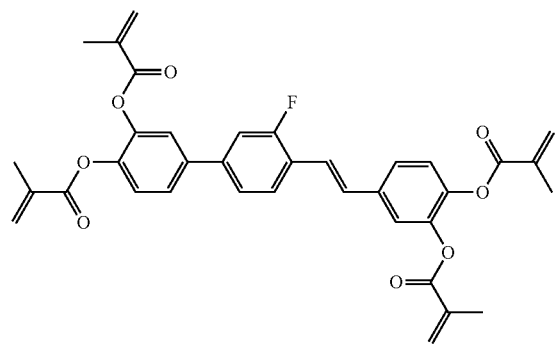
(1-1-66)
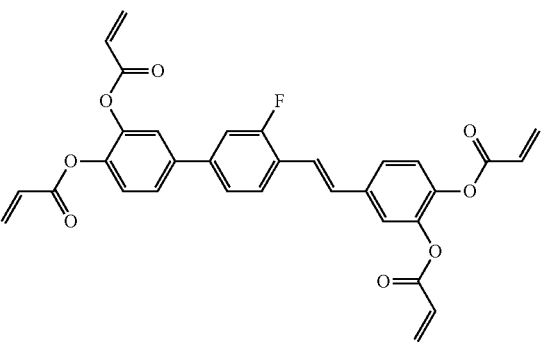
(1-1-67)
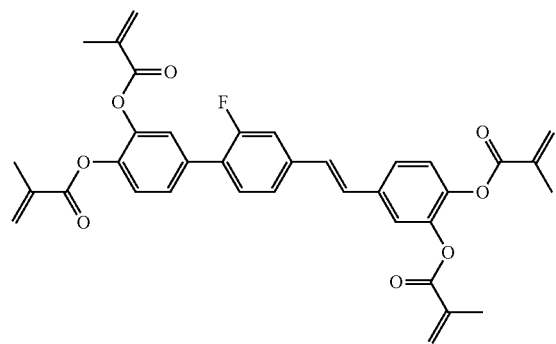
(1-1-68)
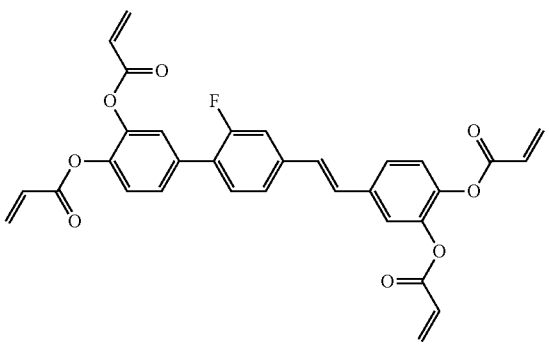
(1-1-69)
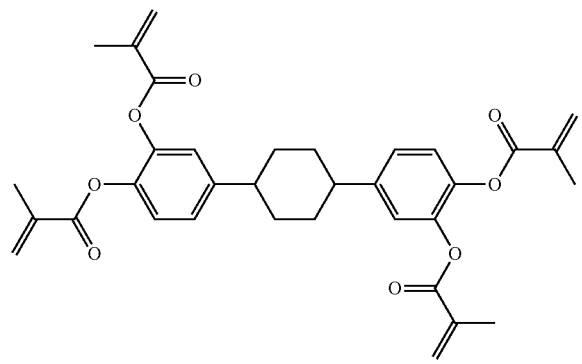
(1-1-70)
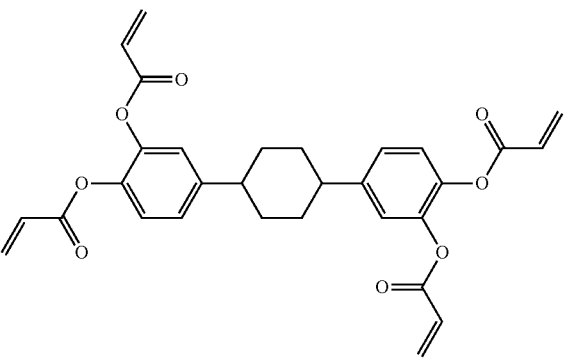
(1-1-71)
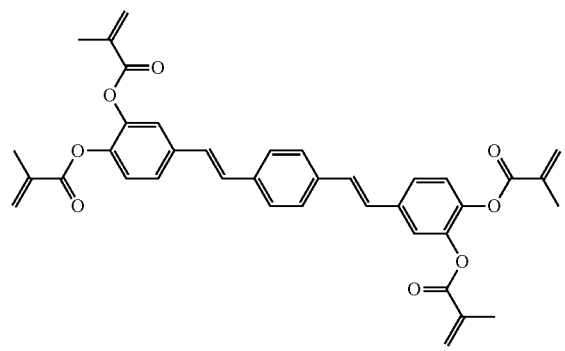
(1-1-72)
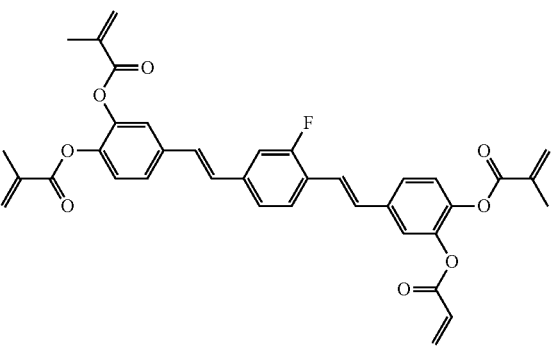

-continued
(1-1-73)
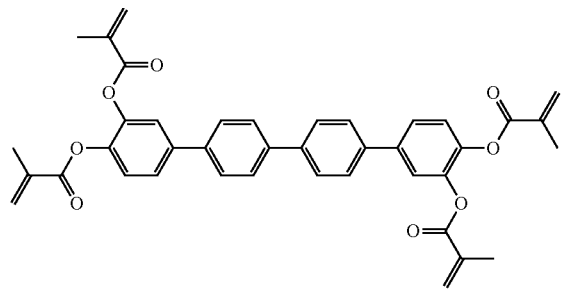
(1-1-74)
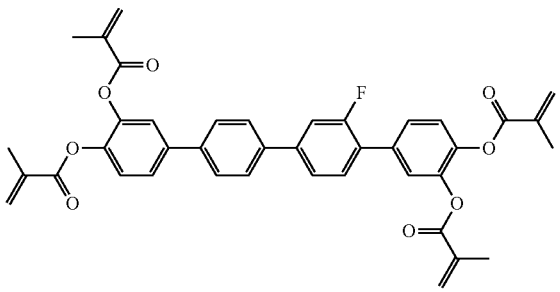
(1-1-75)
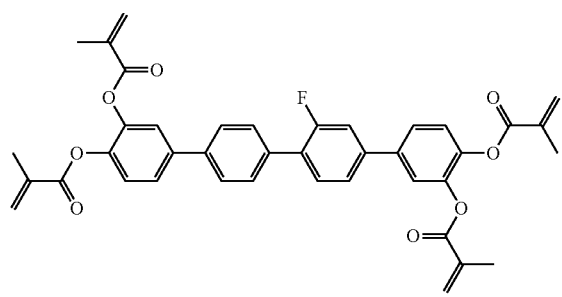
(1-1-76)
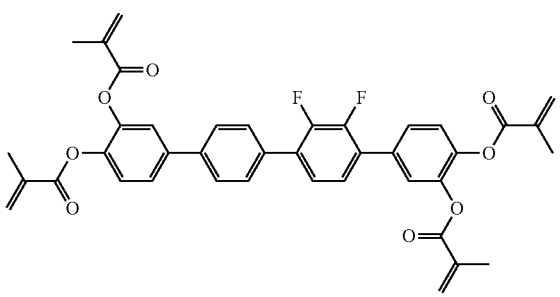
(1-1-77)
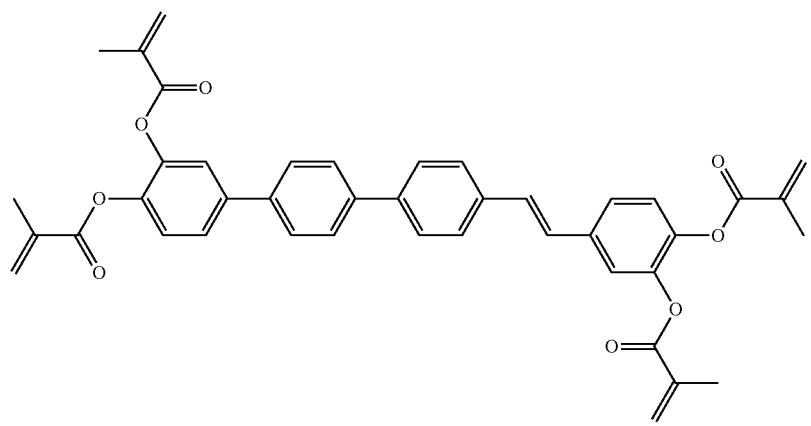
(1-1-78)
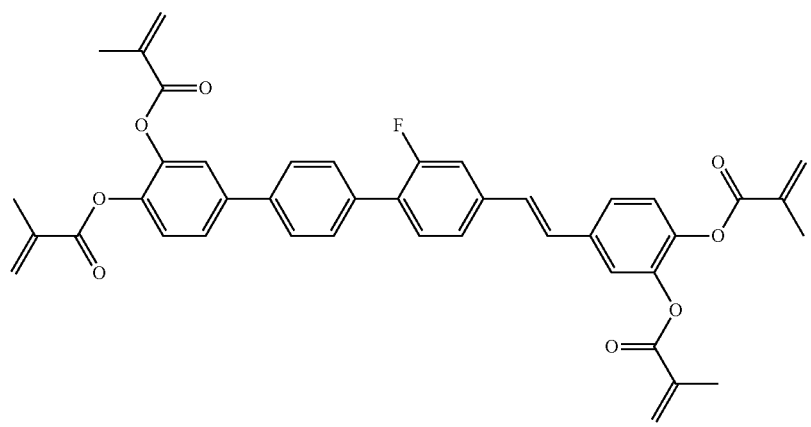

-continued
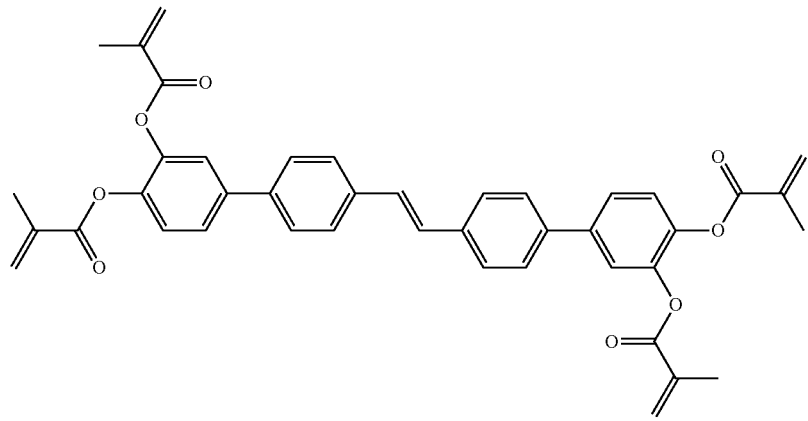
(1-1-79)
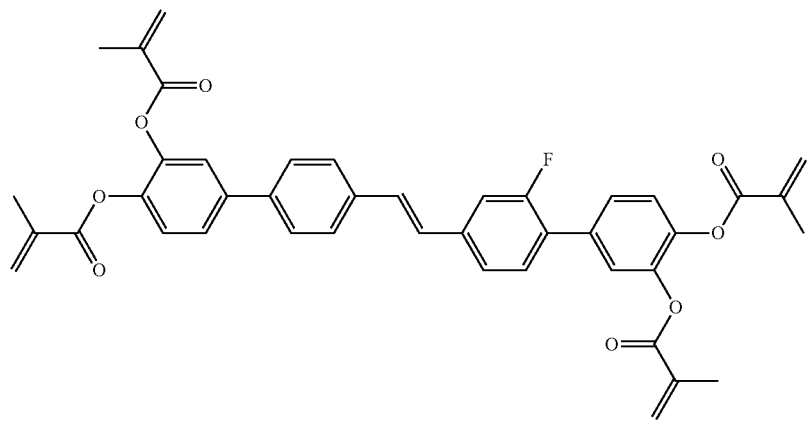
(1-1-80)
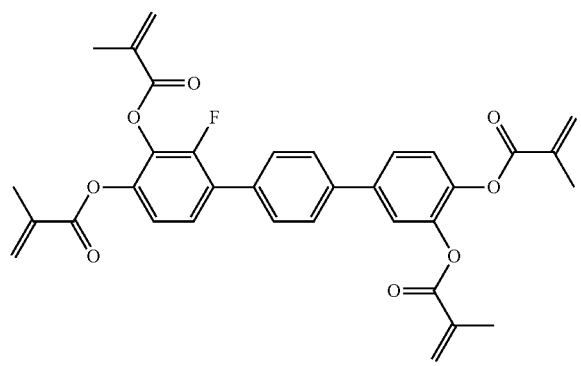
(1-1-81)
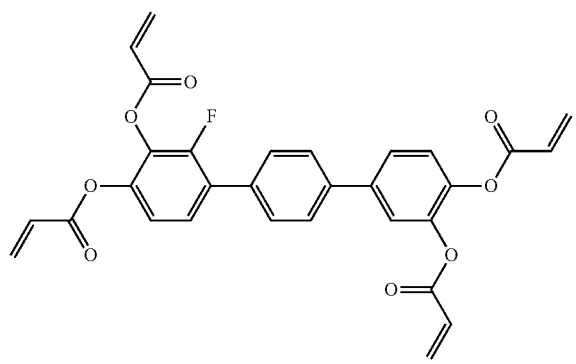
(1-1-82)
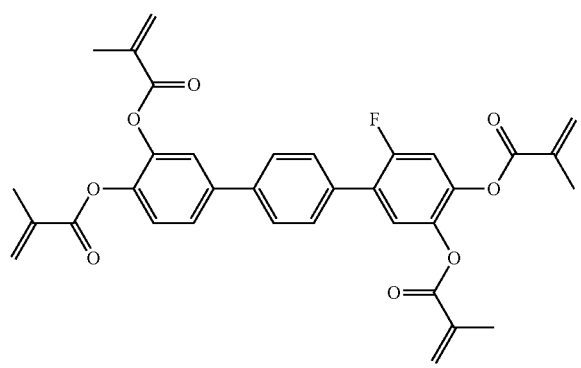
(1-1-83)
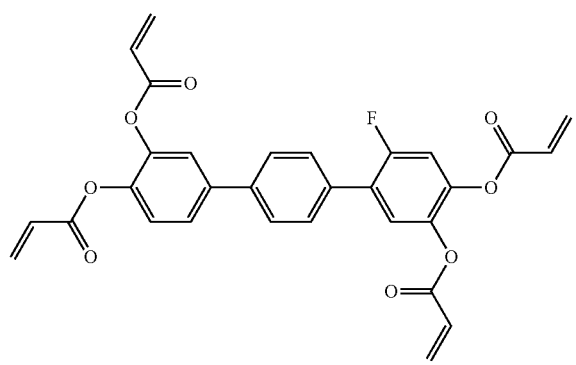
(1-1-84)

-continued
(1-1-85)
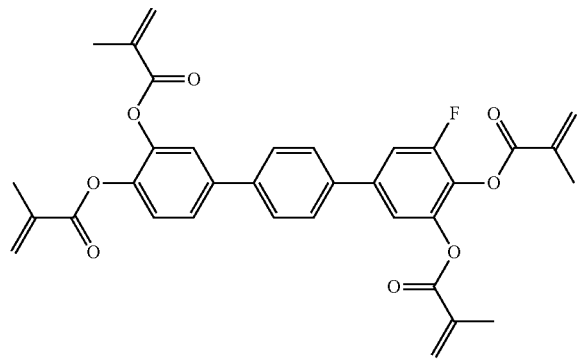
(1-1-86)
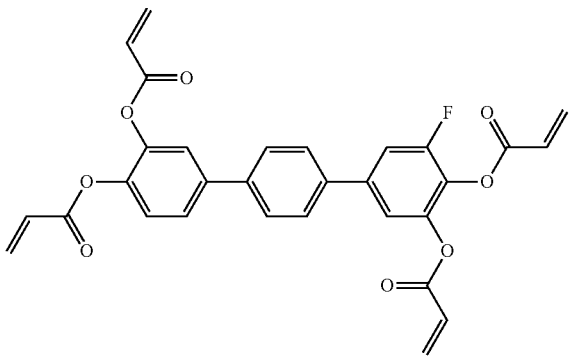
(1-1-87)
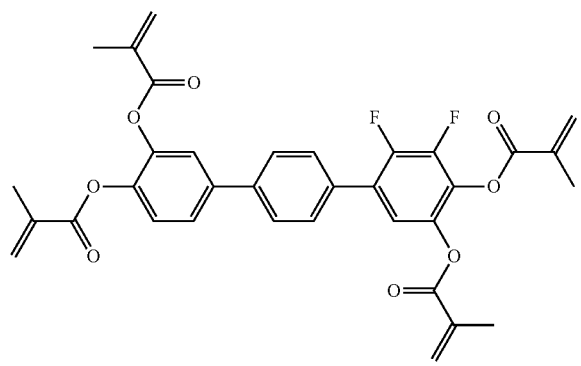
(1-1-88)
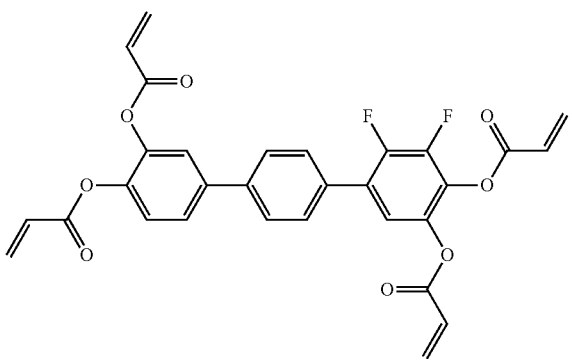
(1-1-89)
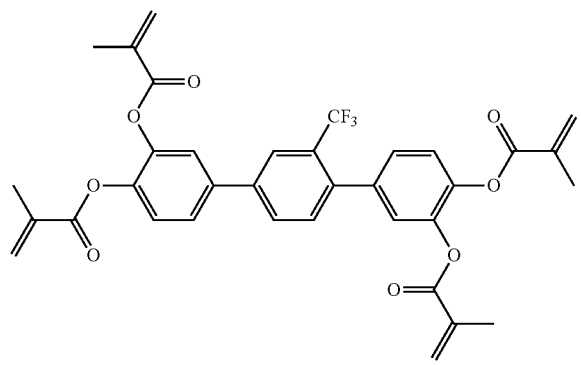
(1-1-90)
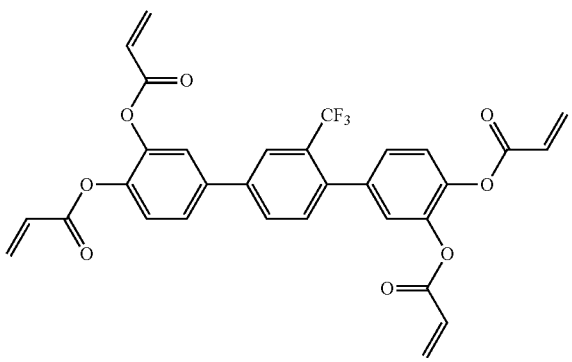
(1-1-91)
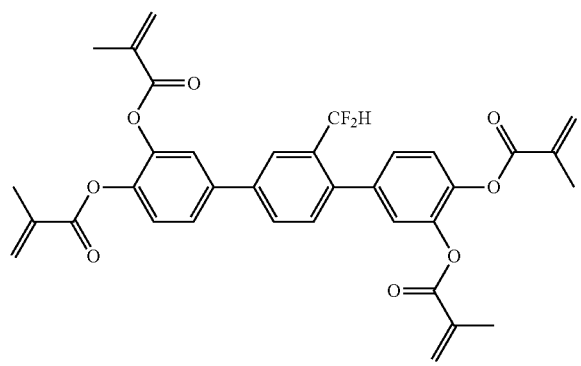
(1-1-92)
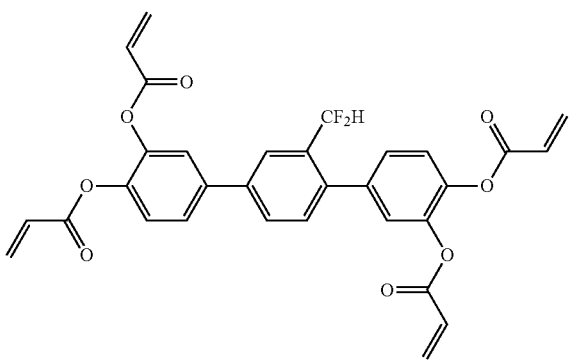

-continued
(1-1-93)
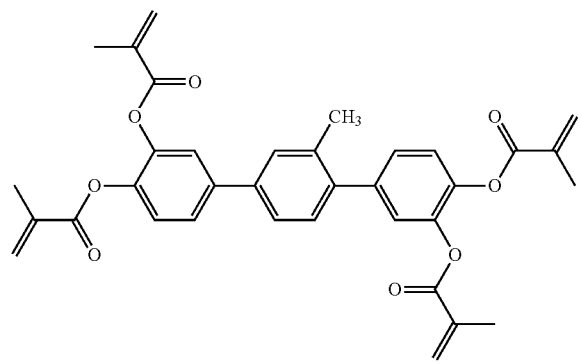
(1-1-94)
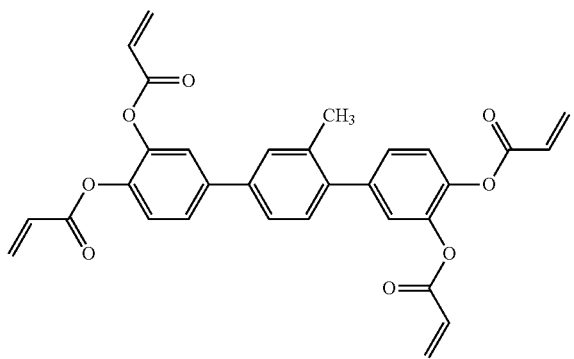
(1-1-95)
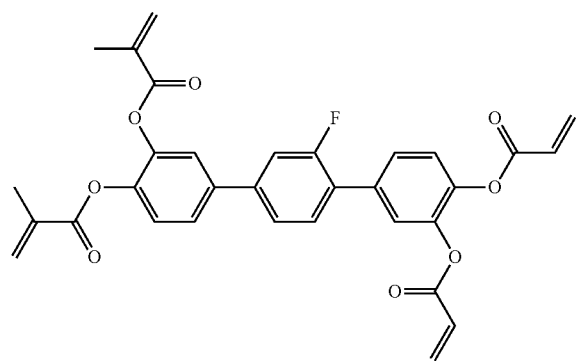
(1-1-96)
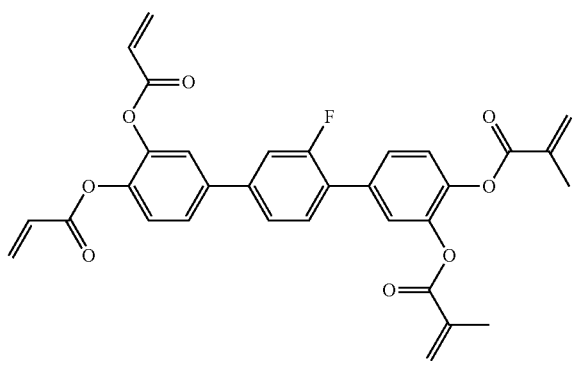
(1-2-1)
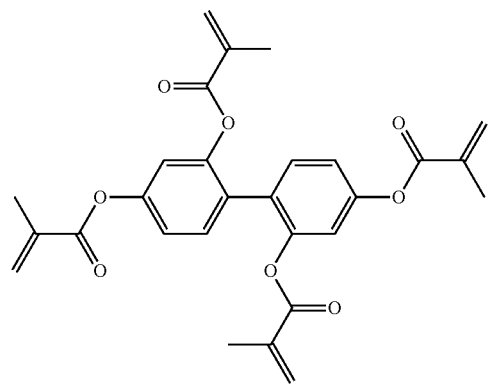 [SMILES: C=C(C)C(=O)Oc1ccc(-c2ccc(OC(=O)C(=C)C)cc2OC(=O)C(=C)C)c(OC(=O)C(=C)C)c1]
(1-2-2)
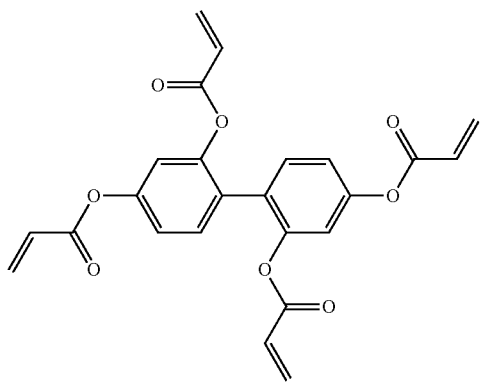
(1-2-3)
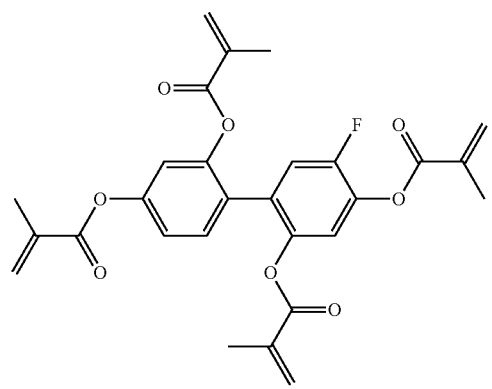
(1-2-4)
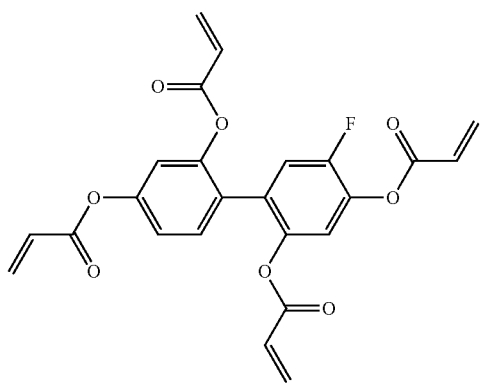

-continued
(1-2-5)
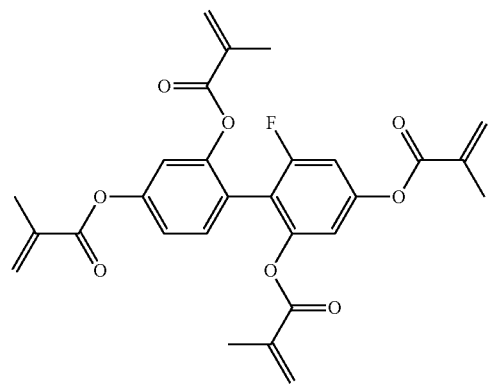
(1-2-6)
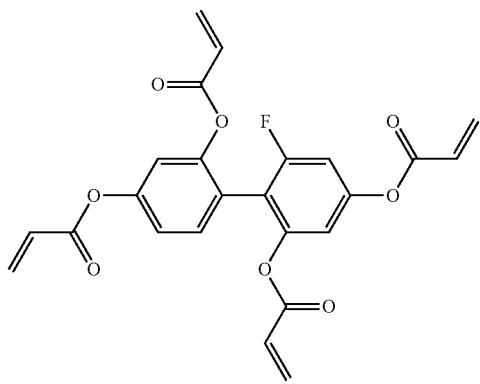
(1-2-7)
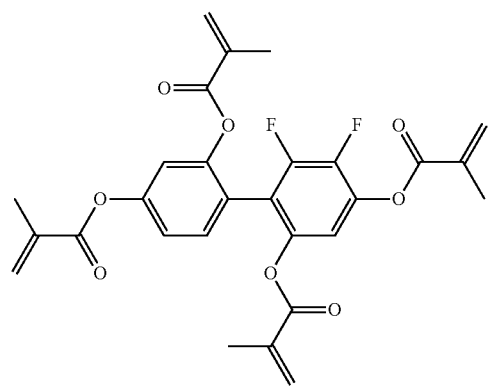
(1-2-8)
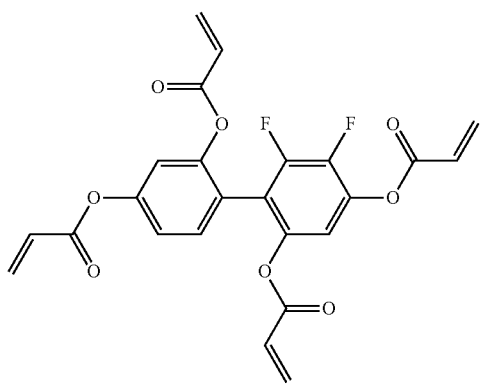
(1-2-9)
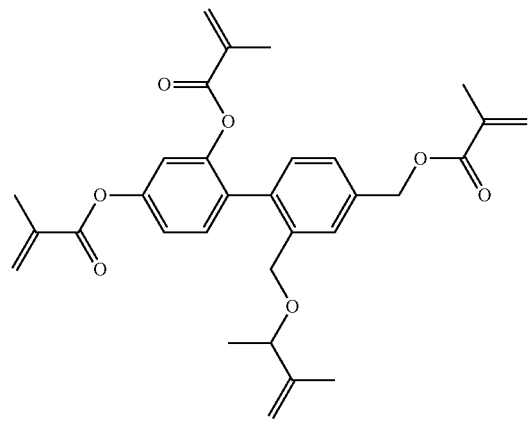
(1-2-10)
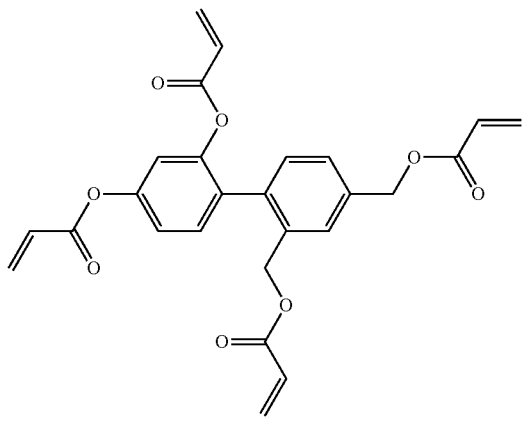
(1-2-11)
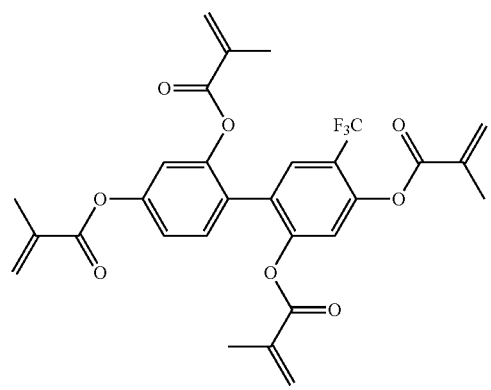
(1-2-12)

-continued
(1-2-13)
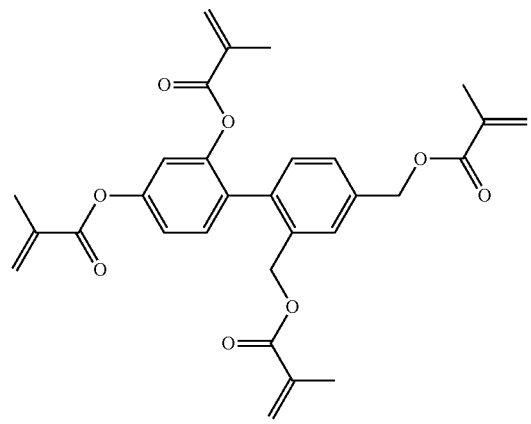
(1-2-14)
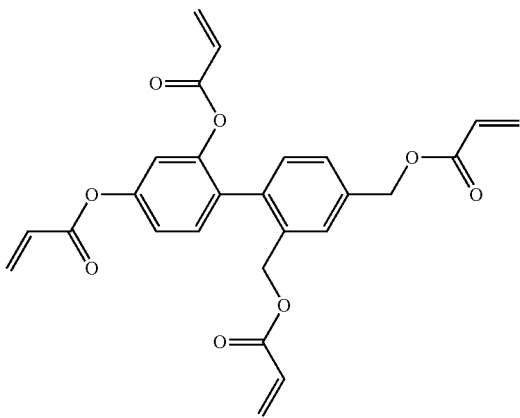
(1-2-15)
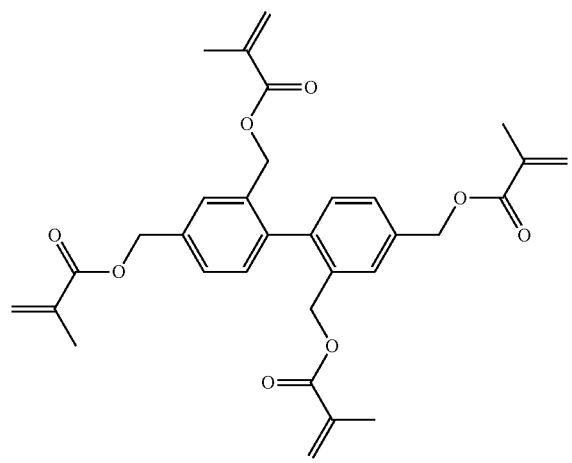
(1-2-16)
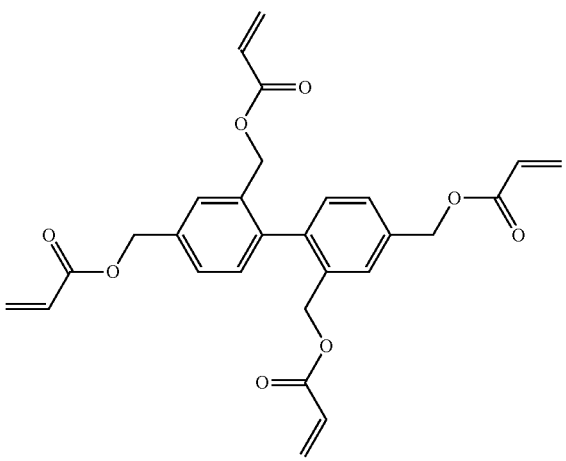
(1-2-17)
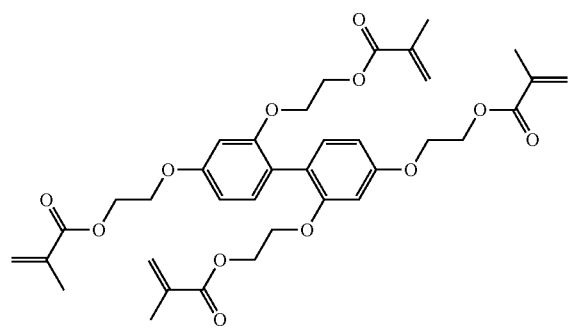
(1-2-18)
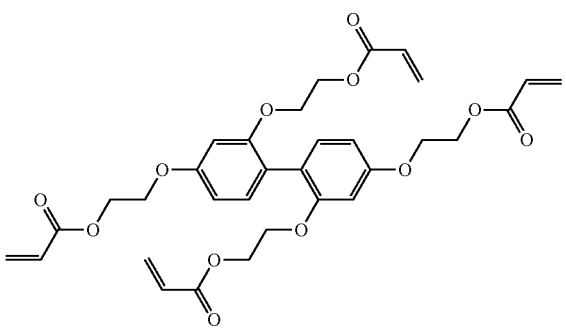
(1-2-19)
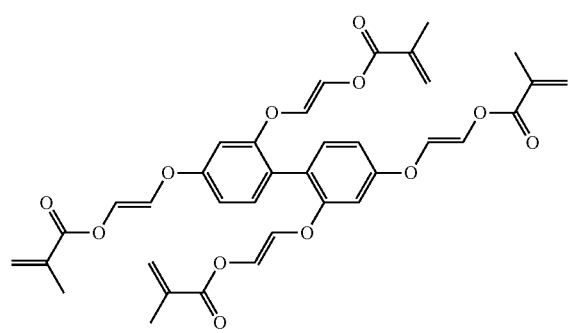
(1-2-20)
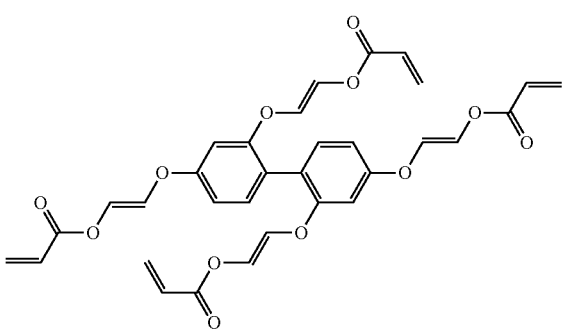

-continued
(1-2-21)
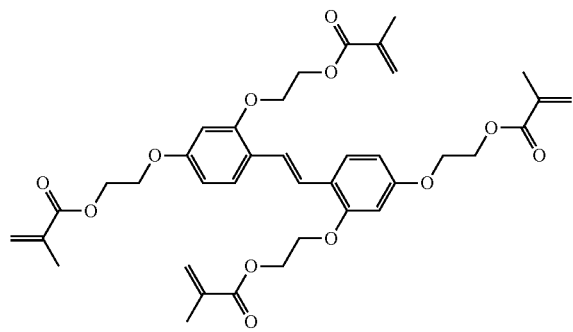
(1-2-22)
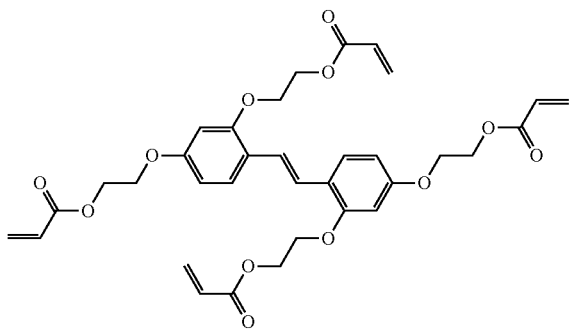
(1-2-23)
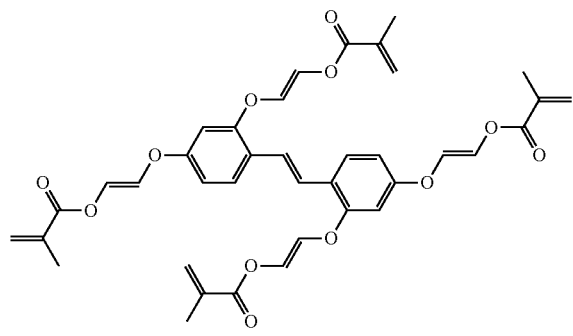
(1-2-24)
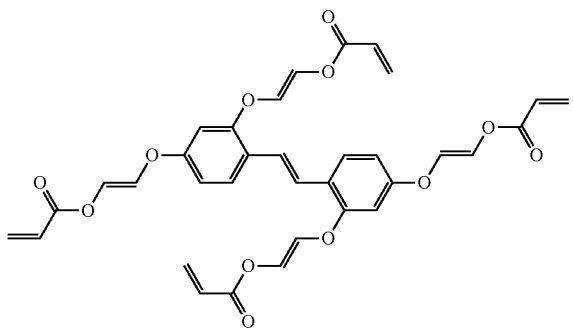
(1-2-25)
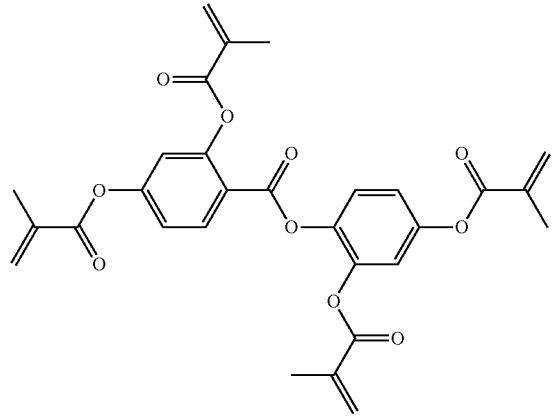
(1-2-26)
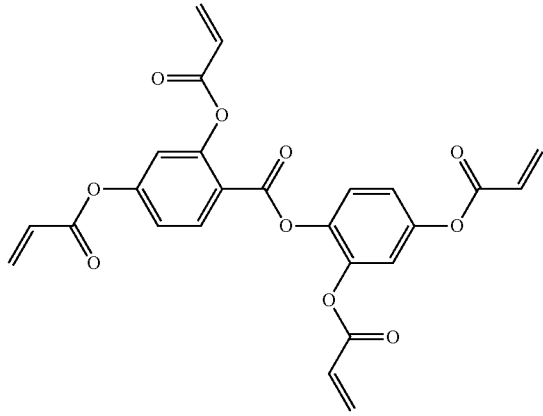
(1-2-27)
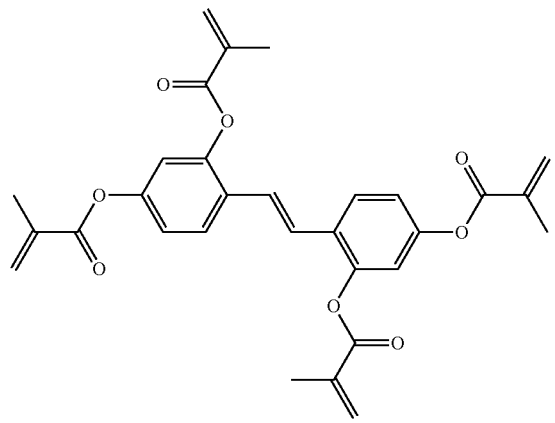
(1-2-28)
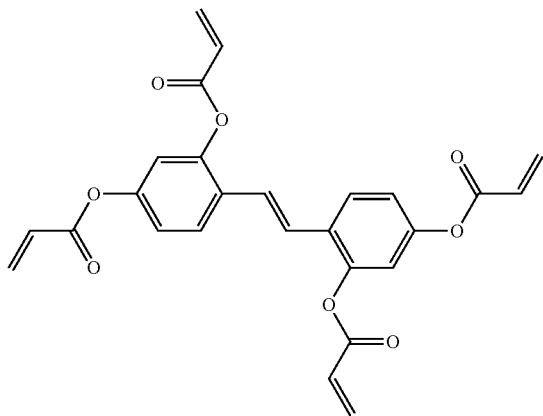

(1-2-29)
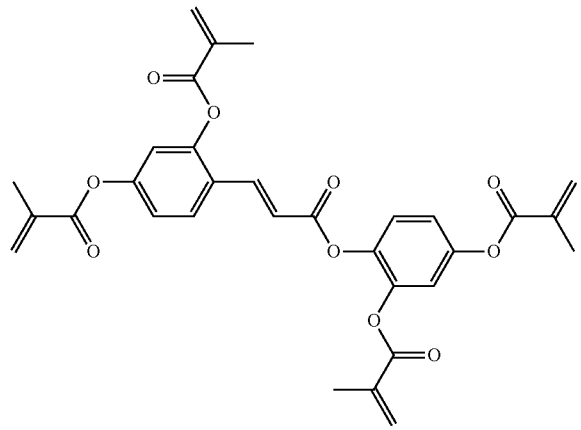
(1-2-30)
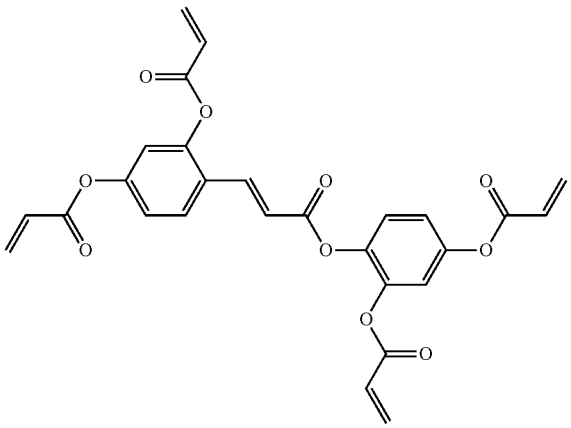
(1-2-31)
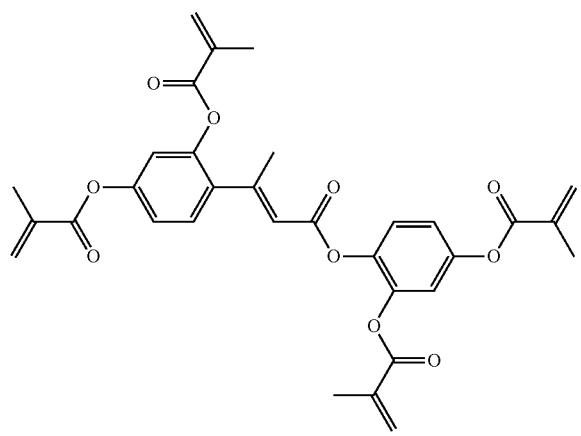
(1-2-32)
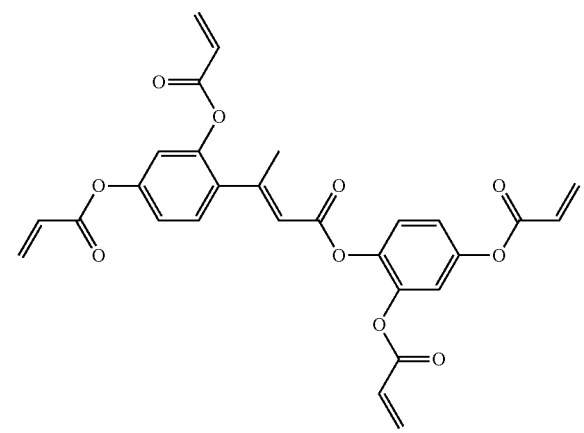
(1-2-33)
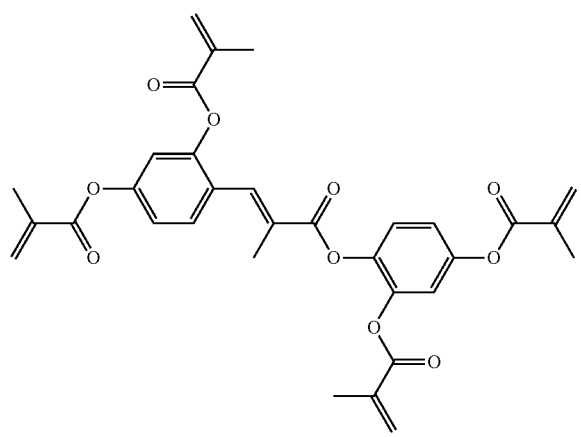
(1-2-34)
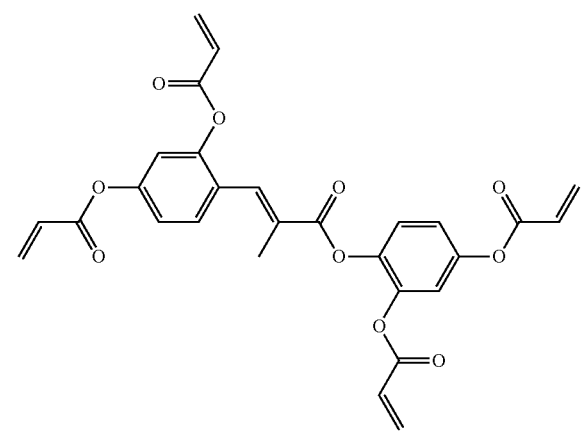

-continued
(1-2-35)
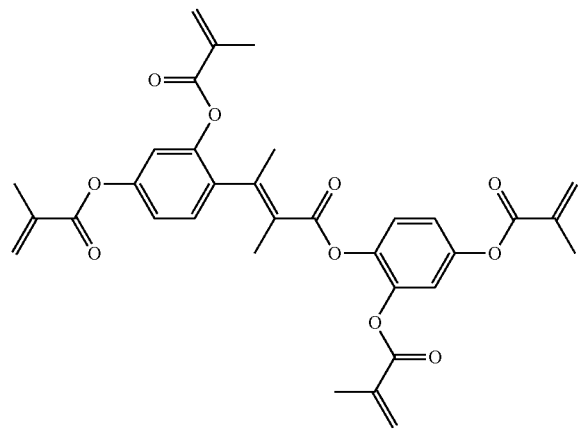
(1-2-36)
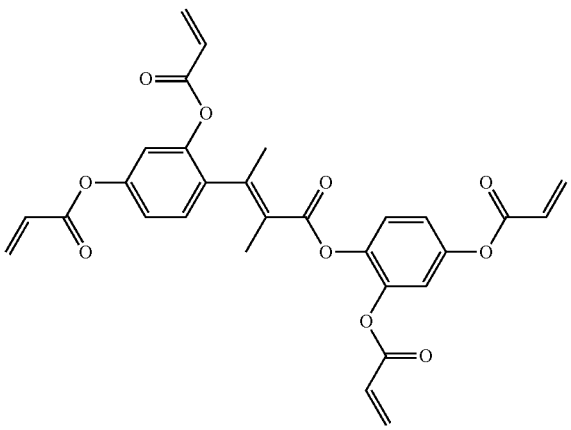
(1-2-37)
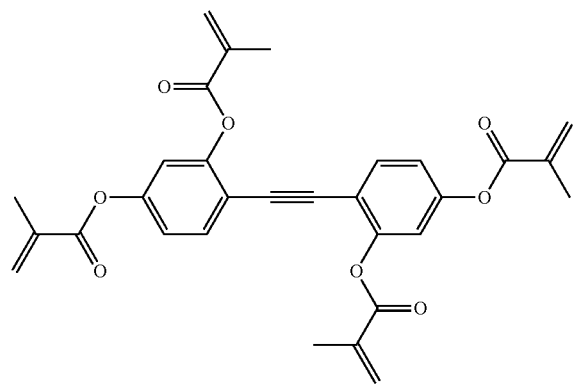
(1-2-38)
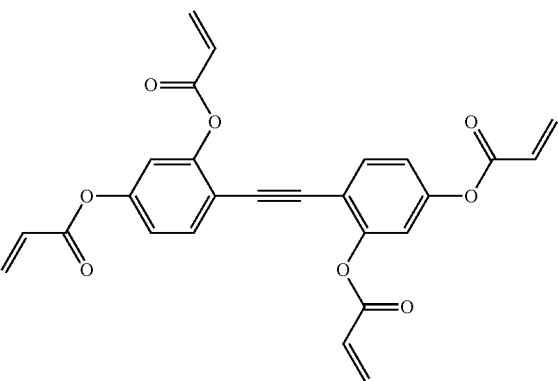
(1-2-39)
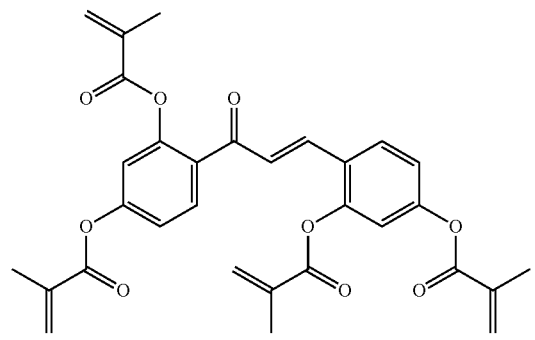
(1-2-40)
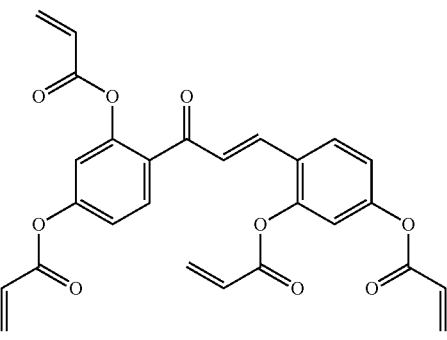
(1-2-41)
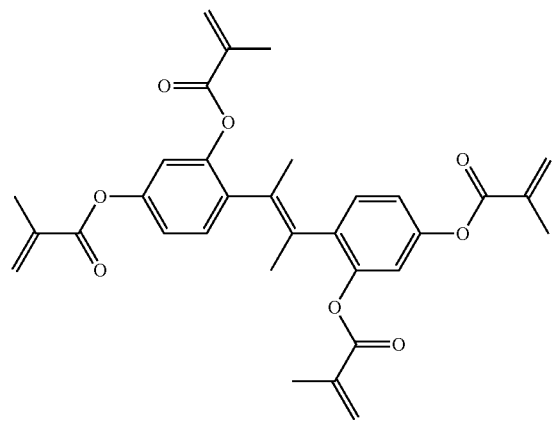
(1-2-42)
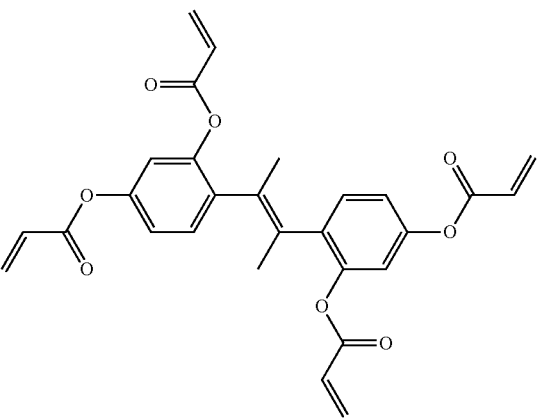

(1-2-43)
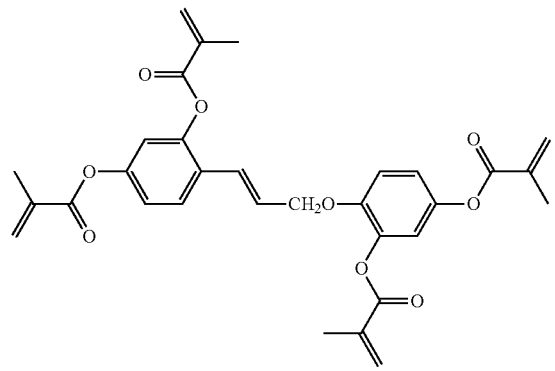
(1-2-44)
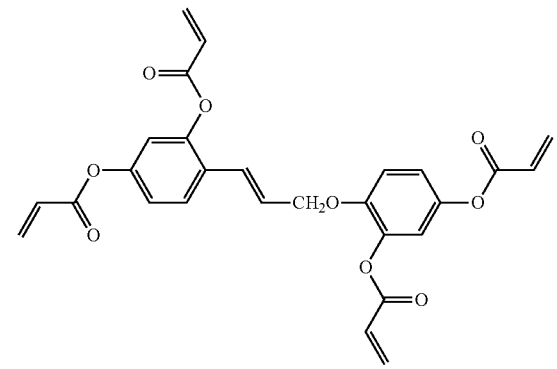
(1-2-45)
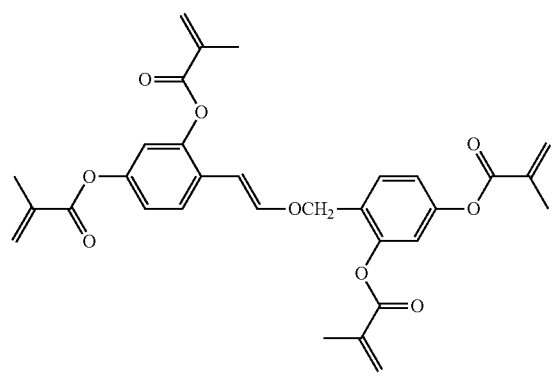
(1-2-46)
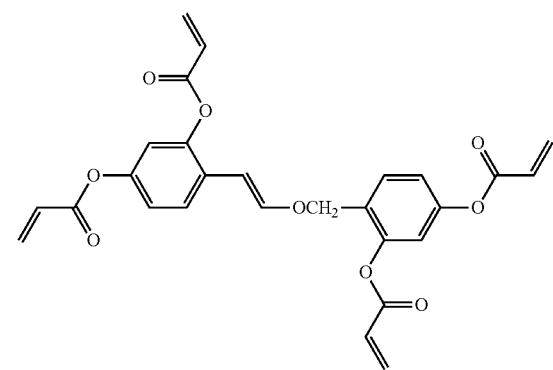
(1-2-47)
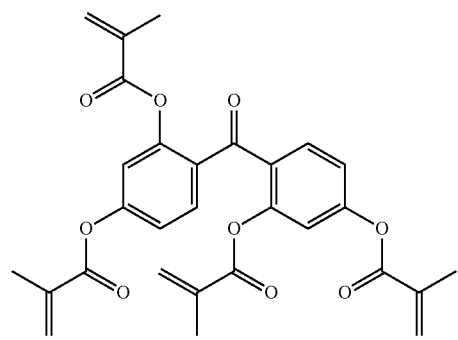
(1-2-48)
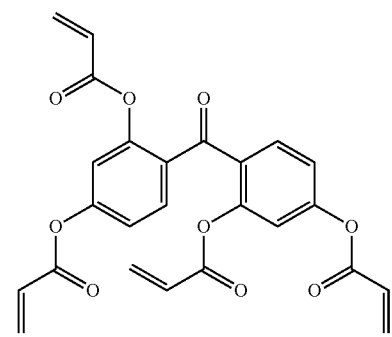
(1-2-49)
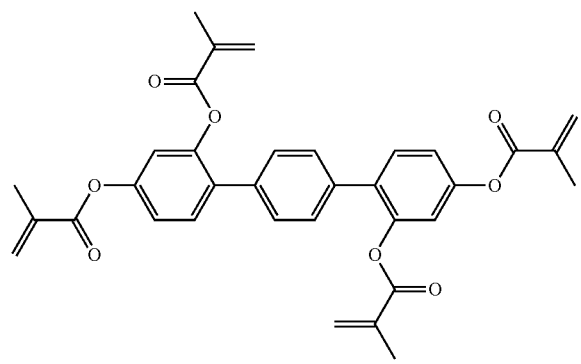
(1-2-50)
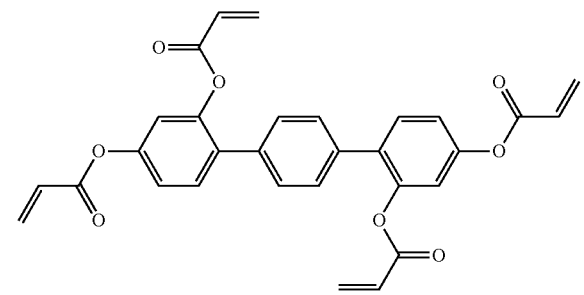

-continued
(1-2-51)
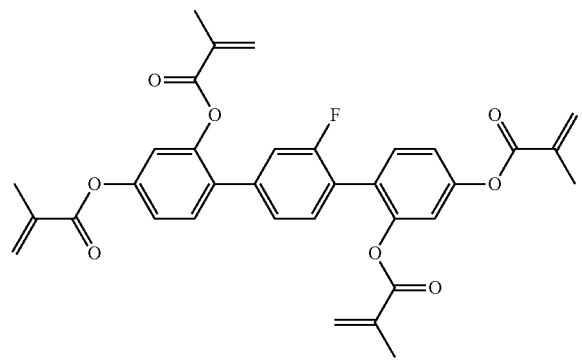
(1-2-52)
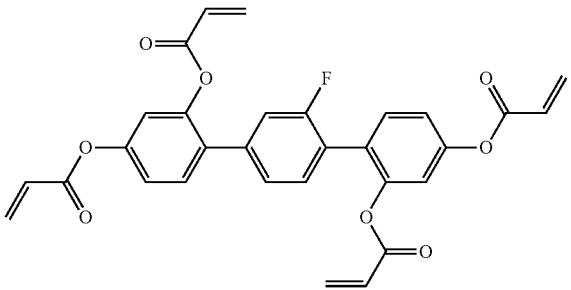
(1-2-53)
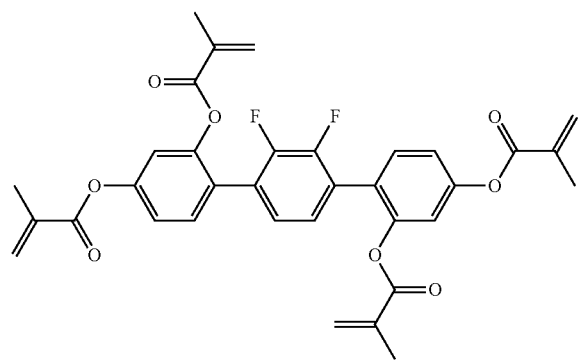
(1-2-54)
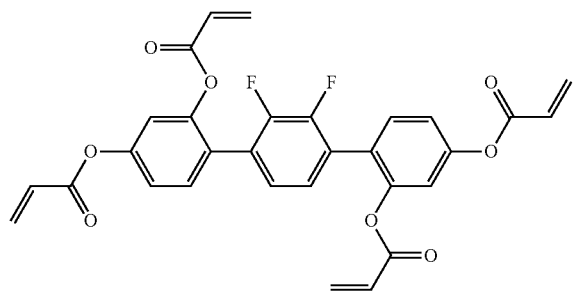
(1-2-55)
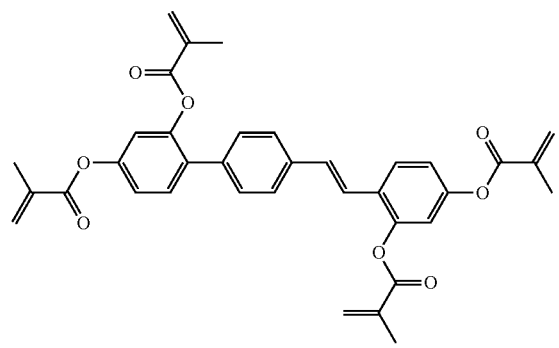
(1-2-56)
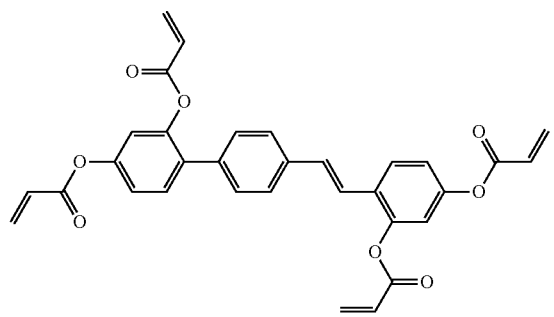
(1-2-57)
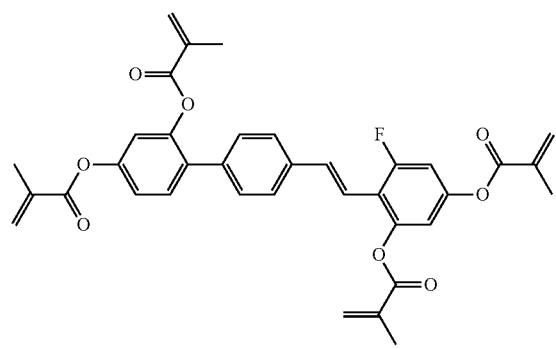
(1-2-58)
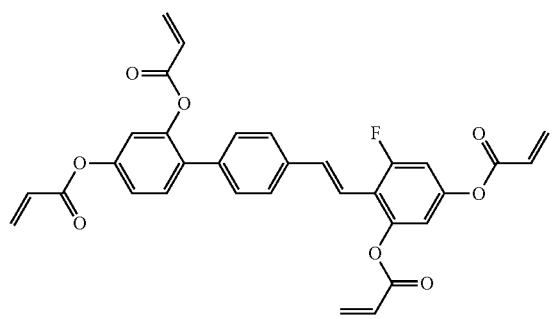

(1-2-59)
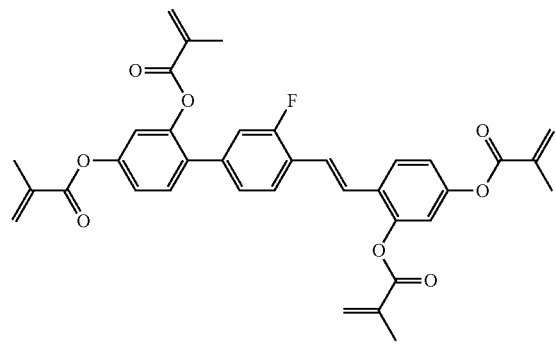
(1-2-60)
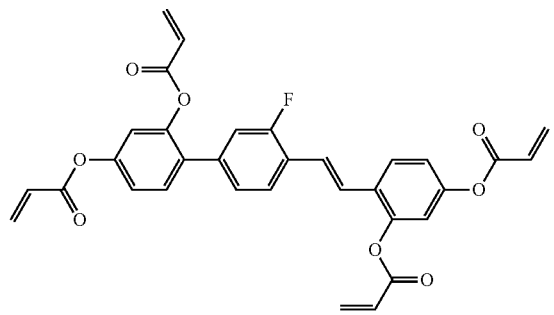
(1-2-61)
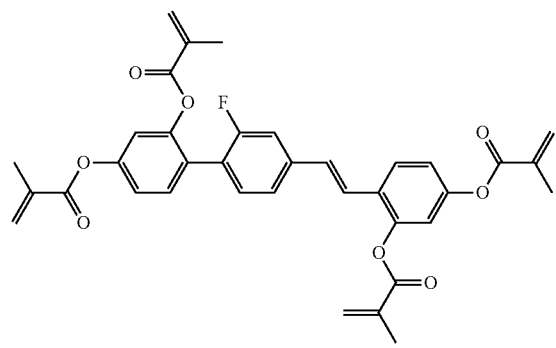
(1-2-62)
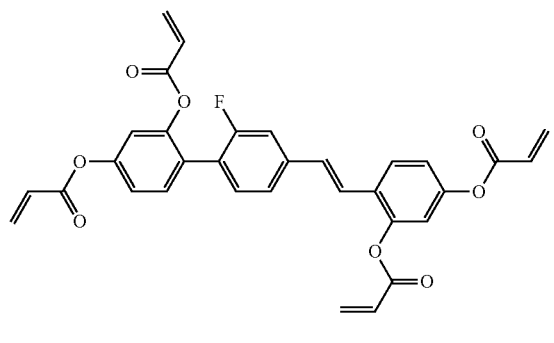
(1-2-63)
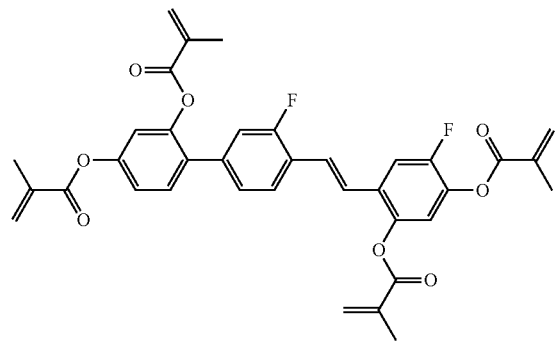
(1-2-64)
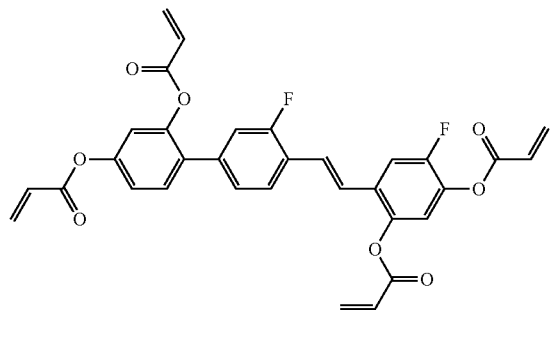
(1-2-65)
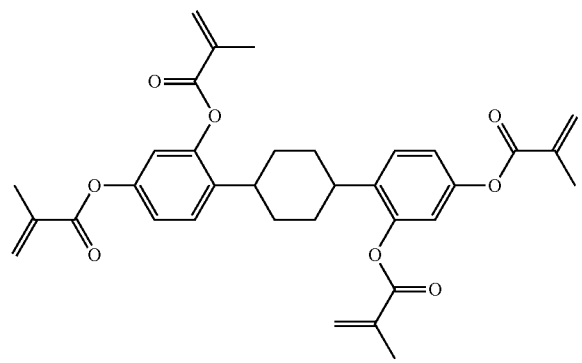
(1-2-66)
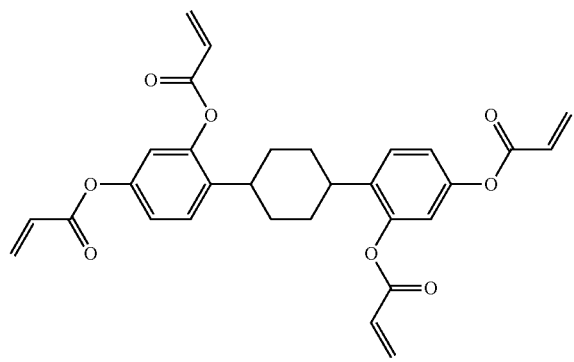

-continued
(1-2-67)
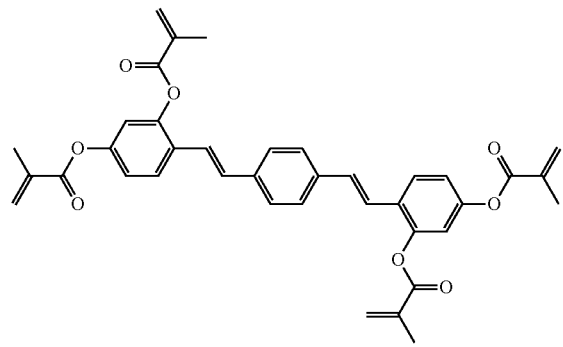
(1-2-68)
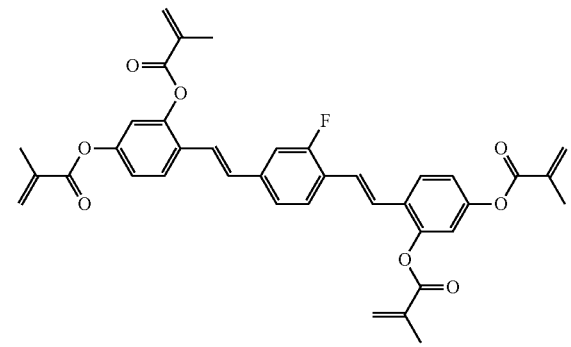
(1-2-69)
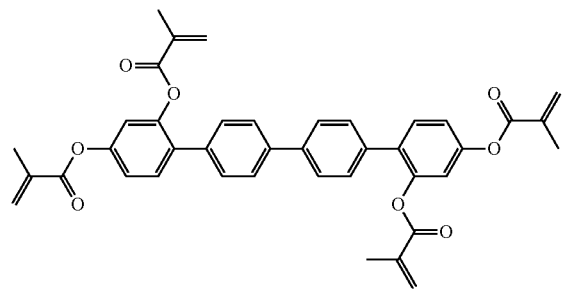
(1-2-70)
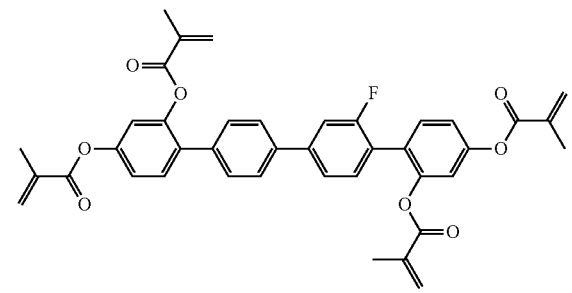
(1-2-71)
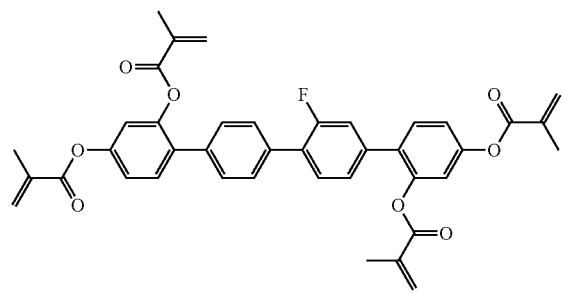
(1-2-72)
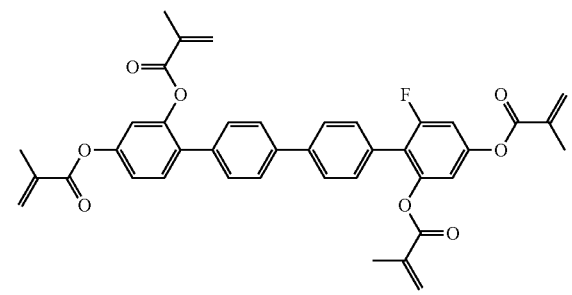
(1-2-73)
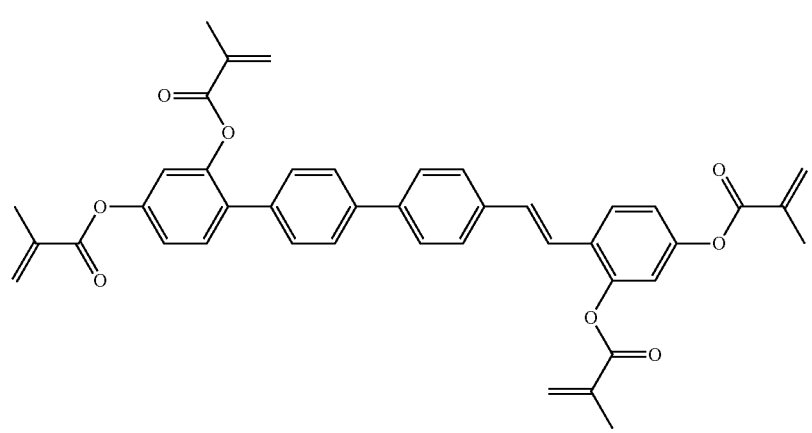

(1-2-74)
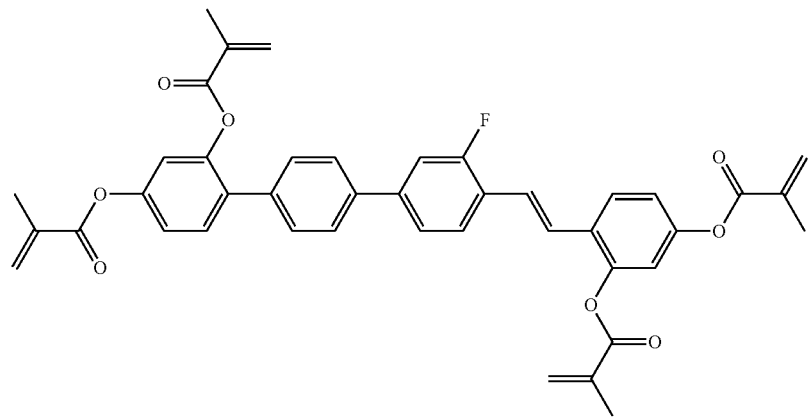
(1-2-75)
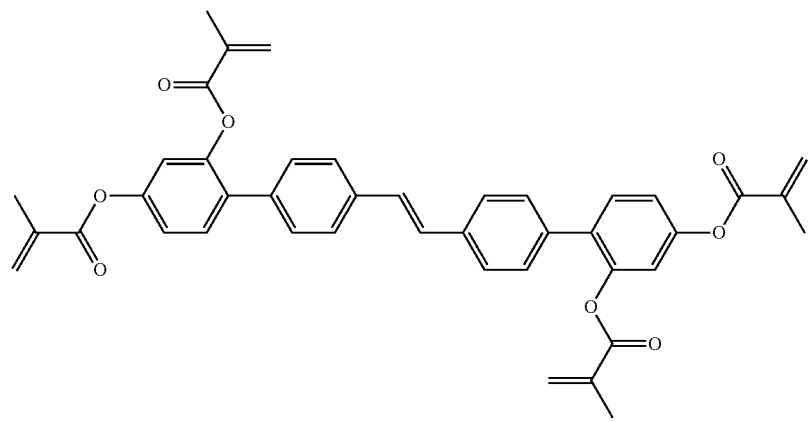
(1-2-76)
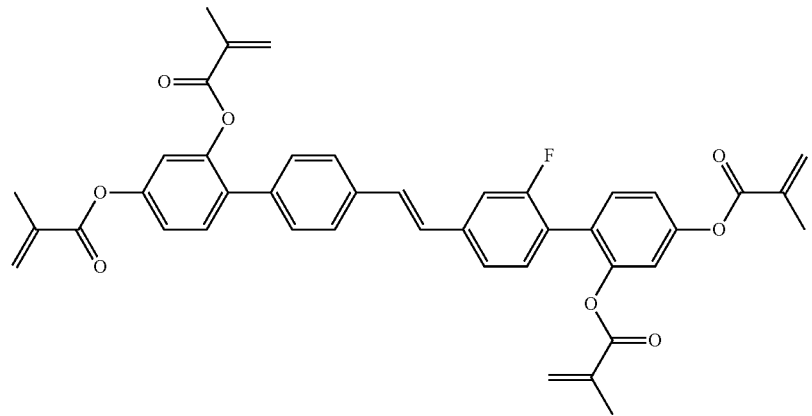
(1-2-77) (1-2-78)
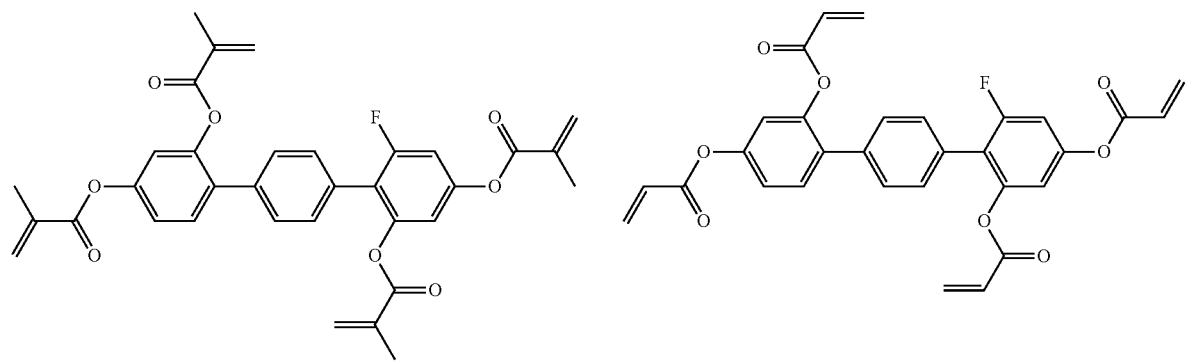

-continued
(1-2-79)
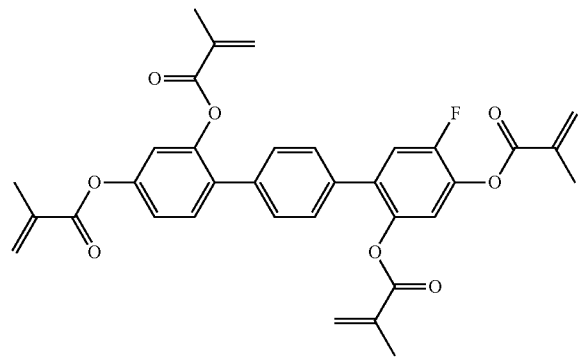
(1-2-80)
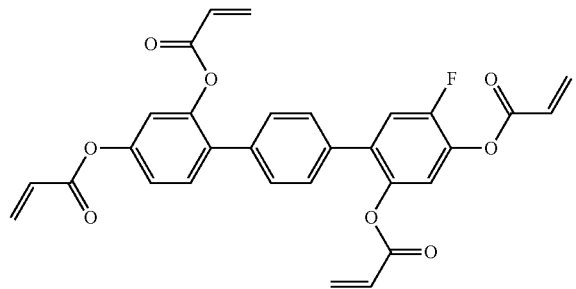
(1-2-81)
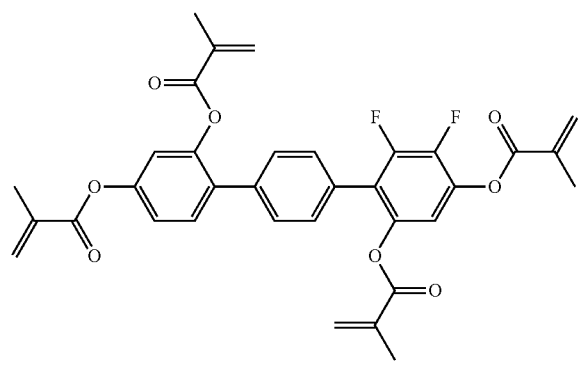
(1-2-82)
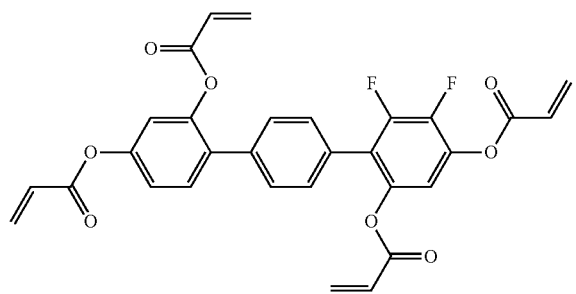
(1-2-83)
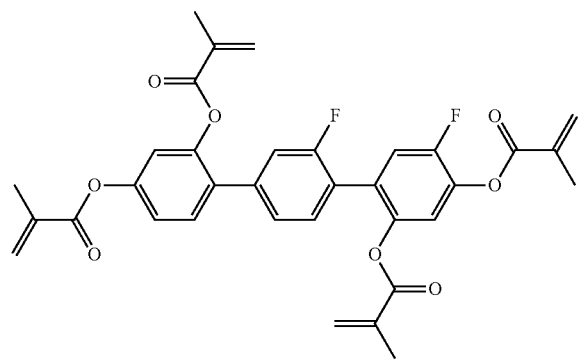
(1-2-84)
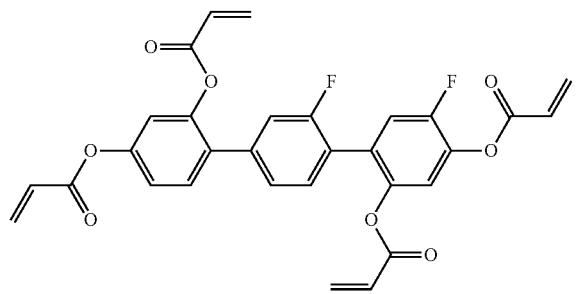
(1-2-85)
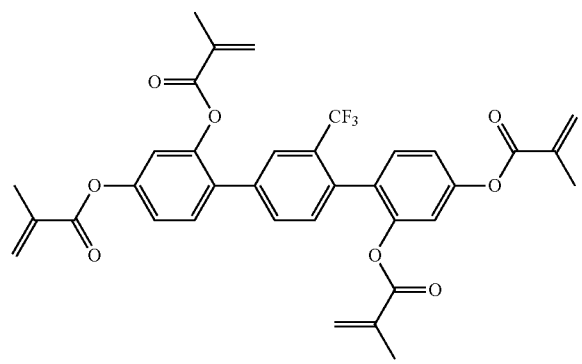
(1-2-86)
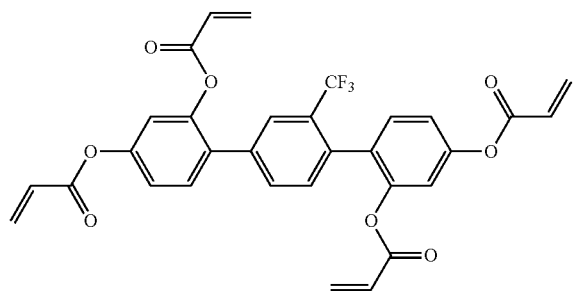

-continued
(1-2-87)
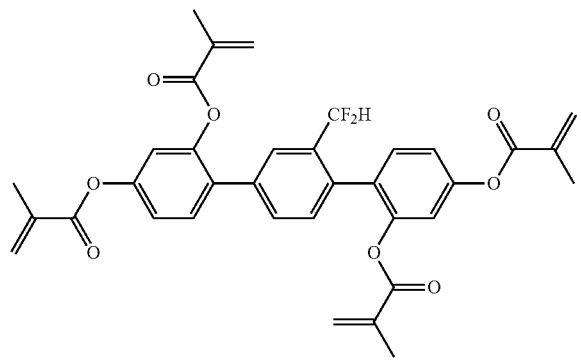
(1-2-88)
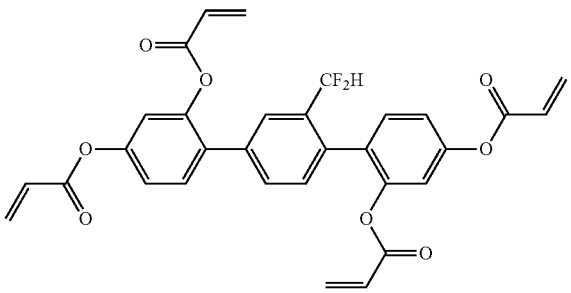
(1-2-89)
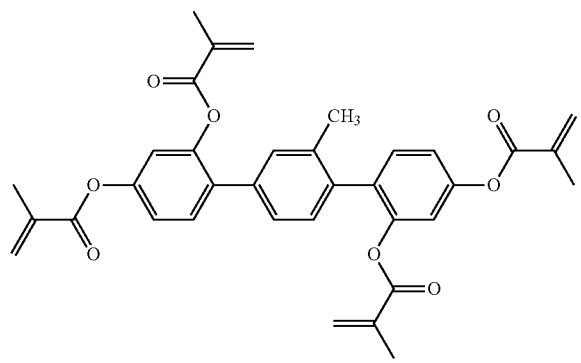
(1-2-90)
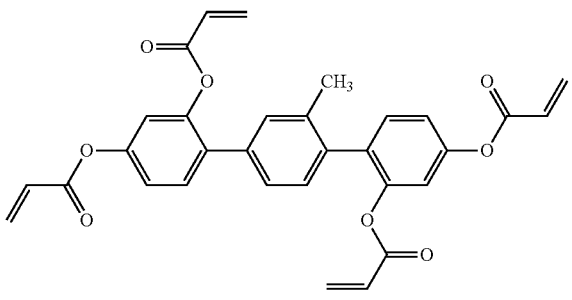
(1-3-1)
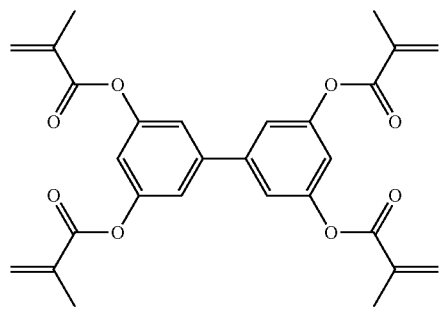 [SMILES: C=C(C)C(=O)Oc1cc(OC(=O)C(=C)C)cc(-c2cc(OC(=O)C(=C)C)cc(OC(=O)C(=C)C)c2)c1]
(1-3-2)
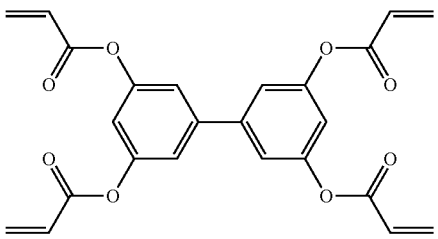
(1-3-3)
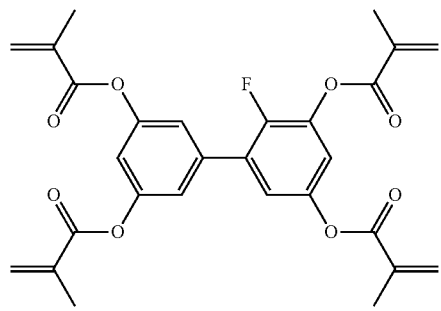
(1-3-4)
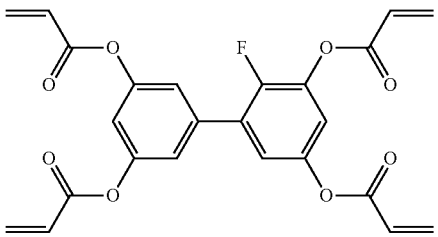

-continued
(1-3-5)
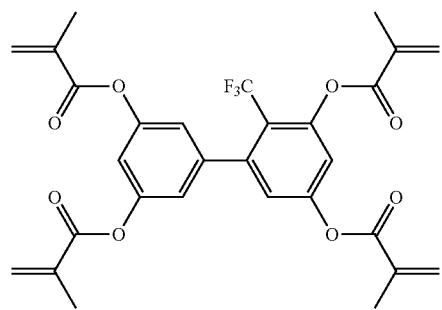 [SMILES: C=C(C)C(=O)Oc1cc(OC(=O)C(=C)C)cc(-c2cc(OC(=O)C(=C)C)cc(OC(=O)C(=C)C)c2)c1]
(1-3-6)
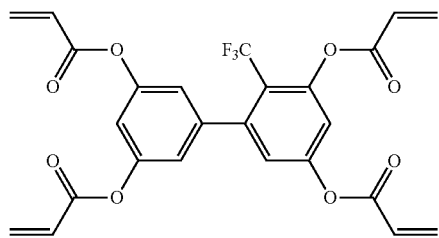
(1-3-7)
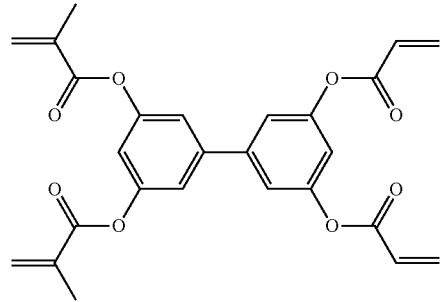
(1-3-8)
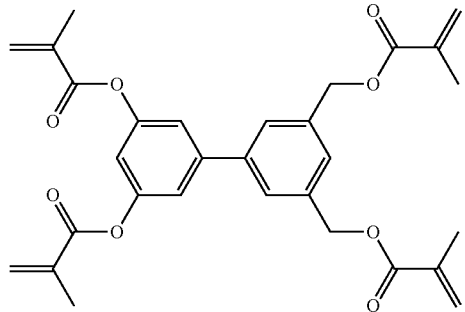
(1-3-9)
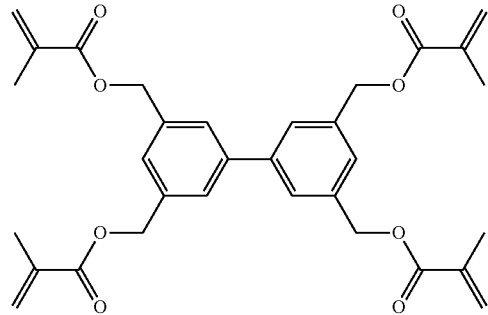
(1-3-10)
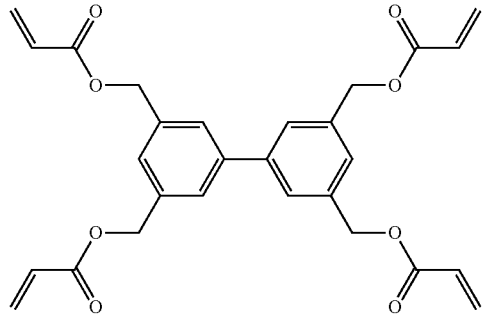
(1-3-11)
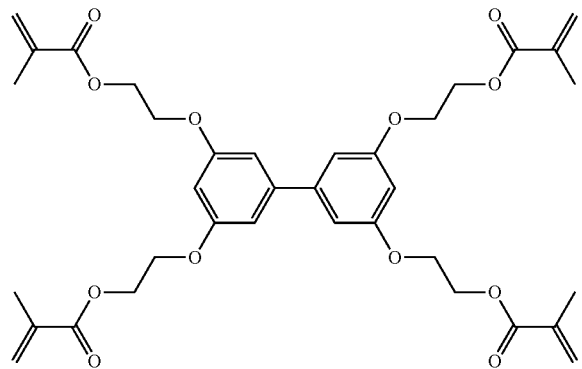
(1-3-12)
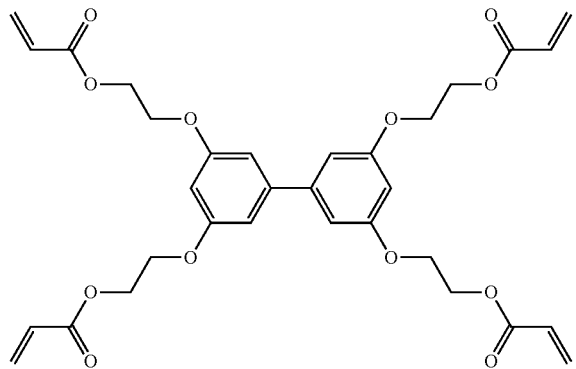

-continued
(1-3-13) (1-3-14)
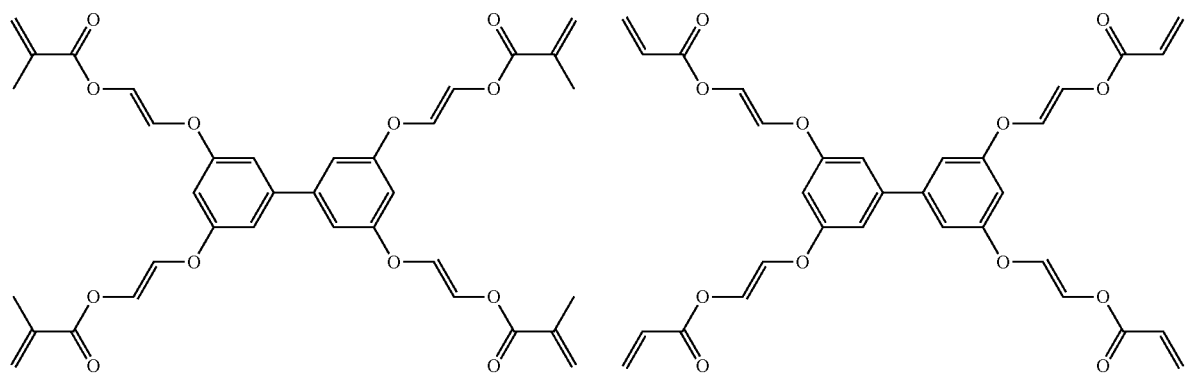
(1-3-15) (1-3-16)
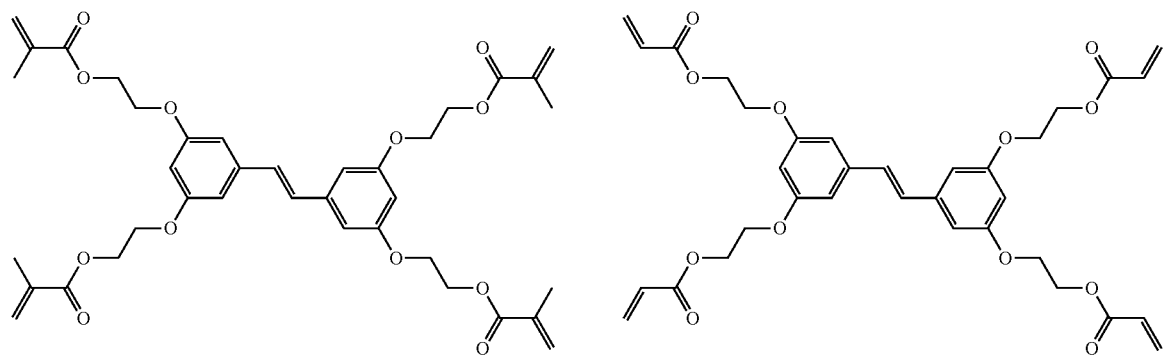
(1-3-17) (1-3-18)
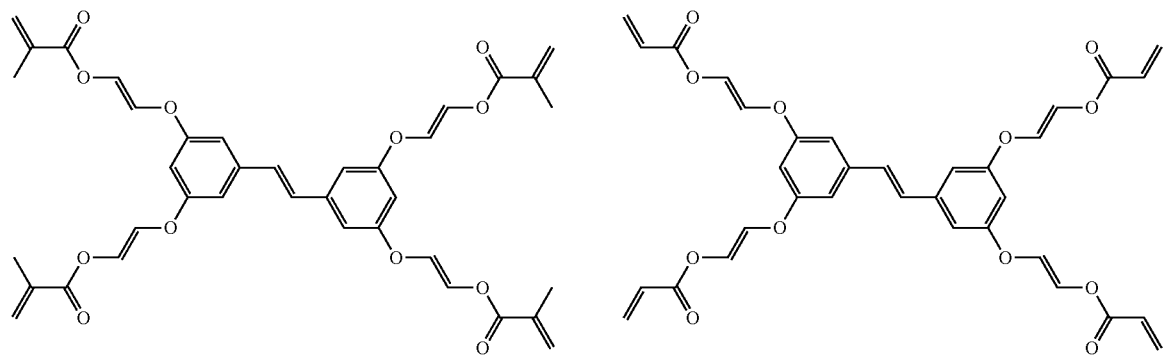
(1-3-19) (1-3-20)
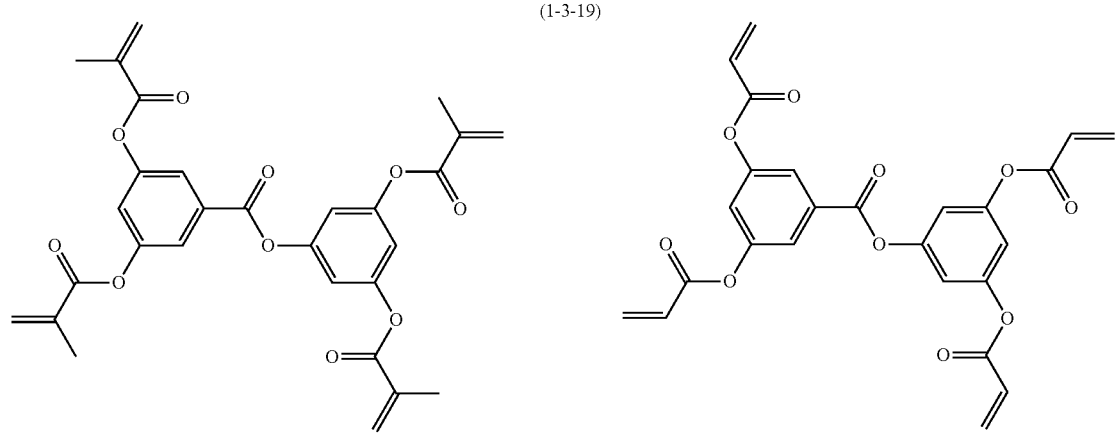

-continued
(1-3-21)
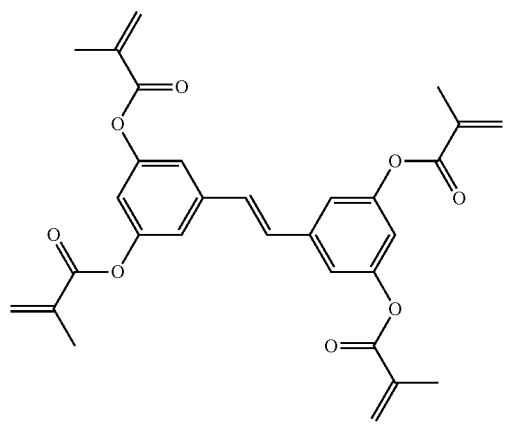
(1-3-22)
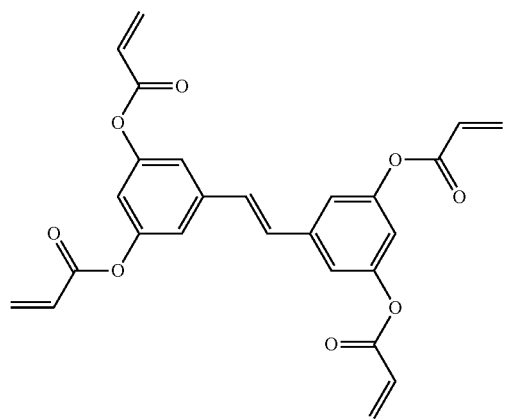
(1-3-23)
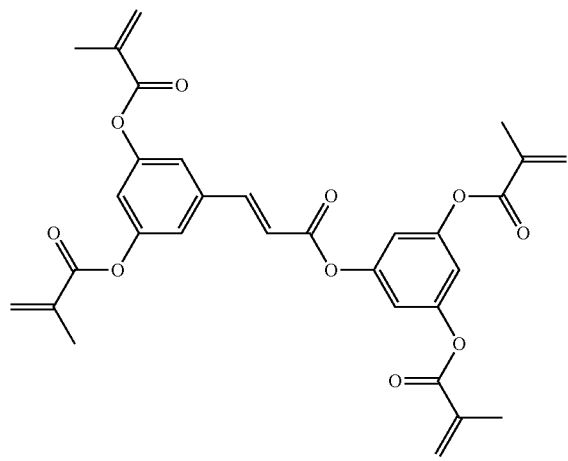
(1-3-24)
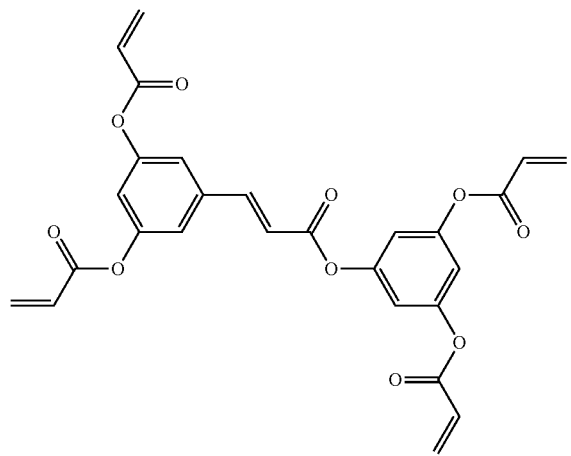
(1-3-25)
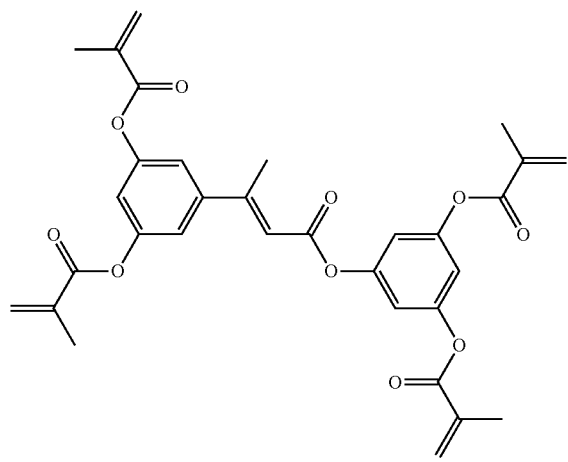
(1-3-26)
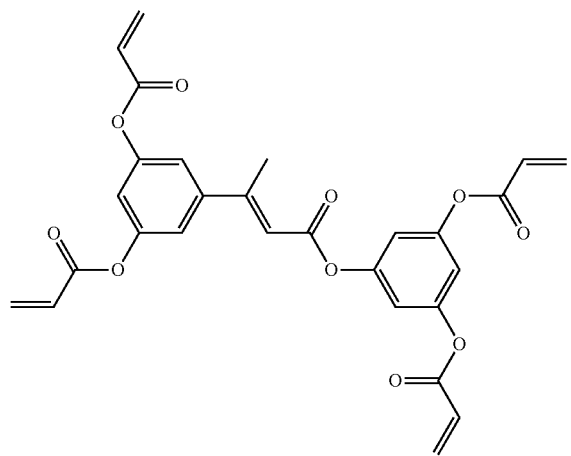

-continued
(1-3-27)
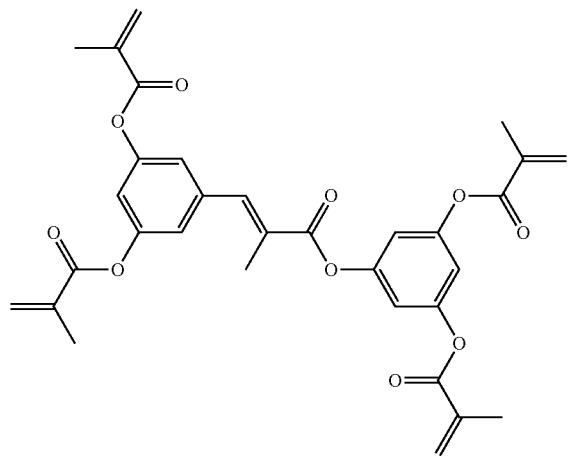
(1-3-28)
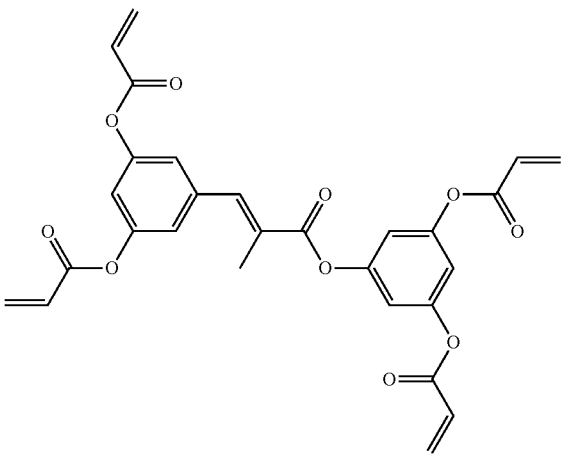
(1-3-29)
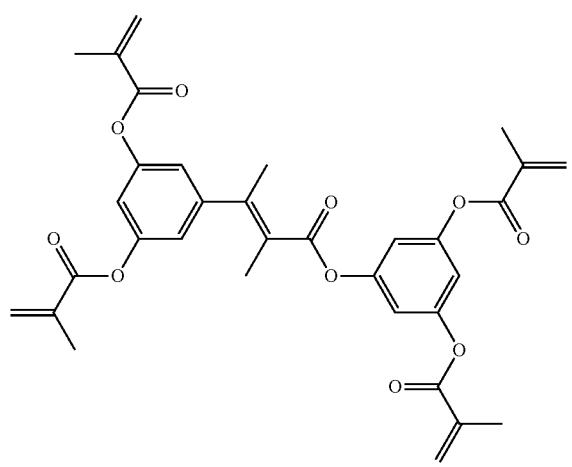
(1-3-30)
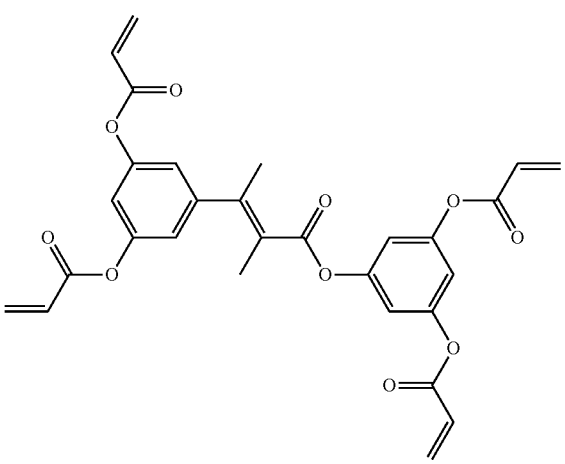
(1-3-31)
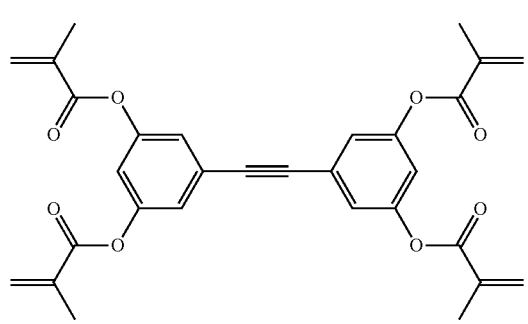
(1-3-32)
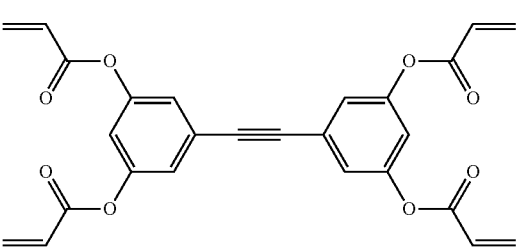
(1-3-33)
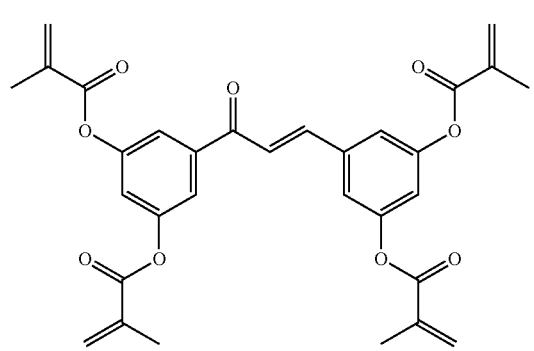
(1-3-34)
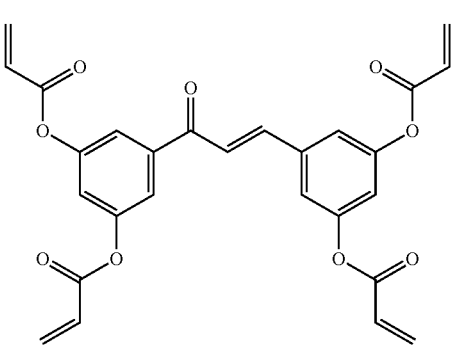

-continued
(1-3-35)
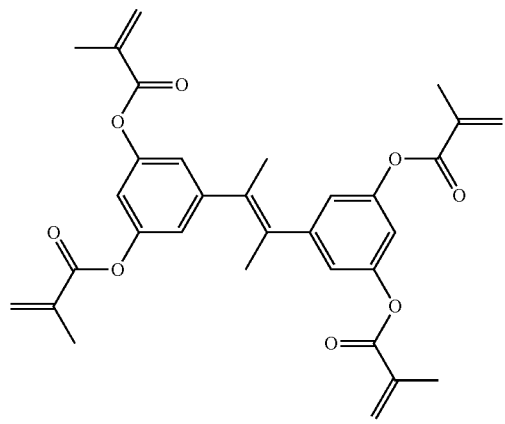
(1-3-36)
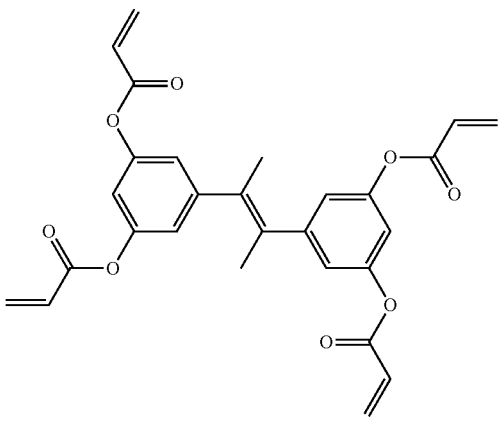
(1-3-37)
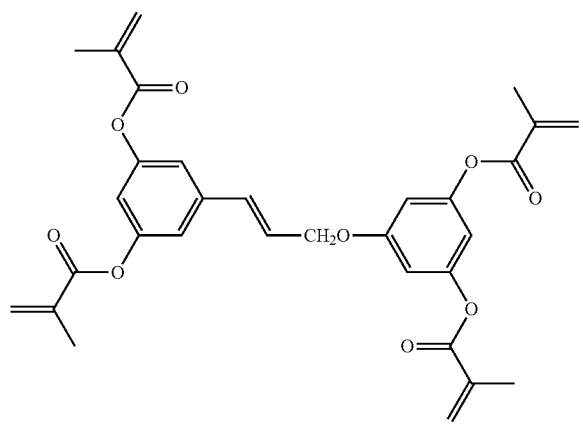
(1-3-38)
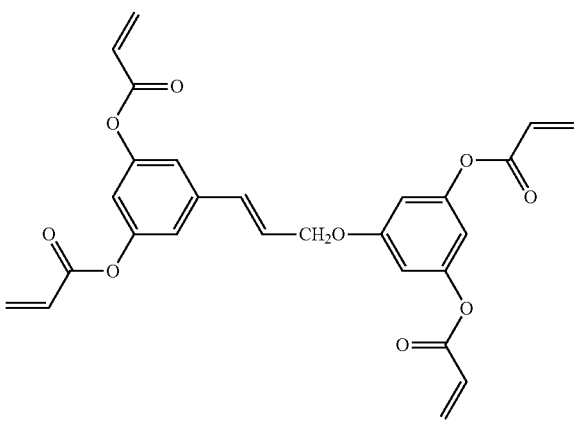
(1-3-39)
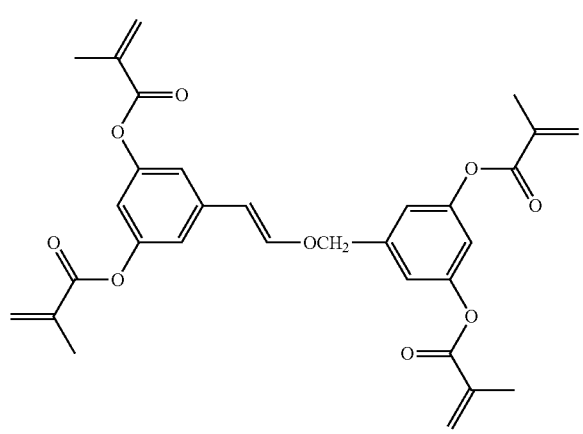
(1-3-40)
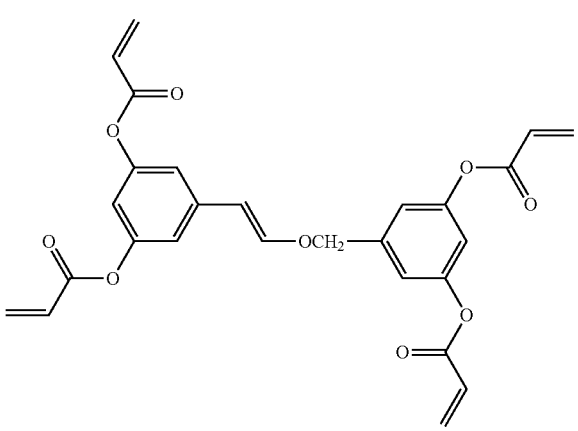
(1-3-41)
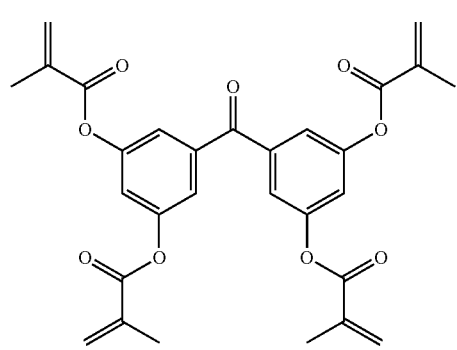
(1-3-42)
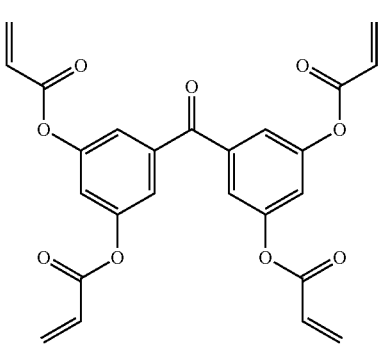

-continued
(1-3-43)
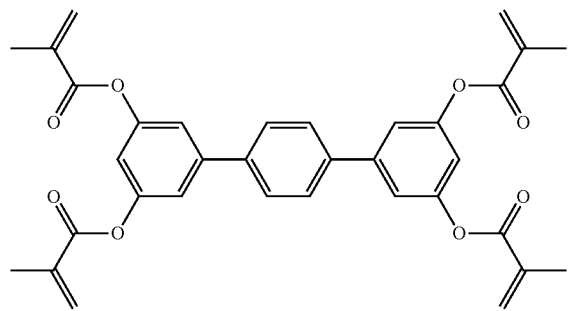
(1-3-44)
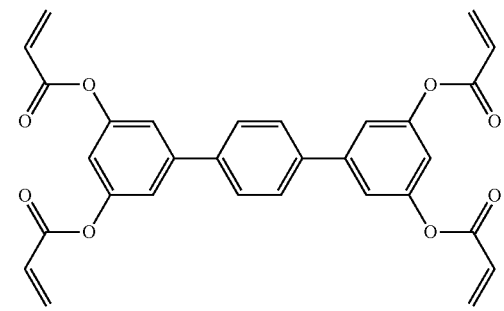
(1-3-45)
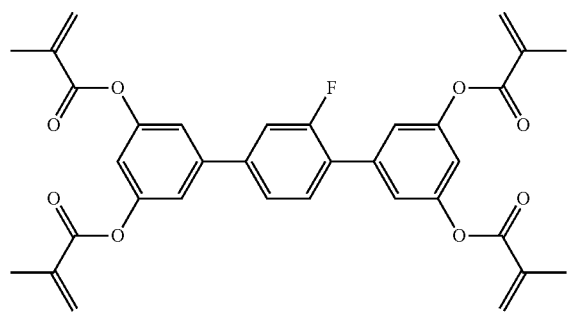
(1-3-46)
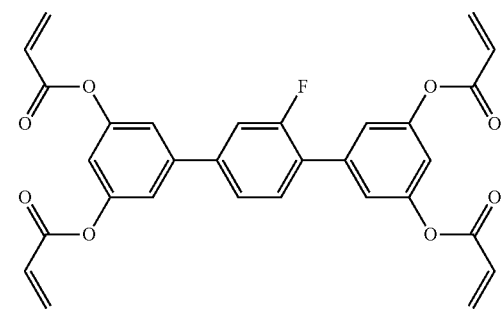
(1-3-47)
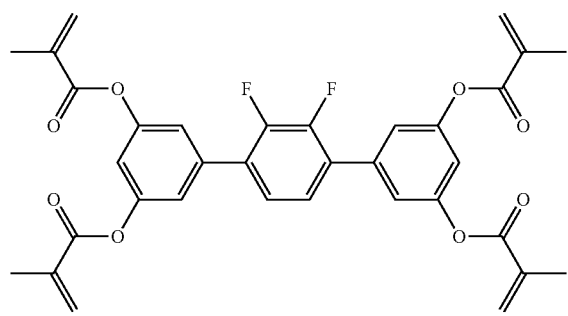
(1-3-48)
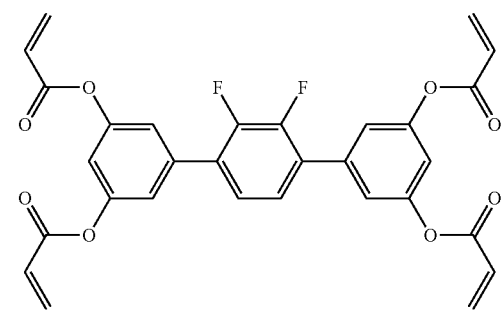
(1-3-49)
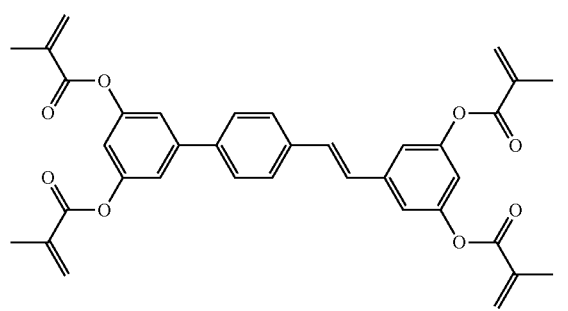
(1-3-50)
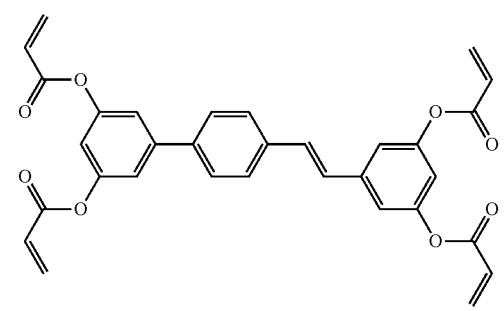

-continued
(1-3-51)
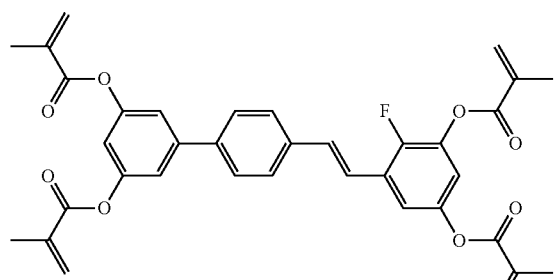
(1-3-52)
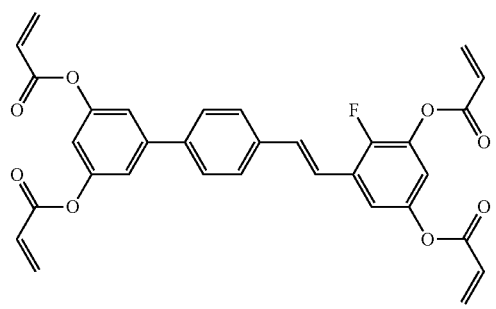
(1-3-53)
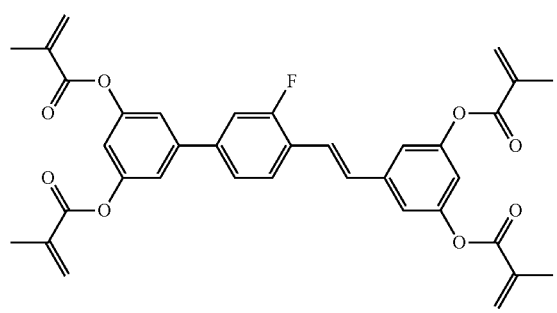
(1-3-54)
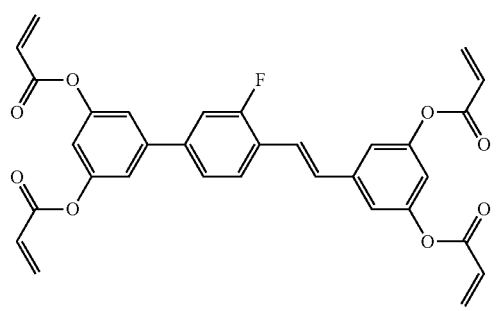
(1-3-55)
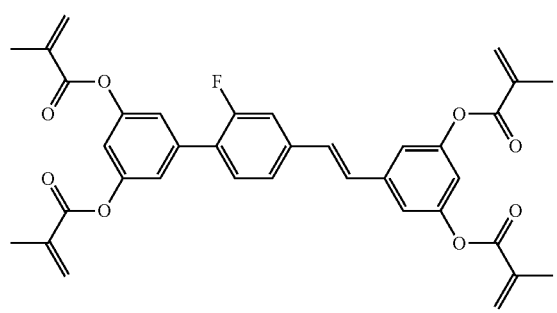
(1-3-56)
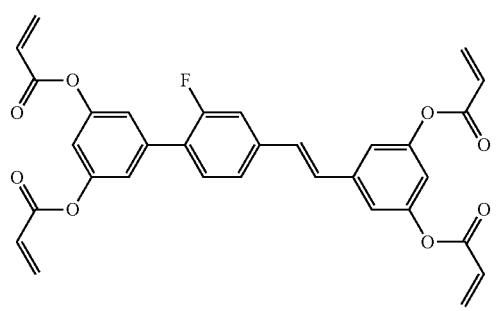
(1-3-57)
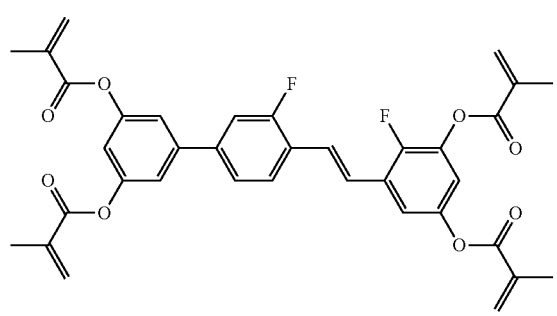
(1-3-58)
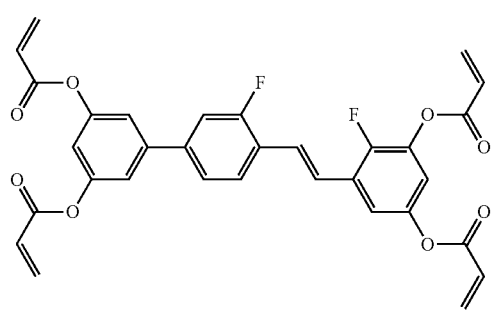
(1-3-59)
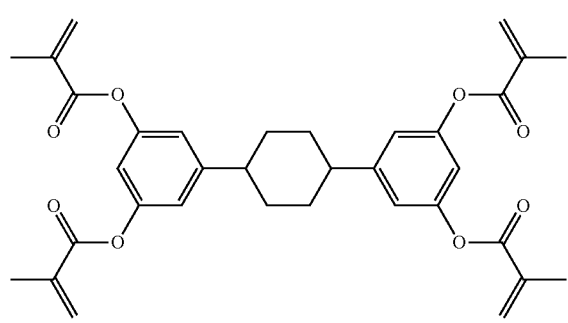
(1-3-60)
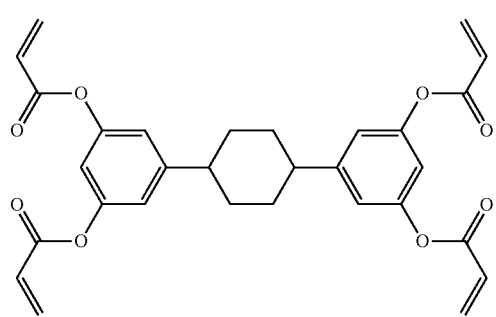

-continued
(1-3-61)
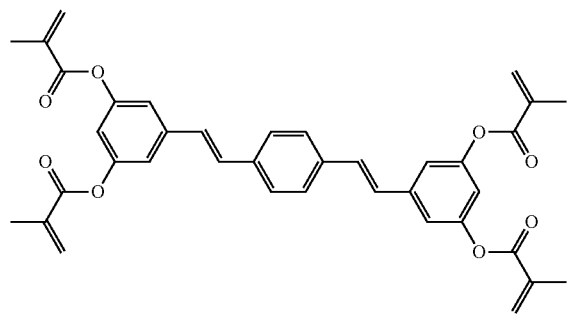
(1-3-62)
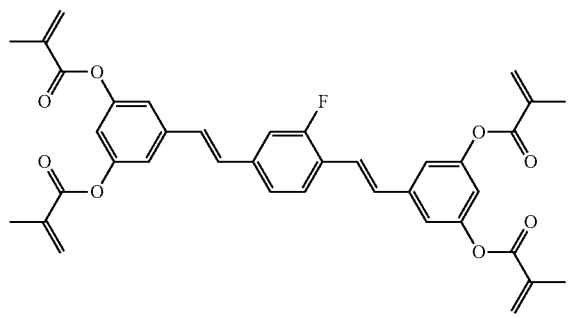
(1-3-63)
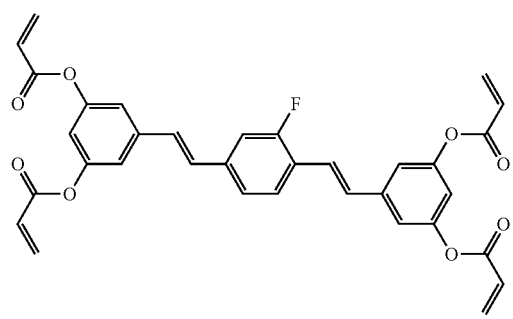
(1-3-64)
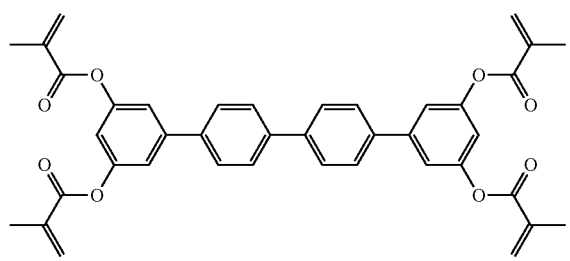
(1-3-65)
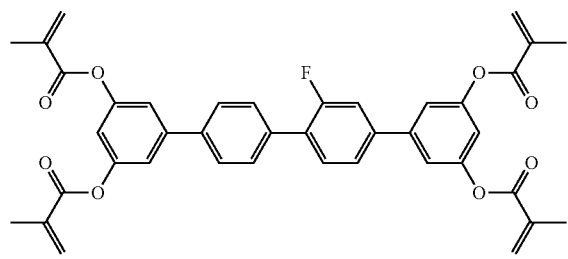
(1-3-66)
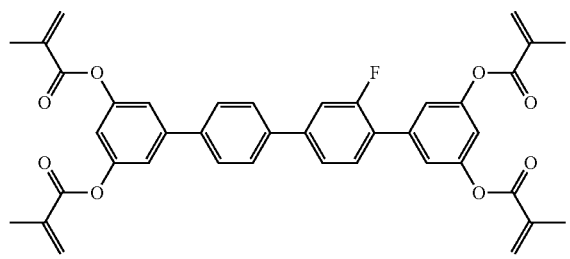
(1-3-67)
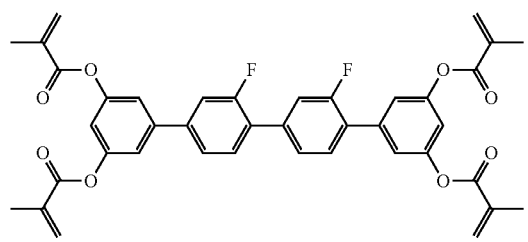
(1-3-68)
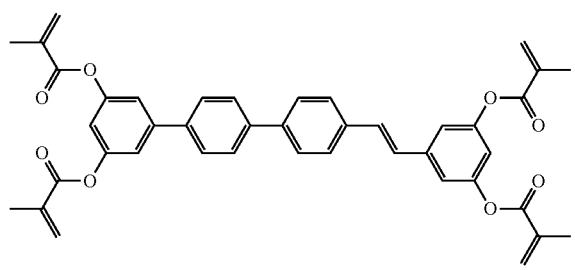
(1-3-69)
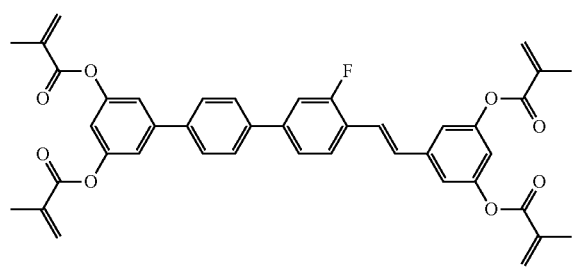
(1-3-70)
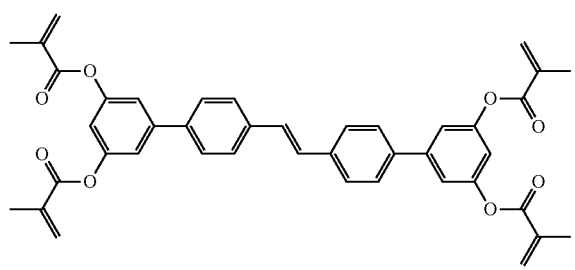

-continued
(1-3-71)
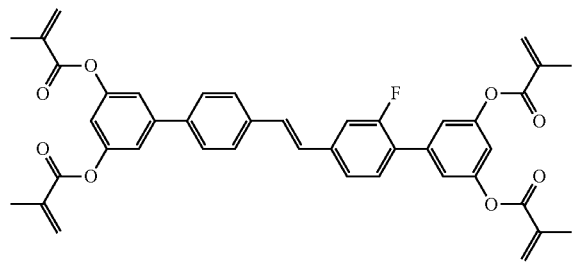
(1-3-72)
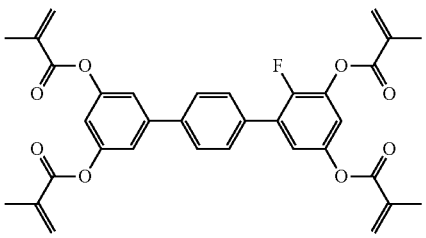
(1-3-73)
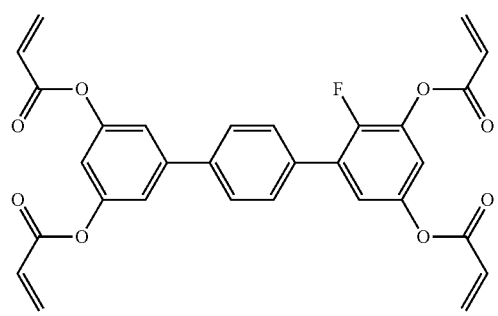
(1-3-74)
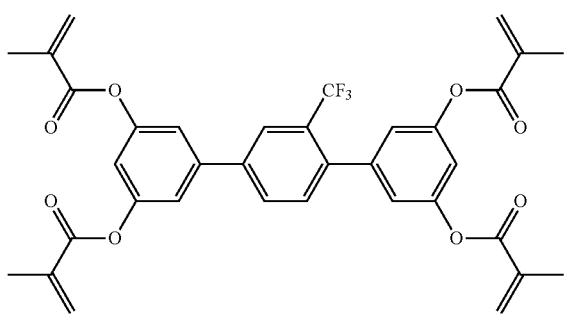
(1-3-75)
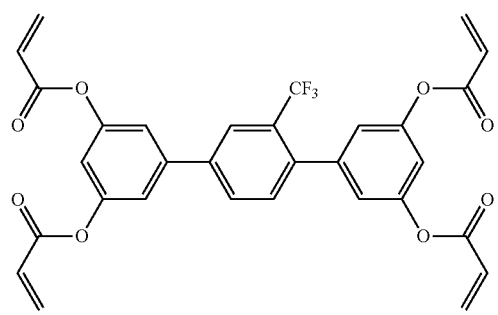
(1-3-76)
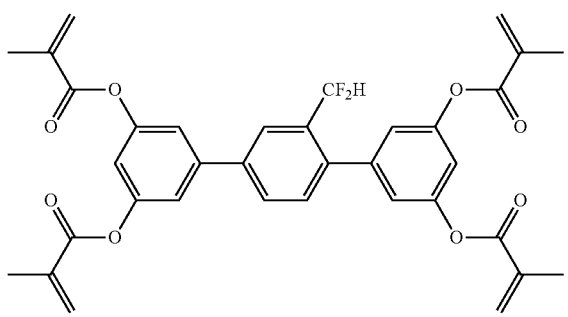
(1-3-77)
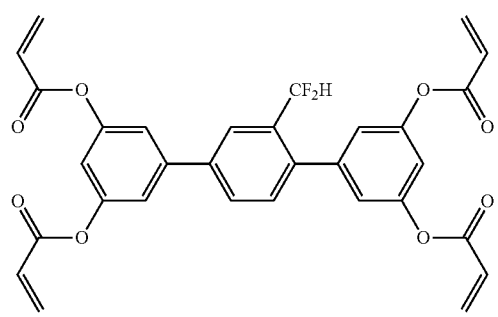
(1-3-78)
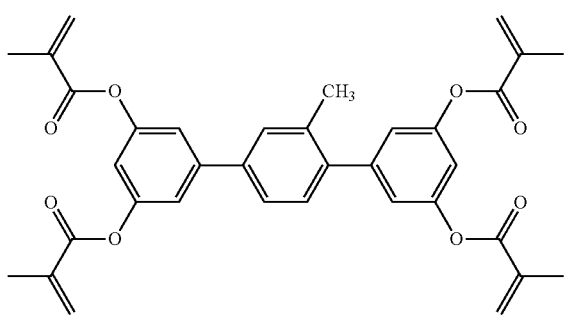

-continued
(1-3-79)
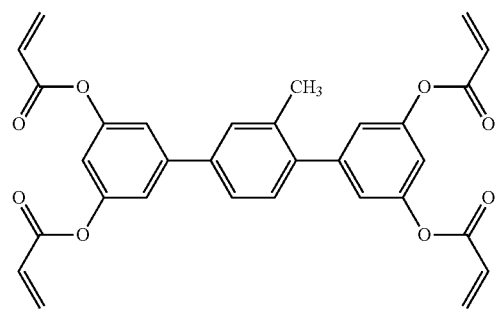
(1-4-1)
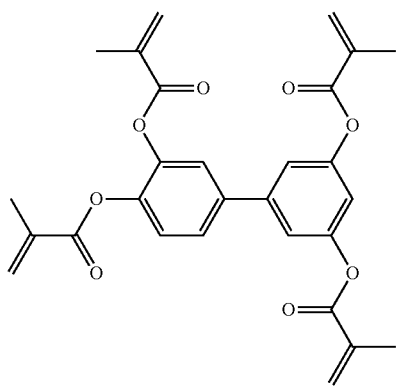
(1-4-2)
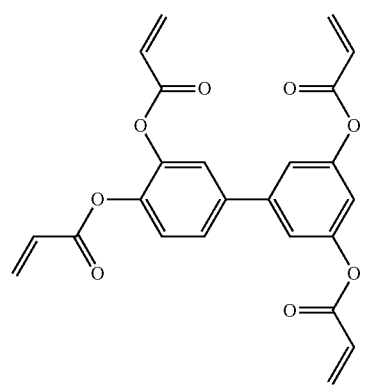
(1-4-3)
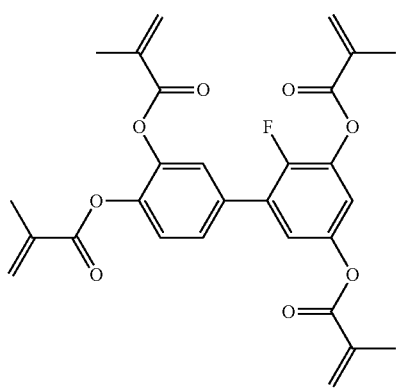
(1-4-4)
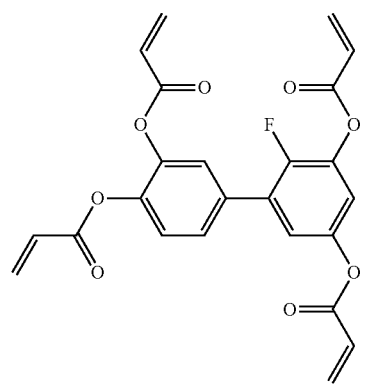
(1-4-5)
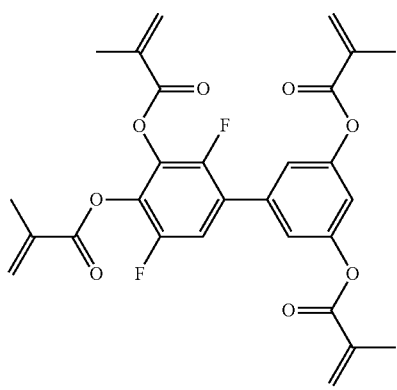
(1-4-6)
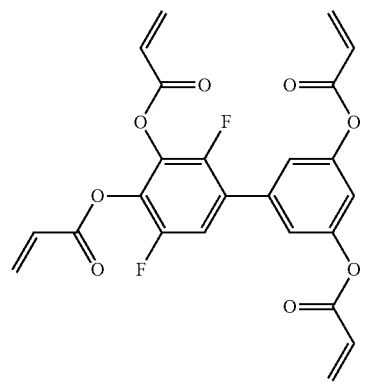
(1-4-7)
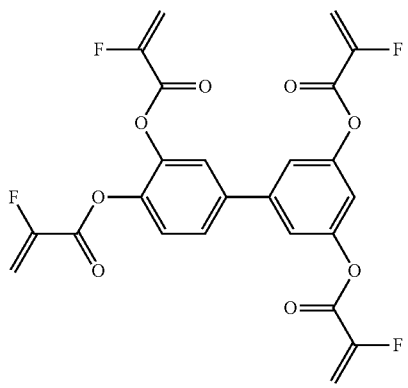

-continued
(1-4-8)
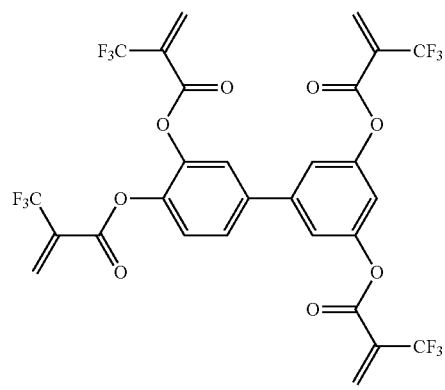
(1-4-9)
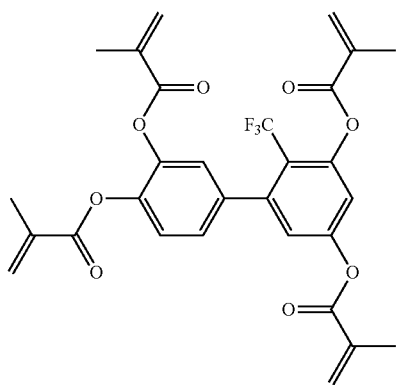
(1-4-10)
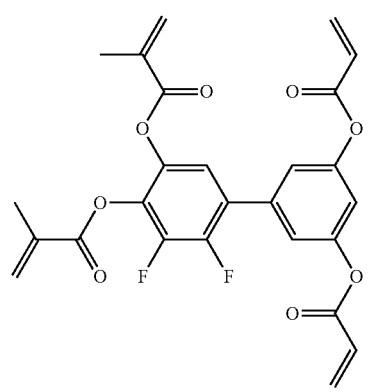
(1-4-11)
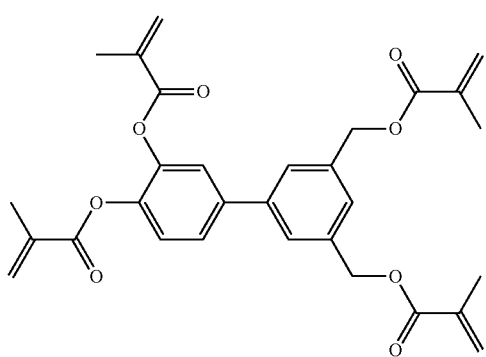
(1-4-12)
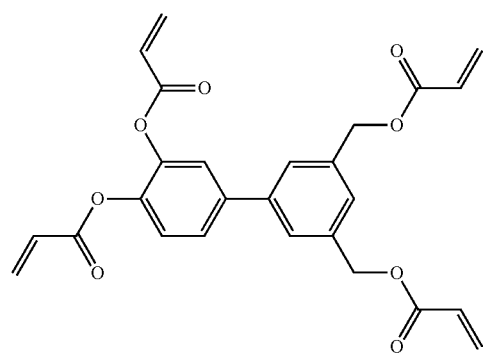
(1-4-13)
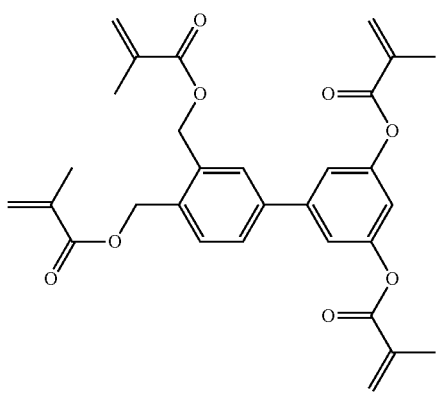
(1-4-14)
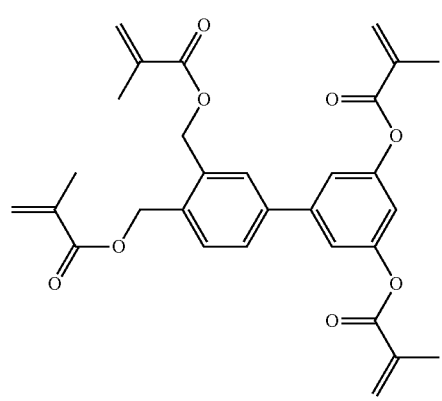
(1-4-15)
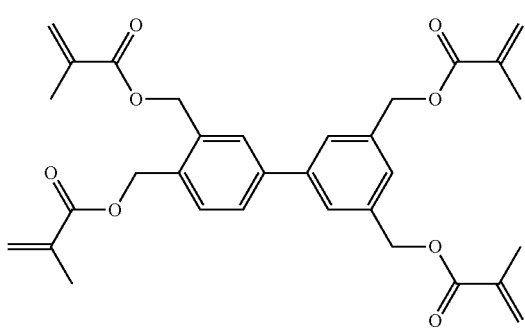

-continued
(1-4-16)
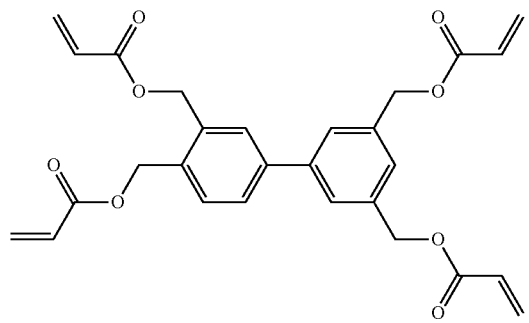
(1-4-17)
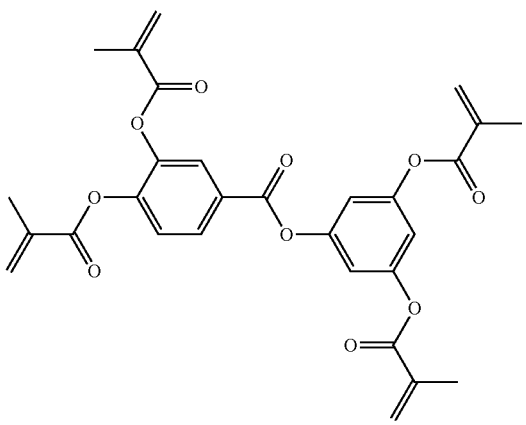
(1-4-18)
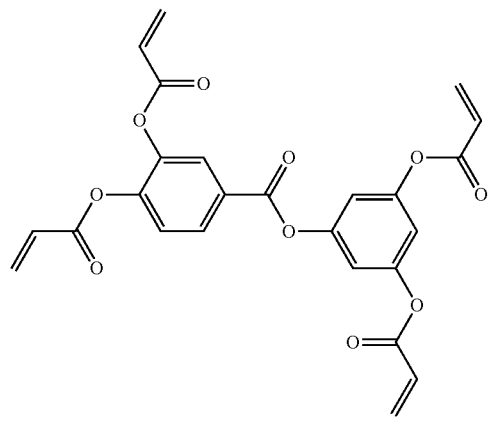
(1-4-19)
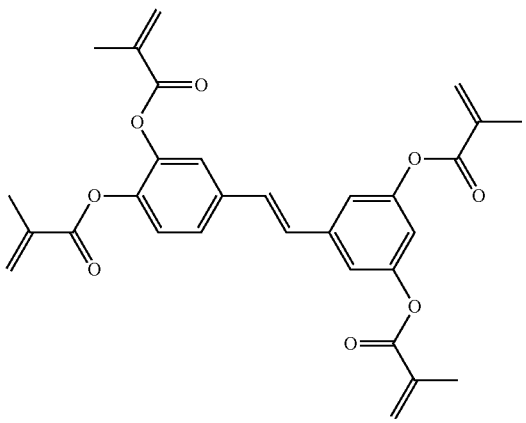
(1-4-20)
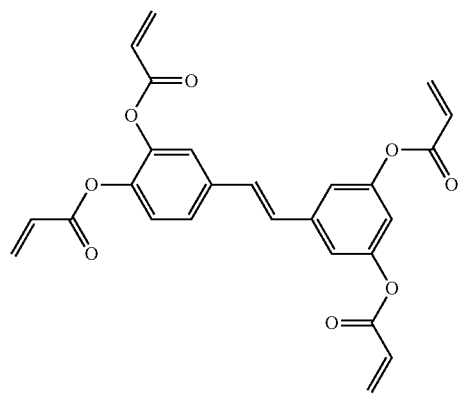
(1-4-21)
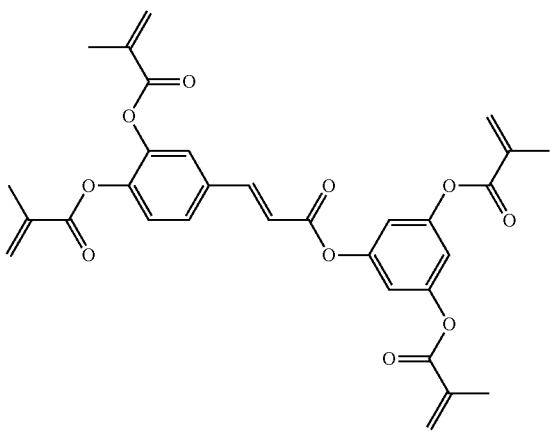

-continued
(1-4-22)
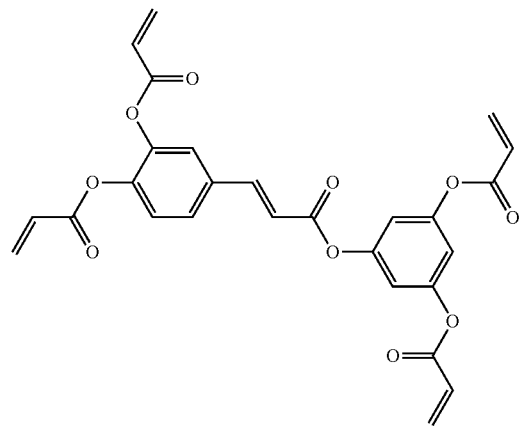
(1-4-23)
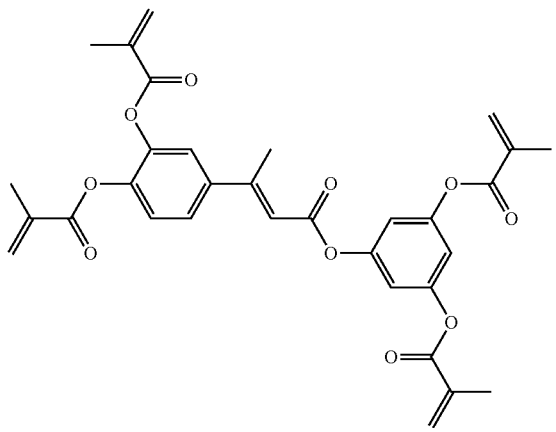
(1-4-24)
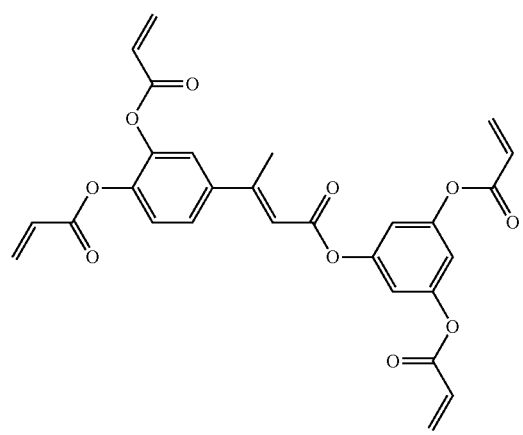
(1-4-25)
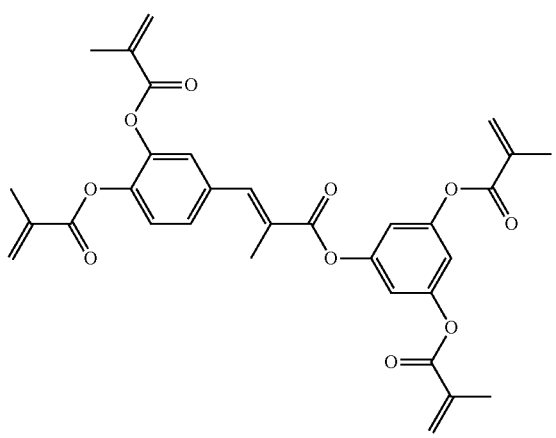
(1-4-26)
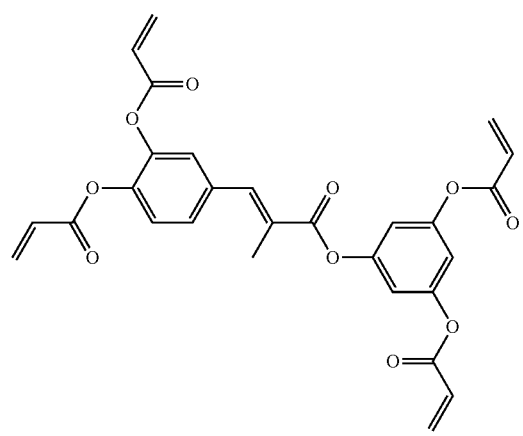
(1-4-27)
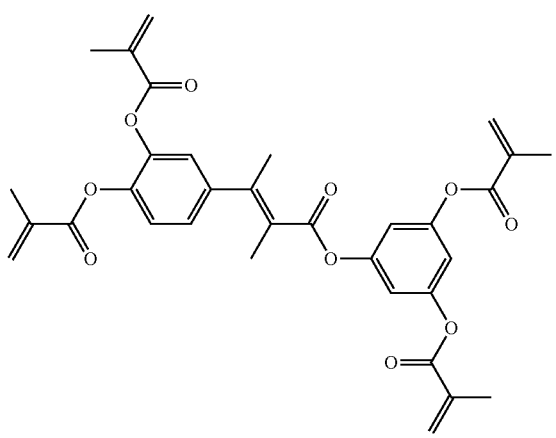

(1-4-28)
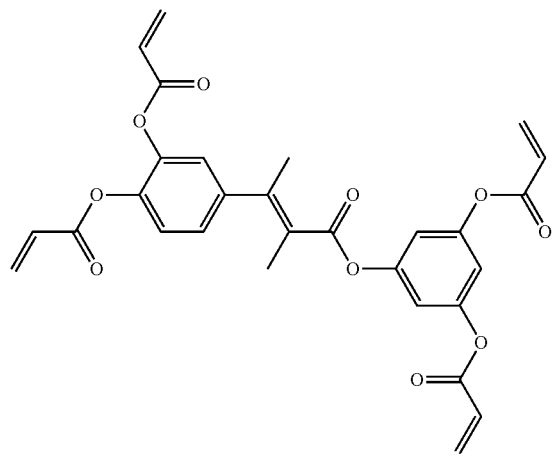
(1-4-29)
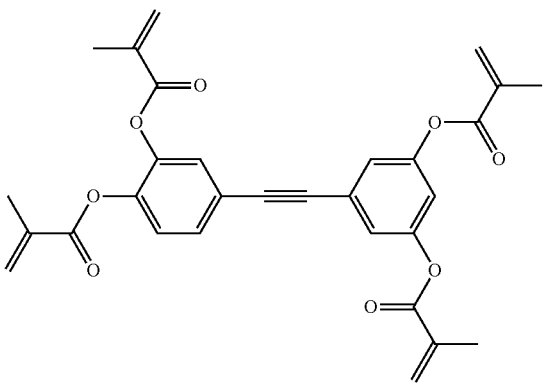
(1-4-30)
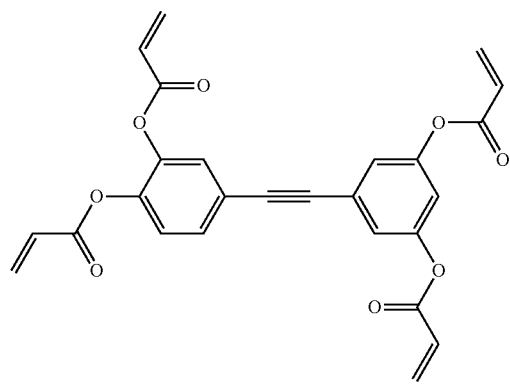
(1-4-31)
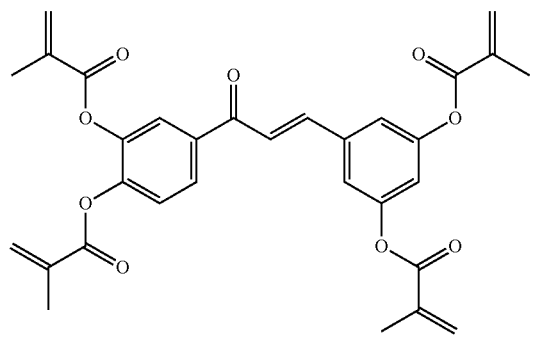
(1-4-32)
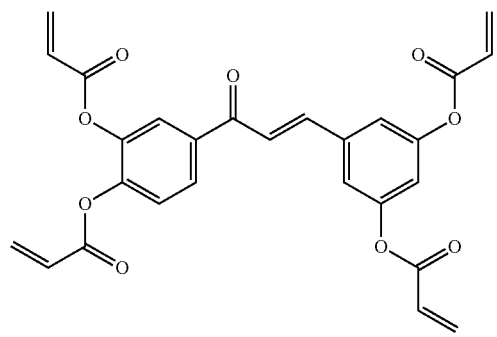
(1-4-33)
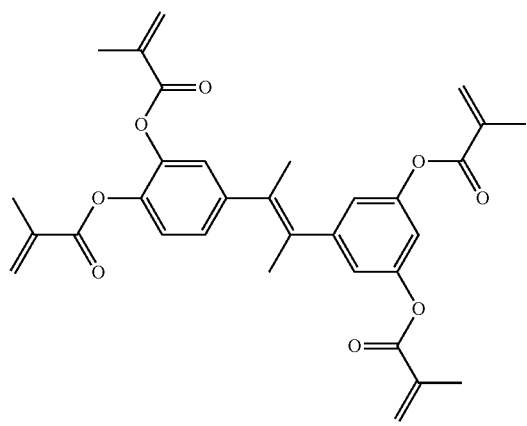

-continued
(1-4-34)
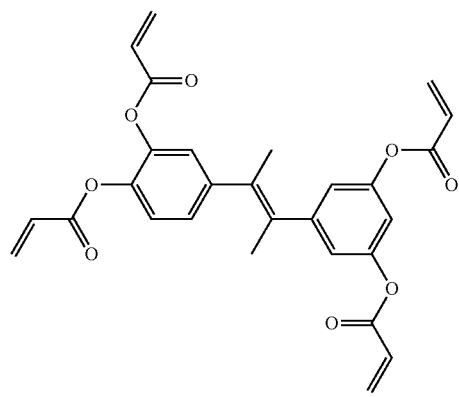
(1-4-35)
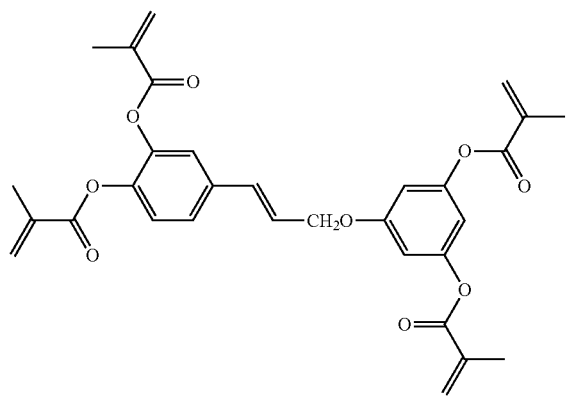
(1-4-36)
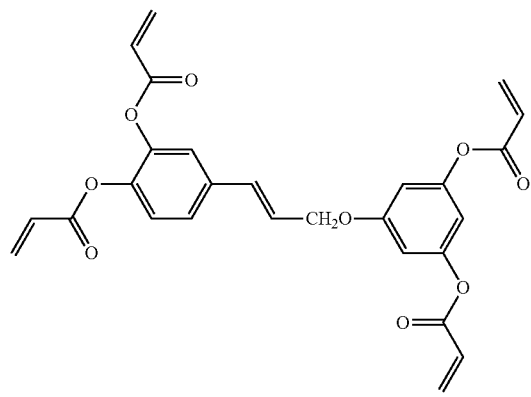
(1-4-37)
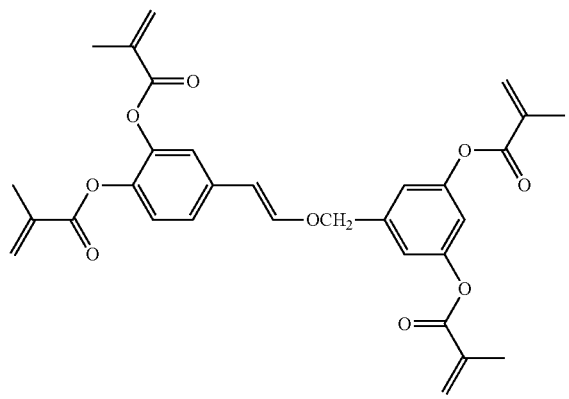
(1-4-38)
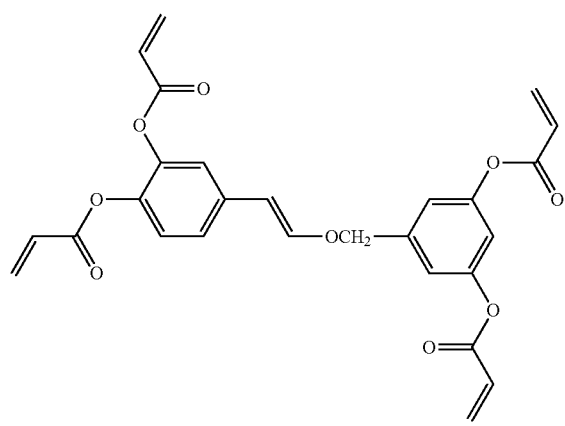
(1-4-39)
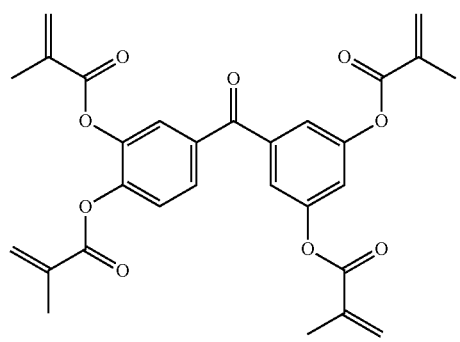
(1-4-40)
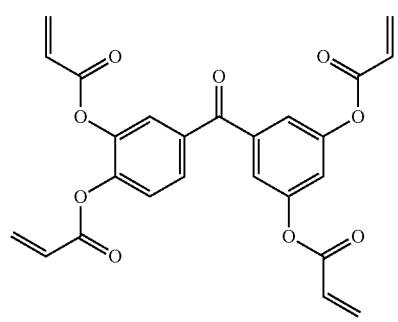
(1-4-41)
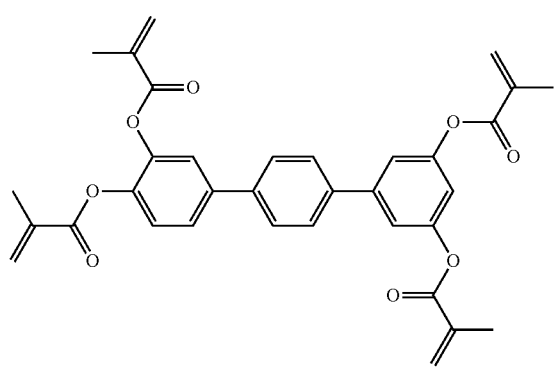

-continued
(1-4-42)
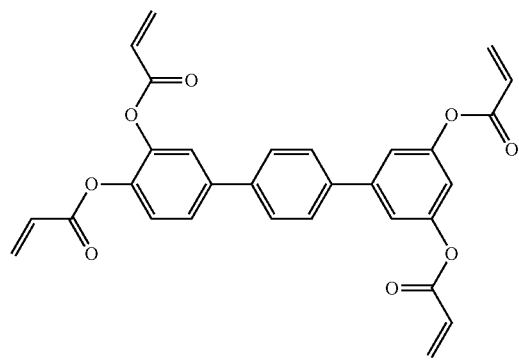
(1-4-43)
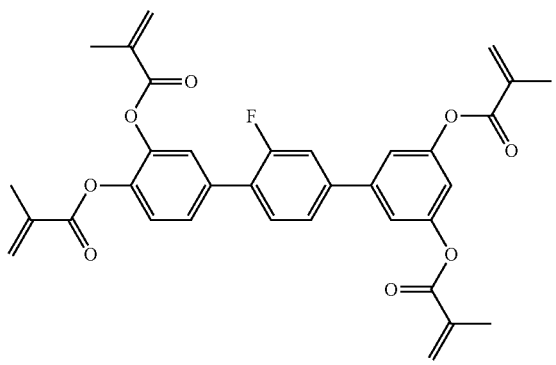
(1-4-44)
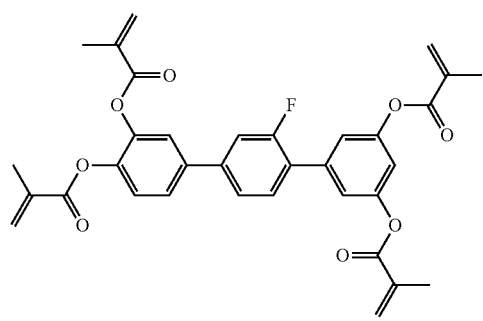
(1-4-45)
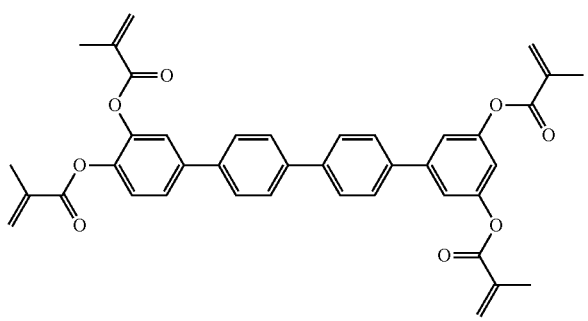
(1-4-46)
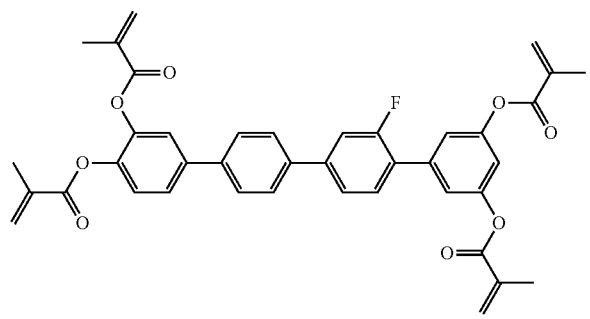
(1-5-1)
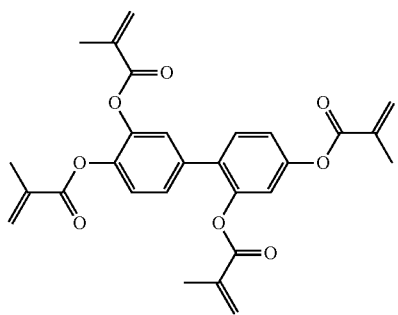
(1-5-2)
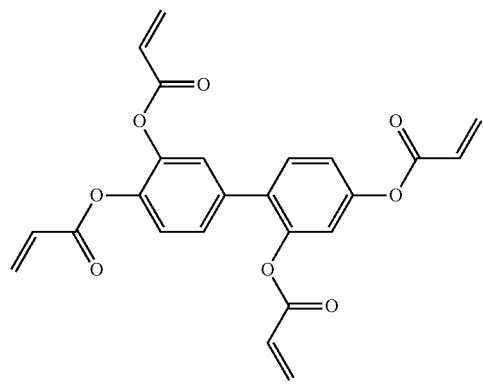
(1-5-3)
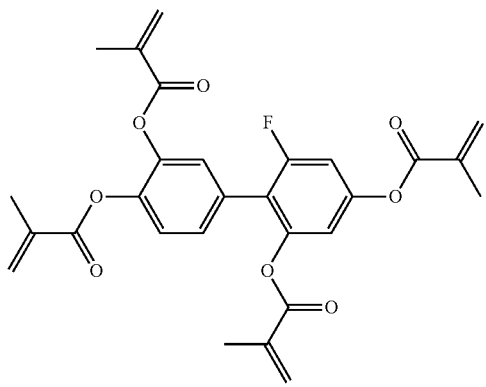

-continued
(1-5-4)
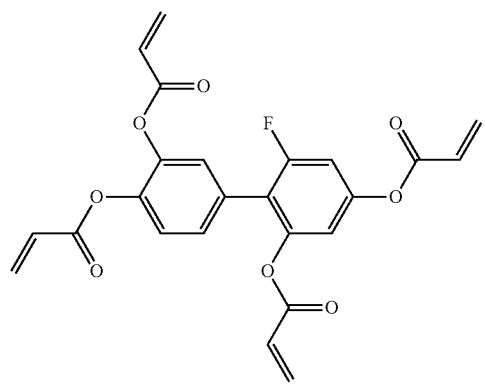
(1-5-5)
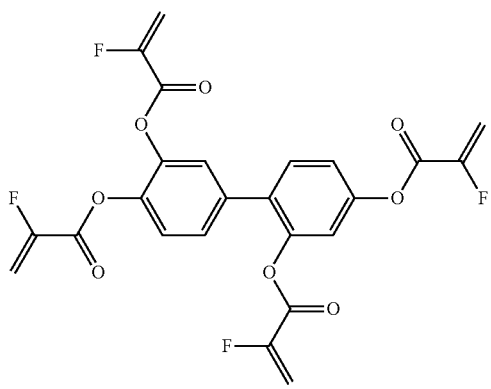
(1-5-6)
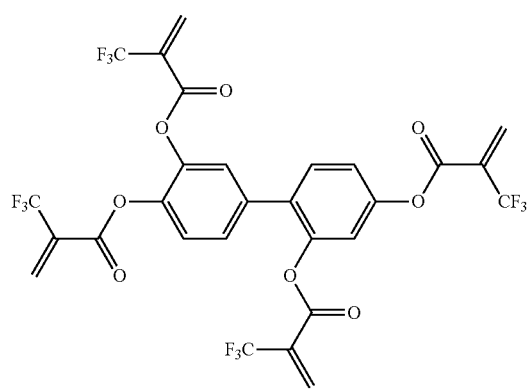
(1-5-7)
(1-5-8)
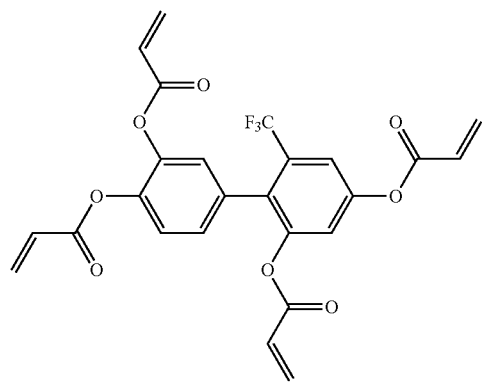
(1-5-9)
(1-5-10)
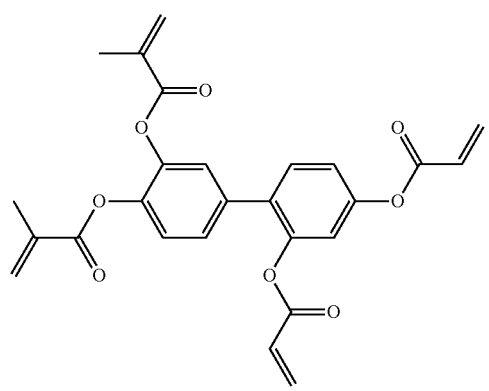
(1-5-11)
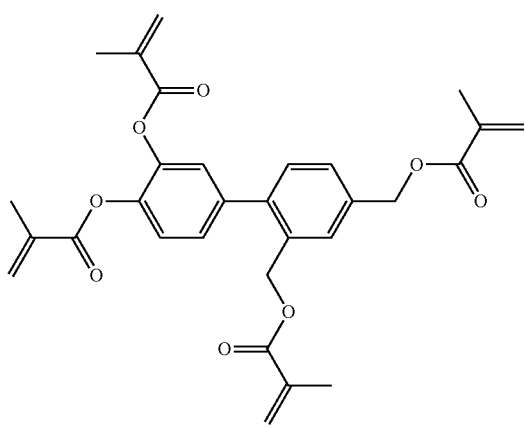

-continued
(1-5-12)
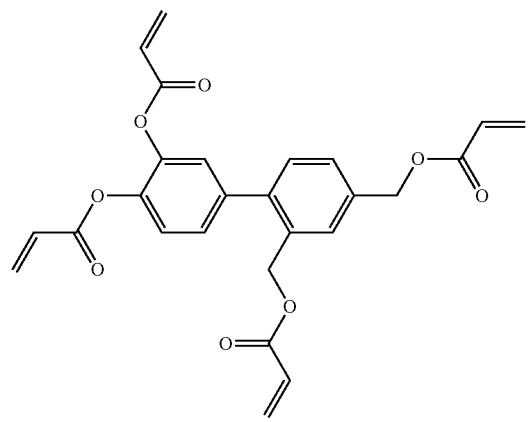
(1-5-13)
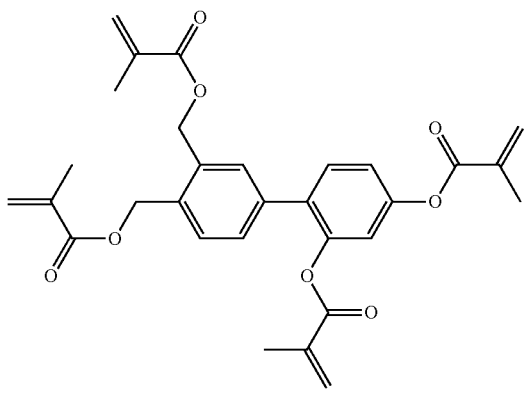
(1-5-14)
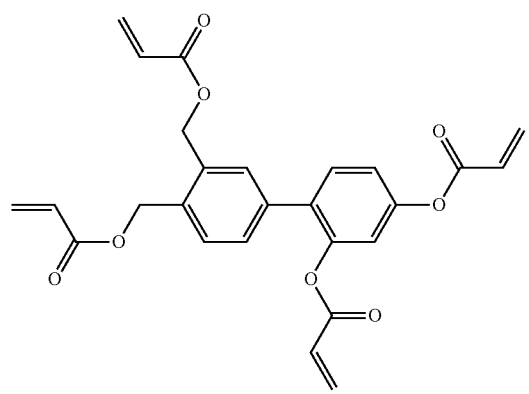
(1-5-15)
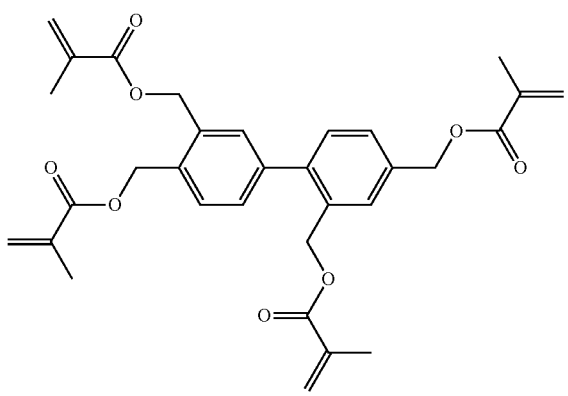
(1-5-16)
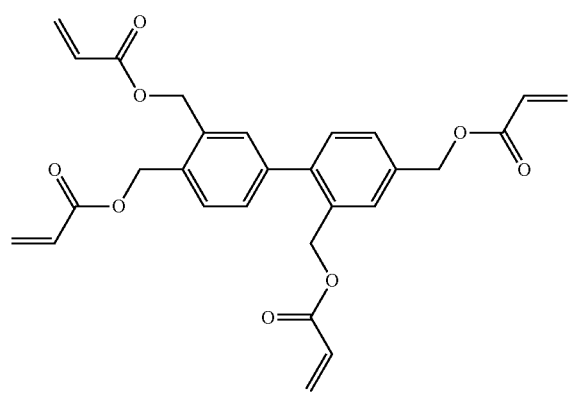
(1-5-17)
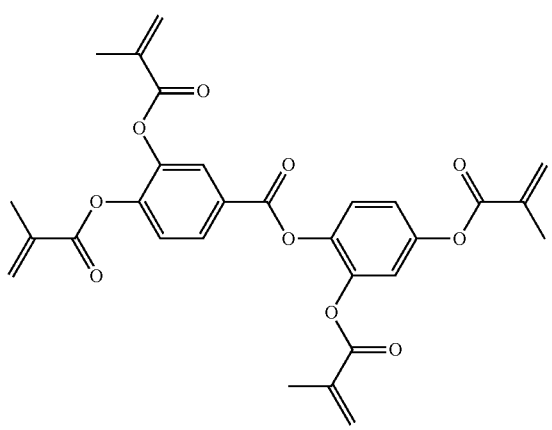

(1-5-18)
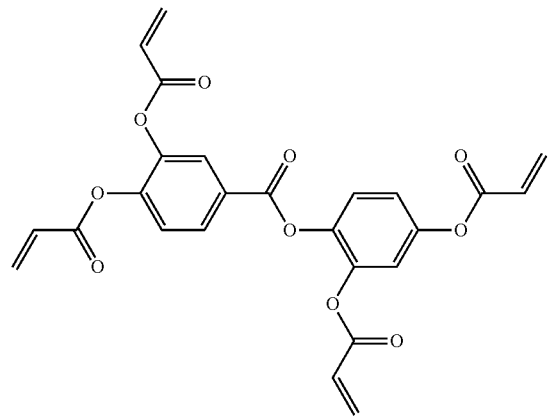
(1-5-19)
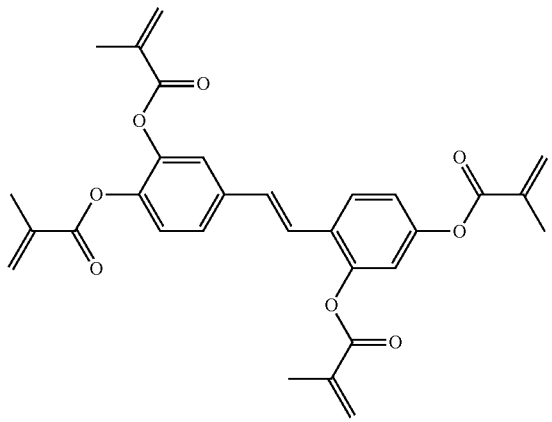
(1-5-20)
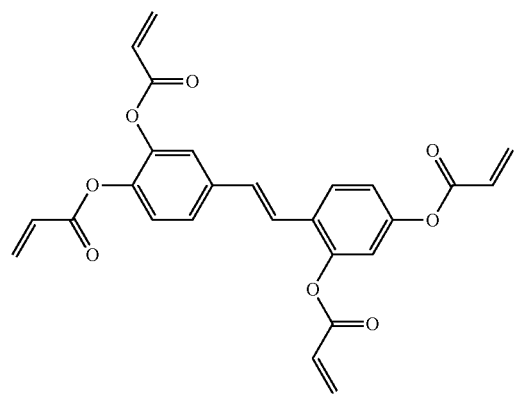
(1-5-21)
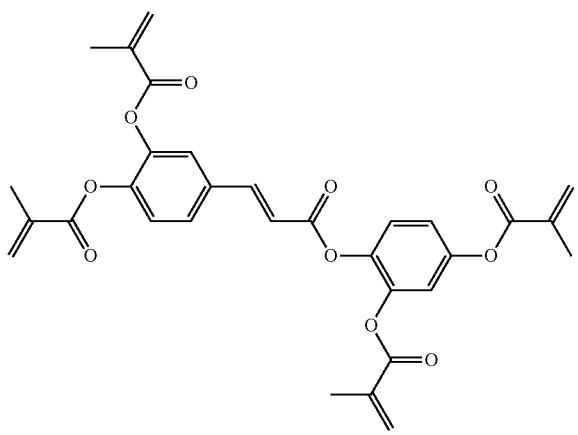
(1-5-22)
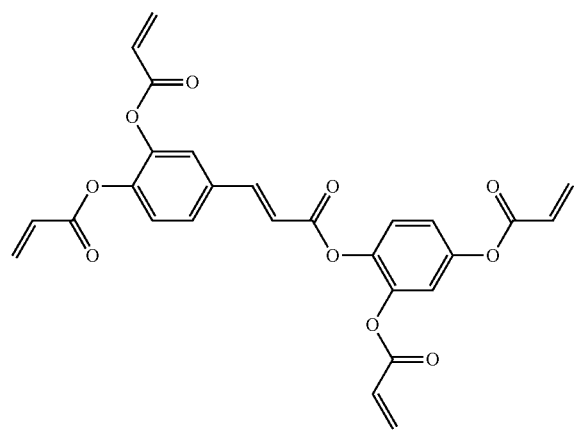
(1-5-23)
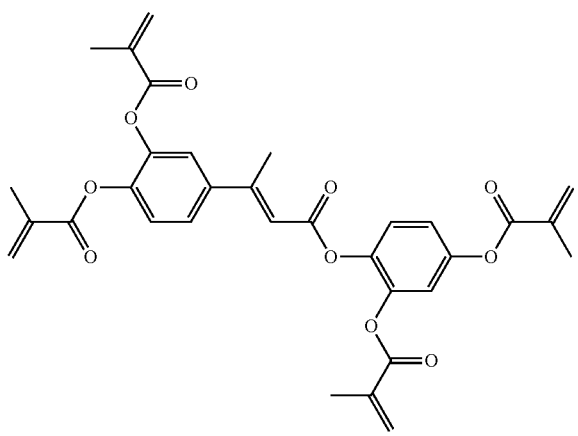

-continued
(1-5-24)
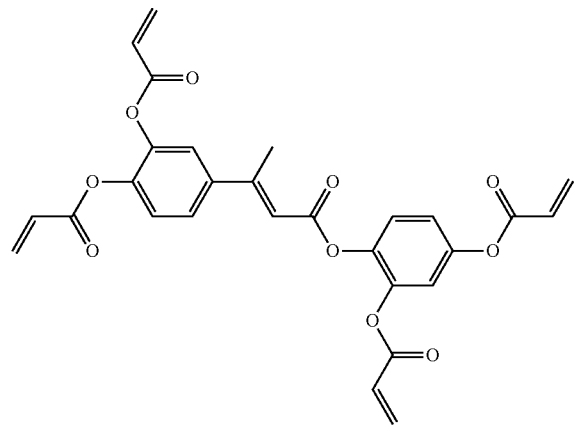
(1-5-25)
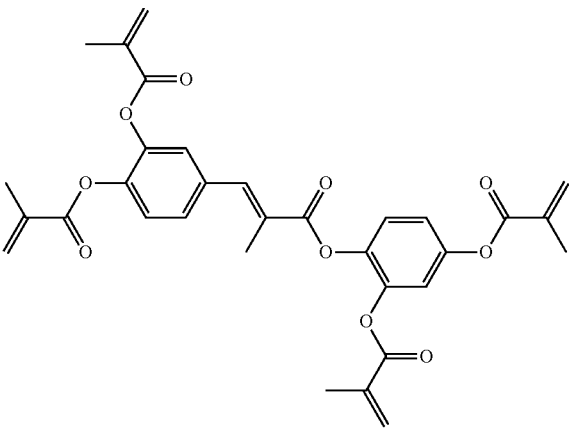
(1-5-26)
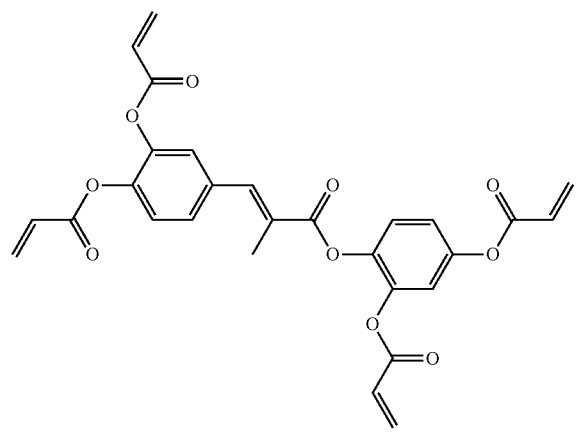
(1-5-27)
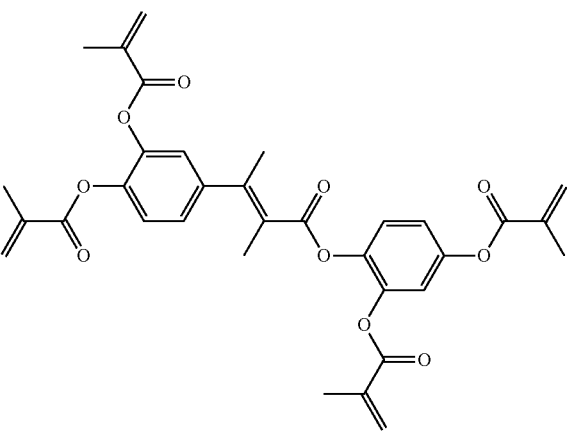
(1-5-28)
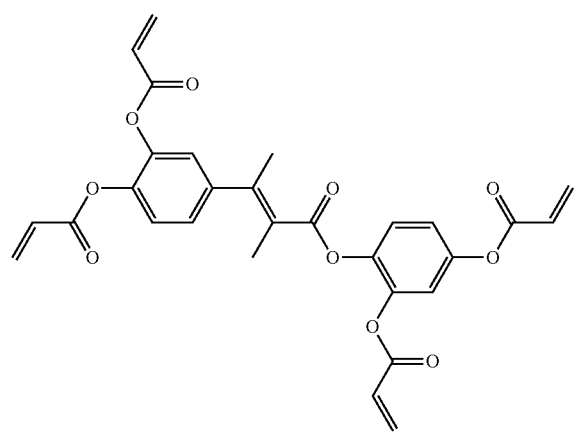
(1-5-29)
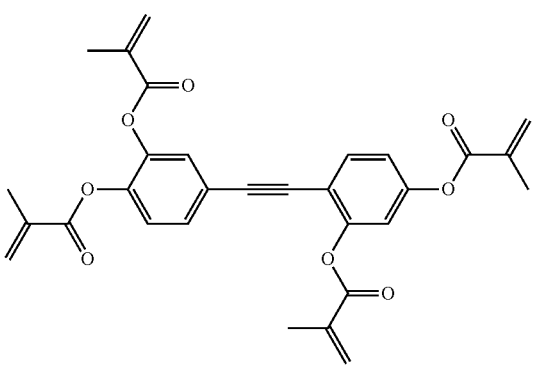

(1-5-30)
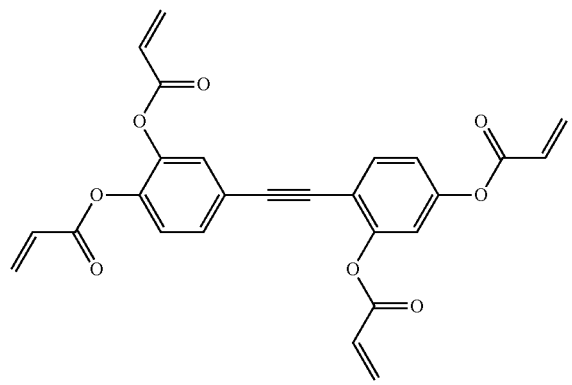
(1-5-31)
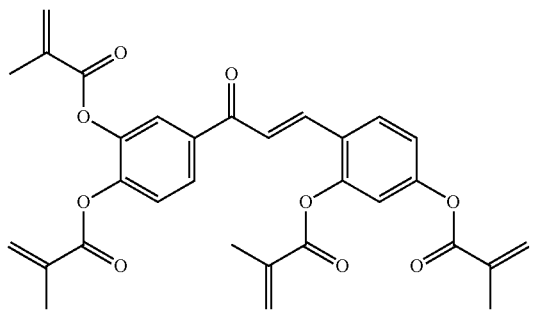
(1-5-32)
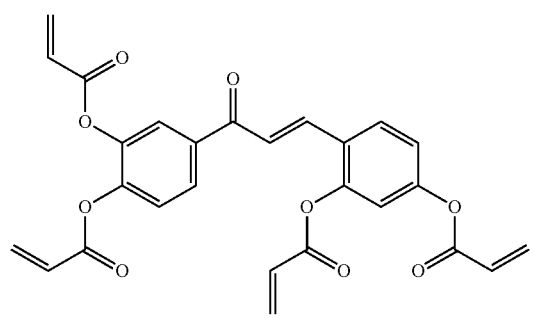
(1-5-33)
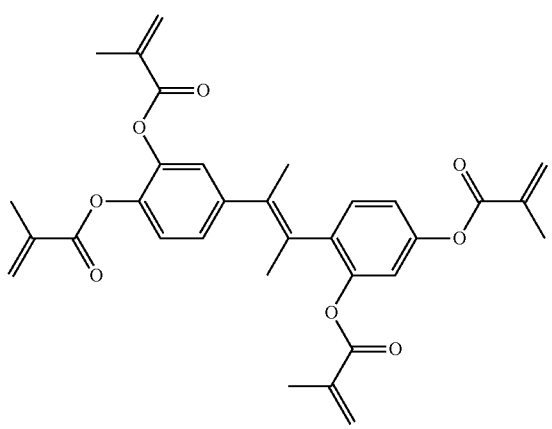
(1-5-34)
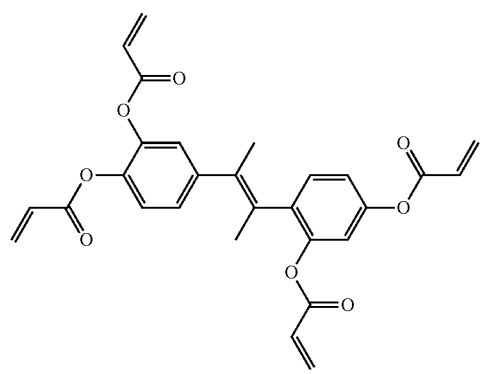
(1-5-35)
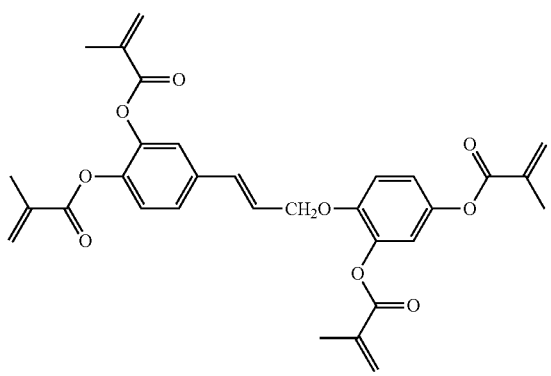
(1-5-36)
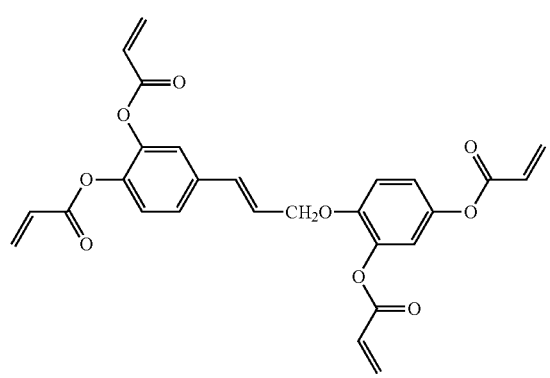
(1-5-37)
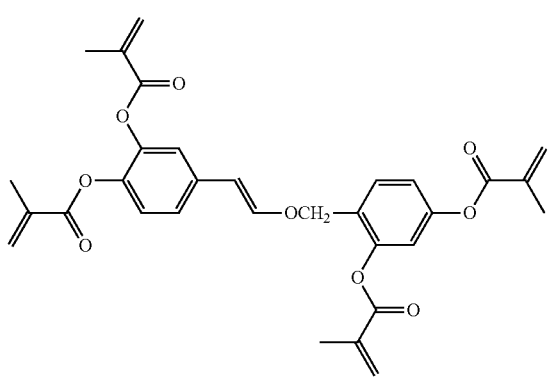

-continued
(1-5-38)
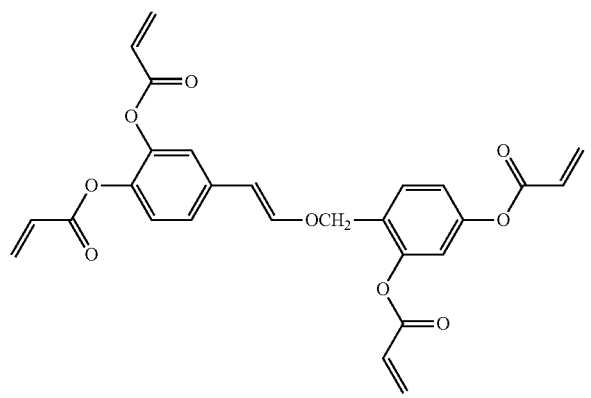
(1-5-39)
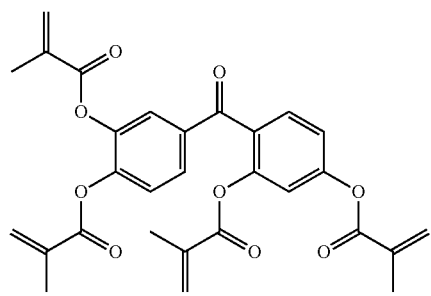
(1-5-40)
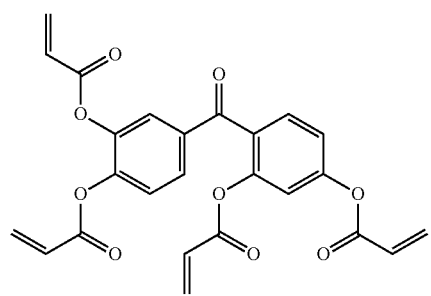
(1-5-41)
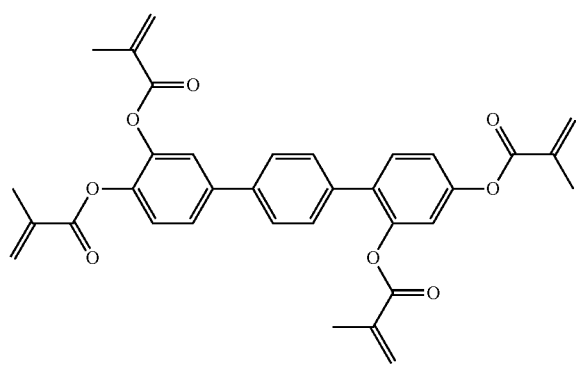
(1-5-42)
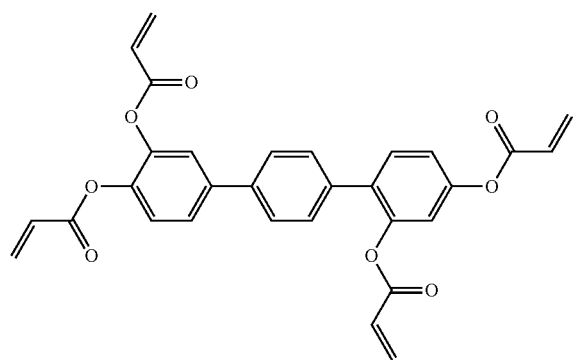
(1-5-43)
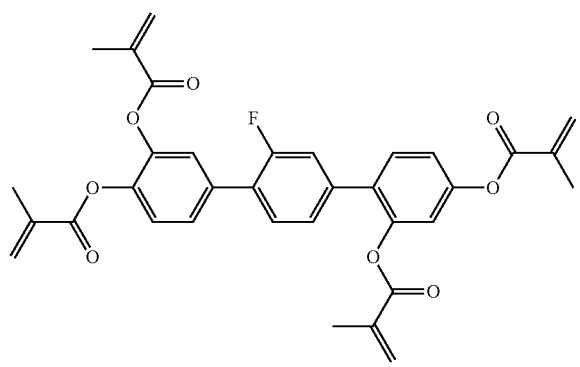
(1-5-44)
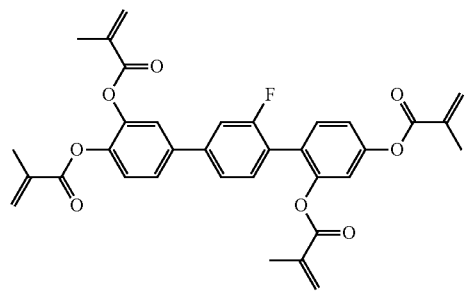
(1-5-45)
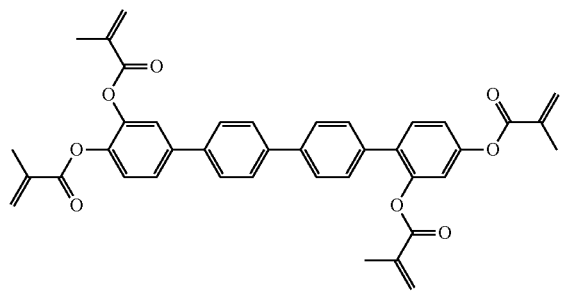

-continued
(1-5-46)
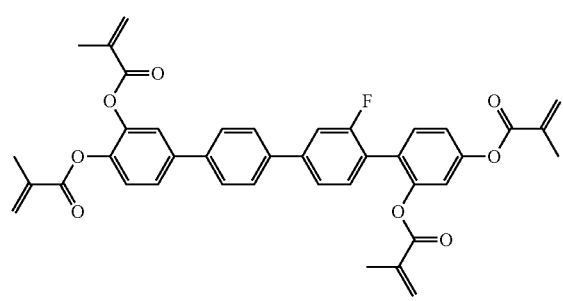
(1-6-1)
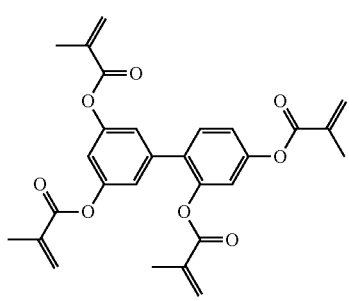
(1-6-2)
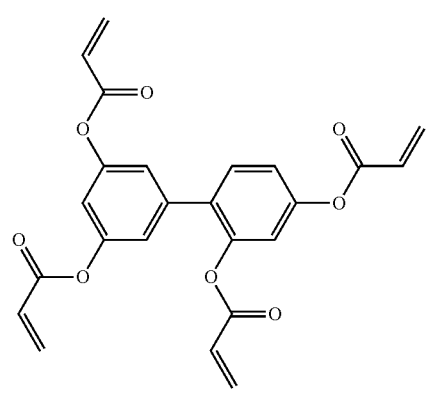
(1-6-3)
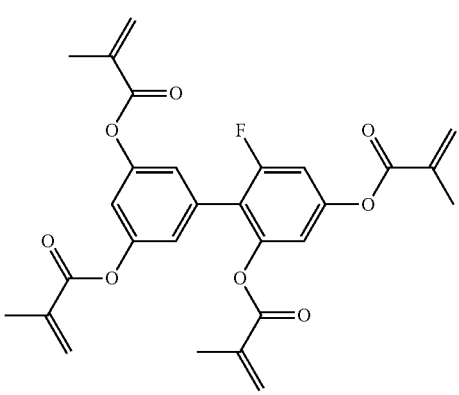
(1-6-4)
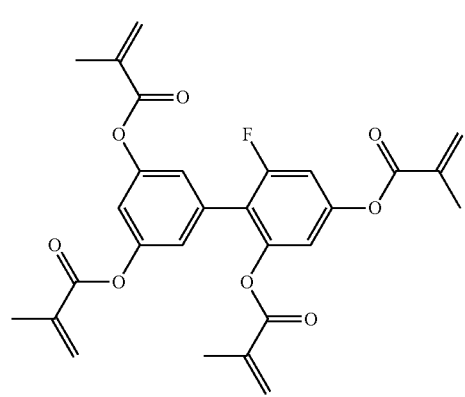
(1-6-5)
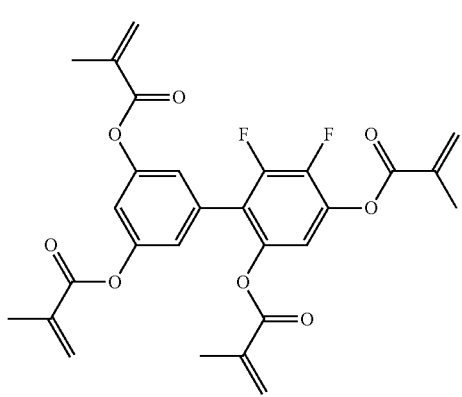
(1-6-6)
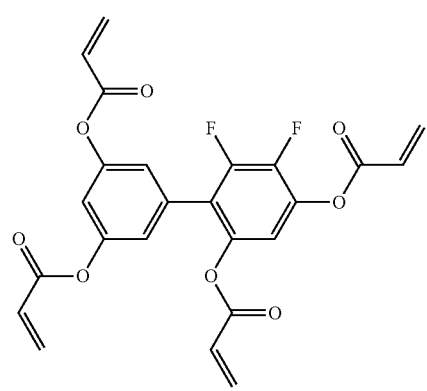
(1-6-7)
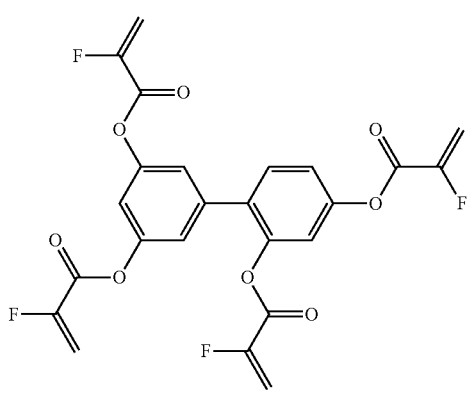

(1-6-8)
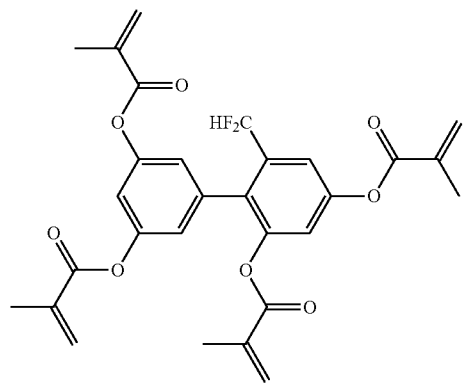
(1-6-9)
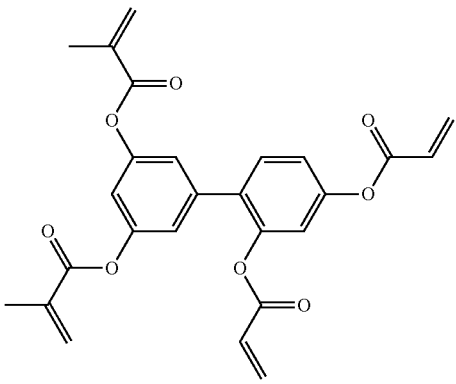
(1-6-10)
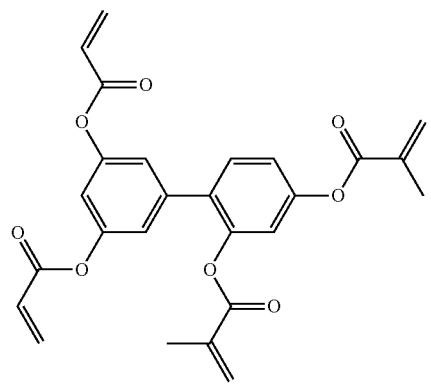
(1-6-11)
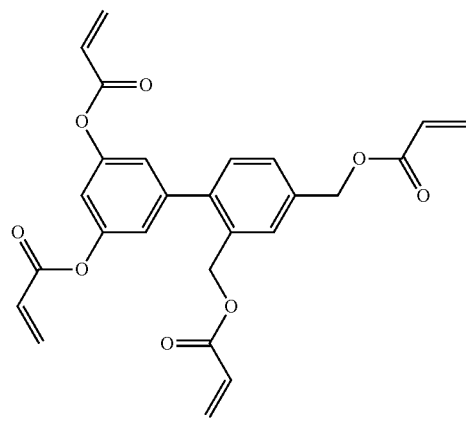
(1-6-12)
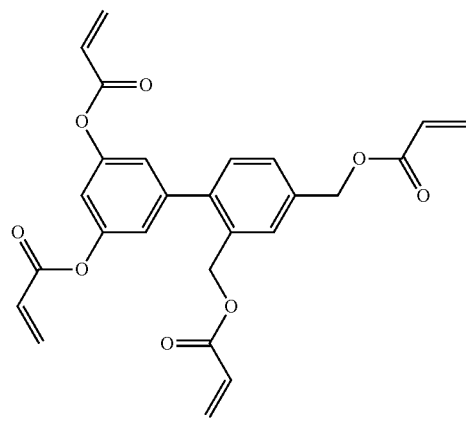
(1-6-13)
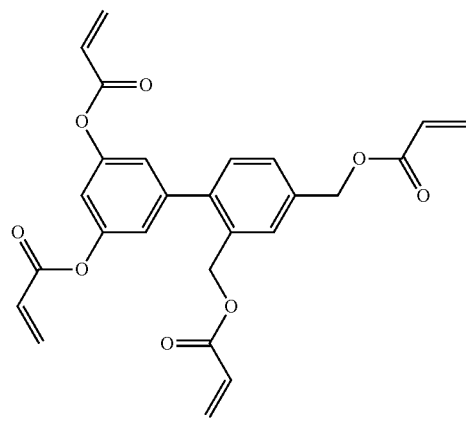
(1-6-14)
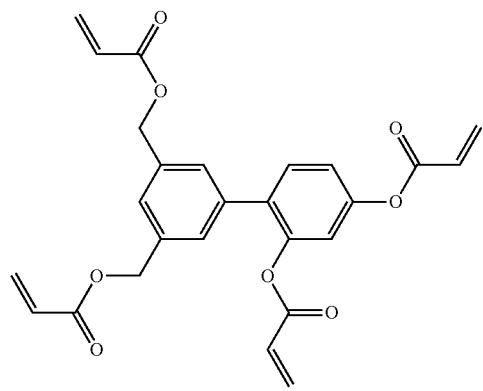
(1-6-15)
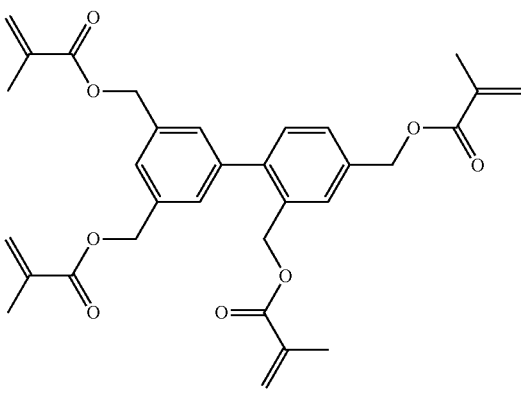

-continued
(1-6-16)
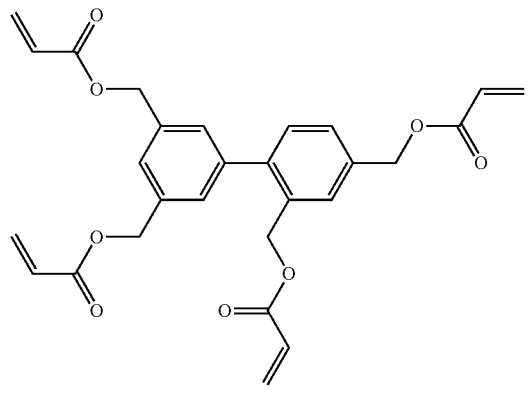
(1-6-17)
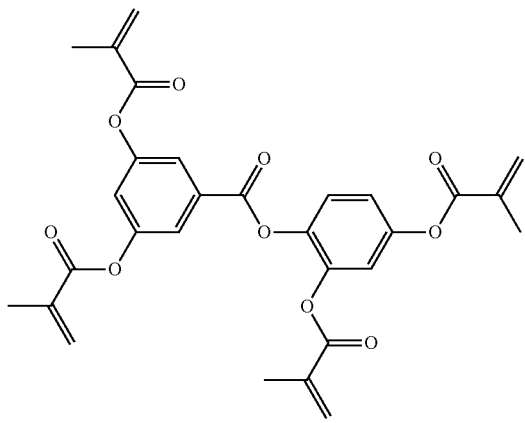
(1-6-18)
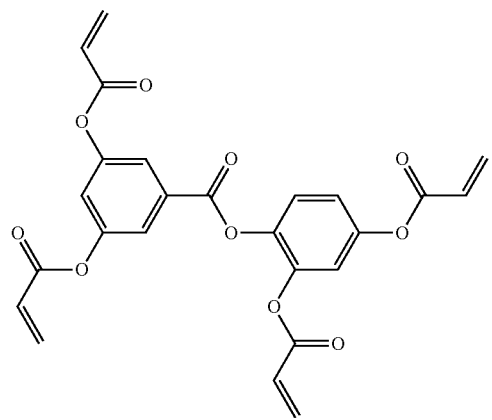
(1-6-19)
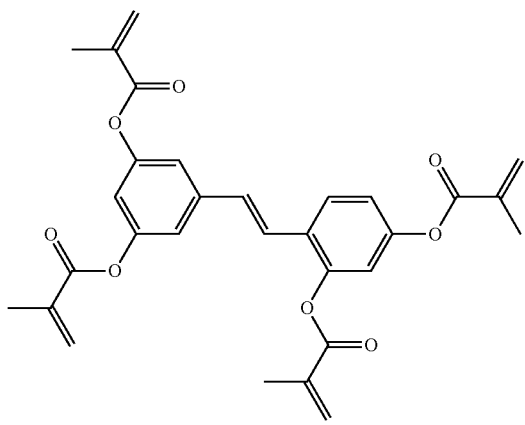
(1-6-20)
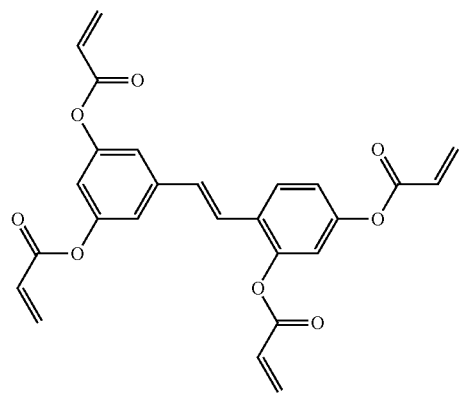
(1-6-21)
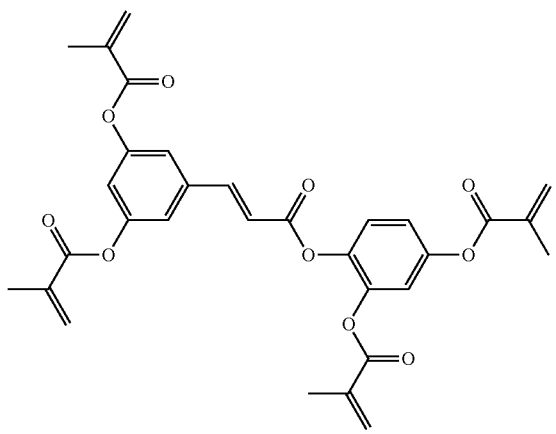

-continued
(1-6-22)
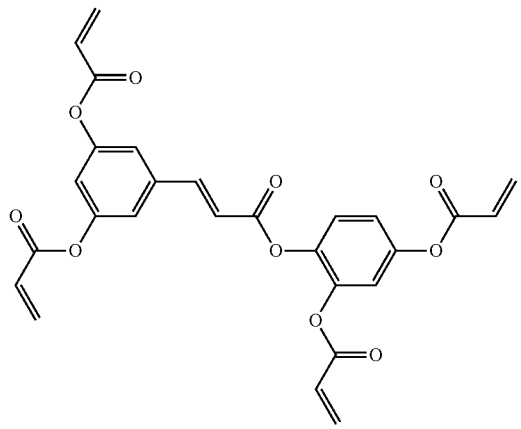
(1-6-23)
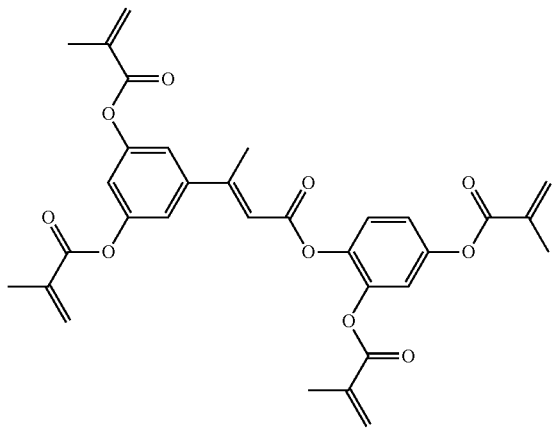
(1-6-24)
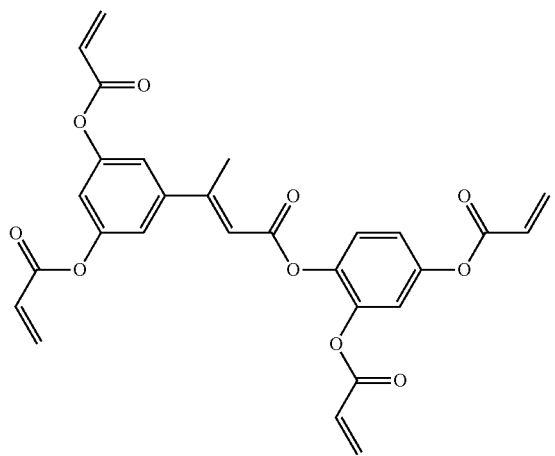
(1-6-25)
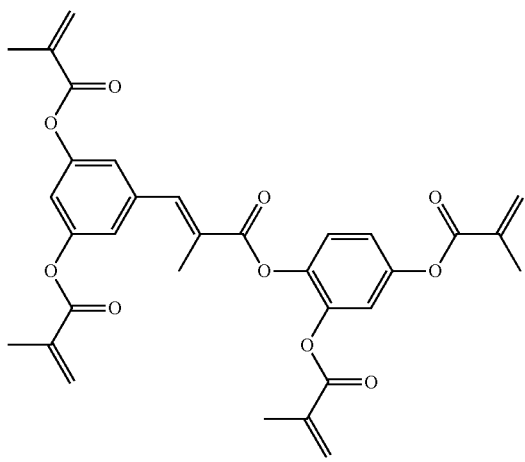
(1-6-26)
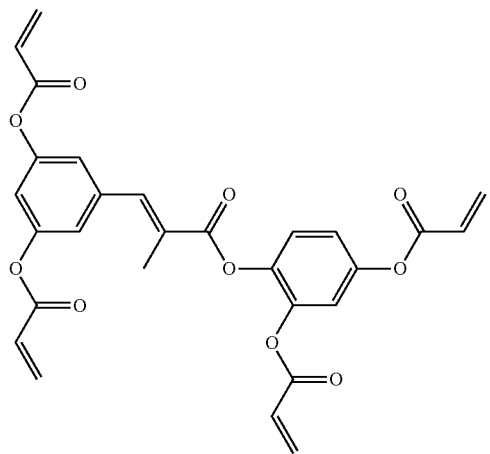
(1-6-27)
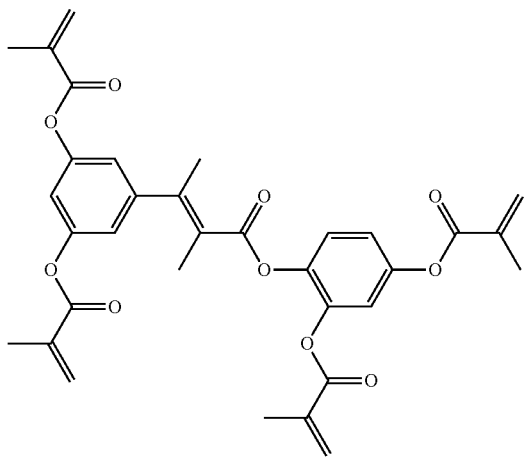

-continued
(1-6-28)
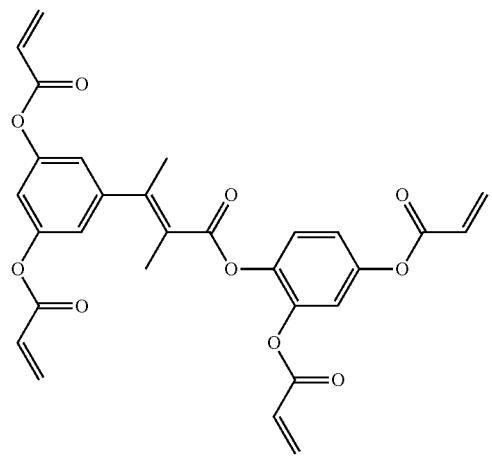
(1-6-29)
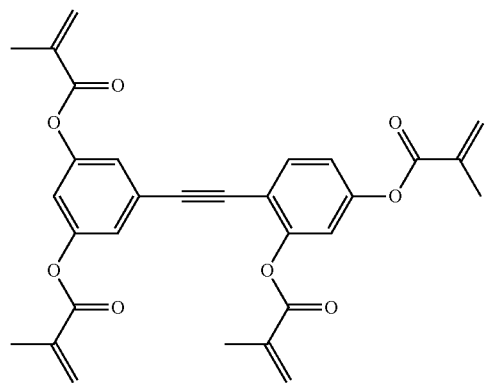
(1-6-30)
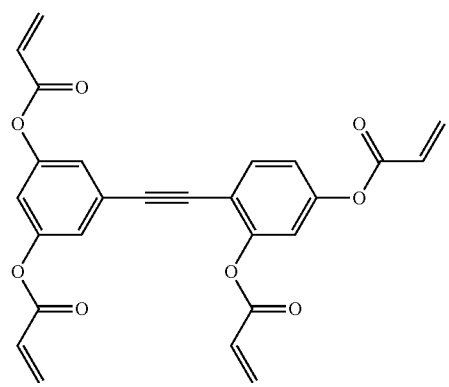
(1-6-31)
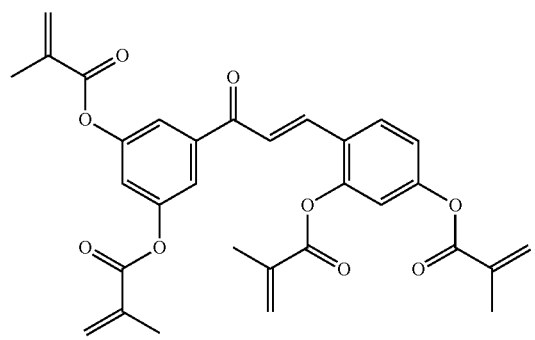
(1-6-32)
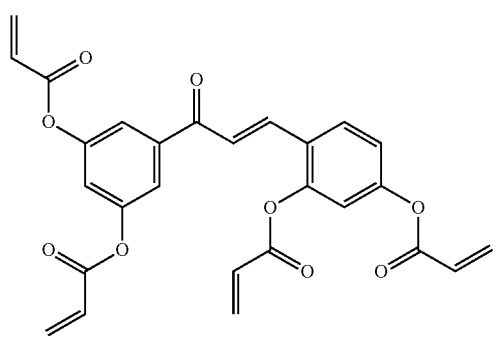
(1-6-33)
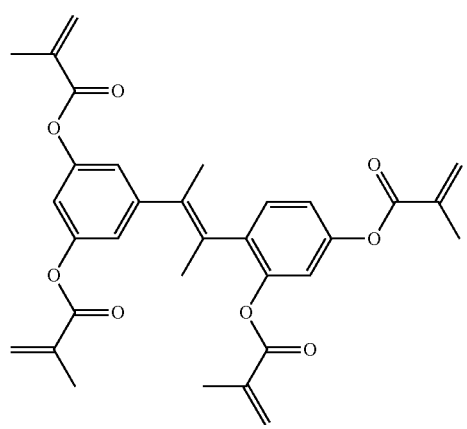

(1-6-34)
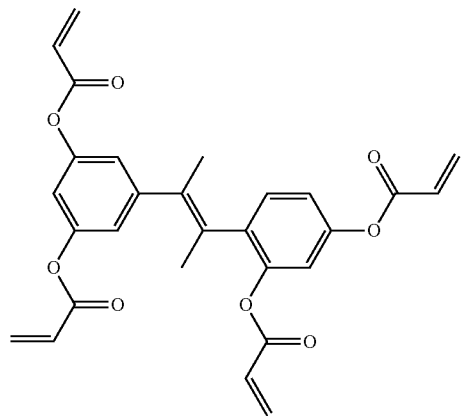
(1-6-35)
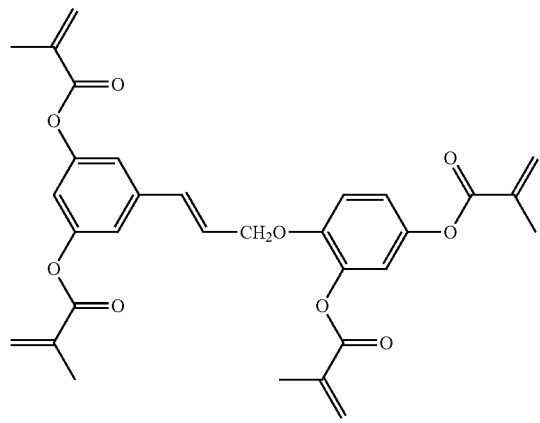
(1-6-36)
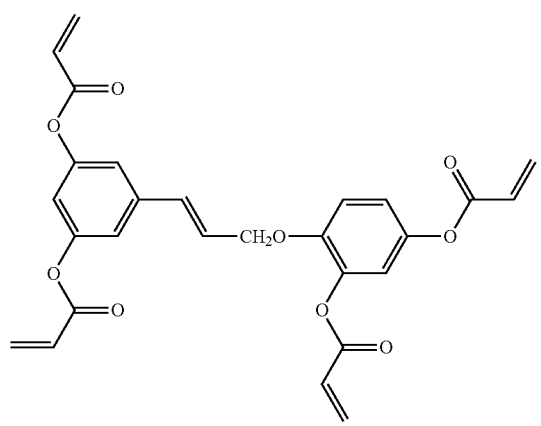
(1-6-37)
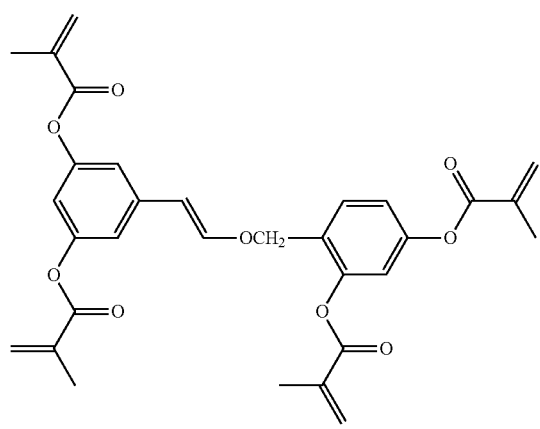
(1-6-38)
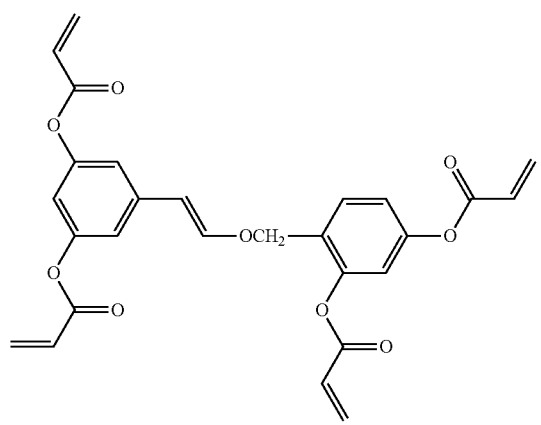
(1-6-39)
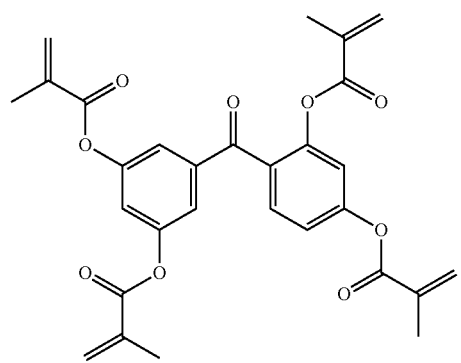

-continued
(1-6-40)
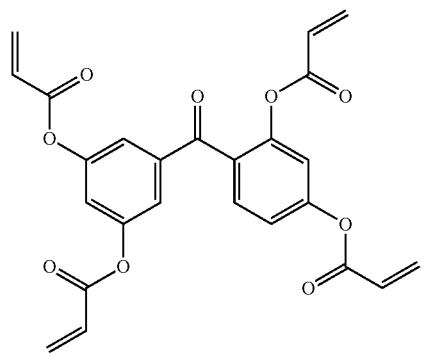
(1-6-41)
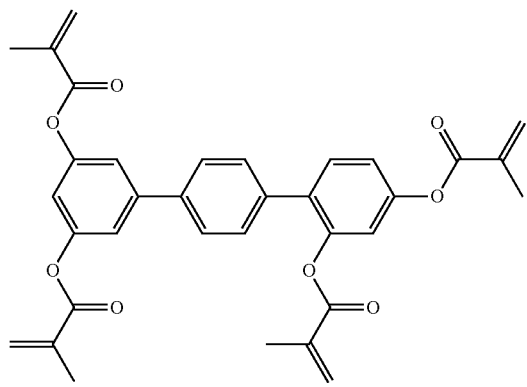
(1-6-42)
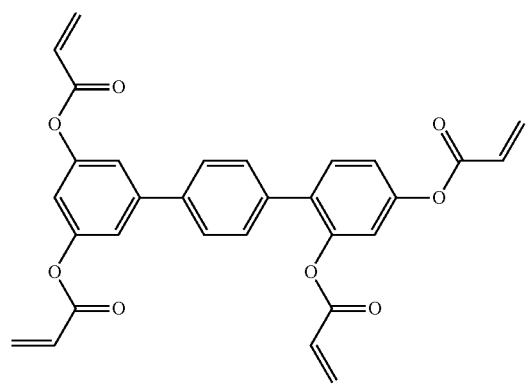
(1-6-43)
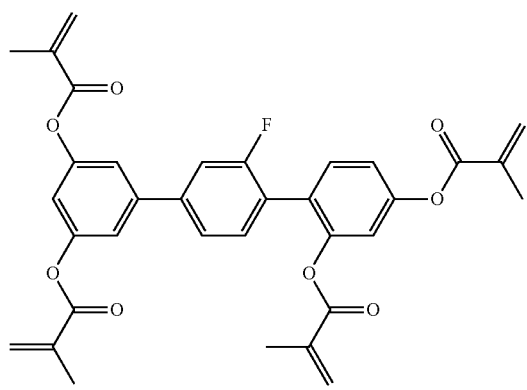
(1-6-44)
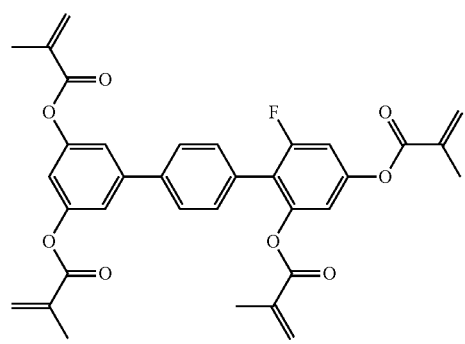
(1-6-45)
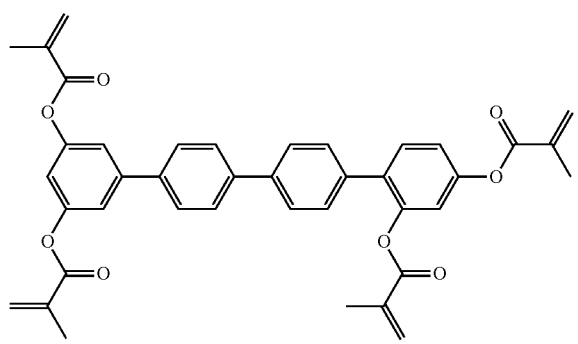
(1-6-46)
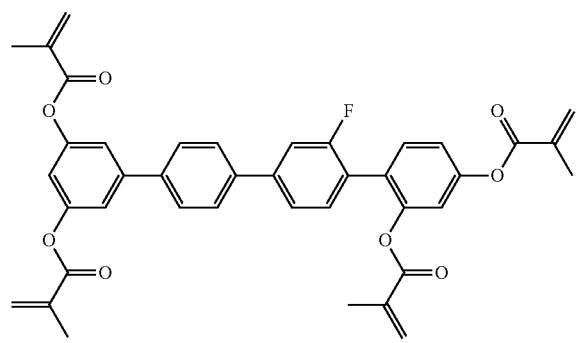
(1-A-1)
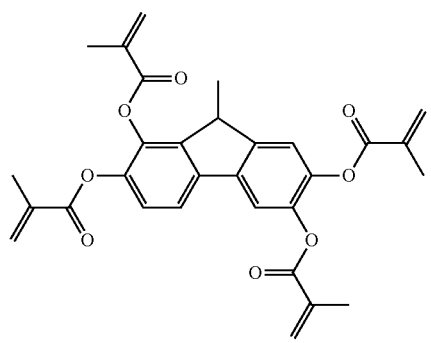

-continued
(1-A-2)
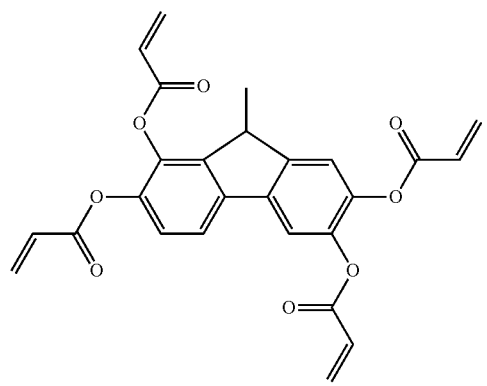
(1-A-3)
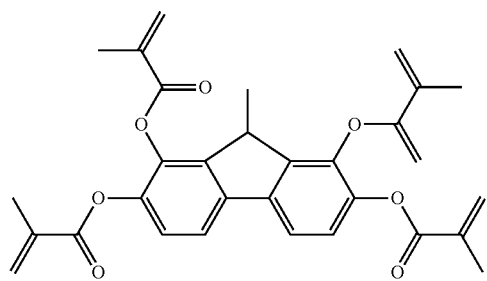
(1-A-4)
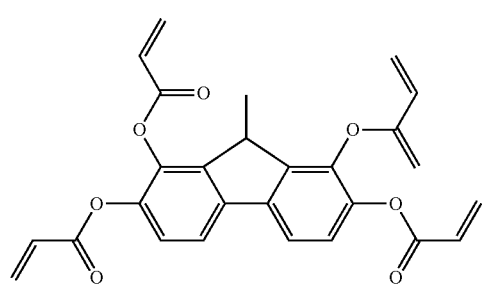
(1-A-5)
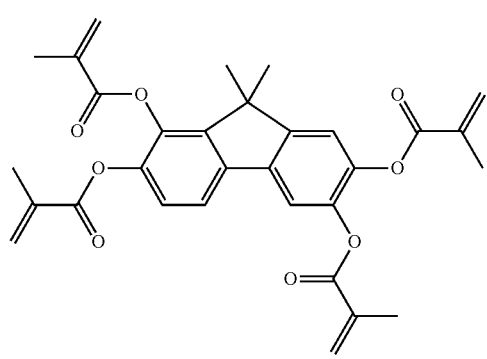
(1-A-6)
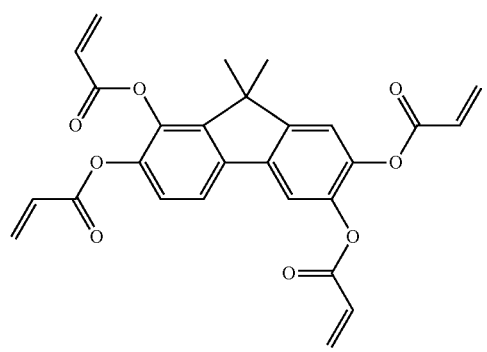
(1-A-7)
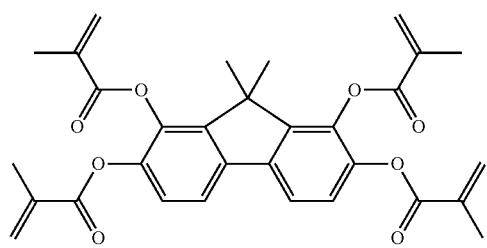
(1-A-8)
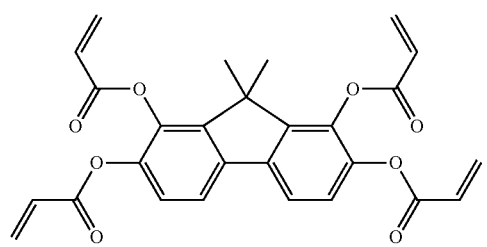
(1-A-9)
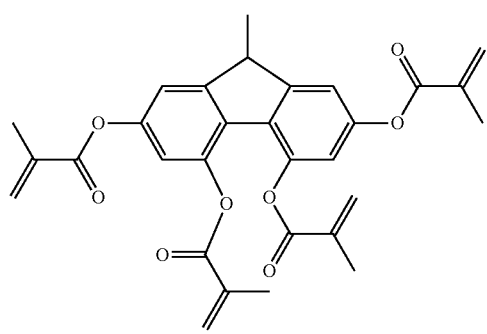

-continued
(1-A-10)
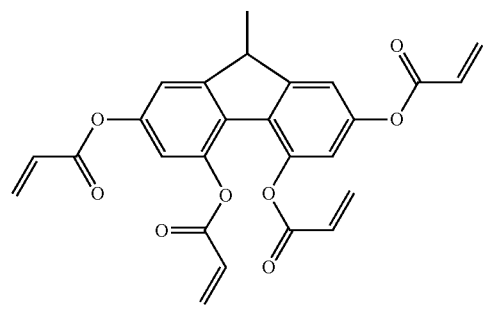
(1-A-11)
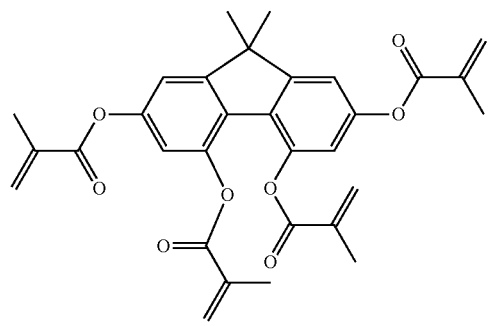
(1-A-12)
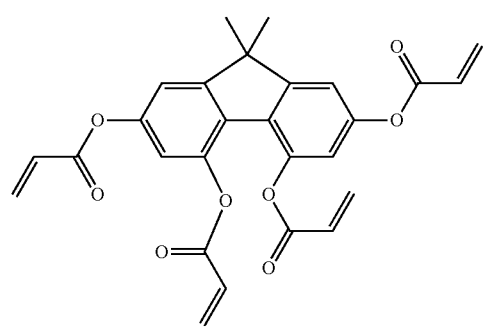
(1-A-13)
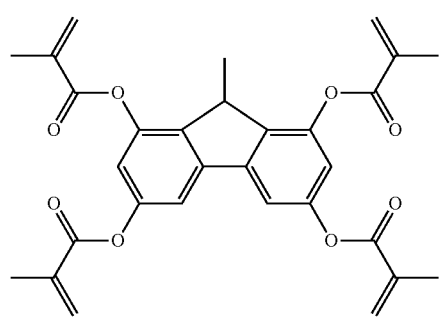
(1-A-14)
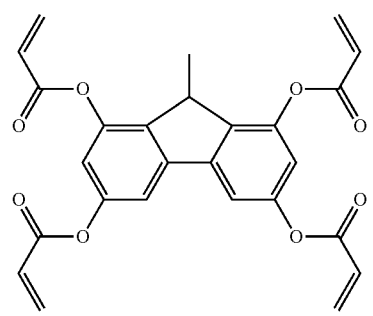
(1-A-15)
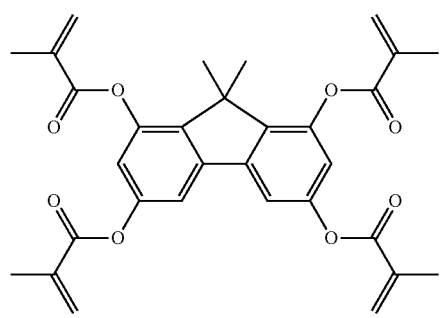
(1-A-16)
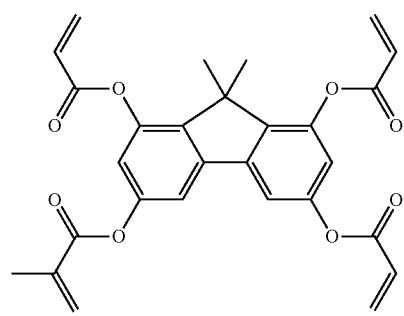
(1-B-1)
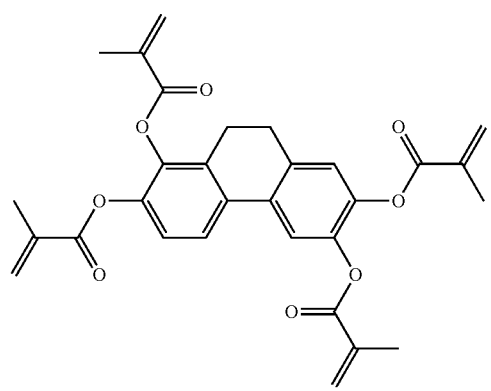

-continued
(1-B-2)
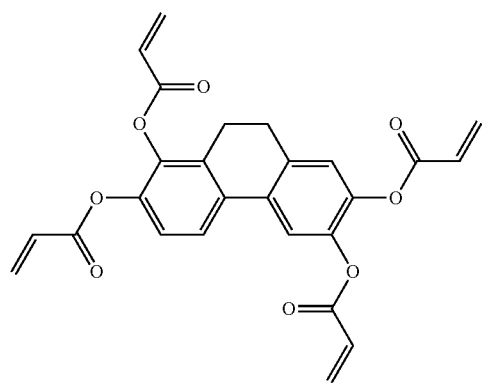
(1-B-3)
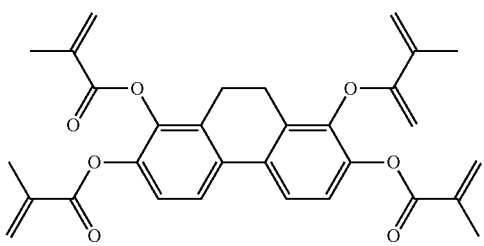
(1-B-4)
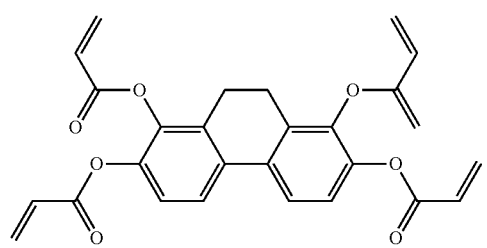
(1-B-5)
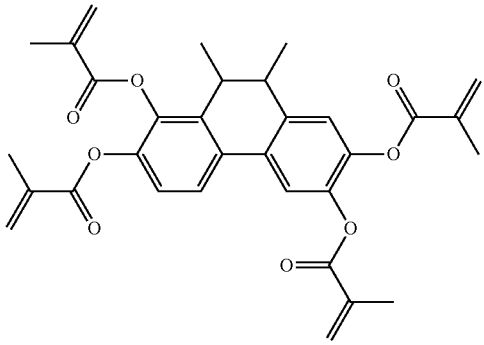
(1-B-6)
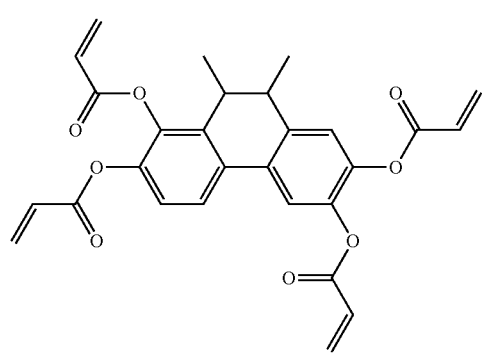
(1-B-7)
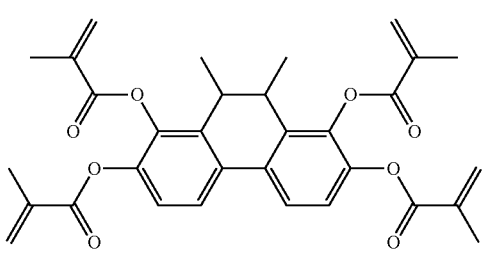
(1-B-8)
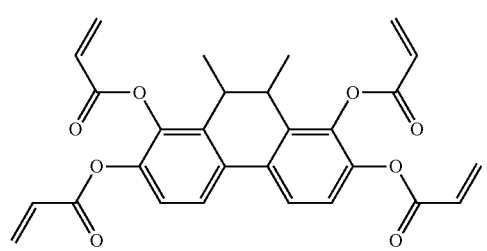
(1-B-9)
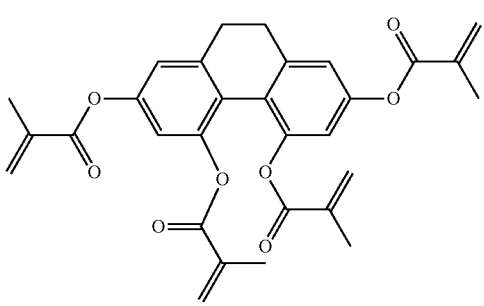

-continued
(1-B-10)
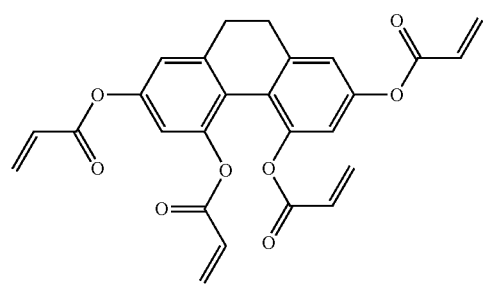
(1-B-11)
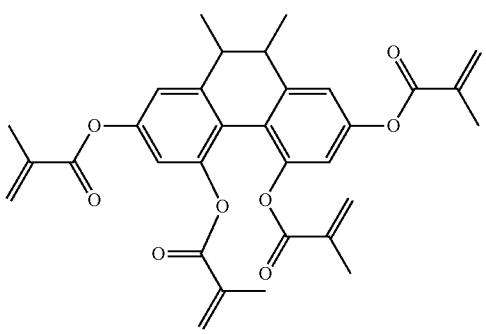
(1-B-12)
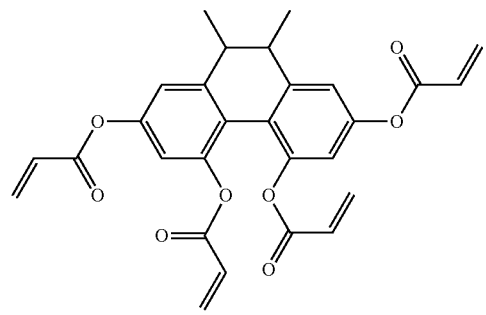
(1-B-13)
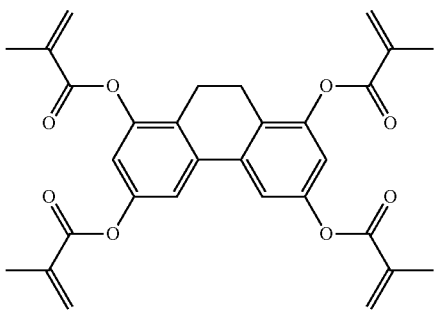
(1-B-14)
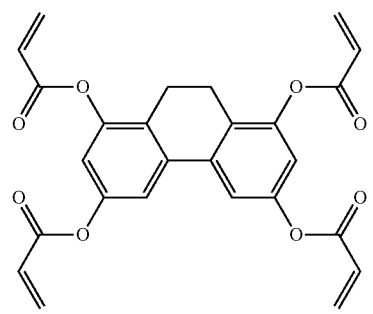
(1-B-15)
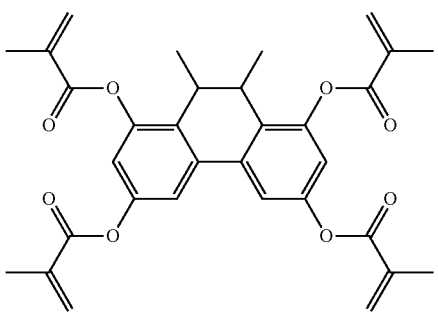
(1-B-16)
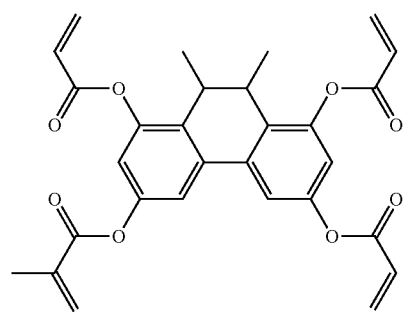

Preparation of Comparative Compounds

Comparative Example 1

Preparation of [1,1'-biphenyl]-4,4'-diyl bis(2-methacrylate) (R-1)

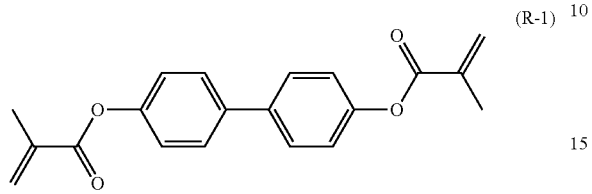

First Step:

Colorless crystals of the comparative compound (R-1) were obtained in the same manner as described in Example 1, except for the replacement of the compound (T-1) with 4-bromophenol.

$^1$H-NMR (DMSO-d; δ ppm): 7.24(d, 4H), 6.96(d, 4H), 6.41(d, 2H), 6.26(d, 2H) and 1.98(s, 6H).

The physical properties of the comparative compound (R-1) were as follows: Melting point: 150° C.; starting temperature of polymerization: 152° C.

Comparative Example 2

Preparation of ([1,1'-biphenyl]-4,4'-diylbis(oxy))bis(ethane-2,1-diyl)bis(2-methacrylate) (R-2)

Preparation of the Compound (S-17)

The compound (S-16) (161 g, 0.845 mol) was added dropwise to a mixture of the compound (S-15) (100 g, 0.768 mol), toluene (300 mL) and pyridine (100 mL) under ice-cooling under an atmosphere of nitrogen, and the stirring was continued at room temperature for 18 hours. Water was added and the mixture was stirred at 40° C. for 4 hours. The reaction solution was extracted with toluene and the organic layer was washed with water and dried over anhydrous magnesium sulfate. The organic solvent was distilled off under reduced pressure to give the compound (S-17) as colorless oil (207 g).

Preparation of the Compound (R-2)

Sodium hydride (55%; 16.8 g, 0.386 mol) was added to a mixture of the compound (S–1) (30.0 g, 0.161 mol) and DMF (200 mL) under an atmosphere of nitrogen, and the stirring was continued at 80° C. for 1 hour. After BHT (5.000 mg, 0.0220 mmol) and DMF (600 mL) had been added to the reaction solution, the compound (S-17) (110 g, 0.387 mol) was added, and the stirring was continued at 60° C. for 4 hours. Water was added to the reaction solution, which was extracted with toluene. The organic layer was washed with water and dried over anhydrous magnesium sulfate. The organic solvent was distilled off under reduced pressure. The residue was purified by silica gel column chromatography (toluene:ethyl acetate=9:1 by volume) and then recrystallized from ethanol to give the comparative compound (R-2) (22.3 g) as colorless crystals.

$^1$H-NMR (DMSO-d; δ ppm): 7.47(d, 4H), 6.98(d, 4H), 6.15(s, 2H), 5.60(t, 2H), 4.52(t, 4H), 4.26(t, 4H) and 1.96(s, 6H).

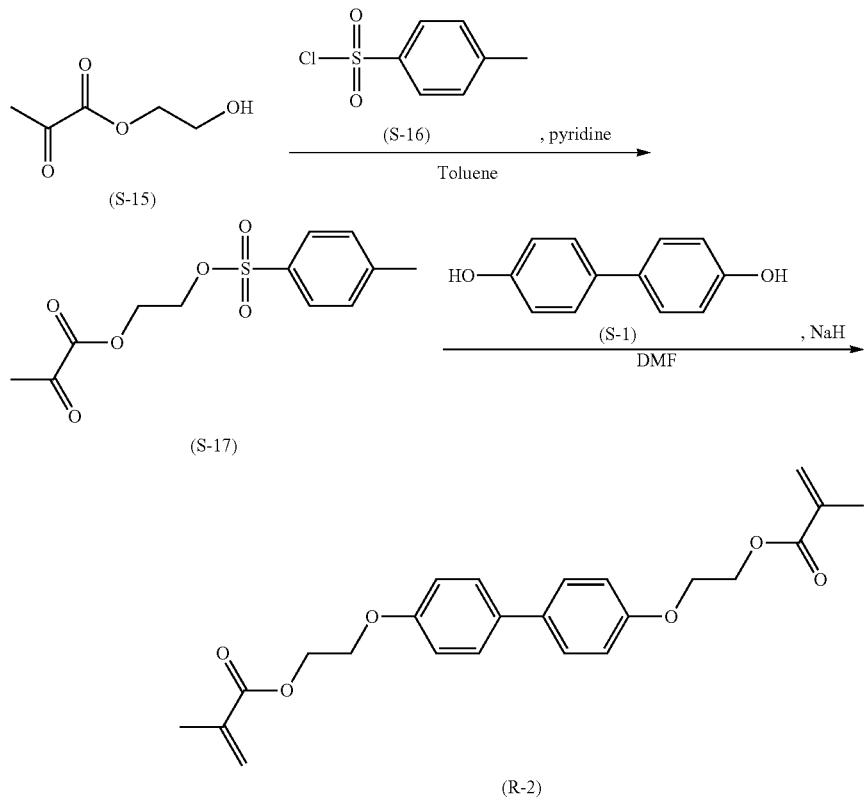

The physical properties of the comparative compound (R-2) were as follows: Melting point: 89° C.; starting temperature of polymerization: 184° C.

Comparative Experiment 1

Comparison of Solubility in a Liquid Crystal Composition

The polymerizable compound (1-1-1), (1-2-1) or (1-3-1) of the invention was added to the liquid crystal composition A described below in the ratio of 0.3% by weight. The mixture was heated at 50° C. for 30 minutes to give a homogeneous solution. After the solution had been allowed to stand under the conditions of Solubility-1 (at room temperature for 2 days) and Solubility-2 (at −20° C. for 10 days), it was observed visually whether or not crystals were deposited. The comparative compound (R-1) or (R-2) was observed in the same way. Table 1 shows the results. In the symbols in Table 1, "o" shows that no crystals were deposited, and "x" shows that crystals were deposited. From Table 1, it is clear that the polymerizable compound of the invention has good solubility in the liquid crystal composition A.

Incidentally, the component of liquid crystal composition A was as follows.

| | | |
|---|---|---|
| 3-H2B (2F, 3F)-O2 | (6-4) | 18% |
| 5-H2B (2F, 3F)-O2 | (6-4) | 17% |
| 3-HH1OCro (7F, 8F)-5 | (10-6) | 6% |
| 3-HBB (2F, 3F)-O2 | (7-7) | 10% |
| 4-HBB (2F, 3F)-O2 | (7-7) | 6% |
| 5-HBB (2F, 3F)-O2 | (7-7) | 6% |
| 2-HH-3 | (12-1) | 14% |
| 3-HH-4 | (12-1) | 8% |
| 3-HHB-1 | (13-1) | 5% |
| 3-HHB-3 | (13-1) | 6% |
| 3-HHB-O1 | (13-1) | 4% |

TABLE 1

Comparison of solubility in a liquid crystal composition

| Polymerizable compound | Structural formula | Solubility-1 (room temp., 2 days) | Solubility-2 (−20° C., 10 days) |
|---|---|---|---|
| Compound (1-1-1) | | o | o |
| Compound (1-2-1) | | o | o |

TABLE 1-continued

Comparison of solubility in a liquid crystal composition

| Polymerizable compound | Structural formula | Solubility-1 (room temp., 2 days) | Solubility-2 (−20° C., 10 days) |
|---|---|---|---|
| Compound (1-3-1) | (structure) | O | O |
| Comparative compound (R-1) | (structure) | X | X |
| Comparative compound (R-2) | (structure) | O | O |

Comparative Experiment 2

Unreacted Polymerizable Compound

The polymerizable compound (1-1-1) or (1-3-1) was added and dissolved to the liquid crystal composition A described above in the ratio of 0.3% by weight. The solution was irradiated with ultraviolet light of 11 mW/cm² for 273 seconds. A mercury-xenon lamp, Execure 4000-D made by Hoya Candeo Optronics Corp. was used for irradiation with ultraviolet light. The amount of the polymerizable compound remained in the solution was measured by HPLC. On the other hand, the amount of unreacted polymerizable compound remained in the liquid crystal composition A was measured for the comparative compound (R-2) in the same way. Table 2 shows the results.

TABLE 2

Unreacted polymerizable compound

| Compound | Structural formula | unreacted reactant (% by weight) |
|---|---|---|
| Compound (1-1-1) | | 0.02 |
| Compound (1-3-1) | | 0.07 |
| Comparative compound (R-2) | | 0.20 |

It is found from Table 2 that in the polymerizable compound of the invention, the amount of unreacted reactant is small in comparison with that of the comparative compound. Accordingly, it can be said that the compound (1) has a high conversion yield in the polymerization. It is concluded from the results on Table 1 and Table 2 that the polymerizable compound (1-1-1) has a higher conversion yield than the comparative compound and is excellent in compatibility with another liquid crystal compound.

2. Examples of the Liquid Crystal Composition

The compounds described in Examples were expressed in terms of symbols according to the definition in Table 3 described below. In Table 3, the configuration of 1,4-cyclohexylene is trans. The parenthesized number next to the symbols in Example indicates the number of the compound. The symbol (-) means other liquid crystal compound. The contents (percentage) of liquid crystal compounds mean the percentages by weight (% by weight) based on the total weight of the liquid crystal compounds. Last, the values of physical properties of the composition were summarized. The physical properties were measured according to the method described above, and measured values themselves were reported (without extrapolation).

TABLE 3

Method of Description of Compound using Symbols
$R-(A_1)-Z_1-...-Z_n-(A_n)-R'$

| 1) Left-terminal Group R— | Symbol |
|---|---|
| $C_nH_{2n+1}-$ | n- |
| $C_nH_{2n+1}O-$ | nO— |
| $C_mH_{2m+1}OC_nH_{2n}-$ | mOn— |
| $CH_2=CH-$ | V— |
| $C_nH_{2n+1}-CH=CH-$ | nV— |
| $CH_2=CH-C_nH_{2n}-$ | Vn— |
| $C_mH_{2m+1}-CH=CH-C_nH_{2n}-$ | mVn— |

TABLE 3-continued

Method of Description of Compound using Symbols
R—(A₁)—Z₁—...—Zₙ—(Aₙ)—R'

| | |
|---|---|
| CF₂=CH— | VFF— |
| CF₂=CH—CₙH₂ₙ— | VFFn— |

| 2) Right-terminal Group —R' | Symbol |
|---|---|
| —CₙH₂ₙ₊₁ | -n |
| —OCₙH₂ₙ₊₁ | —On |
| —COOCH₃ | —EMe |
| —CH=CH₂ | —V |
| —CH=CH—CₙH₂ₙ₊₁ | —Vn |
| —CₙH₂ₙ—CH=CH₂ | —nV |
| —CₘH₂ₘ—CH=CH—CₙH₂ₙ₊₁ | —mVn |
| —CH=CF₂ | —VFF |
| —F | —F |
| —Cl | —CL |
| —OCF₃ | —OCF3 |
| —OCF₂H | —OCF2H |
| —CF₃ | —CF3 |
| —CF=CH—CF₃ | —FVCF3 |
| —C≡N | —C |

| 3) Bonding Group —Zₙ— | Symbol |
|---|---|
| —CₙH₂ₙ— | n |
| —COO— | E |
| —CH=CH— | V |
| —CH₂O— | 1O |
| —OCH₂— | O1 |
| —CF₂O— | X |
| —C≡C— | T |

| 4) Ring Structure —Aₙ— | Symbol |
|---|---|
| 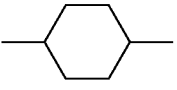 | H |
|  | B |
| 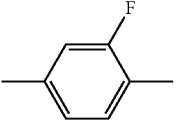 | B(F) |
| 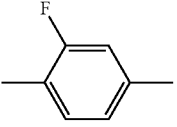 | B(2F) |
| 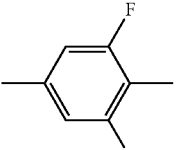 | B(F,F) |
| 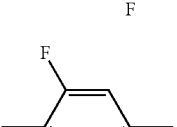 | B(2F,5F) |
| 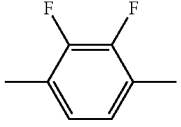 | B(2F,3F) |
| 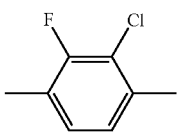 | B(2F,3CL) |
| 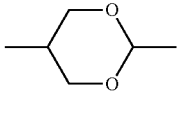 | G |
| 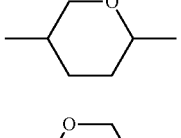 | dh |
| 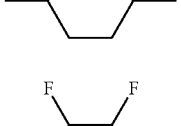 | Dh |
| 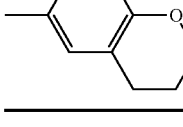 | Cro(7F,8F) |

5) Examples of Description

Example 1. 3-BB(F,F)XB(F,F)—F

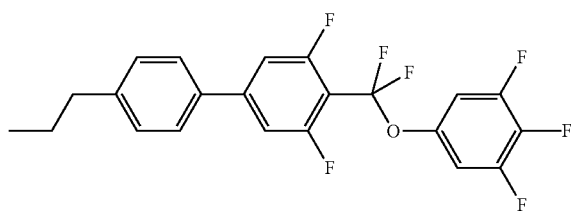

Example 2. 3HBB(2F,3F)—O2

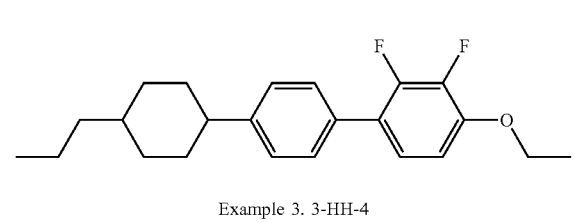

Example 3. 3-HH-4

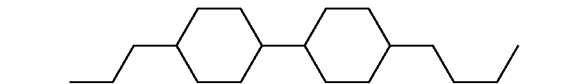 [SMILES: CCCCC1CCC(C2CCC(CCC)CC2)CC1]

TABLE 3-continued

Method of Description of Compound using Symbols
R—(A$_1$)—Z$_1$—...—Z$_n$—(A$_n$)—R'

Example 4. 3HBB(F,F)—F

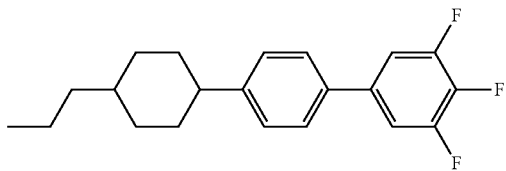 [SMILES: CCCC1CCC(c2ccc(-c3cc(F)c(F)c(F)c3)cc2)CC1]

Example 6

| | | |
|---|---|---|
| 3-HBB (F, F) XB (F, F)-F | (4-38) | 10% |
| 4-BB (F) B (F, F) XB (F, F)-F | (4-47) | 8% |
| 5-BB (F) B (F, F) XB (F, F)-F | (4-47) | 3% |
| 3-HH-O1 | (12-1) | 3% |
| 3-HH-V | (12-1) | 39% |
| 3-HH-V1 | (12-1) | 6% |
| V-HHB-1 | (13-1) | 5% |
| 1-BB (F) B-2V | (13-6) | 5% |
| 5-HBB (F) B-2 | (14-5) | 4% |
| 3-HXB (F, F)-F | (2-13) | 4% |
| 3-HHXB (F, F)-CF3 | (3-100) | 6% |
| 3-BB (F, F) XB (F, F)-F | (3-97) | 7% |
| 3-BB (F, F) XB (F, F)-F | (3-97) | 6% |
| 3-GB (F, F) XB (F, F)-F | (3-118) | 5% |
| 3-HHBB (F, F)-F | (4-6) | 3% |

The following compound (1-2-1) was added in the ratio of 0.3% by weight based on the preceding composition.

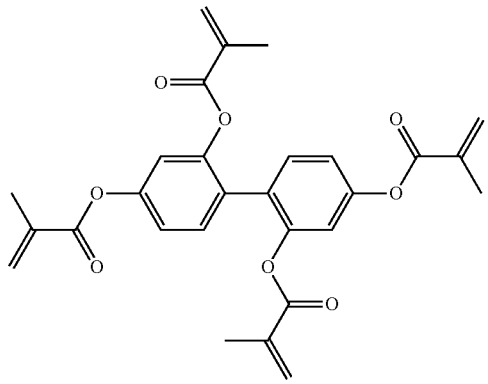

(1-2-1)

NI=75.6° C.; Δn=0.105; Δ∈=6.7; η=13.6 mPa·s.

Example 7

| | | |
|---|---|---|
| 5-HB (F) B (F, F) XB (F, F)-F | (4-41) | 5% |
| 3-BB (F) B (F, F) XB (F, F)-F | (4-47) | 4% |
| 4-BB (F) B (F, F) XB (F, F)-F | (4-47) | 7% |
| 3-GB (F) B (F, F) XB (F, F)-F | (4-56) | 3% |
| 3-HH-V | (12-1) | 36% |
| 3-HH-V1 | (12-1) | 7% |
| 3-HHEH-5 | (13-13) | 3% |
| 3-HHB-1 | (13-1) | 4% |
| V-HHB-1 | (13-1) | 9% |
| V2-BB (F) B-1 | (13-6) | 5% |
| 1V2-BB-F | (12-8) | 3% |

The following compound (1-1-1) was added in the ratio of 0.4% by weight based on the preceding composition.

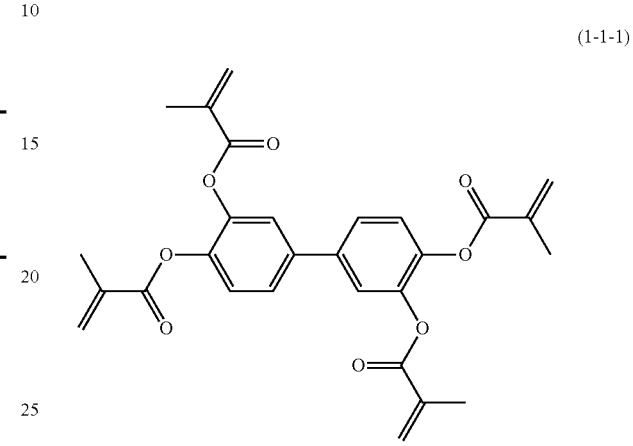

(1-1-1)

NI=85.9° C.; Δn=0.106; Δ∈=7.2; η=15.3 mPa·s.

Example 8

| | | |
|---|---|---|
| 5-HB-F | (2-2) | 12% |
| 6-HB-F | (2-2) | 9% |
| 7-HB-F | (2-2) | 7% |
| 2-HHB-OCF3 | (3-1) | 7% |
| 3-HHB-OCF3 | (3-1) | 7% |
| 4-HHB-OCF3 | (3-1) | 7% |
| 5-HHB-OCF3 | (3-1) | 5% |
| 3-HH2B-OCF3 | (3-4) | 4% |
| 5-HH2B-OCF3 | (3-4) | 4% |
| 3-HHB (F, F)-OCF2H | (3-3) | 4% |
| 3-HHB (F, F)-OCF3 | (3-3) | 5% |
| 3-HH2B (F)-F | (3-5) | 3% |
| 3-HBB (F)-F | (3-23) | 10% |
| 5-HBB (F)-F | (3-23) | 10% |
| 5-HBBH-3 | (14-1) | 3% |
| 3-HB (F) BH-3 | (14-2) | 3% |

The following compound (1-3-1) was added in the ratio of 0.3% by weight based on the preceding composition.

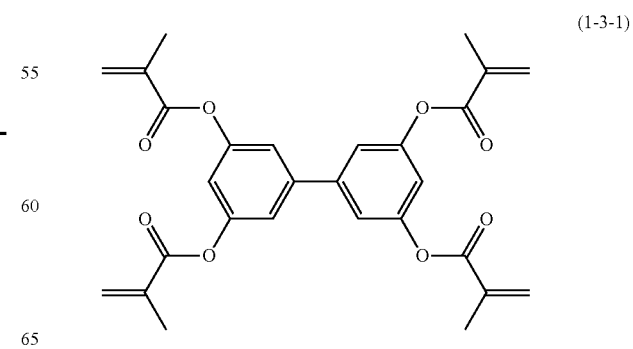

(1-3-1)

NI=85.4° C.; Δn=0.092; Δ∈=4.5; η=15.6 mPa·s.

Example 9

| | | |
|---|---|---|
| 5-HB-CL | (2-2) | 11% |
| 3-HH-4 | (12-1) | 8% |
| 3-HHB-1 | (13-1) | 5% |
| 3-HHB (F, F)-F | (3-3) | 8% |
| 3-HBB (F, F)-F | (3-24) | 20% |
| 5-HBB (F, F)-F | (3-24) | 15% |
| 3-HHEB (F, F)-F | (3-12) | 10% |
| 4-HHEB (F, F)-F | (3-12) | 3% |
| 5-HHEB (F, F)-F | (3-12) | 3% |
| 2-HBEB (F, F)-F | (3-39) | 3% |
| 3-HBEB (F, F)-F | (3-39) | 5% |
| 5-HBEB (F, F)-F | (3-39) | 3% |
| 3-HHBB (F, F)-F | (4-6) | 6% |

The following compound (1-1-1) was added in the ratio of 0.3% by weight based on the preceding composition.

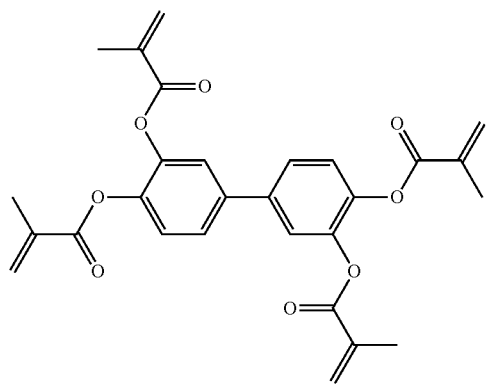

(1-1-1)

NI=80.4° C.; Δn=0.103; Δ∈=8.7; η=23.2 mPa·s.

Example 10

| | | |
|---|---|---|
| 2-HH-3 | (12-1) | 7% |
| 3-HH-4 | (12-1) | 16% |
| 3-HB-O2 | (12-5) | 12% |
| 3-H2B (2F, 3F)-O2 | (6-4) | 14% |
| 5-H2B (2F, 3F)-O2 | (6-4) | 14% |
| 3-HHB (2F, 3CL)-O2 | (7-12) | 4% |
| 2-HBB (2F, 3F)-O2 | (7-7) | 4% |
| 3-HBB (2F, 3F)-O2 | (7-7) | 9% |
| 5-HBB (2F, 3F)-O2 | (7-7) | 9% |
| 3-HHB-1 | (13-1) | 4% |
| 3-HHB-3 | (13-1) | 4% |
| 3-HHB-O1 | (13-1) | 3% |

The following compound (1-2-1) was added in the ratio of 0.4% by weight based on the preceding composition.

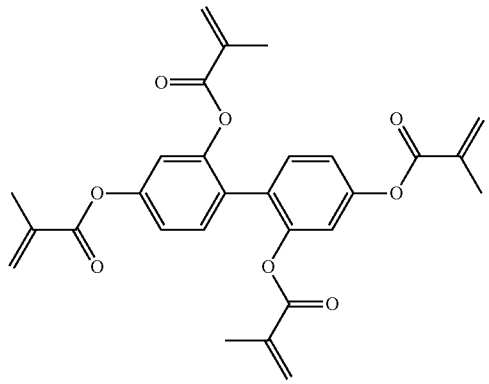

(1-2-1)

NI=75.2° C.; Δn=0.092; Δ∈=−3.9; η=19.0 mPa·s.

Example 11

| | | |
|---|---|---|
| 3-HH-V | (12-1) | 25% |
| 1-BB-3 | (12-8) | 8% |
| 3-HB-O2 | (12-5) | 5% |
| 3-BB (2F, 3F)-O2 | (6-3) | 8% |
| 5-BB (2F, 3F)-O2 | (6-3) | 6% |
| 2-HH1OB (2F, 3F)-O2 | (7-5) | 13% |
| 3-HH1OB (2F, 3F)-O2 | (7-5) | 21% |
| 3-HHB-1 | (13-1) | 5% |
| 3-HHB-O1 | (13-1) | 3% |
| 2-BB (2F, 3F) B-3 | (8-1) | 6% |

The following compound (1-1-1) was added in the ratio of 0.3% by weight based on the preceding composition.

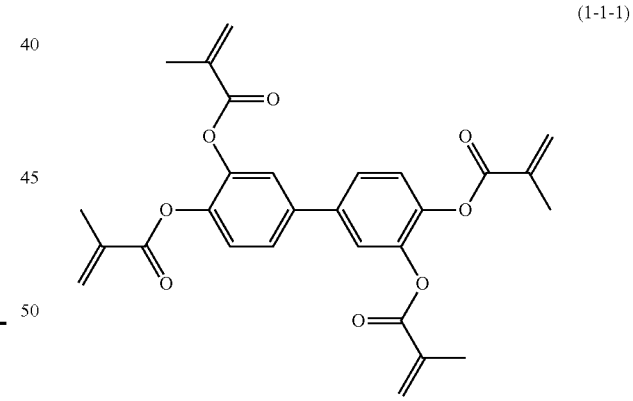

(1-1-1)

NI=77.3° C.; Δn=0.105; Δ∈=−3.2; η=15.6 mPa·s.

Example 12

| | | |
|---|---|---|
| 2-HH-3 | (12-8) | 19% |
| 7-HB-1 | (12-8) | 7% |
| 5-HB-O2 | (12-8) | 8% |
| 3-HB (2F, 3F)-O2 | (6-1) | 15% |
| 5-HB (2F, 3F)-O2 | (6-1) | 15% |
| 5-HBB (2F, 3F)-O2 | (7-7) | 3% |
| 3-HDhB (2F, 3F)-O2 | (7-3) | 5% |

-continued

| | | |
|---|---|---|
| 3-HH1OCro (7F, 8F)-5 | (10-6) | 5% |
| 3-HHB-1 | (13-1) | 4% |
| 3-HHB-3 | (13-1) | 4% |
| 5-HBB (F) B-2 | (13-6) | 7% |
| 5-HBB (F) B-3 | (13-6) | 8% |

The following compound (1-3-1) was added in the ratio of 0.3% by weight based on the preceding composition.

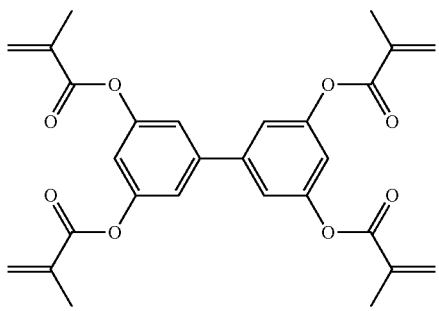

(1-3-1)

NI=76.2° C.; Δn=0.100; Δ∈=−2.5; η=19.8 mPa·s.

Example 13

| | | |
|---|---|---|
| 1-BB-3 | (12-8) | 10% |
| 3-HH-V | (12-1) | 29% |
| 3-BB (2F, 3F)-O2 | (6-3) | 8% |
| 5-BB (2F, 3F)-O2 | (6-3) | 6% |
| 2-HH1OB (2F, 3F)-O2 | (7-5) | 20% |
| 3-HH1OB (2F, 3F)-O2 | (7-5) | 13% |
| 3-HHB-1 | (13-1) | 8% |
| 5-B (F) BB-2 | (13-6) | 6% |

The following compound (1-1-1) was added in the ratio of 0.4% by weight based on the preceding composition.

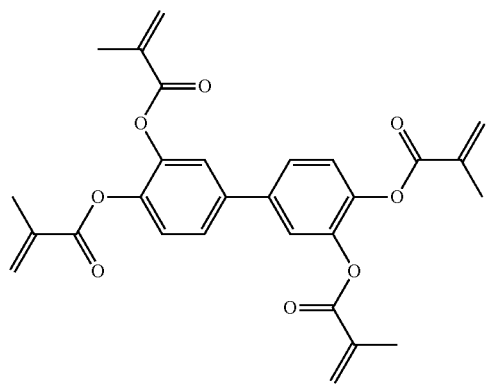

(1-1-1)

NI=73.4° C.; Δn=0.106; Δ∈=−3.0; η=14.8 mPa·s.

Example 14

| | | |
|---|---|---|
| 3-HH-V | (12-1) | 26% |
| 5-HH-V | (12-1) | 8% |
| V-HHB-1 | (13-1) | 12% |
| V2-HHB-1 | (13-1) | 4% |
| 1-BB (F) B-2V | (13-6) | 5% |
| 3-HHXB (F, F)-F | (3-100) | 10% |
| 3-BB (F, F) XB (F, F)-F | (3-97) | 7% |
| 3-GB (F, F) XB (F, F)-F | (3-118) | 7% |
| 3-HBBXB (F, F)-F | (4-32) | 7% |
| 3-HBB (F, F) XB (F, F)-F | (4-38) | 5% |
| 3-BB (F) B (F, F) XB (F, F)-F | (4-47) | 4% |
| 4-GB (F) B (F, F) XB (F, F)-F | (4-56) | 5% |

The following compound (1-1-1) was added in the ratio of 0.3% by weight based on the preceding composition.

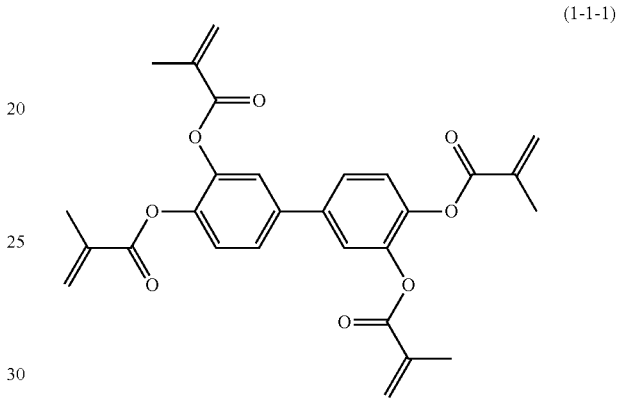

(1-1-1)

NI=86.4° C.; Δn=0.105; Δ∈=8.5; η=16.2 mPa·s.

INDUSTRIAL APPLICABILITY

The polymerizable compound of the invention has a suitable polymerization reactivity, a high conversion yield and a high solubility in a liquid crystal composition. The liquid crystal composition of the invention includes this compound and has physical properties such as a high maximum temperature of a nematic phase, a low minimum temperature of a nematic phase, a small viscosity, a suitable optical anisotropy, a large dielectric anisotropy, a suitable elastic constant, a large specific resistance and a suitable pretilt. The composition has a suitable balance between at least two of the physical properties. The polymerizable compound gives a polymer by polymerization. The composition is suitable for a liquid crystal display device having a PSA mode. A liquid crystal display device containing the composition has a wide temperature range in which the device can be used, a short response time, a large voltage holding ratio, a low threshold voltage, a large contrast ratio and a long service life. Accordingly, the device can widely be utilized for the display of personal computers, televisions and so forth.

What is claimed is:

1. A compound represented by formula (1):

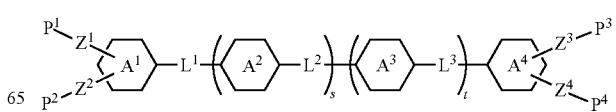

(1)

wherein ring $A^1$, ring $A^2$, ring $A^3$ and ring $A^4$ are independently phenylene or cyclohexylene, and in these groups at least one hydrogen may be replaced by alkyl having 1 to 10 carbons, fluorine, —$CF_2H$ or —$CF_3$;

$Z^1$, $Z^2$, $Z^3$ and $Z^4$ are independently a single bond, —COO—, —$CH_2O$— or —CH=CHO—;

$L^1$, $L^2$ and $L^3$ are independently a single bond, —CH=CH—, —CH=CH—COO—, —$C(CH_3)$=CH—COO—, —CH=$C(CH_3)$—COO—, —$C(CH_3)$=$C(CH_3)$—COO—, —C≡C—, —COCH=CH—, —$C(CH_3)$=$C(CH_3)$—, —CH=CH—$CH_2O$—, —CH=CH—$OCH_2$— or —CO—, and at least one of $L^1$, $L^2$ and $L^3$ is —CH=CH—, —CH=CH—COO—, —$C(CH_3)$=CH—COO—, —CH=$C(CH_3)$—COO—, —$C(CH_3)$=$C(CH_3)$—COO—, —C≡C—, —COCH=CH—, —$C(CH_3)$=$C(CH_3)$—, —CH=CH—$CH_2O$—, —CH=CH—$OCH_2$— or —CO—;

s and t are independently 0 or 1, and the sum of s and t is 0, 1 or 2;

$P^1$, $P^2$, $P^3$ and $P^4$ are the group (P-1):

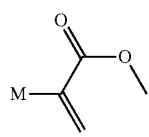
(P-1)

wherein M is hydrogen, fluorine, -$CH_3$ or -$CF_3$.

2. The compound according to claim 1, wherein the compound is represented by any one of formulas (1-1) to (1-6):

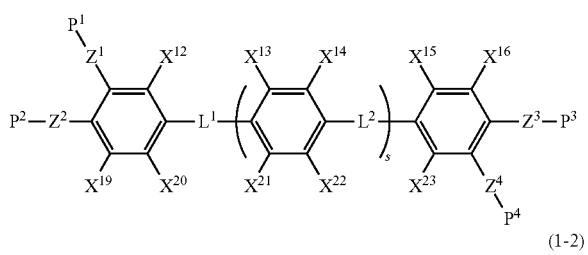
(1-1)

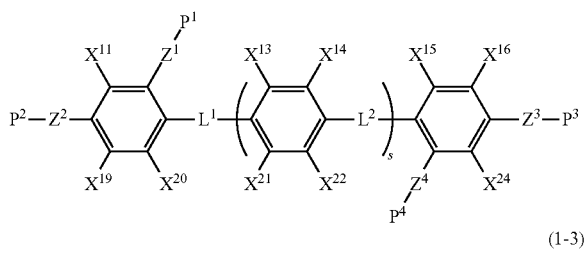
(1-2)

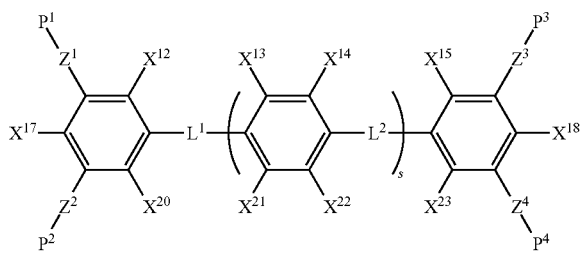
(1-3)

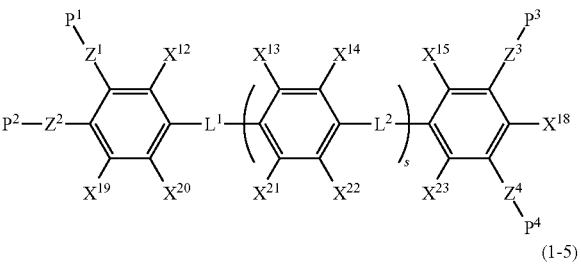
(1-4)

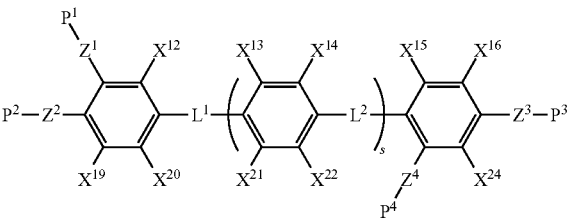
(1-5)

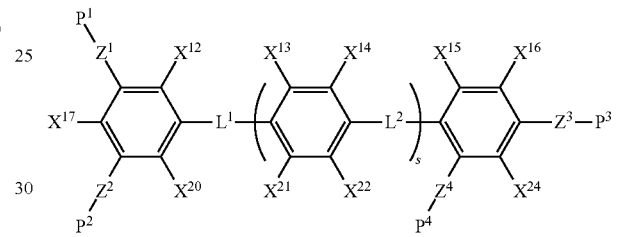
(1-6)

wherein $Z^1$, $Z^2$, $Z^3$ and $Z^4$ are independently a single bond, —COO—, —$CH_2O$— or —CH=CHO—; $L^1$ and $L^2$ are independently a single bond, —CH=CH—, —CH=CH—COO—, —$C(CH_3)$=CH—COO—, —CH=$C(CH_3)$—COO—, —$C(CH_3)$=$C(CH_3)$—COO—, —C≡C—, —COCH=CH—, —$C(CH_3)$=$C(CH_3)$—, —CH=CH—$CH_2O$—, —CH=CH—$OCH_2$— or —CO—, and at least one of $L^1$ and $L^2$ is —CH=CH—, —CH=CH—COO—, —$C(CH_3)$=CH—COO—, —CH=$C(CH_3)$—COO—, —$C(CH_3)$=$C(CH_3)$—COO—, —C≡C—, —COCH=CH—, —$C(CH_3)$=$C(CH_3)$—, —CH=CH—$CH_2O$—, —CH=CH—$OCH_2$— or —CO—; $X^{11}$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$ and $X^{24}$ are independently hydrogen, alkyl having 1 to 10 carbons, fluorine, —$CF_2H$ or —$CF_3$; s is 0 or 1; and $P^1$, $P^2$, $P^3$ and $P^4$ are the group (P-1):

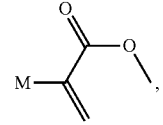
(P-1)

wherein M is hydrogen, fluorine, —$CH_3$ or —$CF_3$.

3. The compound according to claim 2, wherein in formulas (1-1) to (1-6), s is 0.

4. The compound according to claim 2, wherein in formulas (1-1) to (1-6), $Z^1$, $Z^2$, $Z^3$ and $Z^4$ are independently a single bond; s is 0 or 1; and P is $CH_2$=CH—COO—, or $CH_2$=$C(CH_3)$—COO—.

5. The compound according to claim 2, wherein in formulas (1-1) to (1-6), $Z^1$, $Z^2$, $Z^3$ and $Z^4$ are independently —COO—, —CH$_2$O— or —CH=CHO—; s is 0 or 1; and P is CH$_2$=CH—COO— or CH$_2$=C(CH$_3$)—COO—.

6. The compound according to claim 2, wherein in formulas (1-1) to (1-3), Z$^1$, Z$^2$, Z$^3$ and Z$^4$ are independently a single bond; s is 0 or 1; L$^1$ and L$^2$ are independently a single bond, —CH=CH— or —CH=CHCOO—; and P is CH$_2$=CH—COO— or CH$_2$=C(CH$_3$)—COO—.

7. The compound according to claim 2, wherein in formulas (1-1) to (1-3), Z$^1$, Z$^2$, Z$^3$ and Z$^4$ are —CH=CHO—; s is 0 or 1; L$^1$ and L$^2$ are independently a single bond, —CH=CH— or —CH=CHCOO—; and P is CH$_2$=CH—COO— or CH$_2$=C(CH$_3$)—COO—.

8. A polymer obtained from the compound according to claim 1.

9. A liquid crystal composition including the compound according to claim 1.

10. The liquid crystal composition according to claim 9, further including at least one compound selected from the group consisting of compounds represented by formulas (2), (3) and (4):

wherein R$^3$ is alkyl having 1 to 10 carbons or alkenyl having 2 to 10 carbons, and in these groups at least one hydrogen may be replaced by fluorine and at least one —CH$_2$— may be replaced —O—;
X$^1$ is independently fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;
ring B$^1$, ring B$^2$ and ring B$^3$ are independently 1,4-cyclohexylene, 1,3-dioxane-2,5-diyl, pyrimidine-2,5-diyl, tetrahydropyran-2,5-diyl, or 1,4-phenylene in which at least one hydrogen may be replaced by fluorine;
Y$^1$ and Y$^2$ are independently —(CH$_2$)$_2$—, —(CH$_2$)$_4$—, —COO—, —CF$_2$O—, —OCF$_2$—, —CH=CH—, —C≡C—, —CH$_2$O— or a single bond; and
Q$^1$ and Q$^2$ are independently hydrogen or fluorine.

11. The liquid crystal composition according to claim 9, further including at least one compound selected from the group consisting of compounds represented by formula (5):

(5)

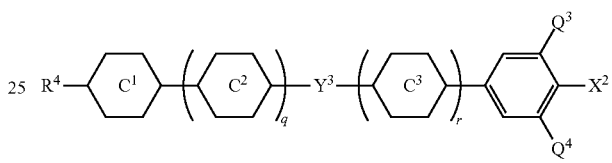

wherein R$^4$ is alkyl having 1 to 10 carbons or alkenyl having 2 to 10 carbons, and in these groups at least one hydrogen may be replaced by fluorine and at least one —CH$_2$— may be replaced by —O—;
X$^2$ is —CN or —C≡C—CN;
ring C$^1$, ring C$^2$ and ring C$^3$ are independently 1,4-cyclohexylene, 1,4-phenylene in which at least one hydrogen may be replaced by fluorine, 1,3-dioxane-2,5-diyl, tetrahydropyran-2,5-diyl or pyrimidine-2,5-diyl;
Y$^3$ is —(CH$_2$)$_2$—, —COO—, —CF$_2$O—, —OCF$_2$—, —C≡C—, —CH$_2$O— or a single bond;
Q$^3$ and Q$^4$ are independently hydrogen or fluorine; and
q is 0, 1 or 2, and r is 0 or 1.

12. The liquid crystal composition according to claim 9, further including at least one compound selected from the group consisting of compounds represented by formulas (6), (7), (8), (9), (10) and (11):

(2)

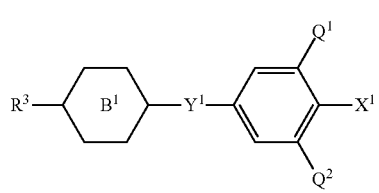

(3)

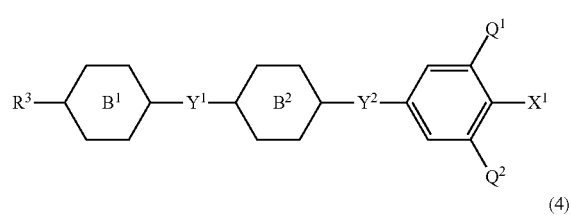

(4)

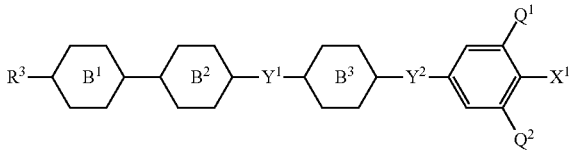

(6)

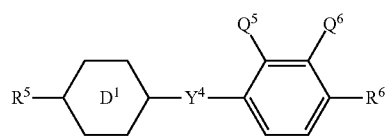

(7)

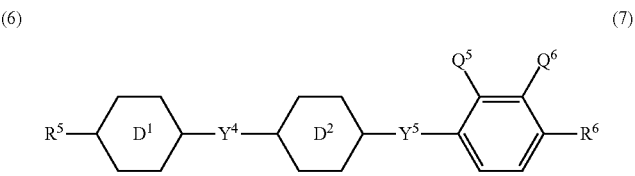

(8)

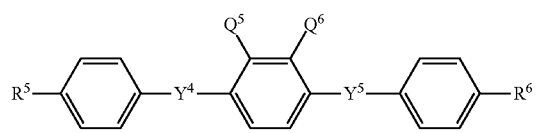

(9)

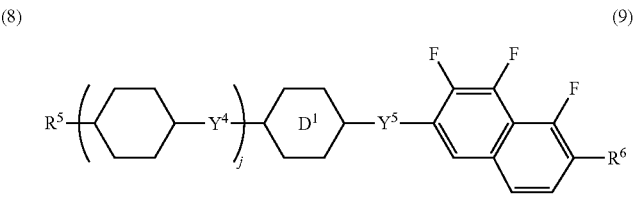

-continued

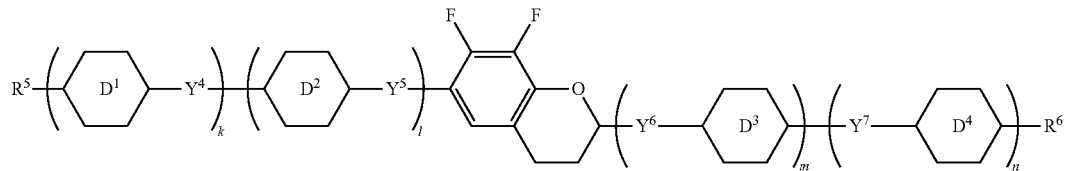
(10)

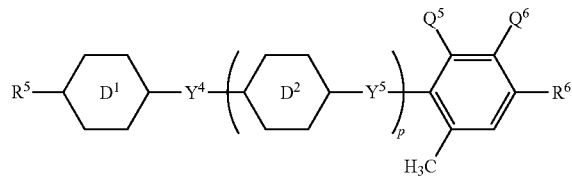
(11)

wherein R⁵ and R⁶ are independently alkyl having 1 to 10 carbons or alkenyl having 2 to 10 carbons, and in these groups at least one hydrogen may be replaced by fluorine and at least one —CH₂— may be replaced by —O—;
ring D¹, ring D², ring D³ and ring D⁴ are independently 1,4-cyclohexylene, 1,4-cyclohexenylene, 1,4-phenylene in which at least one hydrogen may be replaced by fluorine, tetrahydropyran-2,5-diyl or decahydro-2,6-naphthalene;
Y⁴, Y⁵, Y⁶ and Y⁷ are independently —(CH₂)₂—, —COO—, —CH₂O—, —OCF₂—, —OCF₂(CH₂)₂— or a single bond;
Q⁵ and Q⁶ are independently fluorine or chlorine; and
j, k, l, m, n and p are independently 0 or 1, and the sum of k, l, m and n is 1 or 2.

13. The liquid crystal composition according to claim 9, further including at least one compound selected from the group consisting of compounds represented by formulas (12), (13) and (14):

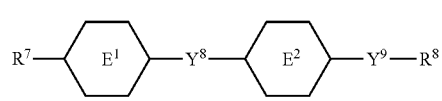
(12)

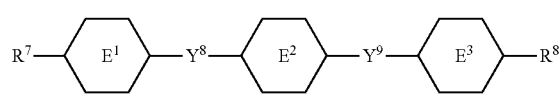
(13)

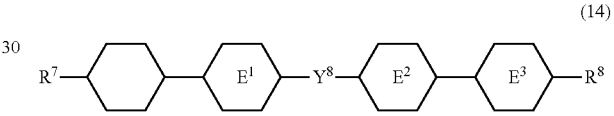
(14)

wherein R⁷ and R⁸ are independently alkyl having 1 to 10 carbons or alkenyl having 2 to 10 carbons, and in these groups at least one hydrogen may be replaced by fluorine and at least one —CH₂— may be replaced by —O—;
ring E¹, ring E² and ring E³ are independently 1,4-cyclohexylene, pyrimidine-2,5-diyl, 1,4-phenylene, 2-fluoro-1,4-phenylene or 2,5-difluoro-1,4-phenylene; and
Y⁸ and Y⁹ are independently —C≡C—, —COO—, —(CH₂)₂—, —CH=CH— or a single bond.

14. The liquid crystal composition according to claim 10, further including at least one compound selected from the group consisting of compounds represented by formulas (12), (13) and (14):

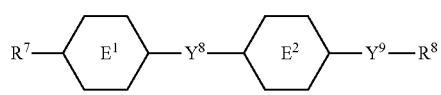
(12)

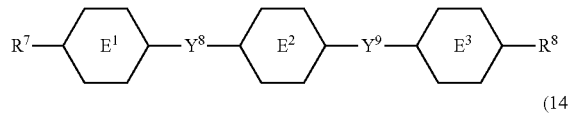
(13)

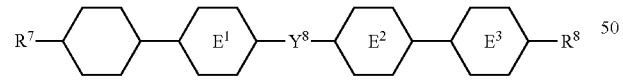
(14)

wherein R⁷ and R⁸ are independently alkyl having 1 to 10 carbons or alkenyl having 2 to 10 carbons, and in these groups at least one hydrogen may be replaced by fluorine and at least one —CH₂— may be replaced by —O—;
ring E¹, ring E² and ring E³ are independently 1,4-cyclohexylene, pyrimidine-2,5-diyl, 1,4-phenylene, 2-fluoro-1,4-phenylene or 2,5-difluoro-1,4-phenylene; and
Y⁸ and Y⁹ are independently —C≡C—, —COO—, —(CH₂)₂—, —CH=CH— or a single bond.

15. The liquid crystal composition according to claim 11, further including at least one compound selected from the group consisting of compounds represented by formulas (12), (13) and (14):

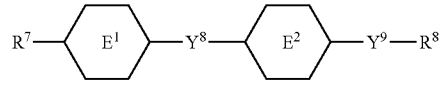
(12)

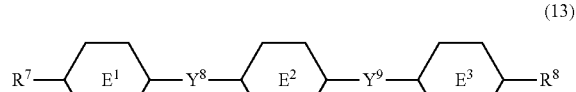
(13)

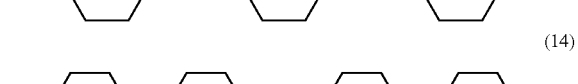
(14)

wherein R⁷ and R⁸ are independently alkyl having 1 to 10 carbons or alkenyl having 2 to 10 carbons, and in these groups at least one hydrogen may be replaced by fluorine and at least one —CH$_2$— may be replaced by —O—;

ring E$^1$, ring E$^2$ and ring E$^3$ are independently 1,4-cyclohexylene, pyrimidine-2,5-diyl, 1,4-phenylene, 2-fluoro-1,4-phenylene or 2,5-difluoro-1,4-phenylene; and Y$^8$ and Y$^9$ are independently —C≡C—, —COO—, —(CH$_2$)$_2$—, —CH═CH— or a single bond.

16. The liquid crystal composition according to claim 12, further including at least one compound selected from the group consisting of compounds represented by formulas (12), (13) and (14):

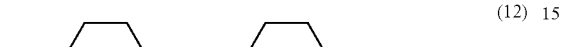
(12)

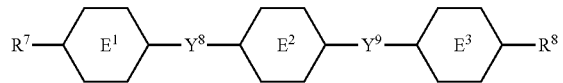
(13)

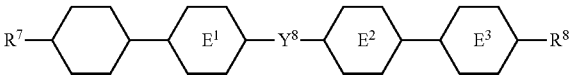
(14)

wherein R$^7$ and R$^8$ are independently alkyl having 1 to 10 carbons or alkenyl having 2 to 10 carbons, and in these groups at least one hydrogen may be replaced by fluorine and at least one —CH$_2$— may be replaced by —O—;

ring E$^1$, ring E$^2$ and ring E$^3$ are independently 1,4-cyclohexylene, pyrimidine-2,5-diyl, 1,4-phenylene, 2-fluoro-1,4-phenylene or 2,5-difluoro-1,4-phenylene; and Y$^8$ and Y$^9$ are independently —C≡C—, —COO—, —(CH$_2$)$_2$—, —CH═CH— or a single bond.

17. A liquid crystal display device containing the liquid crystal composition according to claim 9.

* * * * *